(12) United States Patent
Cutler et al.

(10) Patent No.: US 10,919,943 B2
(45) Date of Patent: Feb. 16, 2021

(54) MUTANT PROTEINS ENABLING AGROCHEMICAL CONTROL OF PLANT GENE EXPRESSION

(71) Applicant: The Regents of the University of California, Oakland, CA (US)

(72) Inventors: Sean R. Cutler, Riverside, CA (US); Sang-Youl Park, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/087,024

(22) PCT Filed: Mar. 24, 2017

(86) PCT No.: PCT/US2017/024153
§ 371 (c)(1),
(2) Date: Sep. 20, 2018

(87) PCT Pub. No.: WO2017/165855
PCT Pub. Date: Sep. 28, 2017

(65) Prior Publication Data
US 2019/0389914 A1     Dec. 26, 2019

Related U.S. Application Data

(60) Provisional application No. 62/313,290, filed on Mar. 25, 2016.

(51) Int. Cl.
*C07K 14/415*     (2006.01)
*C12N 15/82*     (2006.01)

(52) U.S. Cl.
CPC ........ *C07K 14/415* (2013.01); *C12N 15/8238* (2013.01)

(58) Field of Classification Search
None
See application file for complete search history.

(56) References Cited

U.S. PATENT DOCUMENTS

| 9,738,902 B2 * | 8/2017 | Cutler ............... C12N 15/8273 |
| 2010/0216643 A1 | 8/2010 | Cutler et al. |
| 2011/0271408 A1 | 11/2011 | Cutler et al. |
| 2014/0259226 A1 | 9/2014 | Cutler et al. |

FOREIGN PATENT DOCUMENTS

| WO | WO 2014/159394 A1 | 10/2014 |
| WO | WO 2016/043985 A1 | 3/2016 |

OTHER PUBLICATIONS

Yu et al 2016 PLOS ONE 1-17 (Year: 2016).*
Sugimoto et al 2014 Journal of Experimental Botany 18:5385-5400 (Year: 2014).*
International Application No. PCT/US2017/024153, International Search Report and Written Opinion dated Sep. 13, 2017, 15 pages.
Mosquna et al., "Potent and Selective Activation of Abscisic Acid Receptors In Vivo by Mutational Stabilization of their Agonist-Bound Conformation," PNAS, vol. 108, No. 51, Dec. 20, 2011, pp. 20838-20843.
Park et al., "Abscisic Acid Inhibits PP2Cs via the PYR/PYL Family of ABA-binding START Proteins," Science, vol. 324, Issue 5930, May 22, 2009, pp. 1068-1071.
Soon et al., "Molecular Mimicry Regulates ABA Signaling by SnRK2 Kinases and PP2C Phosphatases," Science, NIH Public Access, Author Manuscript (10 pages) plus final edited form as Science, vol. 335 (6064), Jan. 6, 2012, pp. 85-88.

* cited by examiner

*Primary Examiner* — Brent T Page
(74) *Attorney, Agent, or Firm* — Kilpatrick Townsend & Stockton LLP

(57) ABSTRACT

Mutated PYR/PYL receptor polypeptides and mutated type 2C protein phosphatases (PP2Cs) are provided. In some embodiments, the mutated PYR/PYL receptor polypeptide is agonized by an orthogonal ligand that does not significantly agonize a wild-type PYR/PYL receptor polypeptide and comprises one or more mutations that disrupts binding to a wild-type PP2C, and the mutated PP2C comprises one or more mutations that disrupts binding to a wild-type PYR/PYL receptor polypeptide, wherein the mutated PYR/PYL receptor polypeptide and the mutated PP2C interact with each other.

21 Claims, 15 Drawing Sheets

Specification includes a Sequence Listing.

MUTANT PROTEINS ENABLING AGROCHEMICAL CONTROL OF PLANT GENE EXPRESSION

CROSS-REFERENCE TO RELATED APPLICATIONS

This application claims priority to U.S. Provisional Patent Application No. 62/313,290, filed Mar. 25, 2016, the entire content of which is incorporated by reference herein.

STATEMENT AS TO RIGHTS TO INVENTIONS MADE UNDER FEDERALLY SPONSORED RESEARCH AND DEVELOPMENT

This invention was made with Government support under Grant No. 1258175, awarded by the National Science Foundation. The Government has certain rights in this invention.

BACKGROUND OF THE INVENTION

Systems for regulating biological responses with small molecules have broad biotechnological utility and are generally built by modifying natural regulatory circuits, as first exemplified by engineering the Lac operon from *E. coli* for inducible production of recombinant proteins in the 1970s. Numerous regulatory mechanisms can be coopted for creating inducible inducible regulatory circuits, including allostery, subcellular localization, and chemically induced dimerization (CID). The first chemically induced heterodimerization system harnessed immunosuppressant regulated protein-protein interactions to build rapamycin-controlled three-hybrid systems (Belshaw, Ho, Crabtree, & Schreiber, 1996; Bier, Thiel, Briels, & Ottmann, 2015; Licitra & Liu, 1996), in which transcription of a target gene is controlled by a CID module that controls the physical association of a transcriptional activation (AD) and DNA binding domain (DBD). The most common three-hybrid systems use rapamycin, or related rapalogs, to direct the formation of a complex between and the prolyl-isomerase FKBP (FK506 binding protein 12) and FRB (the FKBP-rapamycin binding domain of mammalian Target of Rapamycin Complex 1) (Rutkowska & Schultz, 2012). Several CID systems based on different protein-protein interaction modules have been developed (Bier et al., 2015), and CID is a general process that can be exploited for many synthetic biological processes. For example, CID can be used to regulate the enzymatic activity of enzymes split into two non-functional halves, as recently Illustrated with CAS9 (Zetsche, Volz, & Zhang, 2015). It can also be used to regulate the activity of proteins that function in specific subcellular locations. For example, the "anchor away" method uses a FRB domain fused to cytoplasmic anchors (such as abundant ribosomal or plasma membrane proteins) to relocalize target-FKBP fusion proteins away from sites of action in response to rapamycin, enabling construction of inducible loss-of-function phenotypes (Haruki, Nishikawa, & Laemmli, 2008). Proteins can also be recruited to the proteasome or mitochondrial membrane using CID to create chemically inactivated protein functions (Janse, Crosas, Finley, & Church, 2004). The converse creation of chemically activatable protein forms can be engineered using an unstable FKBP allele that is rapidly degraded under basal conditions, but stabilized upon rapamycin treatment by interaction FRB (Banaszynski, Chen, Maynard-Smith, Ooi, & Wandless, 2006). Thus, CID modules are powerful tools that can be leveraged to engineer many modes of chemically regulated activities, with many examples beyond those provided above.

The plant abscisic acid (ABA) response module has been coopted to build a chemically induced proximity (CIP) system controlled by ABA, which is a non-toxic dietary metabolite (Liang, Ho, & Crabtree, 2011). ABA is perceived by the soluble receptor PYR1 (Pyrabactin Resistance 1), and related PYR1-like (PYL) ABA receptors (Cutler, Rodriguez, Finkelstein, & Abrams, 2010). These proteins indirectly control the activity of a subfamily of three Sucrose non-fermenting 1-related (SnRK2) protein kinases in response to drought and other environmental stresses. The SnRK2s autoactivate by cis- and trans-autophosphorylation on their activation loops, but are continuously inactivated by clade A type 2C protein phosphatases (PP2Cs), which results in low basal kinase activity (Ng et al., 2011; Soon et al., 2012). When ABA rises during stress it binds to PYR1 and PYR1-like (PYL) receptors and stabilizes their activated conformations, enabling them to bind to and inhibit the PP2Cs (Ma et al., 2009; Melcher et al., 2009; Miyazono et al., 2009; S.-Y. Park et al., 2009; Yin et al., 2009). This in turn allows accumulation of activated SnRK2 kinases, which triggers downstream signaling events. ABA's ability to stabilize a complex between ABA receptors and PP2Cs has been exploited to create a new CID module regulated by ABA, as have other plant hormones and their perception systems. However, plant hormones are not well-suited for use in plants as ligands for CID.

BRIEF SUMMARY OF THE INVENTION

The present invention provides for cells (e.g., plant, animal, mammalian, bacterial, or fungal cells) or plants (or a plant cell, seed, flower, leaf, fruit, or other plant part from such plants or processed food or food ingredient from such plants) comprising a heterologous expression cassette, the expression cassette comprising a promoter operably linked to one or more polynucleotides encoding a first polypeptide comprising a mutated PYR/PYL receptor polypeptide and a second polypeptide comprising a mutated type 2C protein phosphatase (PP2C), wherein the mutated PYR/PYL receptor polypeptide is agonized by an orthogonal ligand that does not significantly agonize a wild-type PYR/PYL receptor polypeptide and wherein the mutated PYR/PYL receptor polypeptide comprises one or more mutations that disrupts binding to a wild-type PP2C, wherein the mutated PP2C comprises one or more mutations that disrupts binding to a wild-type PYR/PYL receptor polypeptide, and wherein the mutated PYR/PYL receptor polypeptide and the mutated PP2C interact with each other.

In some embodiments, the cell or plant comprises a first heterologous expression cassette and a second heterologous expression cassette, wherein the first expression cassette comprises a first promoter operably linked to a polynucleotide encoding the first polypeptide comprising the mutated PYR/PYL receptor polypeptide, and wherein the second expression cassette comprises a second promoter operably linked to a polynucleotide encoding the second polypeptide comprising the mutated PP2C. In some embodiments, the first promoter and the second promoter are the same promoter. In some embodiments, the first promoter and the second promoter are different promoters.

In some embodiments, the first polypeptide comprises the mutated PYR/PYL receptor polypeptide fused to a transcriptional activation domain and the second polypeptide comprises the mutated PP2C fused to a DNA binding domain. In some embodiments, the first polypeptide comprises the mutated PYR/PYL receptor polypeptide fused to a DNA binding domain and the second polypeptide comprises the mutated PP2C fused to a transcriptional activation domain. In some embodiments, one or both of the polynucleotide that encodes the first polypeptide and the polynucleotide that encodes the second polypeptide is operably linked to a promoter that comprises a polynucleotide sequence that binds the DNA binding domain.

In some embodiments, the one or more mutations in the PYR/PYL receptor polypeptide that disrupts binding to a wild-type PP2C comprises a mutation at an amino acid corresponding to position F61, I62, K63, I84, S85, G86, L87, P88, A89, H115, R116, L117, P148, G150, N151, D155, T156, M158, F159, T162, or K170 in PYR1 (SEQ ID NO:1). In some embodiments, the one or more mutations in the PYR/PYL receptor polypeptide that disrupts binding to a wild-type PP2C comprises a mutation selected from F61D/E/G/H/I/K/N/P/Q/R/S, I62D/E/G/K/R/W/Y, K63P, I84L, S85A/C/D/E/F/G/H/I/K/L/M/N/P/Q/R/V/W/Y, G86A/C/D/E/F/H/I/K/L/M/N/P/Q/R/S/T/V/W/Y, L87A/C/D/E/G/H/K/N/Q/R/S/T/V/W/Y, P88C/D/E/F/G/H/I/K/L/M/N/Q/R/S/T/V/W/Y, A89C/D/E/F/H/I/K/L/M/N/P/Q/R/S/T/V/Y, H115A/C/D/E/F/G/I/K/L/M/P/Q/R/S/T/V/W/Y, R116A/C/D/E/F/G/H/I/P/S/T/V/W/Y, L117A/D/E/G/H/K/N/P/Q/R/S/T/V/W/Y, P148C/D/E/F/G/H/I/K/L/M/N/Q/R/S/T/V/W/Y, G150I/N/V/W, N151C/D/E/F/G/H/I/K/L/M/P/Q/R/V/W/Y, D155C/F/G/I/K/L/M/P/R/V/W/Y, T156E/F/G/H/I/K/L/M/N/P/Q/R/W/Y, M158P, F159D/E/G/H/K/N/P/Q/R/S/W/Y, T162D/E/F/P, or K170P. In some embodiments, the one or more mutations in the PYR/PYL receptor polypeptide that disrupts binding to a wild-type PP2C comprises a mutation at an amino acid corresponding to position F61, S85, T156, or T162 in PYR1. In some embodiments, the one or more mutations in the PYR/PYL receptor polypeptide that disrupts binding to a wild-type PP2C comprises a mutation selected from F61K, S85P, T156P, and T162D.

In some embodiments, the mutated PYR/PYL receptor polypeptide further comprises a mutation at one or more amino acids corresponding to positions Y58, K59, V81, A89, F108, S122, M158, F159, or A160 in PYR1 (SEQ ID NO:1), wherein the mutation is selected from Y58H, K59R, V81C, V81I, V81T, A89W, F108A, F108C, F108E, F108G, F108I, F108L, F108N, F108Q, F108S, F108T, F108V, S122G, M158I, M158V, F159A, F159C, F159I, F159L, F159M, F159T, F159V, A160C, A160V, or combinations thereof. In some embodiments, the mutated PYR/PYL receptor comprises:
  mutations corresponding to Y58H, K59R, V81I, F108A, S122G, M158I, F159V, A160V, and T162D in PYR1;
  mutations corresponding to Y58H, K59R, V81I, F108A, S122G, M158V, F159V, A160V, and T162D in PYR1; or
  mutations corresponding to Y58H, K59R, V81I, F108A, S122G, M158I, F159V, A160C, and T162D in PYR1.

In some embodiments, the mutated PYR/PYL receptor polypeptide as described herein is substantially identical (at least 70%, at least 75%, at least 80%, at least 85%, at least 90%, at least 91%, at least 92%, at least 93%, at least 94%, at least 95%, at least 96%, at least 97%, at least 98%, or at least 99% identical) to any of SEQ ID NOs:1-14, 19-21, or 41-115. In some embodiments, the mutated PYR/PYL receptor polypeptide as described herein is substantially identical (at least 70%, at least 75%, at least 80%, at least 85%, at least 90%, at least 91%, at least 92%, at least 93%, at least 94%, at least 95%, at least 96%, at least 97%, at least 98%, or at least 99% identical) to any of SEQ ID NOs:1-14, 19-21, or 41-115 and further comprises one or more mutations as described herein (e.g., a substitution at one or more amino acid residues corresponding to F61, I62, K63, I84, S85, G86, L87, P88, A89, H115, R116, L117, P148, G150, N151, D155, T156, M158, F159, T162, or K170 in SEQ ID NO:1).

In some embodiments, the one or more mutations in the PP2C that disrupts binding to a wild-type PYR/PYL receptor polypeptide comprises a mutation at an amino acid corresponding to position E201, E203, H245, G246, G247, E323, K381, I383, W385, R389, F391, G392, V393, or Y404 in HAB1 (SEQ ID NO:22). In some embodiments, the one or more mutations in the PP2C that disrupts binding to a wild-type PYR/PYL receptor polypeptide comprises a mutation selected from E201H/K, E203A/C/D/F/G/H/I/K/L/M/N/P/R/S/T/V/W/Y, H245A/C/D/E/F/G/I/K/L/M/N/P/Q/R/S/T/V/W/Y, G246A/C/D/E/F/H/I/K/L/M/N/P/Q/R/S/T/V/W/Y, G247A/E/F/I/K/M/P/Q/R/T/V/W/Y, E323L, K381W, I383D/E/G/H/K/N/P/Q/R/S/T/W/Y, W385A/C/D/E/F/G/H/I/K/L/M/N/P/Q/R/S/T/V/Y, R389A/C/D/E/F/G/H/I/K/L/M/P/Q/T/V/W/Y, F391D/E/P, G392A/D/C/E/F/H/I/K/L/M/N/P/Q/R/T/V/W/Y, V393D/E/G/K/N/P/Q/R/S, or Y404D/E/G/K/N/P/Q/R/S/T. In some embodiments, the one or more mutations in the PP2C that disrupts binding to a wild-type PYR/PYL receptor polypeptide comprises a mutation at an amino acid corresponding to position E203, I383, or V393 in HAB1. In some embodiments, the one or more mutations in the PP2C that disrupts binding to a wild-type PYR/PYL receptor polypeptide comprises a mutation selected from E203D, E203T, E203W, I383G, V393K, V393R, or V393Q.

In some embodiments, the mutated PP2C further comprises one or more mutations that disrupts the catalytic activity of the mutated PP2C. In some embodiments, the mutated PP2C comprises a mutation at one or more amino acids corresponding to positions R199, D204, S322, or R505 in HAB1 (SEQ ID NO:22) wherein the mutation is selected from R199A, D204A, S322D, S322E, R505A, or combinations thereof. In some embodiments, the mutated PP2C comprises:
  mutations corresponding to D204A, V393R, and R505A in HAB1; or
  mutations corresponding to R199A, D204A, S322D, V393R, and R505A in HAB1.

In some embodiments, the mutated PP2C as described herein is substantially identical (at least 70%, at least 75%, at least 80%, at least 85%, at least 90%, at least 91%, at least 92%, at least 93%, at least 94%, at least 95%, at least 96%, at least 97%, at least 98%, or at least 99% identical) to any of SEQ ID NOs:22-31. In some embodiments, and comprises one or more mutations as described herein (e.g., a substitution at one or more amino acid residues corresponding to E201, E203, H245, G246, G247, E323, K381, I383, W385, R389, F391, G392, V393, or Y404 in SEQ ID NO:22).

In some embodiments,
  (a) the mutated PYR/PYL receptor polypeptide comprises a mutation corresponding to F61K in PYR1 and the mutated PP2C comprises a mutation corresponding to V393Q in HAB1;
  (b) the mutated PYR/PYL receptor polypeptide comprises a mutation corresponding to S85P in PYR1 and the mutated PP2C comprises a mutation corresponding to E203D in HAB1;
  (c) the mutated PYR/PYL receptor polypeptide comprises a mutation corresponding to S85P in PYR1 and the mutated PP2C comprises a mutation corresponding to E203T in HAB1;

(d) the mutated PYR/PYL receptor polypeptide comprises a mutation corresponding to S85P in PYR1 and the mutated PP2C comprises a mutation corresponding to E203W in HAB1;
(e) the mutated PYR/PYL receptor polypeptide comprises a mutation corresponding to T156P in PYR1 and the mutated PP2C comprises a mutation corresponding to I383G in HAB1;
(f) the mutated PYR/PYL receptor polypeptide comprises a mutation corresponding to T162D in PYR1 and the mutated PP2C comprises a mutation corresponding to V393K in HAB1; or
(g) the mutated PYR/PYL receptor polypeptide comprises a mutation corresponding to T162D in PYR1 and the mutated PP2C comprises a mutation corresponding to V393R in HAB1.

In some embodiments, the orthogonal ligand is an agrochemical. In some embodiments, the orthogonal ligand is mandipropamid.

In another aspect, methods of activating an orthogonal PYR/PYL-PP2C interaction in a cell (e.g., plant, animal, mammalian, bacterial, or fungal cell) or plant are provided. In some embodiments, the method comprises contacting a cell or plant as described herein with the orthogonal ligand, wherein the step of contacting the plant or cell with the orthogonal ligand activates an interaction between the mutated PYR/PYL and the mutated PP2C but does not significantly activate an endogenous abscisic acid (ABA) signaling pathway in the cell or plant.

In another aspect, methods of controlling expression of a gene, protein, or phenotype in a cell (e.g., plant, animal, mammalian, bacterial, or fungal cell) or plant are provided. In some embodiments, the method comprises:
expressing in a plant or a cell an expression cassette comprising a promoter operably linked to one or more polynucleotides encoding a first polypeptide comprising a mutated PYR/PYL receptor polypeptide as described herein fused to one of a transcriptional activation domain or a DNA binding domain, and a second polypeptide comprising a mutated PP2C as described herein fused to the other of a transcriptional activation domain or a DNA binding domain, wherein the promoter comprises a polynucleotide sequence that binds the DNA binding domain; and
contacting the plant or cell with the orthogonal ligand activates an interaction between the mutated PYR/PYL and the mutated PP2C, thereby associating the DNA binding domain and the transcriptional activation domain and activating expression of the gene, protein, or phenotype.

In another aspect, expression cassettes (and expression vectors comprising the expression cassette) comprising a promoter operably linked to one or more polynucleotides encoding a mutated PYR/PYL receptor polypeptide and a mutated type 2C protein phosphatase (PP2C) are provided, wherein the mutated PYR/PYL receptor polypeptide is agonized by an orthogonal ligand that does not significantly agonize a wild-type PYR/PYL receptor polypeptide and wherein the mutated PYR/PYL receptor polypeptide comprises a mutation that disrupts binding to a wild-type PP2C, wherein the mutated PP2C comprises a mutation that disrupts binding to a wild-type PYR/PYL receptor polypeptide, and wherein the mutated PYR/PYL receptor polypeptide and the mutated PP2C interact with each other.

In some embodiments, a first expression cassette and a second expression cassette are provided, wherein the first expression cassette comprises a first promoter operably linked to a polynucleotide encoding the first polypeptide comprising the mutated PYR/PYL receptor polypeptide, and wherein the second expression cassette comprises a second promoter operably linked to a polynucleotide encoding the second polypeptide comprising the mutated PP2C. In some embodiments, the first promoter and the second promoter are the same promoter. In some embodiments, the first promoter and the second promoter are different promoters.

In some embodiments, the one or more mutations in the PYR/PYL receptor polypeptide that disrupts binding to a wild-type PP2C comprises a mutation at an amino acid corresponding to position F61, I62, K63, I84, S85, G86, L87, P88, A89, H115, R116, L117, P148, G150, N151, D155, T156, M158, F159, T162, or K170 in PYR1 (SEQ ID NO:1). In some embodiments, the one or more mutations in the PYR/PYL receptor polypeptide that disrupts binding to a wild-type PP2C comprises a mutation selected from F61D/E/G/H/I/K/N/P/Q/R/S, I62D/E/G/K/R/W/Y, K63P, I84L, S85A/C/D/E/F/G/H/I/K/L/M/N/P/Q/R/V/W/Y, G86A/C/D/E/F/H/I/K/L/M/N/P/Q/R/S/T/V/W/Y, L87A/C/D/E/G/H/K/N/Q/R/S/T/W/Y, P88C/D/E/F/G/H/I/K/L/M/N/Q/R/S/T/V/W/Y, A89C/D/E/F/H/I/K/L/M/N/P/Q/R/S/T/V/Y, H115A/C/D/E/F/G/I/K/L/M/P/Q/R/S/T/V/W/Y, R116A/C/D/E/F/G/H/I/P/S/T/V/W/Y, L117A/D/E/G/H/K/N/P/Q/R/S/T/V/W/Y, P148C/D/E/F/G/H/I/K/L/M/N/Q/R/S/T/V/W/Y, G150I/N/V/W, N151C/D/E/F/G/H/I/K/L/M/P/Q/R/V/W/Y, D155C/F/G/I/K/L/M/P/R/V/W/Y, T156E/F/G/H/I/K/L/M/N/P/Q/R/W/Y, M158P, F159D/E/G/H/K/N/P/Q/R/S/W/Y, T162D/E/F/P, or K170P. In some embodiments, the one or more mutations in the PYR/PYL receptor polypeptide that disrupts binding to a wild-type PP2C comprises a mutation at an amino acid corresponding to position F61, S85, T156, or T162 in PYR1. In some embodiments, the one or more mutations in the PYR/PYL receptor polypeptide that disrupts binding to a wild-type PP2C comprises a mutation selected from F61K, S85P, T156P, and T162D.

In some embodiments, the mutated PYR/PYL receptor polypeptide further comprises a mutation at one or more amino acids corresponding to positions Y58, K59, V81, A89, F108, S122, M158, F159, or A160 in PYR1 (SEQ ID NO:1), wherein the mutation is selected from Y58H, K59R, V81C, V81I, V81T, A89W, F108A, F108C, F108E, F108G, F108I, F108L, F108N, F108Q, F108S, F108T, F108V, S122G, M158I, M158V, F159A, F159C, F159I, F159L, F159M, F159T, F159V, A160C, A160V, or combinations thereof. In some embodiments, the mutated PYR/PYL receptor comprises:
mutations corresponding to Y58H, K59R, V81, F108A, S122G, M158, F159V, A160V, and T162D in PYR1;
mutations corresponding to Y58H, K59R, V81, F108A, S122G, M158V, F159V, A160V, and T162D in PYR1; or
mutations corresponding to Y58H, K59R, V81, F108A, S122G, M158, F159V, A160C, and T162D in PYR1.

In some embodiments, the mutated PYR/PYL receptor polypeptide as described herein is substantially identical (at least 70%, at least 75%, at least 80%, at least 85%, at least 90%, at least 91%, at least 92%, at least 93%, at least 94%, at least 95%, at least 96%, at least 97%, at least 98%, or at least 99% identical) to any of SEQ ID NOs:1-14 or 19-21.

In some embodiments, the one or more mutations in the PP2C that disrupts binding to a wild-type PYR/PYL receptor polypeptide comprises a mutation at an amino acid corresponding to position E201, E203, H245, G246, G247, E323, K381, I383, W385, R389, F391, G392, V393, or Y404 in HAB1 (SEQ ID NO:22). In some embodiments, the one or more mutations in the PP2C that disrupts binding to a wild-type PYR/PYL receptor polypeptide comprises a mutation selected from E201H/K, E203A/C/D/F/G/H/I/K/L/M/ N/P/R/S/T/V/W/Y, H245A/C/D/E/F/G/I/K/L/M/N/P/Q/R/S/ T/V/W/Y, G246A/C/D/E/F/H/I/K/L/M/N/P/Q/R/S/T/V/W/ Y, G247A/E/F/I/K/M/P/Q/R/T/V/W/Y, E323L, K381W, I383D/E/G/H/K/N/P/Q/R/S/T/W/Y, W385A/C/D/E/F/G/H/ I/K/L/M/N/P/Q/R/S/T/V/Y, R389A/C/D/E/F/G/H/I/K/L/M/ P/Q/T/V/W/Y, F391D/E/P, G392A/D/C/E/F/H/I/K/L/M/N/ P/Q/R/T/V/W/Y, V393D/E/G/K/N/P/Q/R/S, or Y404D/E/G/ K/N/P/Q/R/S/T. In some embodiments, the one or more mutations in the PP2C that disrupts binding to a wild-type PYR/PYL receptor polypeptide comprises a mutation at an amino acid corresponding to position E203, I383, or V393 in HAB1. In some embodiments, the one or more mutations in the PP2C that disrupts binding to a wild-type PYR/PYL receptor polypeptide comprises a mutation selected from E203D, E203T, E203W, I383G, V393K, V393R, or V393Q.

In some embodiments, the mutated PP2C further comprises one or more mutations that disrupts the catalytic activity of the mutated PP2C. In some embodiments, the mutated PP2C comprises a mutation at one or more amino acids corresponding to positions R199, D204, S322, or R505 in HAB1 (SEQ ID NO:22) wherein the mutation is selected from R199A, D204A, S322D, S322E, R505A, or combinations thereof. In some embodiments, the mutated PP2C comprises:
mutations corresponding to D204A, V393R, and R505A in HAB1; or
mutations corresponding to R199A, D204A, S322D, V393R, and R505A in HAB1.

In some embodiments, the mutated PP2C as described herein is substantially identical (at least 70%, at least 75%, at least 80%, at least 85%, at least 90%, at least 91%, at least 92%, at least 93%, at least 94%, at least 95%, at least 96%, at least 97%, at least 98%, or at least 99% identical) to any of SEQ ID NOs:22-31.

In yet another aspect, the present invention provides for isolated nucleic acids comprising a polynucleotide encoding a polypeptide comprising a mutated PYR/PYL receptor polypeptide as described herein fused to a transcriptional activation domain or a DNA binding domain, wherein the mutated PYR/PYL receptor polypeptide is agonized by an orthogonal ligand that does not significantly agonize a wild-type PYR/PYL receptor polypeptide and wherein the mutated PYR/PYL receptor polypeptide comprises a mutation that disrupts binding to a wild-type PP2C.

In some embodiments, the one or more mutations in the PYR/PYL receptor polypeptide that disrupts binding to a wild-type PP2C comprises a mutation at an amino acid corresponding to position F61, I62, K63, I84, S85, G86, L87, P88, A89, H115, R116, L117, P148, G150, N151, D155, T156, M158, F159, T162, or K170 in PYR1 (SEQ ID NO:1). In some embodiments, the one or more mutations in the PYR/PYL receptor polypeptide that disrupts binding to a wild-type PP2C comprises a mutation selected from F61D/ E/G/H/I/K/N/P/Q/R/S, I62D/E/G/K/R/W/Y, K63P, I84L, S85A/C/D/E/F/G/H/I/K/L/M/N/P/Q/R/V/W/Y, G86A/C/D/ E/F/H/I/K/L/M/N/P/Q/R/S/T/V/W/Y, L87A/C/D/E/G/H/K/ N/Q/R/S/T/W/Y, P88C/D/E/F/G/H/I/K/L/MN/Q/R/S/T/V/ W/Y, A89C/D/E/F/H/I/K/L/M/N/P/Q/R/S/T/V/Y, H115A/C/ D/E/F/G/I/K/L/M/P/Q/R/S/T/V/W/Y, R116A/C/D/E/F/G/H/ I/P/S/T/V/W/Y, L117A/D/E/G/H/K/N/P/Q/R/S/T/V/W/Y, P148C/D/E/F/G/H/I/K/L/M/N/Q/R/S/T/V/W/Y, G150I/N/ V/W, N151C/D/E/F/G/H/I/K/L/M/P/Q/R/V/W/Y, D155C/F/ G/I/K/L/M/P/R/V/W/Y, T156E/F/G/H/I/K/L/M/N/P/Q/R/ W/Y, M158P, F159D/E/G/H/K/N/P/Q/R/S/W/Y, T162D/E/ F/P, or K170P. In some embodiments, the one or more mutations in the PYR/PYL receptor polypeptide that disrupts binding to a wild-type PP2C comprises a mutation at an amino acid corresponding to position F61, S85, T156, or T162 in PYR1. In some embodiments, the one or more mutations in the PYR/PYL receptor polypeptide that disrupts binding to a wild-type PP2C comprises a mutation selected from F61K, S85P, T156P, and T162D.

In some embodiments, the mutated PYR/PYL receptor polypeptide further comprises a mutation at one or more amino acids corresponding to positions Y58, K59, V81, A89, F108, S122, M158, F159, or A160 in PYR1 (SEQ ID NO:1), wherein the mutation is selected from Y58H, K59R, V81C, V81I, V81T, A89W, F108A, F108C, F108E, F108G, F108I, F108L, F108N, F108Q, F108S, F108T, F108V, S122G, M158I, M158V, F159A, F159C, F159I, F159L, F159M, F159T, F159V, A160C, A160V, or combinations thereof. In some embodiments, the mutated PYR/PYL receptor comprises:
mutations corresponding to Y58H, K59R, V81I, F108A, S122G, M158I, F159V, A160V, and T162D in PYR1;
mutations corresponding to Y58H, K59R, V81I, F108A, S122G, M158V, F159V, A160V, and T162D in PYR1; or
mutations corresponding to Y58H, K59R, V81I, F108A, S122G, M158I, F159V, A160C, and T162D in PYR1.

In some embodiments, the mutated PYR/PYL receptor polypeptide as described herein is substantially identical (at least 70%, at least 75%, at least 80%, at least 85%, at least 90%, at least 91%, at least 92%, at least 93%, at least 94%, at least 95%, at least 96%, at least 97%, at least 98%, or at least 99% identical) to any of SEQ ID NOs:1-14, 19-21, or 41-115.

In some embodiments, the polypeptide comprises a mutated PYR/PYL receptor polypeptide as described herein fused to a transcriptional activation domain. In some embodiments, the polypeptide is substantially identical (at least 70%, at least 75%, at least 80%, at least 85%, at least 90%, at least 91%, at least 92%, at least 93%, at least 94%, at least 95%, at least 96%, at least 97%, at least 98%, or at least 99% identical) to SEQ ID NO:32.

In still another aspect, the present invention provides for isolated nucleic acids comprising a polynucleotide encoding a polypeptide comprising a mutated PP2C as described herein fused to a transcriptional activation domain (e.g., SEQ ID NO:35) or a DNA binding domain (e.g., SEQ ID NO:36), wherein the mutated PP2C comprises a mutation that disrupts binding to a wild-type PYR/PYL receptor polypeptide.

In some embodiments, the one or more mutations in the PP2C that disrupts binding to a wild-type PYR/PYL receptor polypeptide comprises a mutation at an amino acid corresponding to position E201, E203, H245, G246, G247, E323, K381, I383, W385, R389, F391, G392, V393, or Y404 in HAB1 (SEQ ID NO:22). In some embodiments, the one or more mutations in the PP2C that disrupts binding to a wild-type PYR/PYL receptor polypeptide comprises a mutation selected from E201H/K, E203A/C/D/F/G/H/I/K/L/M/ N/P/R/S/T/V/W/Y, H245A/C/D/E/F/G/I/K/L/M/N/P/Q/R/S/ T/V/W/Y, G246A/C/D/E/F/H/I/K/L/M/N/P/Q/R/S/T/V/W/ Y, G247A/E/F/I/K/M/P/Q/R/T/V/W/Y, E323L, K381W, I383D/E/G/H/K/N/P/Q/R/S/T/W/Y, W385A/C/D/E/F/G/H/ I/K/L/M/N/P/Q/R/S/T/V/Y, R389A/C/D/E/F/G/H/I/K/L/M/ P/Q/T/V/W/Y, F391D/E/P, G392A/D/C/E/F/H/I/K/L/M/N/ P/Q/R/T/V/W/Y, V393D/E/G/K/N/P/Q/R/S, or Y404D/E/G/ K/N/P/Q/R/S/T. In some embodiments, the one or more mutations in the PP2C that disrupts binding to a wild-type PYR/PYL receptor polypeptide comprises a mutation at an amino acid corresponding to position E203, I383, or V393 in HAB1. In some embodiments, the one or more mutations in the PP2C that disrupts binding to a wild-type PYR/PYL receptor polypeptide comprises a mutation selected from E203D, E203T, E203W, I383G, V393K, V393R, or V393Q.

In some embodiments, the mutated PP2C further comprises one or more mutations that disrupts the catalytic activity of the mutated PP2C. In some embodiments, the mutated PP2C comprises a mutation at one or more amino acids corresponding to positions R199, D204, S322, or R505 in HAB1 (SEQ ID NO:22) wherein the mutation is selected from R199A, D204A, S322D, S322E, R505A, or combinations thereof. In some embodiments, the mutated PP2C comprises:

mutations corresponding to D204A, V393R, and R505A in HAB1; or
   mutations corresponding to R199A, D204A, S322D, V393R, and R505A in HAB1.

In some embodiments, the mutated PP2C as described herein is substantially identical (at least 70%, at least 75%, at least 80%, at least 85%, at least 90%, at least 91%, at least 92%, at least 93%, at least 94%, at least 95%, at least 96%, at least 97%, at least 98%, or at least 99% identical) to any of SEQ ID NOs:22-31.

In some embodiments, the polypeptide comprises a mutated PP2C as described herein fused to a DNA binding domain. In some embodiments, the polypeptide is substantially identical (at least 70%, at least 75%, at least 80%, at least 85%, at least 90%, at least 91%, at least 92%, at least 93%, at least 94%, at least 95%, at least 96%, at least 97%, at least 98%, or at least 99% identical) to SEQ ID NO:33 or 34.

The data show western analyses of protein levels in three transgenic lines, lines #2 and #3 were selected for experimentation.

Figure 12:
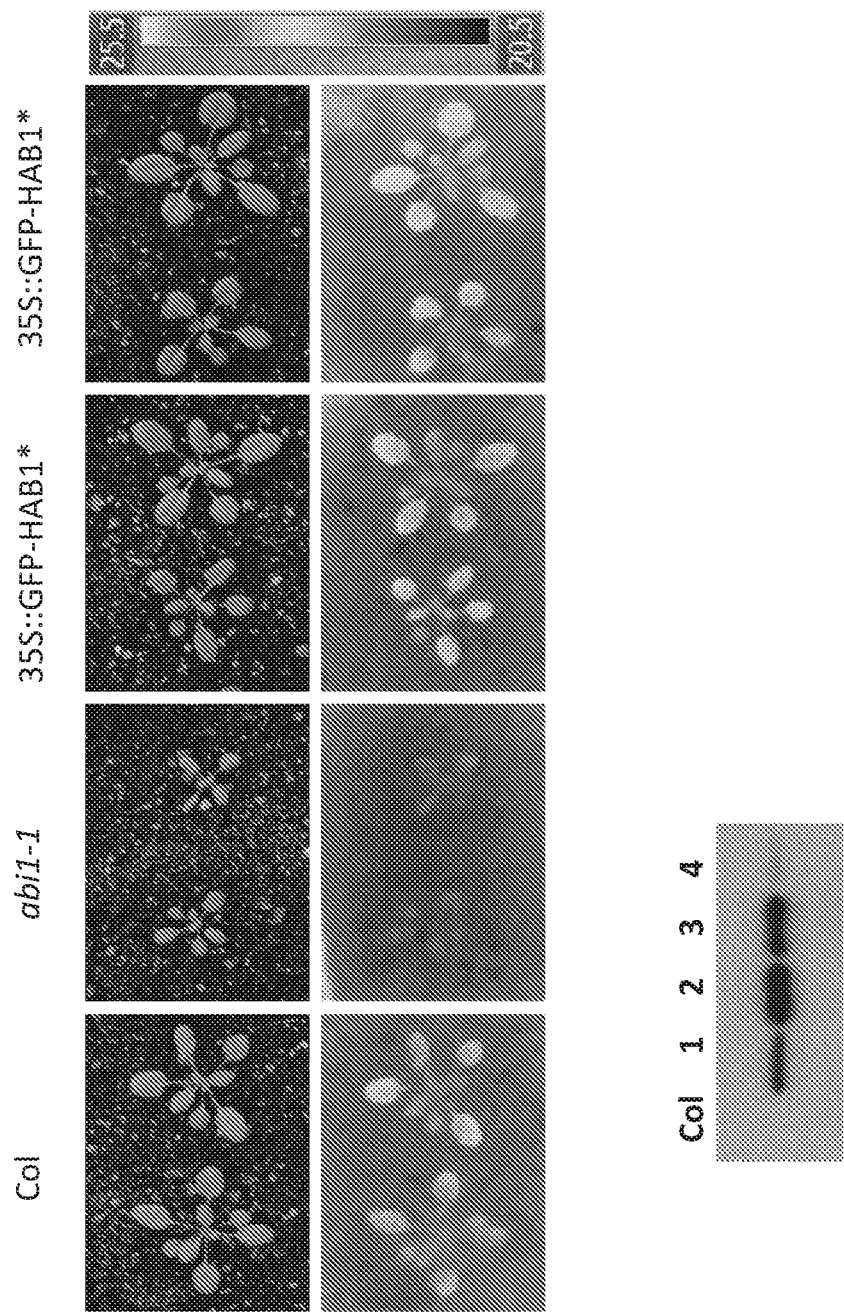

FIG. 12. Expression of HAB1* in planta does not inhibit ABA responses. (Upper panel) The experiment examines the leaf temperature of two independent homozygous 35S::GFP-HAB1* transgenic strains #2 and #3 in comparison to either wild type Columbia of the ABA insensitive mutant abi1-1, as described in Example 5. The data show that expression HAB1* in planta does not strongly interfere with endogenous ABA responses. (Lower panel) The data show Western analyses of fusion protein levels in 4 transgenic lines, lines #2 and #3 were selected for experimentation.

Figure 13:
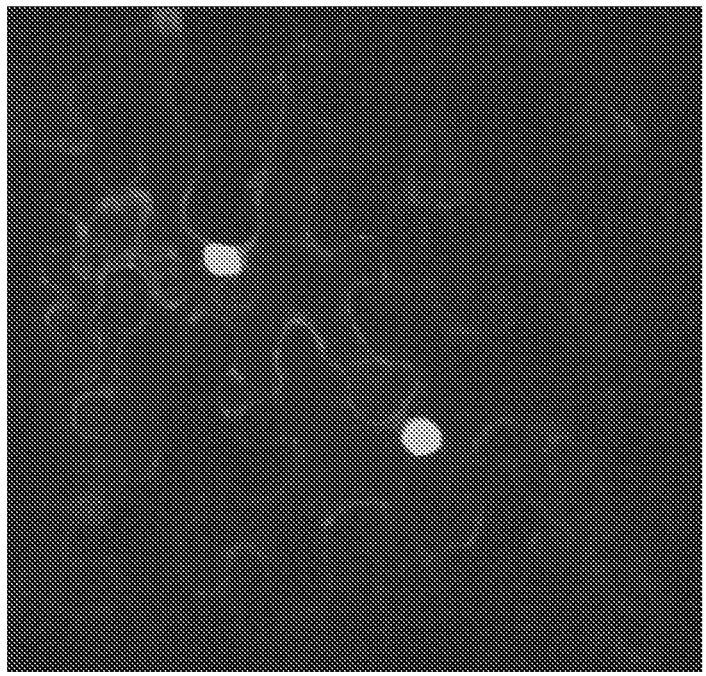
Figure 13:
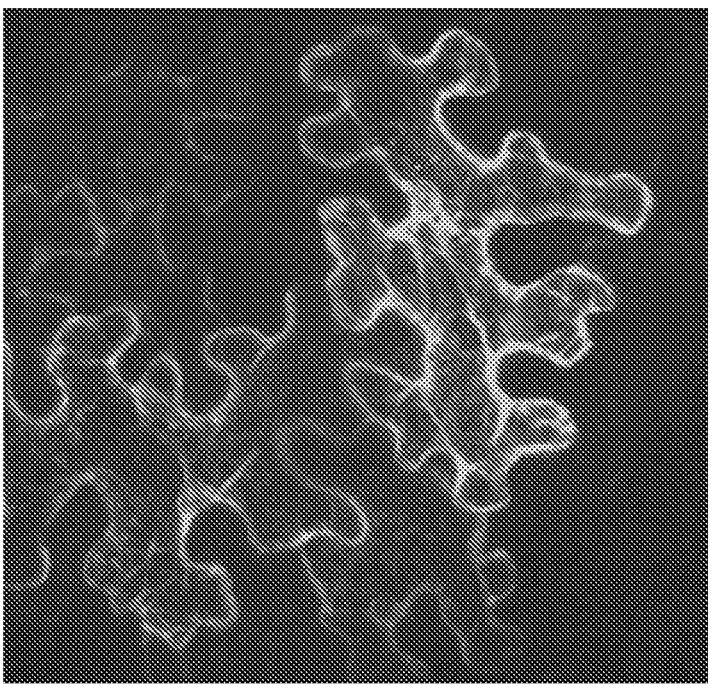

FIG. 13. Mandipropamid-mediated control of protein nuclear localization using the PYR1*-$^{MANDI}$/HAB1* interaction module. 35S::GFP-cyt-HAB1* and 35S::nuc-PY-1*-$^{MANDI}$ were transiently co-expressed in N. benthamiana and plants treated with a mock solution or 50 μM mandipropamid. 35S::GFP-cyt-HAB1* displays the expected cytoplasmic localization in the absence of mandipropamid treatment, however it shows a predominantly nuclear localization pattern after exposure to mandipropamid. Thus, the HAB1*/PYR1*-$^{MANDI}$ module can be used to chemically regulate protein localization.

Figure 14:
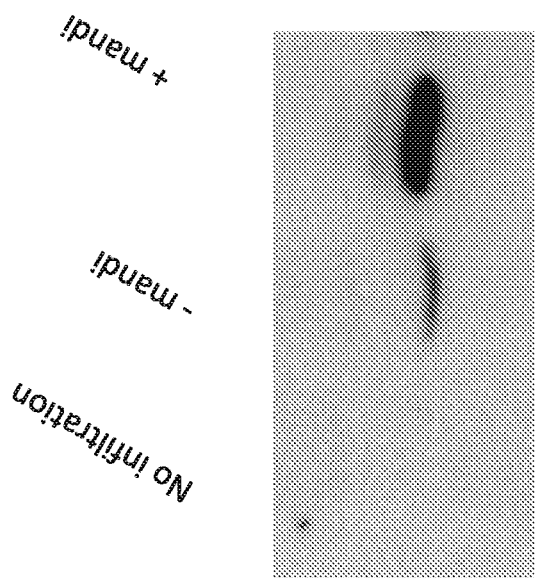

FIG. 14. Mandipropamid-mediated control of transcription using the PYR1*-$^{MANDI}$/HAB1* interaction module. pUAS_GFP_mandi was transiently expressed in N. benthamiana and plants treated with a mock solution or 50 μM mandipropamid and proteins detected by Western blot analyses using an anti-GFP antibody, as described in Example 6. Thus, the HAB1*/PYR1*-$^{MANDI}$ module can be used to chemically regulate transcription in planta. The leftmost lane is a control non-infiltrated leaf sample.

Figure 15:
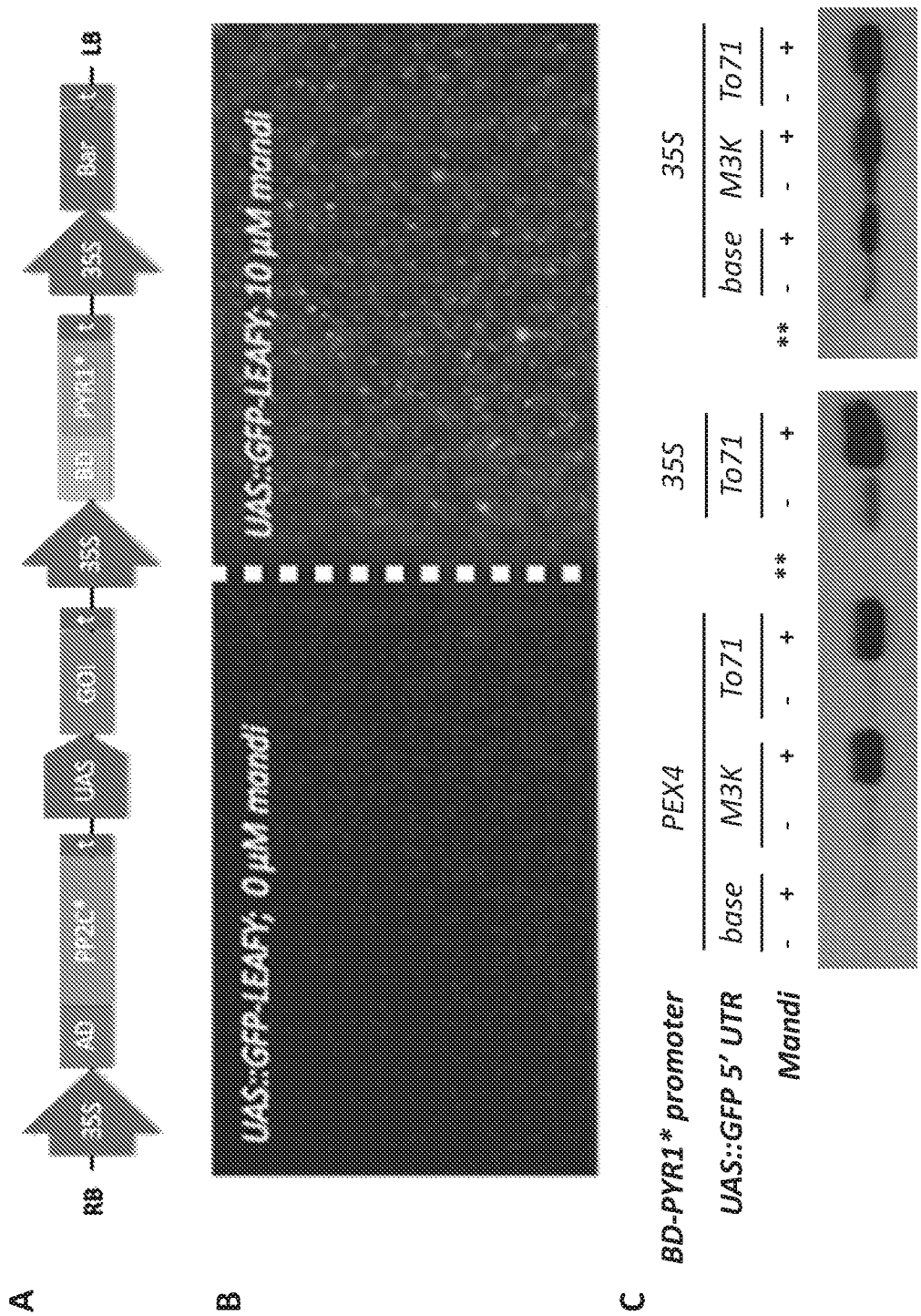

FIG. 15. (A) T-DNA region (~8.5 kb) of pMANDI-GFP vector that was used to construct a UAS::GFP-LEAFY that is mandipropamid inducible. (B) T1 Arabidopsis leaf tissue of the same transgenic plant treated with either control or 10 μM mandipropamid for 24 hours and subsequently imaged by fluorescence microscopy. (C) The pMANDI-GFP base vector was modified by altering expression of its BD-PYR1*-$^{MANDI}$ component with the PEX4 promoter (pPEX4-MANDI-GFP) with or without added MAPKKK18 (M3K) or To71 UTRs appended to GFP. These constructs were transiently expressed in N. benthamiana and their responses to mandipropamid profiled 24 hours after application of 50 μM mandipropamid or control solution, as measured using western blotting with an anti-GFP antibody. Lanes marked "**" are controls that contain protein samples from infiltrated leaf samples. Thus, the HAB1*/PYR1*-$_{MANDI}$ module can be used to chemically regulate transcription in planta.

DEFINITIONS

The term "PYR/PYL receptor polypeptide" refers to a protein characterized in part by the presence of one or more or all of a polyketide cyclase domain 2 (PF10604), a polyketide cyclase domain 1 (PF03364), and a Bet V I domain (PF03364), which in wild-type form mediates abscisic acid (ABA) and ABA analog signaling. A wide variety of PYR/PYL receptor polypeptide sequences are known in the art. PYR/PYL receptor proteins, their structural elements, and their mechanism of activity are described, for example, in Klinger et al., 2010, Journal of Experimental Botany, 61:3199-3210, and in Santiago et al., 2012, Plant Sci, 182:3-11, incorporated by reference herein. In some embodiments, a PYR/PYL receptor polypeptide comprises a polypeptide sequence that is substantially identical to (e.g., at least 70%, at least 75%, at least 80%, at least 85%, at least 90%, at least 91%, at least 92%, at least 93%, at least 94%, at least 95%, at least 96%, at least 97%, at least 98%, or at least 99% identical to) PYR1 (SEQ ID NO:1), PYL1 (SEQ ID NO:2), PYL2 (SEQ ID NO:3), PYL3 (SEQ ID NO:4), PYL4 (SEQ ID NO:5), PYL5 (SEQ ID NO:6), PYL6 (SEQ ID NO:7), PYL7 (SEQ ID NO:8), PYL8 (SEQ ID NO:9), PYL9 (SEQ ID NO:10), PYL10 (SEQ ID NO: 11), PYL11 (SEQ ID NO: 12), PYL12 (SEQ ID NO: 13), or PYL13 (SEQ ID NO: 14), or to any of SEQ ID NOs:41-115.

A "wild-type PYR/PYL receptor polypeptide" refers to a naturally occurring PYR/PYL receptor polypeptide that binds to ABA and mediates ABA signaling via interactions with a PP2C.

A "mutated PYR/PYL receptor polypeptide" or "modified PYR/PYL receptor polypeptide" refers to a PYR/PYL receptor polypeptide that is a variant from a naturally-occurring (i.e., wild-type) PYR/PYL receptor polypeptide. As used herein, a mutated or modified PYR/PYL receptor polypeptide comprises one or more amino acid substitutions relative to a corresponding wild-type PYR/PYL receptor polypeptide. In this context, a "mutated" polypeptide or "modified" polypeptide can be generated by any method for generating non-wild type nucleotide sequences.

The term "type 2C protein phosphatase" or "PP2C" refers to a protein characterized in part by the presence of a serine/threonine phosphatase catalytic site and one or more metal binding sites for binding magnesium or manganese ions. A wide variety of PP2C protein sequences are known in the art. PP2C proteins and their structure and function are described, for example, in Singh et al., 2015, Critical Reviews in Biotechnology, DOI: 10.3109/07388551.2015.1083941, incorporated by reference herein. In some embodiments, a PP2C is a Clade A PP2C. In some embodiments, a PP2C protein comprises a sequence that is substantially identical to (e.g., at least 70%, at least 75%, at least 80%, at least 85%, at least 90%, at least 91%, at least 92%, at least 93%, at least 94%, at least 95%, at least 96%, at least 97%, at least 98%, or at least 99% identical to) HAB1 (SEQ ID NO:22), ABI1 (SEQ ID NO:23), ABI2 (SEQ ID NO:24), HAB2 (SEQ ID NO:25), HAI1 (SEQ ID NO:26), HAI2 (SEQ ID NO:27), HAI3 (SEQ ID NO:28), or At1g43900 (SEQ ID NO:29).

A "wild-type PP2C" refers to a naturally-occurring PP2C protein that negatively regulates ABA signaling.

A "mutated PP2C" or "modified PP2C" refers to a PP2C protein that is a variant from a naturally-occurring (i.e., wild-type) PP2C. As used herein, a mutated or modified PP2C protein comprises one or more amino acid substitutions relative to a corresponding wild-type PP2C protein. In this context, a "mutated" polypeptide or "modified" polypeptide can be generated by any method for generating non-wild type nucleotide sequences.

An amino acid "corresponding to position [X] of [specific sequence]" refers to an amino acid in a polypeptide of interest that aligns with the equivalent amino acid of a specified sequence. Generally, as described herein, the amino acid corresponding to a position of a PYR/PYL receptor polypeptide or PP2C can be determined using an alignment algorithm such as BLAST. With respect to PYR/PYL receptor polypeptide sequences, in typical embodiments of the present invention, "correspondence" of amino acid positions is determined by aligning to a region of the PYR/PYL receptor polypeptide comprising SEQ ID NO:1 (PYR1), as discussed further herein. When a PYR/PYL receptor polypeptide sequence differs from SEQ ID NO: 1

(e.g., by changes in amino acids or addition or deletion of amino acids), it may be that a particular mutation (e.g., a mutation that disrupts binding to a wild-type PP2C) will not be in the same position number as it is in SEQ ID NO:1. For example, amino acid position T192 of PYL1 (SEQ ID NO:2) aligns with amino acid position T162 in SEQ ID NO: 1, as can be readily illustrated in an alignment of the two sequences. In this example, a mutation at amino acid position 192 in SEQ ID NO:2 corresponds to position 162 in SEQ ID NO:1.

Similarly, with respect to PP2C protein sequences, in typical embodiments of the present invention, "correspondence" of amino acid positions is determined by aligning to a region of the PP2C protein comprising SEQ ID NO:22 (HAB1), as discussed further herein. When a PP2C protein differs from SEQ ID NO:22 (e.g., by changes in amino acids or addition or deletion of amino acids), it may be that a particular mutation (e.g., a mutation that disrupts binding to a wild-type PYR/PYL receptor protein) will not be in the same position number as it is in SEQ ID NO:22. For example, amino acid position V308 of ABI1 (SEQ ID NO:23) aligns with amino acid position V393 in SEQ ID NO:22, as can be readily illustrated in an alignment of the two sequences. In this example, a mutation at amino acid position 308 in SEQ ID NO:23 corresponds to position 393 in SEQ ID NO:22.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The phrase "substantially identical," used in the context of two nucleic acids or polypeptides, refers to a sequence that has at least 60% sequence identity with a reference sequence. Alternatively, percent identity can be any integer from 60% to 100%. Some embodiments include at least: 60%, 65%, 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, *Proteins* (1984)).

It is contemplated that a substitution mutation in a mutated PYR/PYL receptor polypeptide and/or a mutated PP2C includes not only those specific amino acid substitutions called out in the specification, e.g. in the Examples section or in any of the Figures or Tables of the specification, but also includes amino acids that are conservative substitutions for those specific amino acids, so long as the conservatively substituted amino acid is not the wild-type amino acid. As a non-limiting example, where a mutated PYR/PYL receptor polypeptide or PP2C comprises a serine-to-threonine substitution, it is contemplated that the mutated PYR/PYL receptor polypeptide or PP2C may alternatively comprise a serine-to-alanine substitution, as threonine and alanine are conservative substitutions for one another; but the mutated PYR/PYL receptor polypeptide or PP2C would not comprise a serine-to-serine substitution, as serine is the amino acid that is present in the wild-type PYR/PYL polypeptide or PP2C.

As used herein, the term "agonist" or "agonists" refers to a molecule identified using in vitro and in vivo assays for activity of a described target protein as described elsewhere herein. Agonists are agents that, e.g., induce or activate the expression of a described target protein or bind to, stimulate, increase, open, activate, facilitate, enhance activation, sensitize or up-regulate the activity of described target protein (or encoding polynucleotide). Agonists include naturally occurring and synthetic molecules. In some embodiments, the agonists are agrichemicals, e.g., fungicides, herbicides, pesticides, and/or fertilizers. Assays for determining whether an agonist "agonizes" or "does not agonize" a target protein include, e.g., contacting putative agonists to purified target protein(s) and then determining the functional effects on the described target protein activity, as described above, or contacting putative agonists to cells expressing the target protein(s) and then determining the functional effects on the described target protein activity, as described above. One of skill in the art will be able to determine whether an assay is suitable for determining whether an agonist agonizes or does not agonize a target protein. Samples or assays comprising described target protein that are treated with a putative agonist are compared to control samples without the agonist to examine the extent of effect. Control samples (untreated with agonists) are assigned a relative activity value of 100%. Agonism of the described target protein is achieved when the activity value relative to the control is 110%, optionally 150%, optionally 200%, 300%, 400%, 500%, or 1000-3000% or more higher.

As used herein, the term "orthogonal receptor" refers to a receptor that has been modified to selectively recognize new ligands ("orthogonal ligands"). As used herein, the term "orthogonal ligand" refers to an agent that agonizes a mutated or modified PYR/PYL receptor polypeptide but which does not agonize a wild-type PYR/PYL receptor polypeptide. In some embodiments, the orthogonal ligands are agrichemicals, e.g., fungicides, herbicides, pesticides, nematicides, plant activators, synergists, herbicide safeners, plant growth regulators, insect repellants, and/or fertilizers. In some embodiments, the orthogonal ligand is mandipropamid.

The term "plant" includes whole plants, shoot vegetative organs and/or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, plant tissue (e.g., vascular tissue, ground tissue, and the like), cells (e.g., guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid, and hemizygous.

The term "promoter," as used herein, refers to a polynucleotide sequence capable of driving transcription of a coding sequence in a cell. Thus, promoters used in the polynucleotide constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "plant promoter" is a promoter capable of initiating transcription in plant cells. A "constitutive promoter" is one that is capable of initiating transcription in nearly all tissue types, whereas a "tissue-specific promoter" initiates transcription only in one or a few particular tissue types.

A polynucleotide sequence is "heterologous" to an organism or a second polynucleotide sequence if it originates from a foreign species, or, if from the same species, is modified from its original form. For example, when a promoter is said to be operably linked to a heterologous coding sequence, it means that the coding sequence is derived from one species whereas the promoter sequence is derived another, different species; or, if both are derived from the same species, the coding sequence is not naturally associated with the promoter (e.g., is a genetically engineered coding sequence, e.g., from a different gene in the same species, or an allele from a different ecotype or variety).

An "expression cassette" refers to a nucleic acid construct that, when introduced into a host cell, results in transcription and/or translation of an RNA or polypeptide, respectively. Antisense or sense constructs that are not or cannot be translated are expressly included by this definition. In the case of both expression of transgenes and suppression of endogenous genes (e.g., by antisense, or sense suppression) one of skill will recognize that the inserted polynucleotide sequence need not be identical, but may be only substantially identical to a sequence of the gene from which it was derived. As explained herein, these substantially identical variants are specifically covered by reference to a specific nucleic acid sequence.

DETAILED DESCRIPTION OF THE INVENTION

I. Introduction

In the abscisic acid (ABA) signaling pathway, PYR/PYL polypeptides are receptors for ABA, while PP2Cs are negative regulators of ABA signaling. In the presence of ABA, the PYR/PYL receptor polypeptide forms a ternary complex with ABA and a PP2C, resulting in the inhibition of the PP2C. It has now been found that components of the ABA signaling pathway can be coopted to generate chemically induced interaction modules that can be expressed in vivo in plants for regulating the expression of a desired gene, protein, or phenotype. As described herein, PYR/PYL receptor polypeptides and PP2Cs can be mutated to disrupt their interactions with endogenous ABA signaling components and enable binding to an orthogonal ligand (such as an agrochemical) that does not activate the endogenous ABA signaling pathway. By linking the mutated PYR/PYL and PP2C proteins described herein to activation domains and DNA binding domains, transcription can be controlled by the presence or absence of the orthogonal ligand.

Thus, in one aspect, the mutated PYR/PYL receptor proteins and mutated PP2Cs described herein can be used to control gene expression in a plant through the use of an orthogonal ligand such as an agrochemical. In another aspect, the mutated PYR/PYL receptor proteins and mutated PP2Cs described herein can be used to control gene expression in a cell (e.g., a plant, animal, mammalian, or fungal cell) through the use of an orthogonal ligand such as an agrochemical.

II. Mutated PYR/PYL Receptor Polypeptides

In one aspect, mutated PYR/PYL receptor polypeptides that (1) are agonized by an orthogonal ligand that does not significantly agonize a wild-type PYR/PYL receptor polypeptide and that (2) comprise one or more mutations that disrupts binding to a wild-type PP2C are provided. Also provided herein are polynucleotides encoding polypeptides comprising the mutated PYR/PYL receptor polypeptides; expression cassettes and expression vectors comprising said polynucleotides; cells (e.g., plant, animal, mammalian, or fungal cells), plants, and plant parts comprising the mutated PYR/PYL receptor polypeptides; methods of making cells or plants comprising the mutated PYR/PYL receptor polypeptides; methods of making the mutated PYR/PYL receptor polypeptides; methods of activating an orthogonal PYR/PYL-PP2C interaction in cells or plants comprising the mutated PYR/PYL receptor polypeptides and mutated PP2Cs as described below; and methods of controlling gene expression in cells or plants comprising the mutated PYR/PYL receptor polypeptides and mutated PP2Cs as described herein.

A wide variety of wild-type (naturally occurring) PYR/PYL polypeptide sequences are known in the art. Although PYR1 was originally identified as an abscisic acid (ABA) receptor in *Arabidopsis*, in fact PYR1 is a member of a group of at least 14 proteins (PYR/PYL proteins) in the same protein family in *Arabidopsis* that also mediate ABA signaling. This protein family is also present in other plants (see, e.g., US 2011/0271408) and is characterized in part by the presence of one or more or all of a polyketide cyclase domain 2 (PF10604), a polyketide cyclase domain 1 (PF03364), and a Bet V I domain (PF00407). START/Bet v 1 superfamily domains are described in, for example, Radauer, *BMC Evol. Biol.* 8:286 (2008). In some embodiments, a wild-type PYR/PYL receptor polypeptide comprises any of SEQ ID NOs:1, 2, 3, 4, 5, 6, 7, 8, 9, 10, 11, 12, 13, 14 or 41-115. In some embodiments, a wild-type PYR/PYL receptor polypeptide is substantially identical to (e.g., at least 70%, 75%, 80%, 85%, 90%, 91%, 92%, 93%, 94% 95%, 96%, 97%, 98%, or 99% identical to) any of SEQ ID NOs:1-14 or 41-115.

PYR/PYL receptor proteins can be described by reference to sequence alignments that identify conserved amino acid or motifs (i.e., where alteration in sequences may alter protein function) and regions where variation occurs in alignment of sequences (i.e., where variation of sequence is not likely to significantly affect protein activity). SEQ ID NOs:15-18 and 116-122 provide consensus sequences useful for identifying wild-type PYR/PYL receptor polypeptides. The consensus sequences of SEQ ID NOs: 15-17 were generated by aligning all 14 members of the *Arabidopsis* PYR/PYL receptor protein family. In the consensus sequences of SEQ ID NOs: 15-17, the capitalized letter represents an amino acid residue that is absolutely conserved among all 14 members of the *Arabidopsis* PYR/PYL receptor protein family, while "x" represents an amino acid residue that is not absolutely conserved among all 14 family members and which can be any amino acid. It will be appreciated that when selecting an amino acid to insert at a position marked by an "x" that in some embodiments, the amino acid is selected from those amino acids found at the corresponding position in a wild-type or mutated PYR/PYL protein.

```
PYR1 to PYL13
                                    (SEQ ID NO: 15)
CxSxxxxxxxxAPxxxxWxxxxxFxxPxxxxxFxxxC (SEQ ID NO: 16)
GxxRxVxxxSxxPAxxSxExLxxxD (SEQ ID NO: 17)
ESxxVDxPxGxxxxxxTxxFxxxxxxxxNLxxL
```

Consensus sequence CxSxxxxxxxxAPxxxxWxxxxxFxxPxxxxxFxxxC (SEQ ID NO:15) comprises the region corresponding to amino acids 30 to 65 of PYR1 (SEQ ID NO: 1). Consensus sequence GxxRxVxxxSxxPAxxSxExLxxxD (SEQ ID NO: 16) comprises the region corresponding to amino acids 76 to 100 of PYR1 (SEQ ID NO:1). ESxxVDxPxGxxxxxxTxxFxxxxxxxxNLxxL (SEQ ID NO: 17) comprises the region corresponding to amino acids 141 to 171 of PYR1 (SEQ ID NO: 1).

In some embodiments, more specific consensus sequences can be generated by aligning subsets of the 14 members of the *Arabidopsis* PYR/PYL proteins, as shown below. The consensus sequences of SEQ ID NOs: 18, 116, and 117 were generated by aligning the *Arabidopsis* PYR/PYL receptor proteins PYR1, PYL1, PYL2, PYL3, PYL4, PYL5, and PYL6. The consensus sequences of SEQ ID NOs:118, 119, and 120 were generated by aligning the *Arabidopsis* PYR/PYL receptor proteins PYL7, PYL8, PYL9, and PYL10. The consensus sequences of SEQ ID NOs: 121 and 122 were generated by aligning the *Arabidopsis* PYR/PYL receptor proteins PYL11, PYL12, and PYL13.

PYR1-PYL6

(SEQ ID NO: 18)
HxxxxxxxxCxSxxxxxxxxAPxxxxWxxxxxFxxPxxYKxFxxxC (SEQ ID NO: 116)
VGRxVxVxSGLPAxxSxExLxxxDxxxxxxxFxxxGGxHRLxNYxSVT (SEQ ID NO: 117)
VxESYxVDxPxGNxxxxTxxFxDxxxxxNLQxL

PYL7-PYL10

(SEQ ID NO: 118)
HxHxxxxxQCxSxLVKxIxAPxHxVWSxVRRFDxPQKYKPFxSRCxVxGx (SEQ ID NO: 119)
ExGxxxREVxxKSGLPATxSTExLExLDDxEHILxIxIxGGDHRLKNYSSxxxxHxExIxGxxGTx (SEQ ID NO: 120)
xxESFVVDVPxGNTKxxTCxFVExLIxCNLxSLAxxxERL

PYL11-PYL13

(SEQ ID NO: 121)
CxSxxVxTIxAPLxLVWSILRxFDxPxxxxxFVKxCxxxSGxGG (SEQ ID NO: 122)
GSVRxVTxVSxxPAxFSxERLxELDDESHVMxxSIIGGxHRLVNYxSKT In some embodiments, the mutated PYR/PYL receptor polypeptides of the present invention comprise one or more of the above-described consensus sequences (SEQ ID NOs: 15-18 and 116-122) or conservative variants thereof.

In some embodiments, a PYR/PYL mutation occurs at a residue within a consensus sequence of SEQ ID NOs:15-18 or 116-122. In some cases, the mutation occurs at a residue that is absolutely conserved among all 14 members of the PYR/PYL receptor protein family or that is absolutely conserved among all members of a PYR/PYL receptor protein subset (e.g., the PYR1-PYL6 subset, the PYL7-PYL10 subset, or the PYL11-PYL13 subset). In some cases, the mutation occurs at a residue that is not absolutely conserved.

Mutations that Disrupt Binding to a Wild-Type PP2C

In some embodiments, a mutated PYR/PYL receptor polypeptide is substantially identical to a SEQ ID listed herein and further comprises at least one (e.g., 1, 2, 3, 4, 5, 6, 7, 8, 9, 10, etc.) mutation at an amino acid position. In some embodiments, a mutated PYR/PYL receptor polypeptide is substantially identical to any of SEQ ID NOs: 1-14 or 41-115 and further comprises at least one mutation at any amino acid position.

In some embodiments, a mutated PYR/PYL receptor polypeptide comprises one or more mutations that disrupts binding to a wild-type PP2C (e.g., wild-type HAB1, ABI1, or ABI2). In some embodiments, a mutated PYR/PYL receptor protein exhibits "disrupted" binding to a wild-type PP2C if the level of binding between the mutated PYR/PYL protein (e.g., a mutated PYR1 protein) and the wild-type PP2C is decreased by at least 10%, at least 20%, at least 30%, at least 40%, at least 50%, at least 60%, at least 70%, at least 80%, at least 90% or more in the presence of ABA as compared to the level of binding between the corresponding wild-type PYR/PYL protein (e.g., wild-type PYR1) and the wild-type PP2C in the presence of ABA. In some embodiments, a mutated PYR/PYL receptor protein exhibits disrupted binding to a wild-type PP2C if no detectable binding occurs in the presence of ABA.

Mammalian or yeast two-hybrid approaches (see, e.g., Bartel, P. L. et al. *Methods Enzymol*, 254:241 (1995)) can be used to determine whether polypeptides interact or bind when expressed together in a cell. Optionally, both positive and negative selection schemes can be utilized in the two-hybrid assay. Binding can also be measured indirectly, such as by measuring inhibition of PP2C activity. Inhibition of PP2C activity can be measured in live cells using the yeast two hybrid or other cell-based methods. It can also be measured in vitro using enzymatic phosphatase assays in the presence of a colorimetric detection reagent (for example, para-nitrophenylphosphate). See, e.g., Park et al., *Science*, 2009, 324:1068-1071, and the Examples section below; see also, US 2010/0216643, US 2011/0271408, and US 2014/0259226, incorporated by reference herein.

In some embodiments, a mutated PYR/PYL receptor that comprises one or more mutations that disrupts binding to a wild-type PP2C comprises a mutation at one or more residues of the PP2C binding interface. The PP2C binding interface of a PYR/PYL receptor polypeptide comprises amino acid residues that are in close proximity (e.g., within about 5 Å) to PP2C when PP2C, the PYR/PYL receptor, and ABA are all bound together in a ternary complex. In total, there are 25 residues that make up the PP2C binding interface in PYR1 (SEQ ID NO:1): H60, F61, I62, K63, I84, S85, G86, L87, P88, A89, H115, R116, L117, P148, G150, N151, D154, D155, T156, M158, F159, T162, V163, L166, and K170. The residues of the PP2C binding interface are also highly conserved among other PYR/PYL family members. Thus, in some embodiments, corresponding mutations can be made in the PP2C binding interface of other PYR/PYL receptor proteins of interest by aligning the sequences of PYR1 (SEQ ID NO: 1) and the PYR/PYL protein of interest.

In some embodiments, a mutated PYR/PYL receptor comprises one, two, three, four, five, six, seven, eight, nine, or more amino acid substitutions in the PP2C binding interface relative to wild-type PYR/PYL. In some embodiments, a mutated PYR/PYL receptor comprises 1-10 mutations, 5-10 mutations, 1-7 mutations, 1-5 mutations, 1-3 mutations, 1-2 mutations, 2-7 mutations, or 2-5 mutations in the PP2C binding interface relative to wild-type PYR/PYL. In some embodiments, a mutated PYR/PYL receptor comprises a substitution at one or more of residues selected from F61, I62, K63, I84, S85, G86, L87, P88, A89, H115, R116, L117, P148, G150, N151, D155, T156, M158, F159, T162, and K170 in PYR1. In some embodiments, a mutated PYR/PYL receptor comprises one or more substitutions selected from F61D/E/G/H/I/K/N/P/Q/R/S, I62D/E/G/K/R/W/Y, K63P, I84L, S85A/C/D/E/F/G/H/I/K/L/M/N/P/Q/R/V/W/Y, G86A/C/D/E/F/H/I/K/L/M/N/P/Q/R/S/T/V/W/Y, L87A/C/D/E/G/H/K/N/Q/R/S/T/W/Y, P88C/D/E/F/G/H/I/K/L/M/N/Q/R/S/T/V/W/Y, A89C/D/E/F/H/I/K/L/M/N/P/Q/R/S/T/V/Y, H115A/C/D/E/F/G/I/K/L/M/P/Q/R/S/T/V/W/Y, R116A/C/D/E/F/G/H/I/P/S/T/V/W/Y, L117A/D/E/G/H/K/N/P/Q/R/S/T/V/W/Y, P148C/D/E/F/G/H/I/K/L/M/N/Q/R/S/T/V/W/Y, G150I/N/V/W, N151C/D/E/F/G/H/I/K/L/M/P/Q/R/V/W/Y, D155C/F/G/I/K/L/M/P/R/V/W/Y, T156E/F/G/H/I/K/L/M/N/P/Q/R/W/Y, M158P, F159D/E/G/H/K/N/P/Q/R/S/W/Y, T162D/E/F/P, K170P, and combinations thereof.

In some embodiments, the mutated PYR/PYL receptor comprises a mutation at position H60. In some embodiments, the mutated PYR/PYL receptor comprises a mutation at position F61 (e.g., a F61D/E/G/H/I/K/N/P/Q/R/S substitution). In some embodiments, the mutated PYR/PYL receptor comprises a mutation at position I62 (e.g., a I62D/E/G/K/R/W/Y substitution). In some embodiments, the mutated PYR/PYL receptor comprises a mutation at position K63 (e.g., a K63P substitution). In some embodiments, the mutated PYR/PYL receptor comprises a mutation at position 184 (e.g., a I84L substitution). In some embodiments, the mutated PYR/PYL receptor comprises a mutation at position S85 (e.g., a S85A/C/D/E/F/G/H/I/K/L/M/N/P/Q/R/V/W/Y substitution). In some embodiments, the mutated PYR/PYL receptor comprises a mutation at position G86 (e.g., a G86A/C/D/E/F/H/I/K/L/M/N/P/Q/R/S/T/V/W/Y substitution). In some embodiments, the mutated PYR/PYL receptor comprises a mutation at position L87 (e.g., a L87A/C/D/E/G/H/K/N/Q/R/S/T/W/Y substitution). In some embodiments, the mutated PYR/PYL receptor comprises a mutation at position P88 (e.g., a P88C/D/E/F/G/H/I/K/L/M/N/Q/R/S/T/V/W/Y substitution). In some embodiments, the mutated PYR/PYL receptor comprises a mutation at position A89 (e.g., a A89C/D/E/F/H/I/K/L/M/N/P/Q/R/S/T/V/Y substitution). In some embodiments, the mutated PYR/PYL receptor comprises a mutation at position H115 (e.g., a H115A/C/D/E/F/G/I/K/L/M/P/Q/R/S/T/V/W/Y substitution). In some embodiments, the mutated PYR/PYL receptor comprises a mutation at position R116 (e.g., a R116A/C/D/E/F/G/H/I/P/S/T/V/W/Y substitution). In some embodiments, the mutated PYR/PYL receptor comprises a mutation at position L117 (e.g., a L117A/D/E/G/H/K/N/P/Q/R/S/T/V/W/Y substitution). In some embodiments, the mutated PYR/PYL receptor comprises a mutation at position P148 (e.g., a P148C/D/E/F/G/H/I/K/L/M/N/Q/R/S/T/V/W/Y substitution). In some embodiments, the mutated PYR/PYL receptor comprises a mutation at position G150 (e.g., a G150I/N/V/W substitution). In some embodiments, the mutated PYR/PYL receptor comprises a mutation at position N151 (e.g., a N151C/D/E/F/G/H/I/K/L/M/P/Q/R/V/W/Y substitution). In some embodiments, the mutated PYR/PYL receptor comprises a mutation at position D154. In some embodiments, the mutated PYR/PYL receptor comprises a mutation at position D155 (e.g., a D155C/F/G/I/K/L/M/P/R/V/W/Y substitution). In some embodiments, the mutated PYR/PYL receptor comprises a mutation at position T156 (e.g., a T156E/F/G/H/I/K/L/M/N/P/Q/R/W/Y substitution). In some embodiments, the mutated PYR/PYL receptor comprises a mutation at position M158 (e.g., a M158P substitution). In some embodiments, the mutated PYR/PYL receptor comprises a mutation at position F159 (e.g., a F159D/E/G/H/K/N/P/Q/R/S/W/Y substitution). In some embodiments, the mutated PYR/PYL receptor comprises a mutation at position T162 (e.g., a T162D/E/F/P substitution). In some embodiments, the mutated PYR/PYL receptor comprises a mutation at position V163. In some embodiments, the mutated PYR/PYL receptor comprises a mutation at position L166. In some embodiments, the mutated PYR/PYL receptor comprises a mutation at position K170 (e.g., a K170P substitution).

In some embodiments, the mutated PYR/PYL protein comprises one or more mutations at amino acids corresponding to position F61, S85, T156, or T162 in PYR1. In some embodiments, the mutated PYR/PYL protein comprises one or more substitutions selected from F61D/E/G/H/I/K/N/P/Q/R/S, S85A/C/D/E/F/G/H/I/K/L/M/N/P/Q/R/V/W/Y, T156E/F/G/H/I/K/L/M/N/P/Q/R/W/Y, T162D/E/F/P, and combinations thereof. In some embodiments, the mutated PYR/PYL protein comprises one or more substitutions selected from F61K, S85P, T156P, T162D, and combinations thereof.

Mutations that Promote Agonization by an Orthogonal Ligand

In addition to comprising one or more mutations that disrupts binding to a wild-type PP2C some embodiments, the mutated PYR/PYL receptor polypeptides of the present invention further comprise one or more mutations (e.g., one, two, three, four, five, six, seven, eight, nine, or more substitutions) that confers sensitivity to an orthogonal ligand. In some embodiments, a mutated PYR/PYL receptor comprises 1-10 mutations, 5-10 mutations, 1-7 mutations, 1-5 mutations, 1-3 mutations, 1-2 mutations, 2-7 mutations, or 2-5 mutations, relative to wild-type PYR/PYL, that confer sensitivity to an orthogonal ligand. Mutated PYR/PYL receptor polypeptides that are agonized by orthogonal ligands are described, e.g., in US 2011/0271408 and WO 2014/159394, incorporated by reference herein. In some embodiments, the orthogonal ligand is an agrochemical. Agrochemicals are often prepared and applied to plants as esters or salts, which may improve uptake and efficacy. The action of ubiquitous cellular esterases can convert esters (or homologous compounds such as the S-methyl derivatives of acibenzolar) into free acids or alcohols, which are the bioactive forms. In some embodiments, the agrochemical comprises a fungicide, an herbicide, a pesticide, a nematicide, a plant activator, a synergist, an herbicide safener, a plant growth regulator, an insect repellant, or a fertilizer. In some embodiments, the agrochemical is mandipropamid, bromoxynil, chloroxynil, ioxynil, fludioxonil, coumatetralyl, dichlobenil, fenhexamid, benoxacor, BTH (acibenzolar-s-methyl), or benzothiadiazole.

In some embodiments, an orthogonal ligand (e.g., mandipropamid) agonizes a mutated PYR/PYL receptor polypeptide, but does not significantly agonize a wild-type PYR/PYL receptor polypeptide, when the orthogonal ligand is contacted to the PYR/PYL receptor polypeptide. As used herein, an agent "agonizes" a PYR/PYL receptor protein if the presence of the agent results in activation or up-regulation of activity of the receptor, e.g., to increase downstream signaling from the PYR/PYL receptor. For the present invention, an agent agonizes a PYR/PYL receptor if, when the agent is present at a concentration no greater than 200 µM, contacting the agent to the PYR/PYL receptor results in activation or up-regulation of the activity of the PYR/PYL receptor. If an agent does not induce activation or up-regulation of a PYR/PYL receptor protein's activity when the agent is present at a concentration no greater than 200 µM, then the agent does not significantly agonize the PYR/PYL receptor. As used herein, "activation" requires a minimum threshold of activity to be induced by the agent. Determining whether this minimum threshold of activity has been met can be accomplished, e.g., by using an enzymatic phosphatase assay that sets a minimum value for the level of enzymatic activity that must be induced (e.g., enzymatic activity of a wild-type PP2C), or by using an enzymatic phosphatase assay in the presence of a colorimetric detection reagent (e.g., para-nitrophenylphosphate) wherein the minimum threshold of activity has been met if a color change is observed.

In some embodiments, the mutated PYR/PYL receptor comprises a substitution at a residue corresponding to amino acid position 59 in PYR1 (SEQ ID NO: 1). As described in US 2011/0271408, in some cases, a K59 mutation is not only sufficient to abolish ABA sensitivity in a modified PYR/PYL receptor protein, it is also sufficient to confer sensitivity to an orthogonal ligand (i.e., a molecule other than ABA) on a modified PYR/PYL receptor protein. In some cases, the K59 mutation that results in receptor activation by an orthogonal ligand is a substitution of an alanine residue for the wild-type residue, a substitution of a cysteine residue for the wild-type residue, a substitution of an aspartic acid residue for the wild-type residue, a substitution of a glutamic acid residue for the wild-type residue, a substitution of a phenylalanine residue for the wild-type residue, a substitution of a glycine residue for the wild-type residue, a substitution of a histidine residue for the wild-type residue, a substitution of a leucine residue for the wild-type residue, a substitution of a methionine residue for the wild-type residue, a substitution of an asparagine residue for the wild-type residue, a substitution of a glutamine residue for the wild-type residue, a substitution of an arginine residue for the wild-type residue, a substitution of a serine residue for the wild-type residue, a substitution of a threonine residue for the wild-type residue, a substitution of a valine residue for the wild-type residue, a substitution of a tyrosine residue for the wild-type residue, or a substitution of a tryptophan residue for the wild-type residue. In some embodiments, the mutation at position K59 is a K59R substitution. In some embodiments, the modified PYR/PYL receptor protein may comprise at least one more mutation in addition to the K59 mutation.

In some embodiments, the modified PYR/PYL receptor protein comprises one or more mutations (e.g., one, two, three, four, five, six, seven, eight, nine, or more substitutions) that confers sensitivity to an orthogonal ligand (e.g., mandipropamid), wherein the mutations comprise substitutions at one or more amino acid residues corresponding to positions 58, 59, 81, 83, 87, 89, 108, 122, 158, 159, 160, and/or 164 in PYR 1 (SEQ ID NO:1). In some embodiments, the modified PYR/PYL receptor protein comprises one or more substitutions selected from Y58H, V81C, V81I, V81T, V83L, L87A, A89W, F108A, F108C, F108E, F108G, F108I, F108L, F108N, F108Q, F108S, F108T, F108V, S122G, M158I, M158V, F159A, F159C, F159I, F159L, F159M, F159T, F159V, A160V, V164I, or combinations thereof. In some embodiments, the mutated PYR/PYL receptor protein comprises a mutation at one or more amino acids corresponding to positions Y58, K59, V81, A89, F108, S122, M158, F159, or A160 in PYR1 (SEQ ID NO: 1), wherein the mutation is selected from Y58H, K59R, V81C, V81I, V81T, A89W, F108A, F108C, F108E, F108G, F108I, F108L, F108N, F108Q, F108S, F108T, F108V, S122G, M158I, M158V, F159A, F159C, F159I, F159L, F159M, F159T, F159V, A160C, A160V, or combinations thereof.

In some embodiments, the mutated PYR/PYL receptor polypeptide that is agonized by an orthogonal ligand (e.g., mandipropamid) that does not significantly agonize a wild-type PYR/PYL receptor polypeptide and that comprises one or more mutations that disrupts binding to a wild-type PP2C comprises mutations at one or more amino acid residues corresponding to positions 58, 59, 81, 108, 122, 158, 159, 160, and 162 in PYR1 (SEQ ID NO: 1). In some embodiments, the mutated PYR/PYL receptor comprises one or more substitutions selected from Y58H, V81C, V81I, V81T, F108A, F108C, F108E, F108G, F108I, F108L, F108N, F108Q, F108S, F108T, F108V, S122G, M158I, M158V, F159A, F159C, F159I, F159L, F159M, F159T, F159V, A160V, T162D, T162E, T162F, T162P, and combinations thereof. In some embodiments, the mutated PYR/PYL receptor comprises one or more substitutions selected from Y58H, K59R, V81I, F108A, S122G, M158I, M158V, F159V, A160C, A160V, and T162D.

In some embodiments, a mutated PYR/PYL receptor that is agonized by an orthogonal ligand that does not significantly agonize a wild-type PYR/PYL receptor polypeptide and that is disrupted binding to a wild-type PP2C is substantially identical to (e.g., at least 70%, at least 75%, at least 80%, at least 85%, at least 90%, at least 91%, at least 92%, at least 93%, at least 94%, at least 95%, at least 96%, at least 97%, at least 98%, or at least 99% identical to) any of SEQ ID NO:1, 2, 3, 4, 5, 6, 7, 8, 9, 10, 11, 12, 13, 14 and comprises mutations corresponding to Y58H, K59R, V81I, F108A, S122G, M158I, F159V, A160V, and T162D in PYR1. In some embodiments, the mutated PYR/PYL receptor polypeptide is substantially identical to (e.g., at least 70%, at least 75%, at least 80%, at least 85%, at least 90%, at least 91%, at least 92%, at least 93%, at least 94%, at least 95%, at least 96%, at least 97%, at least 98%, or at least 99% identical to) SEQ ID NO:19. In some embodiments, the mutated PYR/PYL receptor polypeptide comprises the sequence of SEQ ID NO:19.

In some embodiments, a mutated PYR/PYL receptor that is agonized by an orthogonal ligand that does not significantly agonize a wild-type PYR/PYL receptor polypeptide and that is disrupted binding to a wild-type PP2C is substantially identical to (e.g., at least 70%, at least 75%, at least 80%, at least 85%, at least 90%, at least 91%, at least 92%, at least 93%, at least 94%, at least 95%, at least 96%, at least 97%, at least 98%, or at least 99% identical to) any of SEQ ID NO:1, 2, 3, 4, 5, 6, 7, 8, 9, 10, 11, 12, 13, 14 and comprises mutations corresponding to Y58H, K59R, V81I, F108A, S122G, M158V, F159V, A160V, and T162D in PYR1. In some embodiments, the mutated PYR/PYL receptor polypeptide is substantially identical to (e.g., at least 70%, at least 75%, at least 80%, at least 85%, at least 90%, at least 91%, at least 92%, at least 93%, at least 94%, at least 95%, at least 96%, at least 97%, at least 98%, or at least 99% identical to) SEQ ID NO:20. In some embodiments, the mutated PYR/PYL receptor polypeptide comprises the sequence of SEQ ID NO:20.

In some embodiments, a mutated PYR/PYL receptor that is agonized by an orthogonal ligand that does not significantly agonize a wild-type PYR/PYL receptor polypeptide and that is disrupted binding to a wild-type PP2C is substantially identical to (e.g., at least 70%, at least 75%, at least 80%, at least 85%, at least 90%, at least 91%, at least 92%, at least 93%, at least 94%, at least 95%, at least 96%, at least 97%, at least 98%, or at least 99% identical to) any of SEQ ID NO:1, 2, 3, 4, 5, 6, 7, 8, 9, 10, 11, 12, 13, 14 and comprises mutations corresponding to Y58H, K59R, V81I, F108A, S122G, M158I, F159V, A160C, and T162D in PYR1. In some embodiments, the mutated PYR/PYL receptor polypeptide is substantially identical to (e.g., at least 70%, at least 75%, at least 80%, at least 85%, at least 90%, at least 91%, at least 92%, at least 93%, at least 94%, at least 95%, at least 96%, at least 97%, at least 98%, or at least 99% identical to) SEQ ID NO:21. In some embodiments, the mutated PYR/PYL receptor polypeptide comprises the sequence of SEQ ID NO:21.

III. Mutated Type 2C Protein Phosphatases

In another aspect, mutated PP2Cs that (1) comprise one or more mutations that disrupts binding to a wild-type PYR/PYL receptor polypeptide and that (2) optionally comprise one or more mutations that disrupts the catalytic activity of the PP2C are provided. Also provided herein are polynucleotides encoding polypeptides comprising the mutated PP2Cs; expression cassettes and expression vectors comprising said polynucleotides; cells (e.g., plant, animal, mammalian, bacterial, or fungal cells), plants, and plant parts comprising the mutated PP2Cs; methods of making cells or plants comprising the mutated PP2Cs; methods of making the mutated PP2Cs; methods of activating an orthogonal PYR/PYL-PP2C interaction in cells or plants comprising the mutated PP2Cs and mutated PYR/PYL receptor polypeptides as described above; and methods of controlling gene expression in cells or plants comprising the mutated PP2Cs and mutated PYR/PYL receptor polypeptides as described herein.

A wide variety of wild-type (naturally occurring) PP2C protein sequences are known in the art. PP2Cs, such as the PP2Cs within the "Clade A" cladogram, are key negative regulators of ABA signaling. For example, HAB1, ABI1, ABI2, and PP2CA have been shown to affect both seed and vegetative responses to ABA. See, e.g., Rubio et al., *Plant Physiology,* 2009, 150:1345-1355, incorporated by reference herein. ABA signaling via PP2Cs is modulated by PYR/PYL receptor polypeptides. In the absence of ABA, PYR/PYL proteins are not bound to PP2Cs, and therefore, PP2C activity is high, which prevents phosphorylation and activation of snRK2s (subfamily 2 SNF1-related kinases) and downstream factors. In the presence of ABA, PYR/PYL proteins bind and inhibit PP2Cs, which allows accumulation of phosphorylated downstream factors and ABA transcriptional responses. See, e.g., Park et al., *Science,* 2009, 324: 1068-1071, incorporated by reference herein.

PP2Cs are found in *Arabidopsis* and other species of plants as well as across kingdoms, and are characterized in part by the presence of a serine/threonine phosphatase catalytic site. In some embodiments, a wild-type PP2C protein comprises a Clade A PP2C protein. In some embodiments, a wild-type PP2C protein comprises any of SEQ ID NOs:22, 23, 24, 25, 26, 27, 28, or 29. In some embodiments, a wild-type PP2C protein is substantially identical to (e.g., at least 70%, 75%, 80%, 85%, 90%, 91%, 92%, 93%, 94% 95%, 96%, 97%, 98%, or 99% identical to) any of SEQ ID NOs:22, 23, 24, 25, 26, 27, 28, or 29.

Mutations that Disrupt Binding to a Wild-Type PYR/PYL Receptor Polypeptide

In some embodiments, a mutated PP2C protein is substantially identical to a SEQ ID listed herein and further comprises at least one (e.g., 1, 2, 3, 4, 5, 6, 7, 8, 9, 10, etc.) mutation at an amino acid position. In some embodiments, a mutated PP2C is substantially identical to any of SEQ ID NOs:22-29 and further comprises at least one mutation at any amino acid position.

In some embodiments, a mutated PP2C protein comprises one or more mutations that disrupts binding to a wild-type PYR/PYL receptor protein (e.g., wild-type PYR1). In some embodiments, a mutated PP2C exhibits "disrupted" binding to a wild-type PYR/PYL receptor protein if the level of binding between the mutated PP2C protein (e.g., a mutated HAB1 protein) and the wild-type PYR/PYL receptor protein is decreased by at least 10%, at least 20%, at least 30%, at least 40%, at least 50%, at least 60%, at least 70%, at least 80%, at least 90% or more in the presence of ABA as compared to the level of binding between the corresponding wild-type PP2C protein (e.g., wild-type HAB1) and the wild-type PYR/PYL receptor protein in the presence of ABA. In some embodiments, a mutated PP2C protein exhibits disrupted binding to a wild-type PYR/PYL receptor protein if no detectable binding occurs in the presence of ABA. Binding between a mutated PP2C and a wild-type PYR/PYL protein can be measured as described herein, e.g., in Section II above.

In some embodiments, a mutated PP2C that comprises one or more mutations that disrupts binding to a wild-type PYR/PYL receptor protein comprises a mutation at one or more residues of the PYR/PYL binding interface. The PYR/PYL binding interface of a PP2C protein comprises amino acid residues that are in close proximity (e.g., within about 5 Å) to the PYR/PYL receptor when PP2C, the PYR/PYL receptor, and ABA are all bound together in a ternary complex. In some embodiments, the PYR/PYL binding interface is determined with reference to the PYR/PYL protein PYR1. In some embodiments, the PYR/PYL binding interface in HAB1 is made up of the following 20 amino acid residues: R199, S200, E201, E203, H245, G246, G247, S322, E323, T324, K381, I383, Q384, W385, Q386, R389, F391, G392, V393, and Y404. The residues of the PYR/PYL binding interface are conserved among other PP2C family members. Thus, in some embodiments, corresponding mutations can be made in the PYR/PYL binding interface of other PP2C proteins of interest by aligning the sequences of HAB1 (SEQ ID NO:22) and the PP2C protein of interest.

In some embodiments, a mutated PP2C comprises one, two, three, four, five, six, seven, eight, nine, or more amino acid substitutions in the PYR/PYL binding interface relative to wild-type PP2C. In some embodiments, a mutated PP2C comprises 1-10 mutations, 5-10 mutations, 1-7 mutations, 1-5 mutations, 1-3 mutations, 1-2 mutations, 2-7 mutations, or 2-5 mutations in the PYR/PYL binding interface relative to wild-type PP2C. In some embodiments, a mutated PP2C comprises a substitution at one or more of residues selected from E201, E203, H245, G246, G247, E323, K381, I383, W385, R389, F391, G392, V393, and Y404 in HAB1. In some embodiments, a mutated PP2C comprises one or more substitutions selected from E201H/K, E203A/C/D/F/G/H/I/K/L/M/N/P/R/S/T/V/W/Y, H245A/C/D/E/F/G/I/K/L/M/N/P/Q/R/S/T/V/W/Y, G246A/C/D/E/F/H/I/K/L/M/N/P/Q/R/S/T/V/W/Y, G247A/E/F/I/K/M/P/Q/R/T/V/W/Y, E323L, K381W, I383D/E/G/H/K/N/P/Q/R/S/T/W/Y, W385A/C/D/E/F/G/H/I/K/L/M/N/P/Q/R/S/T/V/Y, R389A/C/D/E/F/G/H/I/K/L/M/P/Q/T/V/W/Y, F391D/E/P, G392A/D/C/E/F/H/I/K/L/M/N/P/Q/R/T/V/W/Y, V393D/E/G/K/N/P/Q/R/S, Y404D/E/G/K/N/P/Q/R/S/T, and combinations thereof.

In some embodiments, the mutated PP2C comprises a mutation at position R199. In some embodiments, the mutated PP2C comprises a mutation at position S200. In some embodiments, the mutated PP2C comprises a mutation at position E201 (e.g., a E201H/K substitution). In some embodiments, the mutated PP2C comprises a mutation at position E203 (e.g., a E203A/C/D/F/G/H/I/K/L/M/N/P/R/S/T/V/W/Y substitution). In some embodiments, the mutated PP2C comprises a mutation at position H245 (e.g., a H245A/C/D/E/F/G/I/K/L/M/N/P/Q/R/S/T/V/W/Y substitution). In some embodiments, the mutated PP2C comprises a mutation at position G246 (e.g., a G246A/C/D/E/F/H/I/K/L/M/N/P/Q/R/S/T/V/W/Y substitution). In some embodiments, the mutated PP2C comprises a mutation at position G247 (e.g., a G247A/E/F/I/K/M/P/Q/R/T/V/W/Y substitution). In some embodiments, the mutated PP2C comprises a mutation at position S322. In some embodiments, the mutated PP2C comprises a mutation at position E323 (e.g., a E323L substitution). In some embodiments, the mutated PP2C comprises a mutation at position T324. In some embodiments, the mutated PP2C comprises a mutation at position K381 (e.g., a K381W substitution). In some embodiments, the mutated PP2C comprises a mutation at position 1383 (e.g., a I383D/E/G/H/K/N/P/Q/R/S/T/W/Y substitution). In some embodiments, the mutated PP2C comprises a mutation at position Q384. In some embodiments, the mutated PP2C comprises a mutation at position W385 (e.g., a W385A/C/D/E/F/G/H/I/K/L/M/N/P/Q/R/S/T/V/Y substitution). In some embodiments, the mutated PP2C comprises a mutation at position Q386. In some embodiments, the mutated PP2C comprises a mutation at position R389 (e.g., a R389A/C/D/E/F/G/H/I/K/L/M/P/Q/T/V/W/Y substitution). In some embodiments, the mutated PP2C comprises a mutation at position F391 (e.g., a F391D/E/P substitution). In some embodiments, the mutated PP2C comprises a mutation at position G392 (e.g., a G392A/D/C/E/F/H/I/K/L/M/N/P/Q/R/T/V/W/Y substitution). In some embodiments, the mutated PP2C comprises a mutation at position V393 (e.g., a V393D/E/G/K/N/P/Q/R/S substitution). In some embodiments, the mutated PP2C comprises a mutation at position Y404 (e.g., a Y404D/E/G/K/N/P/Q/R/S/T substitution).

In some embodiments, the mutated PP2C protein comprises one or more mutations at amino acids corresponding to position E203, I383, or V393 in HAB1. In some embodiments, the mutated PP2C protein comprises one or more substitutions selected from E203A/C/D/F/G/H/I/K/L/M/N/P/R/S/T/V/W/Y, I383D/E/G/H/K/N/P/Q/R/S/T/W/Y, V393D/E/G/K/N/P/Q/R/S, and combinations thereof. In some embodiments, the mutated PP2C protein comprises one or more substitutions selected from E203D, E203T, E203W, I383G, V393K, V393R, V393Q, and combinations thereof.

Mutations that Disrupt PP2C Catalytic Activity

In some embodiments, the mutated PP2C further comprises one or more mutations that disrupts the catalytic activity of the mutated PP2C. In some embodiments, the mutated PP2C exhibits "disrupted" catalytic activity if the level of phosphatase activity of the mutated PP2C (e.g., a mutated HAB1) is decreased by at least 10%, 20%, 30%, 40%, 50%, 60%, 70%, 80%, 90% or more relative to a corresponding wild-type PP2C (e.g., wild-type HAB1). In some embodiments, the mutated PP2C does not have a detectable level of phosphatase activity. In some embodiments, phosphatase activity is measured in a phosphatase assay, e.g., as described herein in the Examples section. In some embodiments, the catalytic activity of the mutated PP2C is measured by measuring the activity of a downstream signaling pathway component (e.g., measuring the activity of a downstream snRK2 kinase).

In some embodiments, the mutated PP2C comprises a mutation at a residue within the PP2C catalytic active site. In some embodiments, the mutated PP2C comprises a mutation at one or more amino acid residues corresponding to the positions D204 or R505 in HAB1 (SEQ ID NO:22). In some embodiments, the mutated PP2C comprises one or more substitutions selected from R505A and D204A.

In some embodiments, the mutated PP2C further comprises one or more substitutions that stabilizes or strengthens interactions with a mutated PYR/PYL protein (e.g., at a site within the PYR/PYL interface). In some embodiments, the mutated PP2C further comprises a mutation at one or more amino acid residues corresponding to the positions R199 and S322 in HAB1. In some embodiments, the mutated PP2C further comprises one or more substitutions selected from R199A, S322D, and S322E.

In some embodiments, the mutated PP2C is substantially identical to (e.g., at least 70%, at least 75%, at least 80%, at least 85%, at least 90%, at least 91%, at least 92%, at least 93%, at least 94%, at least 95%, at least 96%, at least 97%, at least 98%, or at least 99% identical to) any of SEQ ID NO:22-29 and comprises mutations corresponding to D204A, V393R, and R505A in HAB1. In some embodiments, the mutated PP2C is substantially identical to (e.g., at least 70%, at least 75%, at least 80%, at least 85%, at least 90%, at least 91%, at least 92%, at least 93%, at least 94%, at least 95%, at least 96%, at least 97%, at least 98%, or at least 99% identical to) any of SEQ ID NO:22-29 and comprises mutations corresponding to R199A, D204A, S322D, V393R, and R505A in HAB1. In some embodiments, the mutated PP2C is substantially identical to (e.g., at least 70%, at least 75%, at least 80%, at least 85%, at least 90%, at least 91%, at least 92%, at least 93%, at least 94%, at least 95%, at least 96%, at least 97%, at least 98%, or at least 99% identical to) SEQ ID NO:30 or 31. In some embodiments, the mutated PP2C comprises the sequence of SEQ ID NO:30 or 31.

IV. Methods of Making Mutated PYR/PYL Receptor Polypeptides and Mutated PP2Cs

Embodiments of the present invention provide for use of the above proteins and/or nucleic acid sequences, encoding such polypeptides, in the methods and compositions (e.g., expression cassettes, plants, cells, etc.) of the present invention. The isolation of a polynucleotide sequence encoding a plant wild-type PYR/PYL receptor and/or PP2C (e.g., from plants where PYR/PYL sequences and/or PP2C sequences have not yet been identified) may be accomplished by a number of techniques. For instance, oligonucleotide probes based on the PYR/PYL coding sequences disclosed herein (e.g., as listed in the SEQUENCE LISTING) can be used to identify the desired wild-type PYR/PYL gene in a cDNA or genomic DNA library, or oligonucleotide probes based on the PP2C coding sequences disclosed herein can be used to identify the desired wild-type PP2C gene in a cDNA or genomic DNA library. To construct genomic libraries, large segments of genomic DNA are generated by random fragmentation, e.g., using restriction endonucleases, and are ligated with vector DNA to form concatemers that can be packaged into the appropriate vector. To prepare a cDNA library, mRNA is isolated from the desired tissue, such as a leaf from a particular plant species, and a cDNA library containing the gene transcript of interest is prepared from the mRNA. Alternatively, cDNA may be prepared from mRNA extracted from other tissues in which the PYR/PYL gene and/or PP2C gene is expressed.

The cDNA or genomic library can then be screened using a probe based upon the sequence of a PYR/PYL gene and/or PP2C gene disclosed here. Probes may be used to hybridize with genomic DNA or cDNA sequences to isolate homologous genes in the same or different plant species. Alternatively, antibodies raised against a polypeptide can be used to screen an mRNA expression library.

Alternatively, the nucleic acids encoding a PYR/PYL or a PP2C can be amplified from nucleic acid samples using amplification techniques. For instance, polymerase chain reaction (PCR) technology can be used to amplify the coding sequences of a PYR/PYL and/or a PP2C directly from genomic DNA, from cDNA, from genomic libraries or cDNA libraries. PCR and other in vitro amplification methods may also be useful, for example, to clone polynucleotide sequences encoding the PYR/PYL and/or PP2C to be expressed, to make nucleic acids to use as probes for detecting the presence of the desired mRNA in samples, for nucleic acid sequencing, or for other purposes. For a general overview of PCR see *PCR Protocols: A Guide to Methods and Applications*. (Innis, M., Gelfand, D., Sninsky, J. and White, T., eds.), Academic Press, San Diego (1990). Appropriate primers and probes for identifying sequences from plant tissues are generated from comparisons of the sequences provided here with other related genes.

In some embodiments, the partial or entire genome of a number of plants has been sequenced and open reading frames identified. By a BLAST search, one can identify the coding sequence for a wild-type PYR/PYL or wild-type PP2C in various plants.

Embodiments of the present invention also provide for methods of making mutated PYR/PYL receptor proteins and mutated PP2Cs as described herein. Mutated PYR/PYL receptor polypeptides can be constructed by mutating the DNA sequences that encode the corresponding wild-type PYR/PYL receptor polypeptide (e.g., a wild-type PYR/PYL polypeptide of any of SEQ ID NOs: 1-14 or a corresponding variant from which the mutant PYR/PYL receptor polypeptide of the invention is derived), such as by using techniques commonly referred to as site-directed mutagenesis. Similarly, mutated PP2Cs can be constructed by mutated the DNA sequences that encode the corresponding wild-type PP2C protein (e.g., a wild-type PP2C of any of SEQ ID NOs:22-29 or a corresponding variant from which the mutant PP2C of the invention is derived). Nucleic acid molecules encoding the wild-type PYR/PYL receptor polypeptide and/or PP2C protein can be mutated by a variety of polymerase chain reaction (PCR) techniques well-known to one of ordinary skill in the art. (See, e.g., *PCR Strategies* (M. A. Innis, D. H. Gelfand, and J. J. Sninsky eds., 1995, Academic Press, San Diego, Calif.) at Chapter 14; *PCR Protocols: A Guide to Methods and Applications* (M. A. Innis, D. H. Gelfand, J. J. Sninsky, and T. J. White eds., Academic Press, N Y, 1990).

By way of non-limiting example, mutagenesis may be accomplished by means of error-prone PCR amplification (ePCR), which modifies PCR reaction conditions (e.g., using error-prone polymerases, varying magnesium or manganese concentration, or providing unbalanced dNTP ratios) in order to promote increased rates of error in DNA replication. Kits for ePCR mutagenesis are commercially available, such as the GeneMorph® PCR Mutagenesis kit (Stratagene) and Diversify® PCR Random Mutagenesis Kit (Clontech). Briefly, DNA polymerase (e.g., Taq polymerase), salt (e.g., MgCl2, MgSO4, or MnSO4), dNTPs in unbalanced ratios, reaction buffer, and DNA template are combined and subjected to standard PCR amplification according to manufacturer's instructions. Following ePCR amplification, the reaction products are cloned into a suitable vector to construct a mutagenized library, which can then be transformed into suitable cells (e.g., yeast cells) for subsequent screening (e.g., via a two-hybrid screen) as described below.

Alternatively, mutagenesis can be accomplished by recombination (i.e. DNA shuffling). Briefly, a shuffled mutant library is generated through DNA shuffling using in vitro homologous recombination by random fragmentation of a parent DNA followed by reassembly using PCR, resulting in randomly introduced point mutations. Methods of performing DNA shuffling are known in the art (see, e.g., Stebel, S. C. et al., *Methods Mol Biol* 352:167-190 (2007)).

Optionally, multiple rounds of mutagenesis may be performed in order to improve the efficiency of mutant proteins isolated. Thus, in some embodiments, PYR/PYL mutants and/or PP2C isolated from ePCR and subsequent screening may be pooled and used as templates for later rounds of mutagenesis.

V. Screening Mutated PYR/PYL Receptor Polypeptides and Mutated PP2Cs

Embodiments of the present invention provide for methods of screening mutated PYR/PYL receptor proteins and mutated PP2C proteins to identify sets of mutually suppressing mutations in the mutated PYR/PYL protein and mutated PP2C protein, which as a pair, prevent a PYR/PYL-PP2C complex from forming in the presence of ABA. In some embodiments, the method comprises expressing a mutated PYR/PYL protein (e.g., as described in Section II above) and expressing a mutated PP2C protein (e.g., as described in Section III above) in the presence of ABA in an in vitro or in vivo assay, and evaluating the level of downstream activity in response to the addition of ABA, relative to a corresponding wild-type PYR/PYL protein and wild-type PP2C. In some embodiments, the combination of the mutated PYR/PYL protein and the mutated PP2C protein exhibits at least 2-fold, at least 3-fold, at least 4-fold, at least 5-fold, at least 6-fold, at least 7-fold, at least 8-fold, at least 9-fold or more of a decrease in sensitivity to ABA, relative to a corresponding wild-type PYR/PYL protein and PP2C protein. In some embodiments, the downstream activity is measured by an enzymatic phosphatase assay in the presence of a colorimetric detection reagent (for example, para-nitrophenylphosphate). See, e.g., Park et al., *Science,* 2009, 324:1068-1071, and the Examples section below; see also, US 2010/0216643, US 2011/0271408, and US 2014/0259226, incorporated by reference herein.

Embodiments of the present invention also provide for methods of screening mutated PYR/PYL receptor proteins and mutated PP2C proteins to determine whether the mutated PYR/PYL receptor protein and the PP2C protein interact with each other. In some embodiments, the mutated PYR/PYL receptor protein and the PP2C protein interact with each other if there is a physical interaction between the mutated PYR/PYL protein and the mutated PP2C protein that is detectable in a biochemical assay, e.g., in a yeast-two hybrid assay. Methods for detecting a biochemical interaction between a mutated PYR/PYL protein and a mutated PP2C protein by yeast two-hybrid assay are described herein in the Examples section, and are also described, for example, in Park et al., *Science,* 2009, 324:1068-1071, incorporated by reference herein.

Optionally, binding assays can be used for determining whether the mutated PYR/PYL receptor protein and the PP2C protein interact with each other. Binding assays can involve contacting the mutated PYR/PYL receptor polypeptide with the mutated PP2C and allowing sufficient time for the proteins to form a binding complex. Any binding complexes formed can be detected using any of a number of established analytical techniques. Protein binding assays include, but are not limited to, methods that measure co-precipitation or co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89. The PYR/PYL and PP2C proteins utilized in such assays can be naturally expressed, cloned or synthesized.

In some embodiments, the mutated PYR/PYL proteins and mutated PP2Cs that are initially identified by any of the foregoing screening methods can be further tested to validate the apparent activity and/or determine other biological effects of the mutated PYR/PYL receptor polypeptide and mutated PP2C. In some cases, the mutated PYR/PYL receptor polypeptide and the mutated PP2C are expressed in plants and tested for the ability to effect plant stress (e.g., drought tolerance), seed germination, or another phenotype affected by ABA. A number of such assays and phenotypes are known in the art and can be employed according to the methods of the invention.

VI. PYR/PYL-PP2C Interaction Module for Regulation of Gene Expression

In another aspect, the mutated PYR/PYL proteins and mutated PP2C proteins described herein can be used to regulate gene and protein expression in vivo (e.g., in cells such as plant, animal, mammalian, bacterial, or fungal cells, or in plants such as crops). In some embodiments, the mutated PYR/PYL proteins and mutated PP2C proteins described herein, when expressed in a plant or plant cell, are able to interact with each other (e.g., in the presence of an orthogonal ligand such as mandipropamid) without activating endogenous ABA responses the plant or plant cell. This orthogonal interaction between mutated PYR/PYL and PP2C proteins can be utilized to generate an inducible protein-protein interaction module for regulating gene and protein expression in a cell or in a plant, such as for engineering crops in which a desired protein function or phenotype is regulated agrochemically.

In some embodiments, a PYR/PYL-PP2C interaction module utilizes fusion constructs in which one of the mutated PYR/PYL receptor protein and mutated PP2C protein is fused to a transcriptional activation domain (AD) and the other of the mutated PYR/PYL receptor protein and mutated PP2C protein is fused to a DNA binding domain (BD). In this PYR/PYL-PP2C interaction module, interaction between the mutated PYR/PYL protein and mutated PP2C protein is regulated by the presence or absence of an orthogonal ligand (e.g., an agrochemical such as mandipropamid). In the absence of the orthogonal ligand, the mutated PYR/PYL protein and mutated PP2C do not significantly interact with each other (e.g., do not interact with other at a detectable level). In the presence of the orthogonal ligand, however, the mutated PYR/PYL protein and the mutated PP2C protein interact with each other, which results in the physical association of the AD and BD fused to the mutated PYR/PYL and mutated PP2C, and enables control of transcription of a target gene.

In some embodiments, the mutated PYR/PYL receptor protein is fused to a transcriptional activation domain and the mutated PP2C protein is fused to a DNA binding domain. In some embodiments, the mutated PP2C protein is fused to a transcriptional activation domain and the mutated PYR/PYL receptor protein is fused to a DNA binding domain. In some embodiments, the AD is substantially identical to (e.g., at least 70%, at least 75%, at least 80%, at least 85%, at least 90%, at least 91%, at least 92%, at least 93%, at least 94%, at least 95%, at least 96%, at least 97%, at least 98%, or at least 99% identical to) the AD having the amino acid sequence of SEQ ID NO:35. In some embodiments, the AD comprises the sequence of SEQ ID NO:35. In some embodiments, the BD is substantially identical to (e.g., at least 70%, at least 75%, at least 80%, at least 85%, at least 90%, at least 91%, at least 92%, at least 93%, at least 94%, at least 95%, at least 96%, at least 97%, at least 98%, or at least 99% identical to) the BD having the amino acid sequence of SEQ ID NO:36. In some embodiments, the BD comprises the sequence of SEQ ID NO:36.

In some embodiments, one or more expression cassettes comprising the fusion proteins is expressed in a plant or plant cell. In some embodiments, one expression cassette comprises both a mutated PYR/PYL receptor protein fused to a transcriptional activation domain and a mutated PP2C protein fused to a DNA binding domain, or comprises both a mutated PP2C protein fused to a transcriptional activation domain and a mutated PYR/PYL receptor protein fused to a DNA binding domain, under the control of a heterologous promoter. In some embodiments, a first expression cassette comprises a first heterologous promoter for expressing a mutated PYR/PYL receptor protein fused to one of a transcriptional activation domain or a DNA binding domain, and a second expression cassette comprises a second heterologous promoter for expressing a mutated PP2C protein fused to the other of a transcriptional activation domain or a DNA binding domain. In some embodiments, the first promoter and the second promoter are the same promoter. In some embodiments, the first promoter and the second promoter are different promoters. In some embodiments, the promoter comprises a sequence that is bound by the DNA binding domain.

In some embodiments, one or both of the mutated PYR/PYL receptor protein (or mutant PYR/PYL fusion protein) and mutated PP2C protein (or mutant PP2C fusion protein) further comprises a sequence for localizing the expression of the mutated PYR/PYL protein or mutated PP2C protein, e.g., in the nucleus, in the cytoplasm of a cell, or in an organelle (e.g., mitochondria or chloroplast). Localization of the PYR/PYL-PP2C interaction module to the nucleus of the cell can be advantageous, e.g., for regulating transcription factors or other nuclear proteins that require access to their DNA targets in order to control phenotypic outputs.

In some embodiments, one or both of the mutated PYR/PYL receptor protein (or mutant PYR/PYL fusion protein) and mutated PP2C protein (or mutant PP2C fusion protein) is localized to the nucleus. Thus, in some embodiments, the mutated PYR/PYL receptor protein or fusion protein, or the mutated PP2C protein or fusion protein, further comprises a nuclear localization sequence. In some embodiments, the nuclear localization sequence is substantially identical to (e.g., at least 70%, at least 75%, at least 80%, at least 85%, at least 90%, at least 91%, at least 92%, at least 93%, at least 94%, at least 95%, at least 96%, at least 97%, at least 98%, or at least 99% identical to) the nuclear localization sequence having the amino acid sequence of SEQ ID NO:37. In some embodiments, the nuclear localization sequence comprises the sequence of SEQ ID NO:37.

In some embodiments, one or both of the mutated PYR/PYL receptor protein (or mutant PYR/PYL fusion protein) and mutated PP2C protein (or mutant PP2C fusion protein) is localized to the cytoplasm. Thus, in some embodiments, the mutated PYR/PYL receptor protein or fusion protein, or the mutated PP2C protein or fusion protein, further comprises a nuclear export sequence. In some embodiments, the nuclear export sequence is substantially identical to (e.g., at least 70%, at least 75%, at least 80%, at least 85%, at least 90%, at least 91%, at least 92%, at least 93%, at least 94%, at least 95%, at least 96%, at least 97%, at least 98%, or at least 99% identical to) the nuclear export sequence having the amino acid sequence of SEQ ID NO:38 or 39. In some embodiments, the nuclear export sequence comprises the sequence of SEQ ID NO:38 or 39.

VII. Expression Cassettes and Expression Vectors

Once a polynucleotide sequence encoding a polypeptide comprising a mutated PYR/PYL receptor polypeptide and a polynucleotide sequence encoding a polypeptide comprising a mutated PP2C protein are obtained, the polynucleotide sequences can be used to prepare an expression cassette for expressing the mutated PYR/PYL receptor polypeptide and mutated PP2C in a cell (e.g., a plant, animal, mammalian, bacterial, or fungal cell) or in a transgenic plant, directed by a heterologous promoter. In some embodiments, the polynucleotide sequence encoding the polypeptide comprising the mutated PYR/PYL receptor polypeptide and the polynucleotide sequence encoding the polypeptide comprising the mutated PP2C protein are expressed in a single expression cassette (e.g., under the control of a single heterologous promoter or each polynucleotide under the control of its own promoter). In some embodiments, a first expression cassette is generated comprising the polynucleotide sequence encoding the polypeptide comprising the mutated PYR/PYL receptor polypeptide under the control of a first promoter, and a second expression cassette is generated comprising the polynucleotide sequence encoding the polypeptide comprising the mutated PP2C protein under the control of a second promoter. In some embodiments, the first promoter and the second promoter are identical to each other. In some embodiments, the first promoter and the second promoter are not identical to each other.

To use a polynucleotide sequence for a mutated PYR/PYL receptor polypeptide or a mutated PP2C protein in the above techniques, recombinant DNA vectors suitable for transformation of cells or plants are prepared. Techniques for transforming a wide variety of cells and higher plant species are well known and described in the technical and scientific literature. See, e.g., Weising et al. *Ann. Rev. Genet.* 22:421-477 (1988). A DNA sequence coding for the mutated PYR/PYL receptor polypeptide preferably will be combined with transcriptional and translational initiation regulatory sequences which will direct the transcription of the sequence from the gene in the intended tissues of the transformed plant.

For example, a promoter fragment may be employed to direct expression of the mutated PYR/PYL polynucleotide or mutated PP2C polynucleotide in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the promoter may direct expression of the mutated PYR/PYL receptor protein or mutated PP2C in a specific tissue (tissue-specific promoters) or may be otherwise under more precise environmental control (inducible promoters). Examples of tissue-specific promoters under developmental control include promoters that initiate transcription only in certain tissues, such as leaves, vegetative tissue, or guard cells (including but not limited to those described in WO/2005/085449; U.S. Pat. No. 6,653,535; Li et al; *Sci China C Life Sci.* 2005 April; 48(2):181-6; Husebye, et al., *Plant Physiol*, April 2002, Vol. 128, pp. 1180-1188; and Plesch, et al., *Gene*, Volume 249, Number 1, 16 May 2000, pp. 83-89(7)). Examples of environmental conditions that may affect transcription by inducible promoters include anaerobic conditions, elevated temperature, or the presence of light.

In some embodiments, the promoter comprises a sequence that is bound by a DNA binding domain (e.g., by a PYR/PYL-BD or PP2C-BD fusion protein as described herein).

In some embodiments, an upstream activating sequence (UAS) can also be included for enhancing gene expression.

If proper protein expression is desired, a polyadenylation region at the 3'-end of the coding region should be included. The polyadenylation region can be derived from a naturally occurring PYR/PYL gene or PP2C gene, from a variety of other plant genes, or from T-DNA.

The vector comprising the sequences will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

In some embodiments, the mutated PYR/PYL nucleic acid sequence or the mutated PP2C nucleic acid sequence is expressed recombinantly in the cell or plant. A variety of different expression constructs, such as expression cassettes and vectors suitable for transformation of plant cells can be prepared. Techniques for transforming a wide variety of higher plant species are well known and described in the technical and scientific literature. See, e.g., Weising et al. *Ann. Rev. Genet.* 22:421-477 (1988). A DNA sequence coding for a PYR/PYL protein can be combined with cis-acting (promoter) and trans-acting (enhancer) transcriptional regulatory sequences to direct the timing, tissue type and levels of transcription in the intended tissues of the transformed plant. Translational control elements can also be used.

Constitutive Promoters

A promoter fragment can be employed to direct expression of a mutated PYR/PYL nucleic acid and/or mutated PP2C nucleic acid in all transformed cells or tissues, e.g., as those of a regenerated plant. The term "constitutive regulatory element" means a regulatory element that confers a level of expression upon an operatively linked nucleic molecule that is relatively independent of the cell or tissue type in which the constitutive regulatory element is expressed. A constitutive regulatory element that is expressed in a plant generally is widely expressed in a large number of cell and tissue types. Promoters that drive expression continuously under physiological conditions are referred to as "constitutive" promoters and are active under most environmental conditions and states of development or cell differentiation.

A variety of constitutive regulatory elements useful for ectopic expression in a transgenic plant are well known in the art. The cauliflower mosaic virus 35S (CaMV 35S) promoter, for example, is a well-characterized constitutive regulatory element that produces a high level of expression in all plant tissues (Odell et al., *Nature* 313:810-812 (1985)). The CaMV 35S promoter can be particularly useful due to its activity in numerous diverse plant species (Benfey and Chua, *Science* 250:959-966 (1990); Futterer et al., *Physiol. Plant* 79:154 (1990); Odell et al., supra, 1985). A tandem 35S promoter, in which the intrinsic promoter element has been duplicated, confers higher expression levels in comparison to the unmodified 35S promoter (Kay et al., *Science* 236:1299 (1987)). Other useful constitutive regulatory elements include, for example, the cauliflower mosaic virus 19S promoter; the ubiquitin promoter; the Figwort mosaic virus promoter; and the nopaline synthase (nos) gene promoter (Singer et al., *Plant Mol. Biol.* 14:433 (1990); An, *Plant Physiol.* 81:86 (1986)).

Additional constitutive regulatory elements including those for efficient expression in monocots also are known in the art, for example, the pEmu promoter and promoters based on the rice Actin-1 5' region (Last et al., *Theor. Appl. Genet.* 81:581 (1991); Mcelroy et al., *Mol. Gen. Genet.* 231:150 (1991); Mcelroy et al., *Plant Cell* 2:163 (1990)). Chimeric regulatory elements, which combine elements from different genes, also can be useful for ectopically expressing a nucleic acid molecule encoding a mutated PYR/PYL receptor protein and/or mutated PP2C protein (Comai et al., *Plant Mol. Biol.* 15:373 (1990)).

Other examples of constitutive promoters include the 1'- or 2'-promoter derived from T-DNA of *Agrobacterium* tumafaciens (see, e.g., Mengiste (1997) supra; O'Grady (1995) *Plant Mol. Biol.* 29:99-108); actin promoters, such as the *Arabidopsis* actin gene promoter (see, e.g., Huang (1997) *Plant Mol. Biol.* 1997 33:125-139); alcohol dehydrogenase (Adh) gene promoters (see, e.g., Millar (1996) *Plant Mol. Biol.* 31:897-904); ACT11 from *Arabidopsis* (Huang et al. *Plant Mol. Biol.* 33:125-139 (1996)), Cat3 from *Arabidopsis* (GenBank No. U43147, Zhong et al., *Mol. Gen. Genet.*

251:196-203 (1996)), the gene encoding stearoyl-acyl carrier protein desaturase from *Brassica napus* (Genbank No. X74782, Solocombe et al. *Plant Physiol.* 104:1167-1176 (1994)), GPc1 from maize (GenBank No. X15596, Martinez et al. *J Mol. Biol* 208:551-565 (1989)), Gpc2 from maize (GenBank No. U45855, Manjunath et al., *Plant Mol. Biol.* 33:97-112 (1997)), other transcription initiation regions from various plant genes known to those of skill. See also Holtorf *Plant Mol. Biol.* 29:637-646 (1995).

Inducible Promoters

Alternatively, a promoter may direct expression of the mutated PYR/PYL polynucleotide and/or mutated PP2C polynucleotide under the influence of changing environmental conditions or developmental conditions. Examples of environmental conditions that may effect transcription by inducible promoters include anaerobic conditions, elevated temperature, drought, or the presence of light. Such promoters are referred to herein as "inducible" promoters. For example, the invention can incorporate a drought-specific promoter such as a drought-inducible promoter of maize (e.g., the maize rab17 drought-inducible promoter (Vilardell et al. (1991) *Plant Mol. Biol.* 17:985-993; Vilardell et al. (1994) *Plant Mol. Biol.* 24:561-569)); or alternatively a cold, drought, and high salt inducible promoter from potato (Kirch (1997) *Plant Mol. Biol.* 33:897-909).

Alternatively, promoters which are inducible upon exposure to plant hormones, such as auxins, can be used to express the mutated PYR/PYL polynucleotide and/or mutated PP2C polynucleotide. For example, the invention can use the auxin-response elements E1 promoter fragment (AuxREs) in the soybean (*Glycine max* L.) (Liu (1997) *Plant Physiol.* 115:397-407); the auxin-responsive *Arabidopsis* GST6 promoter (also responsive to salicylic acid and hydrogen peroxide) (Chen (1996) *Plant J.* 10: 955-966); the auxin-inducible parC promoter from tobacco (Sakai (1996) 37:906-913); a plant biotin response element (Streit (1997) *Mol. Plant Microbe Interact.* 10:933-937); and, the promoter responsive to the stress hormone abscisic acid (Sheen (1996) *Science* 274:1900-1902).

Plant promoters inducible upon exposure to chemicals reagents that may be applied to the plant, such as herbicides or antibiotics, are also useful for expressing the mutated PYR/PYL polynucleotide. For example, the maize In2-2 promoter, activated by benzenesulfonamide herbicide safeners, can be used (De Veylder (1997) *Plant Cell Physiol.* 38:568-577); application of different herbicide safeners induces distinct gene expression patterns, including expression in the root, hydathodes, and the shoot apical meristem. A PYR/PYL and/or PP2C coding sequence can also be under the control of, e.g., a tetracycline-inducible promoter, e.g., as described with transgenic tobacco plants containing the *Avena sativa* L. (oat) arginine decarboxylase gene (Masgrau (1997) *Plant J.* 11:465-473); or, a salicylic acid-responsive element (Stange (1997) *Plant J.* 11:1315-1324; Uknes et al., *Plant Cell* 5:159-169 (1993); Bi et al., *Plant J.* 8:235-245 (1995)).

Examples of useful inducible regulatory elements include copper-inducible regulatory elements (Mett et al., *Proc. Natl. Acad. Sci. USA* 90:4567-4571 (1993); Furst et al., *Cell* 55:705-717 (1988)); tetracycline and chlor-tetracycline-inducible regulatory elements (Gatz et al., *Plant J.* 2:397-404 (1992); Roder et al., *Mol. Gen. Genet.* 243:32-38 (1994); Gatz, *Meth. Cell Biol.* 50:411-424 (1995)); ecdysone inducible regulatory elements (Christopherson et al., *Proc. Natl. Acad. Sci. USA* 89:6314-6318 (1992); Kreutzweiser et al., *Ecotoxicol. Environ. Safety* 28:14-24 (1994)); heat shock inducible regulatory elements (Takahashi et al., *Plant Physiol.* 99:383-390 (1992); Yabe et al., *Plant Cell Physiol.* 35:1207-1219 (1994); Ueda et al., *Mol. Gen. Genet.* 250: 533-539 (1996)); and lac operon elements, which are used in combination with a constitutively expressed lac repressor to confer, for example, IPTG-inducible expression (Wilde et al., *EMBO J.* 11:1251-1259 (1992)). An inducible regulatory element useful in the transgenic plants of the invention also can be, for example, a nitrate-inducible promoter derived from the spinach nitrite reductase gene (Back et al., *Plant Mol. Biol.* 17:9 (1991)) or a light-inducible promoter, such as that associated with the small subunit of RuBP carboxylase or the LHCP gene families (Feinbaum et al., *Mol. Gen. Genet.* 226:449 (1991); Lam and Chua, *Science* 248:471 (1990)).

Tissue-Specific Promoters

Alternatively, the promoter may direct expression of the mutated PYR/PYL polynucleotide and/or mutated PP2C polynucleotide in a specific tissue (tissue-specific promoters). Tissue specific promoters are transcriptional control elements that are only active in particular cells or tissues at specific times during plant development, such as in vegetative tissues or reproductive tissues.

Examples of tissue-specific promoters under developmental control include promoters that initiate transcription only (or primarily only) in certain tissues, such as vegetative tissues, e.g., roots or leaves, or reproductive tissues, such as fruit, ovules, seeds, pollen, pistols, flowers, or any embryonic tissue, or epidermis or mesophyll. Reproductive tissue-specific promoters may be, e.g., ovule-specific, embryo-specific, endosperm-specific, integument-specific, seed and seed coat-specific, pollen-specific, petal-specific, sepal-specific, or some combination thereof. In some embodiments, the promoter is cell-type specific, e.g., guard cell-specific.

Other tissue-specific promoters include seed promoters. Suitable seed-specific promoters are derived from the following genes: MAC1 from maize (Sheridan (1996) *Genetics* 142:1009-1020); Cat3 from maize (GenBank No. L05934, Abler (1993) *Plant Mol. Biol.* 22:10131-1038); vivparous-1 from *Arabidopsis* (Genbank No. U93215); atmyc1 from *Arabidopsis* (Urao (1996) *Plant Mol. Biol.* 32:571-57; Conceicao (1994) *Plant* 5:493-505); napA from *Brassica napus* (GenBank No. J02798, Josefsson (1987) JBL 26:12196-1301); and the napin gene family from *Brassica napus* (Sjodahl (1995) *Planta* 197:264-271).

A variety of promoters specifically active in vegetative tissues, such as leaves, stems, roots and tubers, can also be used. For example, promoters controlling patatin, the major storage protein of the potato tuber, can be used, see, e.g., Kim (1994) *Plant Mol. Biol.* 26:603-615; Martin (1997) *Plant J.* 11:53-62. The ORF13 promoter from *Agrobacterium rhizogenes* that exhibits high activity in roots can also be used (Hansen (1997) *Mol. Gen. Genet.* 254:337-343. Other useful vegetative tissue-specific promoters include: the tarin promoter of the gene encoding a globulin from a major taro (*Colocasia esculenta* L. Schott) corm protein family, tarin (Bezerra (1995) *Plant Mol. Biol.* 28:137-144); the curculin promoter active during taro corm development (de Castro (1992) *Plant Cell* 4:1549-1559) and the promoter for the tobacco root-specific gene TobRB7, whose expression is localized to root meristem and immature central cylinder regions (Yamamoto (1991) *Plant Cell* 3:371-382).

Leaf-specific promoters, such as the ribulose biphosphate carboxylase (RBCS) promoters can be used. For example, the tomato RBCS1, RBCS2 and RBCS3A genes are expressed in leaves and light-grown seedlings, only RBCS1 and RBCS2 are expressed in developing tomato fruits (Meier (1997) *FEBS Lett.* 415:91-95). A ribulose bisphosphate carboxylase promoters expressed almost exclusively in mesophyll cells in leaf blades and leaf sheaths at high levels, described by Matsuoka (1994) *Plant J.* 6:311-319, can be used. Another leaf-specific promoter is the light harvesting chlorophyll a/b binding protein gene promoter, see, e.g., Shiina (1997) *Plant Physiol.* 115:477-483; Casal (1998) *Plant Physiol.* 116:1533-1538. The *Arabidopsis thaliana* myb-related gene promoter (AtmybS) described by Li (1996) *FEBS Lett.* 379:117-121, is leaf-specific. The AtmybS promoter is expressed in developing leaf trichomes, stipules, and epidermal cells on the margins of young rosette and cauline leaves, and in immature seeds. AtmybS mRNA appears between fertilization and the 16 cell stage of embryo development and persists beyond the heart stage. A leaf promoter identified in maize by Busk (1997) *Plant J.* 11:1285-1295, can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, described by Di Laurenzio (1996) *Cell* 86:423-433; and, Long (1996) *Nature* 379:66-69; can be used. Another useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto (1995) *Plant Cell.* 7:517-527). Also useful are knl-related genes from maize and other species which show meristem-specific expression, see, e.g., Granger (1996) *Plant Mol. Biol.* 31:373-378; Kerstetter (1994) *Plant Cell* 6:1877-1887; Hake (1995) *Philos. Trans. R. Soc. Lond. B. Biol. Sci.* 350:45-51. For example, the *Arabidopsis thaliana* KNAT1 promoter (see, e.g., Lincoln (1994) *Plant Cell* 6:1859-1876).

One of skill in the art of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

In another embodiment, the mutated PYR/PYL polynucleotide and/or mutated PP2C polynucleotide is expressed through a transposable element. This allows for constitutive, yet periodic and infrequent expression of the constitutively active polypeptide. The invention also provides for use of tissue-specific promoters derived from viruses including, e.g., the tobamovirus subgenomic promoter (Kumagai (1995) *Proc. Natl. Acad. Sci. USA* 92:1679-1683; the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer (1996) *Plant Mol. Biol.* 31:1129-1139).

VIII. Production of Transgenic Cells and Plants

As detailed herein, embodiments of the present invention provide for transgenic cells (e.g., plant, animal, mammalian, bacterial, or fungal cells) or plants comprising recombinant expression cassettes for expressing a mutant PYR/PYL receptor protein and a mutant PP2C protein as described herein. In some embodiments, a transgenic plant or cell is generated that contains a complete or partial sequence of a polynucleotide that is derived from a species other than the species of the transgenic plant or cell. It should be recognized that transgenic plants encompass the plant or plant cell in which the expression cassette is introduced as well as progeny of such plants or plant cells that contain the expression cassette, including the progeny that have the expression cassette stably integrated in a chromosome.

Recombinant expression vectors comprising a PYR/PYL coding sequence and/or a PP2C coding sequence driven by a heterologous promoter may be introduced into the genome of the desired host (e.g., cell or plant host) by a variety of conventional techniques. For example, the DNA construct may be introduced directly into the genomic DNA of the plant cell using techniques such as electroporation and microinjection of plant cell protoplasts, or the DNA construct can be introduced directly to plant tissue using ballistic methods, such as DNA particle bombardment. Alternatively, the DNA construct may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. While transient expression of mutated PYR/PYL or mutated PP2C is encompassed by the invention, generally expression of construction of the invention will be from insertion of expression cassettes into the plant genome, e.g., such that at least some plant offspring also contain the integrated expression cassette.

Microinjection techniques are also useful for this purpose. These techniques are well known in the art and thoroughly described in the literature. The introduction of DNA constructs using polyethylene glycol precipitation is described in Paszkowski et al. *EMBO J.* 3:2717-2722 (1984). Electroporation techniques are described in Fromm et al. *Proc. Natl. Acad. Sci. USA* 82:5824 (1985). Ballistic transformation techniques are described in Klein et al. *Nature* 327:70-73 (1987).

*Agrobacterium tumefaciens*-mediated transformation techniques, including disarming and use of binary vectors, are well described in the scientific literature. See, for example, Horsch et al. *Science* 233:496-498 (1984), and Fraley et al. *Proc. Natl. Acad. Sci. USA* 80:4803 (1983).

Transformed plant cells derived by any of the above transformation techniques can be cultured to regenerate a whole plant that possesses the transformed genotype and thus the desired phenotype such as enhanced abiotic stress resistance. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987).

One of skill in the art will recognize that after the expression cassette is stably incorporated in transgenic plants and confirmed to be operable, it can be introduced into other plants by sexual crossing. Any of a number of standard breeding techniques can be used, depending upon the species to be crossed.

The expression cassettes of the invention can be expressed in a broad range of cells, such as plant, animal, mammalian, bacterial, or fungal cells. In some embodiments, the cells are eukaryotic cells, including but not limited to fungal cells, algal cells, insect cells, mammalian cells, or plant cells. In some embodiments, the cells are bacterial cells. In some embodiments, the cells are yeast cells. In some embodiments, the cells are plant cells. In some embodiments, the cells are mammalian cells.

The expression cassettes of the invention can also be used over a broad range of plants, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna,* and, *Zea*. In some embodiments, the plant is selected from the group consisting of rice, maize, wheat, soybeans, cotton, canola, turfgrass, and alfalfa. In some embodiments, the plant is an ornamental plant. In some embodiment, the plant is a vegetable- or fruit-producing plant. In some embodiments, the plant is *Arabidopsis*.

Those of skill in the art will recognize that a number of plant species can be used as models to predict the phenotypic effects of transgene expression in other plants. For example, it is well recognized that both tobacco (*Nicotiana*) and *Arabidopsis* plants are useful models of transgene expression, particularly in other dicots.

In some embodiments, for a transgenic plant or cell as described herein, expression of a desired gene, protein, or phenotype can be regulated by contacting the plant or cell with an orthogonal ligand (e.g., an agrochemical such as mandipropamid). For example, in some embodiments, the transgenic plant or cell comprises a first polynucleotide encoding a first polypeptide comprising a mutated PYR/PYL receptor polypeptide fused to one of a transcriptional activation domain or a DNA binding domain, and a second polynucleotide encoding a second polypeptide comprising a mutated PP2C fused to the other of a transcriptional activation domain or a DNA binding domain, under the control of a promoter that comprises a polynucleotide sequence that binds the DNA binding domain. In some embodiments, contacting the plant or cell with the orthogonal ligand (e.g., mandipropamid) activates an interaction between the mutated PYR/PYL and the mutated PP2C, thereby associating the DNA binding domain and the transcriptional activation domain and activating transcription of a target gene.

In some embodiments, methods of controlling gene, protein, or phenotype expression in a transgenic cell or plant as described herein are provided. In some embodiments, the method comprises:

contacting the transgenic cell or plant with an orthogonal ligand, wherein the step of contacting the cell or plant with the orthogonal ligand activates an interaction between the mutated PYR/PYL and the mutated PP2C, thereby associating the DNA binding domain and the transcriptional activation domain and activating transcription of a target gene.

Those of skill in the art will recognize that the PYR/PYL-PP2C interaction modules described herein can be used for regulating the expression of any desired gene, protein, or phenotype of interest. In some embodiments, the mutated PYR/PYL proteins, mutated PP2C proteins, PYR/PYL-PP2C interaction modules, expression cassettes, and/or expression vectors described herein can be used for regulating the expression of a gene, protein, or phenotype relating to cell growth, development, metabolism, cell structure or architecture, stress response, or cell signaling. In some embodiments, the mutated PYR/PYL proteins, mutated PP2C proteins, PYR/PYL-PP2C interaction modules, expression cassettes, and/or expression vectors described herein can be used for regulating a phenotype relating to plant growth (e.g., growth rate or size), yield (e.g., biomass yield or seed yield), plant development (e.g., shoot development, root development, vegetative development, reproductive development, stem elongation, flowering, pattern formation, differentiation, senescence, or time of flowering), plant architecture (e.g., shape, size, color, texture, or patterning), stress tolerance (e.g., environmental stress such as salinity, drought, heat, chilling, freezing, dehydration, flooding, anaerobic stress, aerobic stress, osmotic stress, temperature stress, pollutant, or pathogen-induced stress), or metabolism. In some embodiments, the mutated PYR/PYL proteins, mutated PP2C proteins, PYR/PYL-PP2C interaction modules, expression cassettes, and/or expression vectors described herein can be used for regulating the expression of a particular gene or protein of interest.

EXAMPLES

The following examples are offered to illustrate, but not to limit, the claimed invention.

Example 1: Generation and Characterization of an Orthogonal PYR1/HAB1 Response Module The plant abscisic acid (ABA) response module has been coopted to build a CIP system controlled by ABA, which is a non-toxic dietary metabolite (Liang, Ho, & Crabtree, 2011). ABA is perceived by the soluble receptor PYR1 (Pyrabactin Resistance 1), and related PYR1-like (PYL) ABA receptors (Cutler, Rodriguez, Finkelstein, & Abrams, 2010). These proteins indirectly control the activity of a subfamily of three Sucrose non-fermenting 1-related (SnRK2) protein kinases in response to drought and other environmental stresses. The SnRK2s autoactivate by cis- and trans-autophosphorylation on their activation loops, but are continuously inactivated by clade A type 2C protein phosphatases (PP2Cs), which results in low basal kinase activity (Ng et al., 2011; Soon et al., 2012). When ABA rises during stress it binds to PYR1 and PYR1-like (PYL) receptors and stabilizes their activated conformations, enabling them to bind to and inhibit the PP2Cs (Ma et al., 2009; Melcher et al., 2009; Miyazono et al., 2009; S.-Y. Park et al., 2009; Yin et al., 2009). This in turn allows accumulation of activated SnRK2 kinases, which triggers downstream signaling events. ABA's ability to stabilize a complex between ABA receptors and PP2Cs has been exploited to create a new CID module regulated by ABA, as have other plant hormones and their perception systems.

Although valuable, plant hormones are not well-suited for use in plants as ligands for CID. In this invention we describe mutant proteins that enable CID to be controlled using the agrochemical mandipropamid. The system is based on a modified ABA response module that has the following properties: (1) the receptor contains mutations that enable it to bind mandipropamid, (2) the mutant receptor and phosphatase contain mutations that disrupt their interactions with endogenous ABA signaling components and (3) the PP2C contains a combination of mutations that remove its intrinsic phosphatase activity and enhance its binding affinity for the receptor. This new system can be used to engineer crops in which a desired protein function/phenotype is regulated agrochemically. Due to the broad range of regulatory functions that can be controlled by CID, the agrochemical induced dimerization module described can be used to engineer many different types control systems analogously to other CID systems.

Construction of an Orthogonal PYR1/HAB1 Response Module

The PYR1/HAB1 interaction enables ABA-regulated CIP, but is not appropriate for use in plants. We therefore set out to engineer an orthogonal response module, denoted PYR1$^i$/HAB1$^i$, that is insulated from the endogenous ABA signaling pathway. To reach this engineering target we took the following strategy: we first used site saturation mutagenesis of both PYR1 and HAB1, followed by functional assays of the mutant proteins, to systematically identify disruptive binding-interface mutants. Specific combinations of "dead" alleles that could function together were then identified by co-transforming both set of mutants into S. cerevisiae strains and selecting for mutually suppressing mutant combinations. The best mutant pair identified (PYR1$^{T162D}$/HAB1$^{V193R}$) introduces an acid/base residue pair in close proximity that likely form a salt bridge that stabilizes the mutant PYR1$^i$/HAB1$^i$ interaction but destabilizes both PYR1$^i$/HAB1 and PYR1/HAB1$^i$ interactions.

Use of Site Saturation Mutagenesis to Identify Mutations in PYR1 that Disrupt its Interaction with HAB1

To systematically identify mutations in PYR1 that disrupt its binding to HAB1, we utilized a collection of saturating mutations that contain all possible single amino acid substitutions in 24 conserved interface residues involved in binding HAB1, which was previously constructed for the purpose of engineering constitutively active ABA receptor variants (Mosquna et al., 2011). The interface residues previously mutagenized in this collection are the following: H60, F61, I62, K63, I84, S85, G86, L87, P88, A89, H115, R116, L117, P148, G150, N151, D154, D155, T156, M158, F159, T162, L166, K170. This set was made by mutagenizing a pBD-PYR1 template that encodes a GAL4-DNA binding domain fusion to PYR1, which can be used to assess receptor-HAB1 binding in S. cerevisiae strains co-transformed with pACT-HAB1, which expresses a GAL4 activation domain fusion to HAB1. Mutant pBD-PYR1 clones from the collection are maintained in S. cerevisiae strain Y190 co-transformed with pACT-HAB1. The test strains were spotted onto agar plates containing synthetic dextrose dropout media lacking leucine and tryptophan [SD (-Leu, -Trp)] medium supplemented with 10 µM ABA. After incubating the test plates at 30° C. for two days, colonies were chloroform lysed and stained to reveal β-galactosidase expression levels and "dead" mutants were defined by lack of visible staining in comparison to a wild type control. This effort defined 237 mutations that disrupt ABA-induced binding of PYR1 to HAB1 (Table 1). Premade yeast drop out supplements (Clontech) were utilized in this and other examples for media preparation, amino acids and other standard chemicals were purchased from Sigma-Aldrich (USA). The naturally occurring (+)-ABA isomer was used in all experiments and purchased from Biosynth Ag (Switzerland).

TABLE 1

| Mutations in PYR1 that disrupt ABA-induced binding to PYR1 to HAB1 | | | | | | | | | | | | | | | | | | | | |
|---|---|---|---|---|---|---|---|---|---|---|---|---|---|---|---|---|---|---|---|---|
| | A | C | D | E | F | G | H | I | K | L | M | N | P | Q | R | S | T | V | W | Y |
| F61 | | | x | x | | x | x | x | x | | | | x | x | x | x | x | | | |
| I62 | | | x | x | | | x | | x | | | | | x | | | | | x | x |
| K63 | | | | | | | | | | | | | | x | | | | | | |
| I84 | | | | | | | | | | | x | | | | | | | | | |
| S85 | x | x | x | x | x | x | | x | x | x | x | x | x | x | x | | | x | x | x |
| G86 | x | x | x | x | x | | x | x | x | x | x | x | x | x | x | x | x | x | x | x |
| L87 | x | x | x | x | | x | x | | x | | | x | | x | x | x | x | | x | x |
| P88 | | x | x | x | x | x | x | x | x | x | x | | x | x | x | x | x | x | x | x |
| A89 | | x | x | x | x | | x | x | x | x | x | x | x | x | x | x | x | x | | x |
| H115 | x | x | x | x | x | x | x | x | x | x | x | | x | x | x | x | x | x | x | x |
| R116 | x | x | x | x | x | x | x | x | | | | | | x | | x | x | x | x | x |
| L117 | x | | x | x | | x | x | | x | | | x | x | x | x | x | x | x | x | x |
| P148 | | x | x | x | x | x | x | x | x | x | x | | x | x | x | x | x | x | x | x |
| G150 | | | | | | | x | | | | | x | | | | | | x | x | |
| N151 | | x | x | x | x | x | x | x | x | x | | | x | x | x | | | x | x | x |
| D155 | | x | | | x | x | | x | x | x | x | | x | | x | | | x | x | x |
| T156 | | x | x | x | x | x | x | x | x | x | x | x | x | x | x | | | | x | x |
| M158 | | | | | | | | | | | | x | | | | | | | | |
| F159 | | x | x | | | x | x | | x | | | x | x | x | x | x | | | x | x |
| T162 | | x | x | x | | | | | | | | x | | | | | | | | |
| K170 | | | | | | | | | | | | x | | | | | | | | |

Use of Site Saturation Mutagenesis of HAB1 to Identify Mutations that Disrupt its Interaction with PYR1

To systematically define mutations in HAB1 that disrupt its binding to PYR1, we used site saturation mutagenesis to create a collection all possible single amino acid substitutions in 20 residues lining the PYR1 binding interface, and then assayed the ability of each mutant to bind PYR1 using the yeast two hybrid assay described above. We targeted the following residues for mutagenesis: R199, S200, E201, E203, H245, G246, G247, S322, E323, T324, K381, I383, Q384, W385, Q386, R389, F391, G392, V393, and Y404. To create the collection of mutations, mutagenic "NNK" site directed mutagenesis primers were synthesized for each of the 20 positions and the primers used in QuickChange site-directed mutagenesis reactions using a previously described pACT-HAB1 template (Park et al., 2009). We note that this clone uses a HAB1 cDNA lacking its three N-terminal amino acids. The reaction products were digested with DpnI, and transformed into competent Escherichia coli DH5α cells and plasmid DNA for 96 colonies per site was isolated using Bioneer AccuPrep® Plasmid Mini Extraction Kit (Alameda, Calif.) and sequenced to identify mutants.

This process identified most of the 19 desired mutations per target site; the remaining mutations were constructed directly using specific mutagenic primers. To interrogate the effects of the mutations on PYR1-HAB1 interactions, the mutant clones were individually transformed into *S. cerevisiae* strain Y190 containing pBD-PYR1 (Park et al., 2009). Yeast transformants were selected for the presence of plasmids on selective SD (-Leu,-Trp) plates and then spotted onto SD (-Leu,-Trp) agar plates supplemented with 10 μM ABA. After incubating the test plates at 30° C. for two days, the colonies were lysed with chloroform and stained to reveal β-galactosidase expression levels. "Dead" mutants were defined by lack of detectable staining in comparison to a wild type pBD-PYR1/pACT-HAB1 control. This screening effort defined 163 mutations that disrupt the ABA-induced PYR1/HAB1 interaction (Table 2).

TABLE 3

Mutually suppressing PYR1 and HAB1 mutant pairs

| PYR1 | HAB1 | Strength |
|---|---|---|
| WT | WT | ++++ |
| F61K | V393Q | ++ |
| S85P | E203D | + |
| S85P | E203T | + |
| S85P | E203W | + |
| T156P | I383G | + |
| T162D | V393K | ++ |
| T162D | V393R | +++ |

TABLE 2

Mutations in HAB1 that disrupt HAB1 interaction with PYR1

|  | A | C | D | E | F | G | H | I | K | L | M | N | P | Q | R | S | T | V | W | Y |
|---|---|---|---|---|---|---|---|---|---|---|---|---|---|---|---|---|---|---|---|---|
| E201 |  |  |  |  |  |  | x |  | x |  |  |  |  |  |  |  |  |  |  |  |
| E203 | x | x | x |  | x | x | x | x | x | x | x | x | x |  | x | x | x | x | x | x |
| H245 | x | x | x | x | x | x |  | x | x | x | x | x | x | x | x | x | x | x | x | x |
| G246 | x | x | x | x | x |  | x | x | x | x | x | x | x | x | x | x | x | x | x | x |
| G247 | x |  |  | x | x |  | x | x |  | x |  |  | x | x | x |  | x | x | x | x |
| E323 |  |  |  |  |  |  |  |  |  | x |  |  |  |  |  |  |  |  |  |  |
| K381 |  |  |  |  |  |  |  |  |  |  |  |  |  |  |  |  |  |  | x |  |
| I383 |  | x | x |  | x | x |  | x |  |  | x | x | x | x | x | x |  | x | x |
| W385 | x | x | x | x | x | x | x | x | x | x | x | x | x | x | x | x | x | x |  | x |
| R389 | x | x | x | x | x | x | x | x | x | x | x |  |  | x | x | x |  | x | x | x |
| F391 |  | x | x |  |  |  |  |  |  |  |  |  |  | x |  |  |  |  |  |  |
| G392 | x | x | x | x | x |  | x | x | x | x | x | x | x | x |  | x | x | x | x |  |
| V393 |  | x | x |  | x |  | x |  |  | x | x | x | x | x |  |  |  |  |  |  |
| Y404 |  | x | x |  | x |  | x |  |  | x | x | x | x | x | x |  |  |  |  |  |

Selection for Mutually Suppressing PYR1-Dead/HAB1-Dead Mutant Alleles

Figure 1:
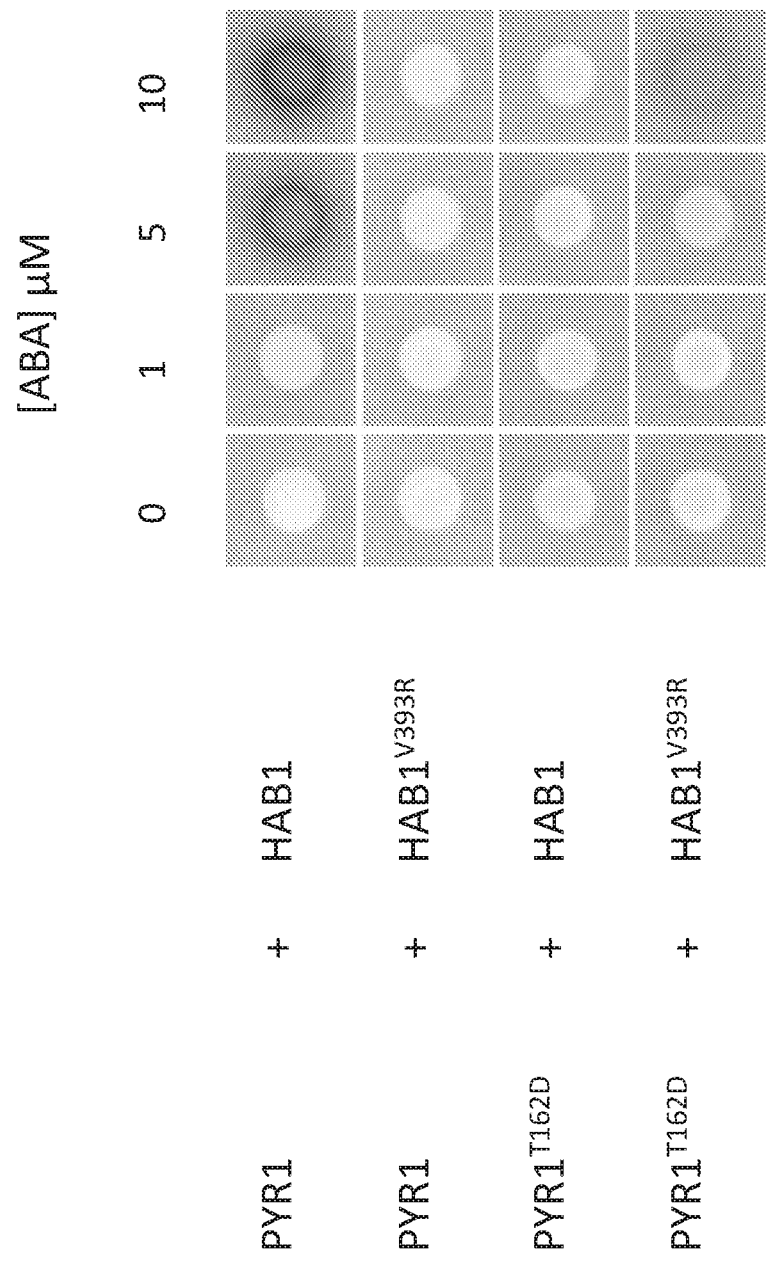
FIG. 1. $PYR1^{T162D}$ and $HAB1^{V393R}$ enable an orthogonal ABA response module. The experiment examines the ABA-promoted interaction of wild type and mutant proteins as measured using a yeast two hybrid assay in which the PYR1 component is expressed as a fusion protein to the GAL4 DNA binding domain and HAB1 component is fused to the GAL4 activation domain, as described in Example 1. $PYR1^{T162D}$ and $HAB1^{V393R}$ (renamed $PYR1^1/HAB1^1$) selectively interact with one another, but not wild type counterparts.

The preceding efforts identified sets of interface "dead" mutations in both PYR1 and HAB1 that in isolation prevent the PYR1/HAB1 complex forming in response to ABA. We next attempted to identify mutually suppressing mutant pairs (i.e. pairs of allele specific suppressors). To do so, a pool of mini-prepped plasmid DNAs for non-functional pACT-HAB1-dead mutants was prepared and transformed into the *S. cerevisiae* strain Y190, yielding ~3200 colonies. The ~3200 yeast colonies were pooled and subsequently transformed with pooled pBD-PYR1-dead mutant plasmids, to generate a library of ~400,000 yeast colonies containing random mutant combinations. The pooled cells were plated onto SD(-Leu,-Trp,-His, +10 mM 3-aminotriazole, +10 μM ABA) and positive, best-growing clones isolated and spotted onto both SD(-Leu,-Trp, -His) and SD(-Leu,-Trp, -His, +10 μM ABA) plates, grown for 2 days growth at 30° C., and stained for β-galactosidase activity after chloroform lysis. This identified 7 pairs of ABA-dependent interacting mutants (Table 3), the strongest of which (PYR1$^{T162D}$/HAB1$^{V393R}$) showed an interaction strength ~4-fold less sensitive to ABA than wild type pBD-PYR1/pACT-HAB1 control cells (FIG. 1). This orthogonal PYR1$^{T162D}$/HAB1$^{V393R}$ mutant pair was selected for subsequent engineering and denoted PYR1$^I$ and HAB1$^I$.

Biochemical Characterization of PYR1$^I$ and HAB1$^I$ Interaction

Figure 2:
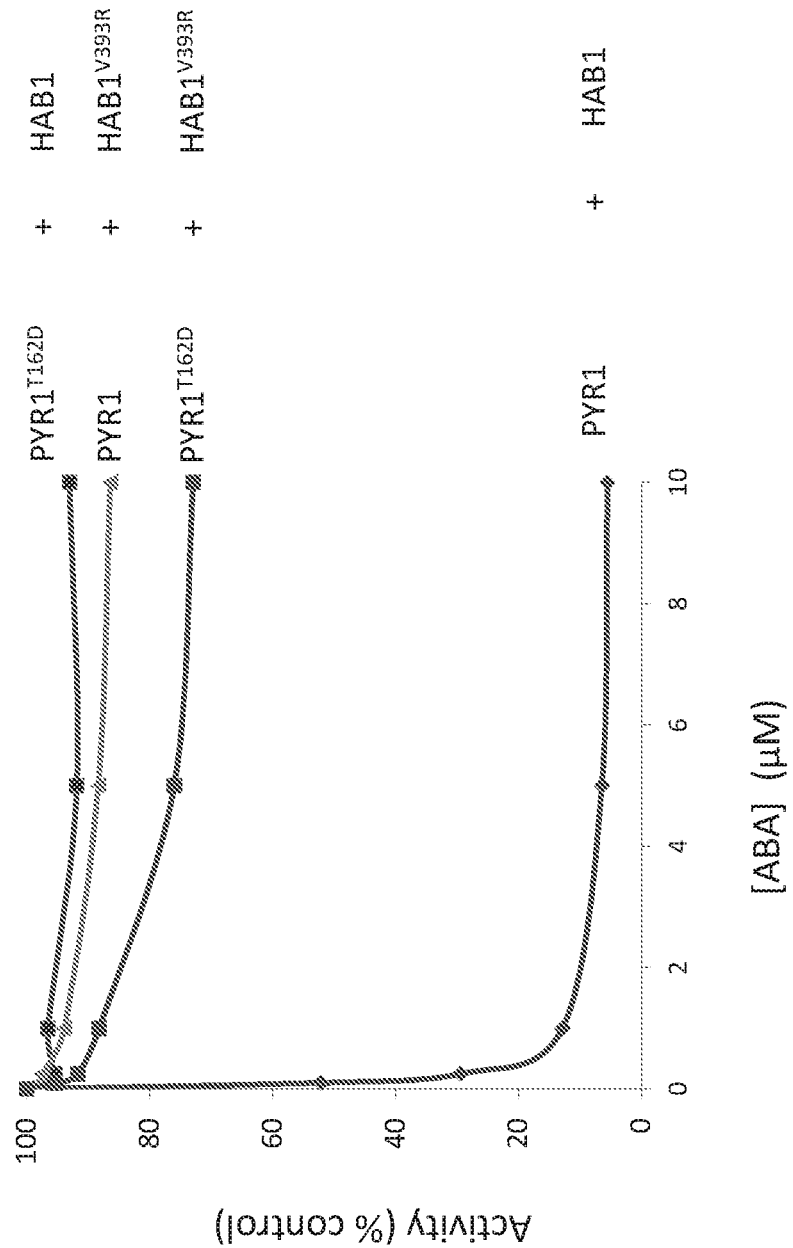
FIG. 2. $PYR1^1$ does not inhibit $HAB1^1$ enzymatic activity. The experiment examines the ABA-promoted inhibition of wild type and mutant HAB1 proteins by either wild type or mutant PYR1, as measured using in vitro PP2C assays, as described in Example 1. The data show that $PYR1^1$ is unable to inhibit the activity of either HAB1 or $HAB1^1$.
Figure 3:
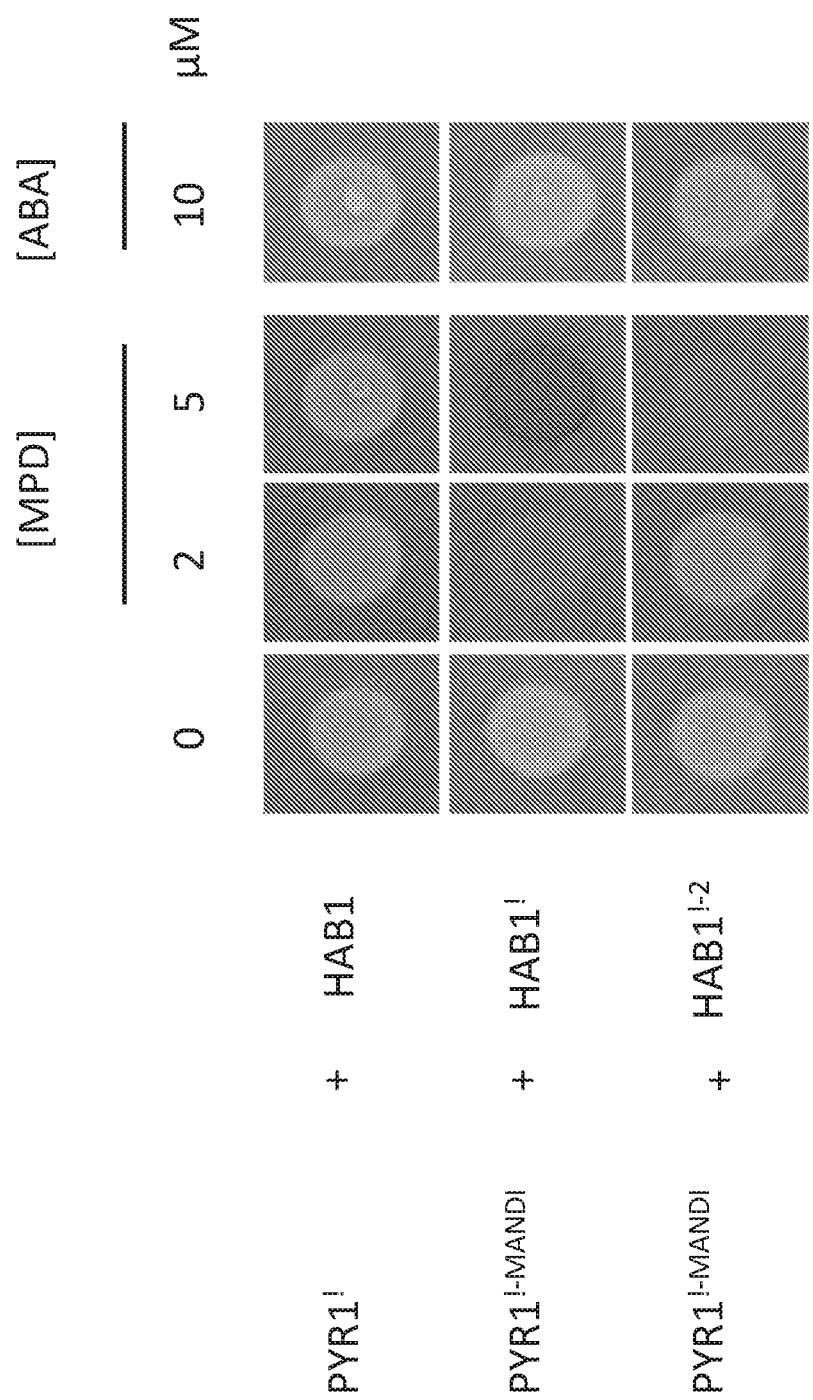
FIG. 3. $PYR1^{1-MANDI}$ selectively interacts with or $HAB1^1$ and $HAB1^{1-2}$. The experiment examines the mandipropamid-promoted interaction of $PYR1^{1-MANDI}$ with HAB1, $HAB1^1$ and $HAB1^{1-2}$, as measured using a yeast two hybrid assay in which the PYR1 component is expressed as a fusion protein to the GAL4 DNA binding domain and HAB1 component is fused to the GAL4 activation domain, as described in Example 2. The data show that $PYR1^{1-MANDI}$ interacts selectively with or $HAB1^1$ and $HAB1^{1-2}$ in response to mandipropamid.
Figure 4:
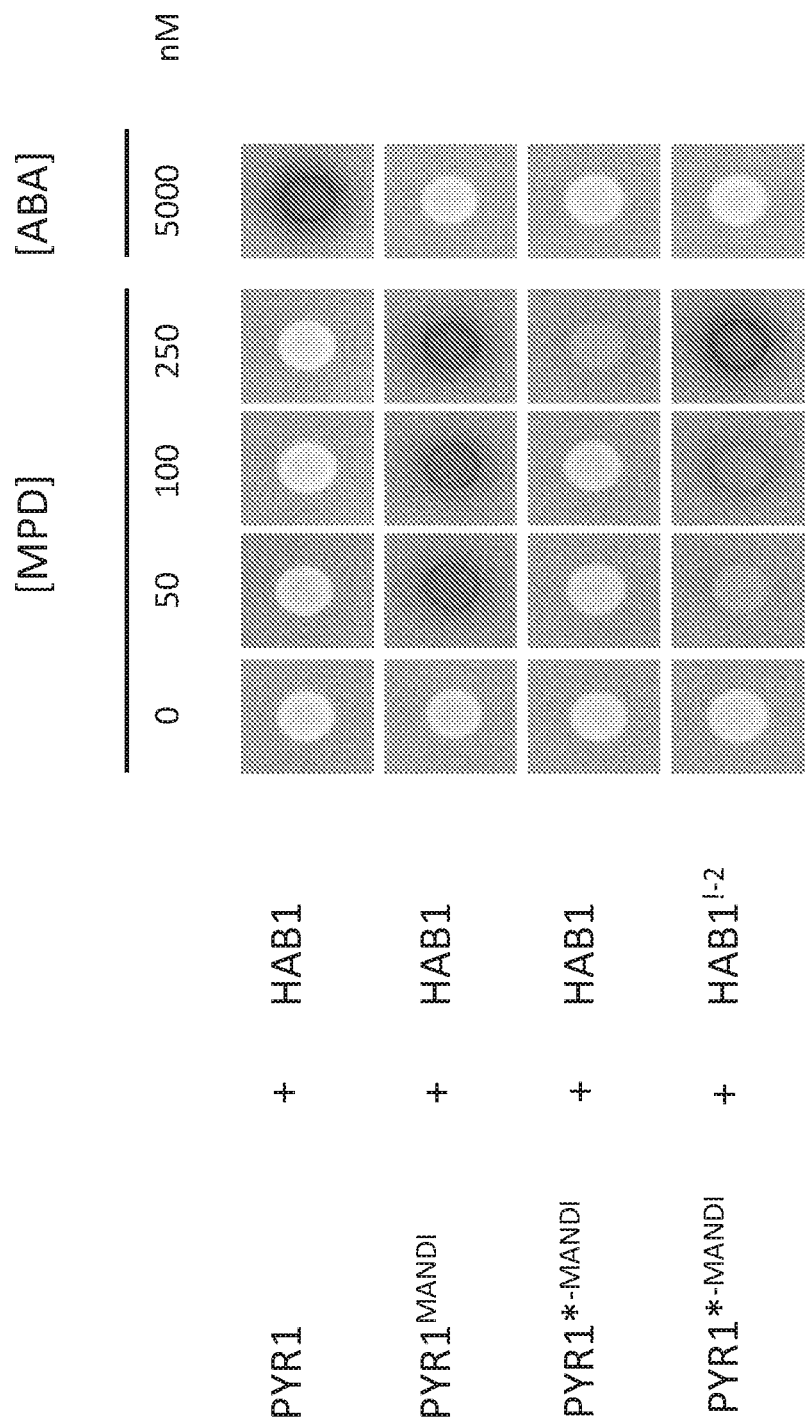
FIG. 4. $PYR1*^{-MANDI}$ selectively interacts with $HAB1^{1-2}$. The experiment examines the mandipropamid-promoted interaction of either $PYR1^{MANDI}$ or $PYR1*^{-MANDI}$ with HAB1 or $HAB1^{1-2}$, as measured using yeast two hybrid assays in which the PYR1 component is expressed as a fusion protein to the GAL4 DNA binding domain and the HAB1 component is fused to the GAL4 activation domain, as described in Example 2. The data show that $PYR1*^{-MANDI}$ interacts selectively with $HAB1^{1-2}$ in response to nM levels of mandipropamid.
Figure 5:
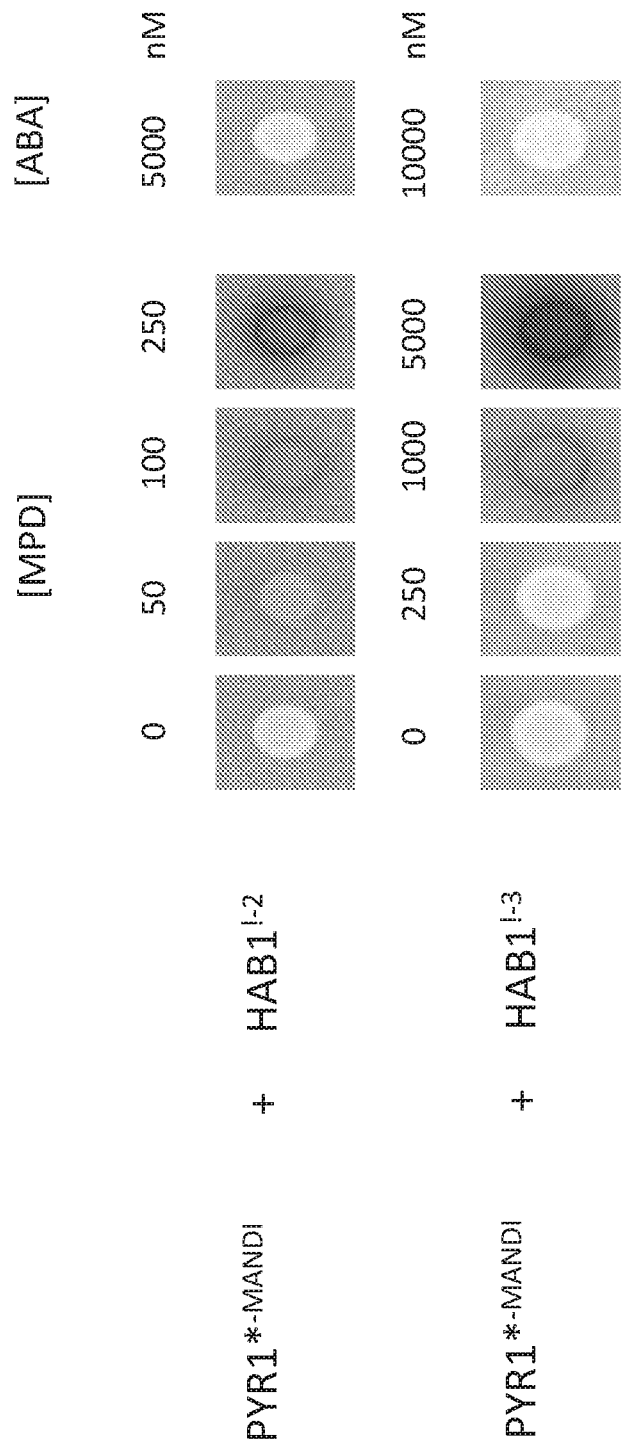
FIG. 5. The catalytically inactive mutant $HAB1^{1-3}$ shows reduced sensitivity in its interaction with $PYR1*^{-MANDI}$ relative to $HAB1^{1-2}$. The experiment examines the mandipropamid-promoted interaction of $PYR1*^{-MANDI}$ with either $HAB1^{1-2}$ or a catalytically inactive mutant $HAB1^{1-3}$, as measured using yeast two hybrid assays in which the PYR1 component is expressed as a fusion protein to the GAL4 DNA binding domain and the HAB1 component is fused to the GAL4 activation domain, as described in Example 3. The data show that $PYR1*^{-MANDI}$ interacts selectively with $HAB1^{1-2}$ in response to nM levels of mandipropamid.

In the presence of ABA, wild type PYR1 binds to HAB1 and docks into its active site, which inhibits its enzymatic activity by blocking access of substrates. To characterize the orthogonal PYR1$^I$ and HAB1$^I$ interaction biochemically, we produced recombinant forms of each protein in *E. coli*, along with the wild type form, and tested the wild type and orthogonal mutant for their ability to inhibit HAB1 and HAB1$^I$ activities in vitro. We cloned PYR1$^I$ into pET28 to generate 6x-His tagged receptor and cloned HAB1$^I$ into pGEX-4T-1 to create a GST-fusion protein. The previously constructed (S.-Y. Park et al., 2009) wild type 6x-His-PYR1 and GST-HAB1 constructs were used for producing recombinant wild type proteins. The 6x-His-tagged receptors and GST-tagged PP2Cs were expressed and purified as previously described. Briefly, the proteins were expressed in BL21 [DE3]pLysS *E. coli* host cells at 18° C. overnight. Fusion proteins were purified from sonicated lysates using Ni-NTA agarose (Qiagen, USA) or Pierce™ Glutathione Agarose (Thermo Scientific) according to the manufacturer's instructions. PP2C assays were conducted in 96-well polystyrene flat-bottom microtitre plates (Greiner). Assays were conducted using the following assay conditions: 100 nM 6x-His-PYR1 or 6x-His-PYR1$^I$, 50 nM GST-HAB1 or 50 nM GST-HAB1$^I$, 100 mM Tris-HCl (pH 7.9), 100 mM NaCl, 1 mM MnCl$_2$, 1% β-mercaptoethanol (3-me) and 0.3% bovine serum albumin (BSA). Reactions were mixed with ABA, mandipropamid, or mock dimethylsulphoxide (DMSO) carrier solvent, equilibrated for 30 minutes, after which 4-methylumbeliferyl phosphate was added (1 mM final concentration). The plates were read using a Victor 2 plate reader (PerkinElmer) (355 nm excitation, 460 nm emission) and assays run in triplicate. The PP2C activity values reported are expressed as percent control values, which were calculated by including the carrier solvent (1% DMSO) and the specific receptor assayed, but no ligand. We note that the recombinant GST-HAB1 had ~50% activity per mg protein in comparison to GST-HAB1. As the data in FIG. 2 show, PYR1$^{!}$ does not strongly inhibit HAB1$^{!}$ in response to ABA. Therefore, the physical interaction indicated by yeast two hybrid assays does not correlate with strong inhibition HAB1$^{!}$'s phosphatase activity in vitro. This suggests that PYR1$^{!}$ binds to HAB1$^{!}$ in a different orientation than the wild type PYR1/HAB1 interaction.

Example 2—Engineering a Sensitive Orthogonal Mandipropamid Response Module

Figure 6:
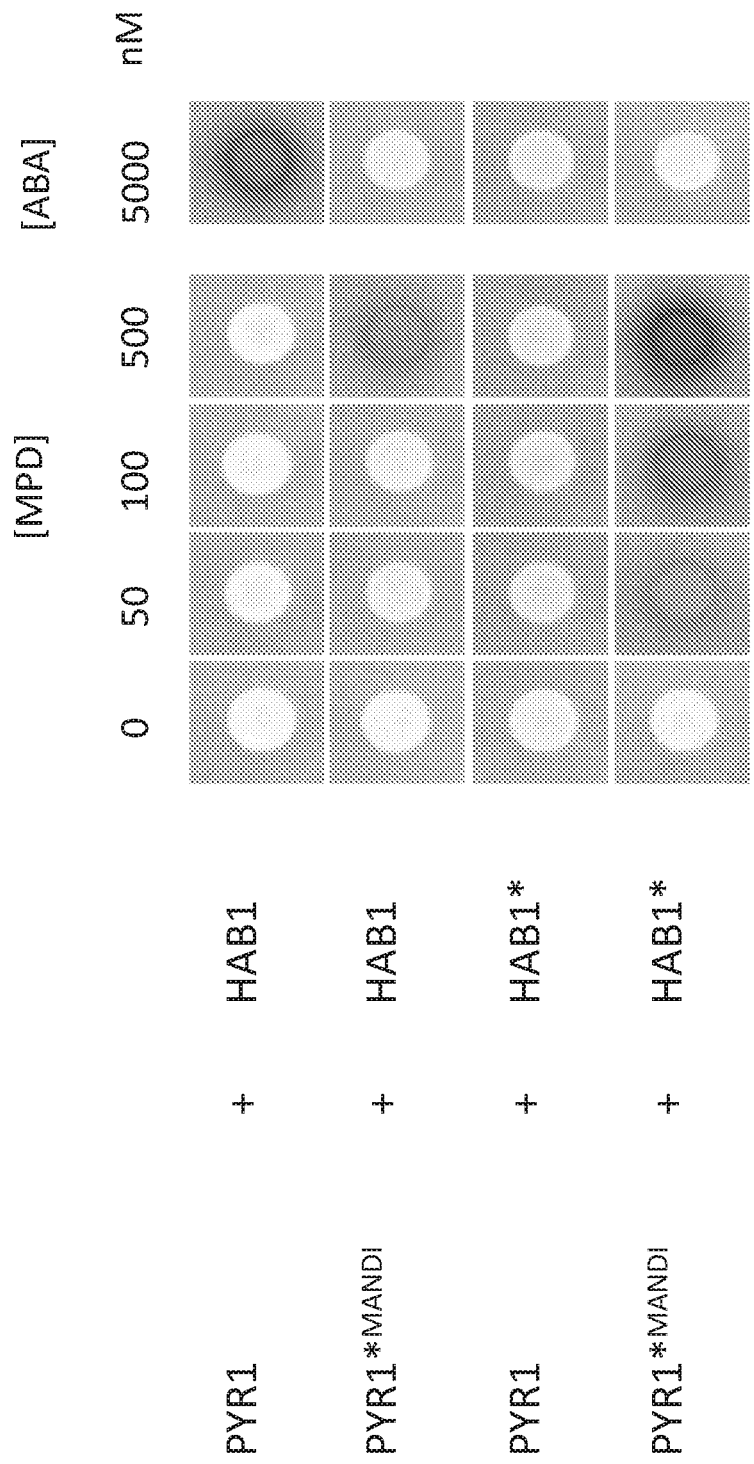
FIG. 6. The catalytically inactive mutant HAB1* shows a high sensitivity interaction with $PYR1*^{-MANDI}$. The experiment examines the mandipropamid-promoted interaction of $PYR1*^{-MANDI}$ with either $HAB1^{1-2}$ or a catalytically inactive mutant $HAB1^{1-3}$, as measured using yeast two hybrid assays in which the PYR1 component is expressed as a fusion protein to the GAL4 DNA binding domain and the HAB1 component is fused to the GAL4 activation domain, as described in Example 3. The data show that $PYR1*^{-MANDI}$ interacts selectively with $HAB1^{1-2}$ in response to nM levels of mandipropamid.

Having generated an orthogonal PYR1$^{!}$/HAB1$^{!}$ ABA-response module, we next set out to build a mandipropamid responsive orthogonal interaction module insulated from the endogenous ABA signaling pathway. Although the interaction of PYR1$^{!}$/HAB1$^{!}$ is orthogonal, HAB1$^{!}$ may still interact with downstream SnRK2 kinases and alter ABA responses in planta. It has previously been shown that the HAB1/SnRK2.6 interaction is stabilized by two modular interactions, one between HAB1's C-terminal basic domain and an SnRK2 "ABA-box" motif, and a second between HAB1's active site and the SnRK2 kinase-domain (Soon et al., 2012). The formation of a stable HAB1/SnRK2 complex in vitro can be abolished by the double mutant HAB1$^{V393R/R505A}$, which disrupts both HAB1/ABA-box and HAB1/kinase-domain interactions (Soon et al., 2012). The V393R mutation is fortuitously present in HAB1$^{!}$, so we introduced R505A to pACT-HAB1 using QuickChange mutagenesis, to create pACT-HAB1$^{!-2}$. This mutant protein should, in principle, affect ABA responses less than HAB1$^{!}$ or HAB1 would in planta.

To engineer orthogonal mandipropamid responsiveness, we introduced the PYR1$^{!}$ mutation into the PYR1$^{MANDI}$ receptor to create a septuple mutant called PYR1$^{!-MANDI}$ (PYR1$^{Y58H;K59R;V81I;F108A;S122G;F159L;T162D}$). This mutant interacts with HAB1$^{!}$ and HAB$^{!-2}$ in response to low μM mandipropamid in yeast two-hybrid assays, but is ~100-fold less sensitive than the PYR1$^{MANDI}$/HAB1 interaction, which responds to concentrations in the low nM range (FIG. 3).

To improve sensitivity, we mutagenized ligand contacting and interface residues in PYR1$^{!-MANDI}$ using NNK primers, pooled the mutant libraries, and used the mutagenized receptors in selection experiments using to identify enhancer mutations. The NNK mutagenesis screen targeted the following residues: P55, H60, F61, I62, K63, V83, S85, G86, L87, P88, A89, S92, E94, I110, H115, R116, L117, Y120, E141, P148, G150, N151, D154, D155, T156, M158, A160, V163, V164, L166, N167, and K170. This pilot screen established that M158I and A160C increase mandipropamid sensitivity. Since M158 and A160 flank the F159V mutation present in PYR1$^{MANDI}$, we inferred that the closely located orthogonalizing T162D mutation in PYR1$^{!-MANDI}$ may have reduced mandipropamid sensitivity by altering the local structure of the C-terminal α3-helix, which participates in ligand-induced conformational changes needed for PP2C binding (Nishimura et al., 2009). We therefore simultaneously mutagenized positions M158, F159 and A160 using a primer with degenerate NNK codons at all three positions. F159 was included in this mutagenesis because we have previously observed that multiple substitutions at F159 (A,C,I,L,M,T, or V) are permissive for mandipropamid responsiveness (S. Y. Park et al., n.d.), and sought to test whether residues other than leucine at position 159 might function better in the context of simultaneous changes to both A160 and M158. The mutagenic primer was used in QuickChange mutagenesis reactions using pBD-PYR1$^{!-MANDI}$ template, and a library of ~12,000 clones was generated. Plasmid DNA for the library was prepared from pooled *E. coli* transformants, and subsequently transformed into *S. cerevisiae* strain MAV99 harboring pACT-HAB1$^{!-2}$. ~20,000 yeast transformants were generated, pooled, and plated onto SD(-Leu,-Trp) agar media supplemented with 0.1% fluorotic acid (to select against mutants that interact in a ligand-independent fashion). The surviving cells were collected and plated onto SD(Leu,-Trp,-Ura) plates supplemented with 50 nM mandipropamid. The colonies displaying the best uracil-independent growth were isolated and retested on different mandipropamid concentrations and then stained in β-galactosidase assays to rank their relative strength. The most sensitive mutant obtained contained the following 9 mutations: PYR1$^{Y58H;K59R;V81I;F108A;S122G;M158I;F159V;A160V;T162D}$, which we refer to as PYR1$^{*-MANDI}$ (SEQ ID NO: 19; see also FIG. 4). The mutants PYR1$^{Y58H;K59R;V81I;F108A;S122G;M158V;F159V;A160V;T162D}$ (SEQ ID NO:20) and PYR1$^{Y58H;K59R;V81I;F108A;S122G;M158I;F159V;A160C;T162D}$ (SEQ ID NO:21) also supported nM responses to mandipropamid, but were slightly less sensitive than PYR1$^{*-MANDI}$. We note that PYR1$^{*-MANDI}$ weakly interacts with wild type HAB1 in yeast two hybrid assays, however as we show below, PYR1$^{*-MANDI}$ does not inhibit HAB1's enzymatic activity in vitro, nor does it activate ABA responses in planta.

Example 3—Engineering a Catalytically Inactive Orthogonal Module

To investigate the effects of overexpressing HAB1$^{!-2}$ in *Arabidopsis*, we used *Agrobacterium* mediated transformation to generate 35S::GFP-HAB1$^{!-2}$ transgenic plants. HAB1$^{!-2}$ was cloned from pACT-HAB1$^{!-2}$ into pEGAD, a binary vector suitable for plant transformation, generating a 35S-driven GFP-HAB1$^{!-2}$ fusion protein. The clone was transformed into *Agrobacterium* and the floral dip method used to transform *Arabidopsis. After selection of* $T_0$ seed on soil containing glufosinate, several $T_1$ seedlings were identified. In spite of the V393R/R505A mutations present (previously reported to prevent SnRK2 binding), the $T_1$ plants displayed symptoms of severe ABA insensitivity, including dwarf stature and high sensitivity to water deficit, and did not survive to produce $T_2$ seed for subsequent analyses. These observations suggest that HAB1$^{!-2}$ retains ability to regulate ABA signaling factors in vivo, in spite of its reported inability to bind SnRK2s, although further characterization of the $T_1$ plants is needed to definitively establish this. As an alternate strategy, we eliminated HAB1's catalytic activity by introducing a mutation in a conserved metal-ion binding residue (D204), which is homologous to D131A mutation in ABI1, previously shown to eliminate phosphatase activity without disrupting wild type receptor-ABI1 interactions (Liang et al., 2011). We used QuickChange mutagenesis to introduce the D204A mutation into pACT-HAB1$^{!-2}$, generating pACT-HAB1$^{!-3}$. When tested for mandipropamid induced interactions with pBD-PYR1$^{*-MANDI}$, HAB1$^{!-3}$ is ~10-fold less sensitive to mandipropamid relative to HAB1$^{!-2}$ (FIG. 5).

D204 is located within HAB1's catalytic active site and binds to one of 3 catalytic $Mg^{++}$ ions that participate in catalysis. Although D204 does not make direct contacts with PYL receptors, the receptors dock into the active site. It is likely that disruptions to active site structure introduced by D204A destabilize the PYR1*-$^{MANDI}$/HAB1$^{1-3}$ interaction relative to HAB1$^{1-2}$. We reasoned that suppressor mutations in other HAB1 interface or active site residues could restore sensitivity by strengthening interactions with PYR1*-$^{MANDI}$. To identify such suppressors, we mutagenized the pACT-HAB1$^{1-3}$ template using NNK mutagenesis in 28 residues located with at the PYR1 binding interface. The residues targeted were: R199, S200, E201, E203, D243, G244, H245, G246, G247, S322, E323, T324, D346, K365, K381, I383, Q384, W385, Q386, R389, F391, G392, Y404, S431, G433, D436, D492 and N394. The pACT-HAB1$^{1-3}$ template was mutagenized in 28 separate NNK mutagenesis reactions using the QuickChange protocol. Mini-libraries, each containing ~1000 clones, were made for each NNK reaction and plasmid DNA for the 28 mutations prepared, pooled, and then transformed into S. cerevisiae strain MAV99 co-transformed with pBD-PYR1*-$^{MANDI}$, and then plated onto selective SD(-Leu,-Trp,-Ura) agar media supplemented with 500 nM mandipropamid. Three mutations in two separate residues were identified that enhance responsiveness of HAB1$^{1-3}$ (S322D, S322E, and R199A). S322D and R199A were combined using the Lightning Multi-site Mutagenesis™ (Agilent, USA) method, and the resultant pentuple mutant tested in combination with pBD-PYR1*-$^{MANDI}$ for sensitivity to mandipropamid using β-galactosidase assays. We refer to the final catalytically inactive orthogonal pentuple mutant (HAB1$^{R199A; D204A; S322D; V393R; R505A}$) as HAB1* (SEQ ID NO:31); this mutant displays nM sensitivity for binding to pBD-PYR1*-$^{MANDI}$ in yeast-two hybrid assays (FIG. 6).

Figure 7:
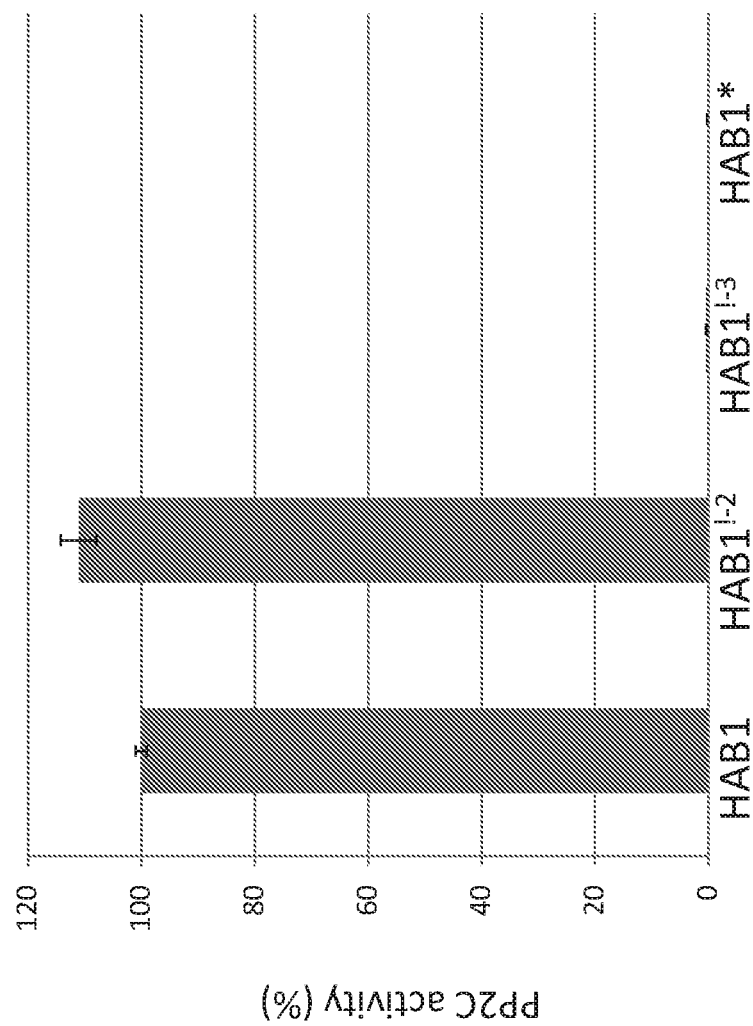
FIG. 7. HAB1* is catalytically inactive. The experiment examines the phosphatase activity of wild type and mutant HAB1 proteins, as measured using in vitro PP2C assays, as described in Example 3. The data confirm that HAB1* is catalytically inactive.

To characterize HAB1$^{1-3}$ and HAB1* in vitro, we cloned them into pGEX-4T-1 to create GST-fusion proteins. Recombinant GST-HAB1, GST-HAB1*, GST-HAB1$^{1-3}$ and GST-HAB1* were prepared from E. coli, as described above in example 1C, and used in phosphatase assays under the following conditions: 1 μg GST-HAB1 and mutants in a buffer containing, 100 mM Tris-HCl (pH 7.9), 100 mM NaCl, 1 mM $MnCl_2$, 1% β-mercaptoethanol and 0.3% bovine serum albumin (BSA); 4-methylumbeliferyl phosphate was added (1 mM final) and plates were read by fluorimetry. The PP2C activity values reported are expressed as percent control (GST-HAB1) from triplicate measurements. Neither HAB1$^{1-3}$ or HAB1* display detectable catalytic activity in vitro, indicating that D204A abolishes catalytic activity as expected, and that the suppressors do not increase mandipropamid sensitivity by restoring catalytic activity (FIG. 7).

Figure 8:
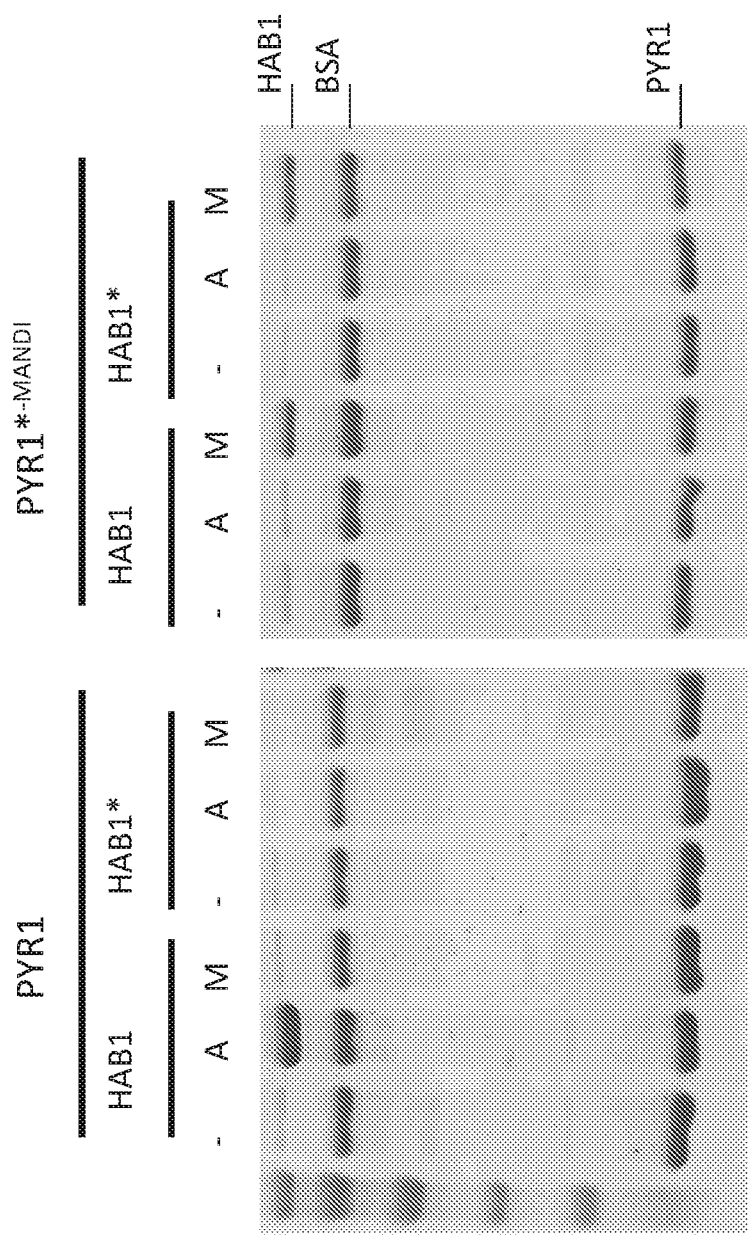
FIG. 8. HAB1* does not bind to wild type PYR1 in the presence of ABA or mandipropamid. The experiment examines the physical interactions of mutant and wild type protein in response to either 10 μM mandipropamid or 10 μM ABA using pull down assays, as described in Example 4. The data indicate that HAB1* does not bind to wild type PYR1 in response to either ligand, however $PYR1*^{-MANDI}$ is able to bind to wild type HAB1 in response to mandipropamid.

Example 4—Characterization of PYR1*-$^{MANDI}$ and HAB1* Interactions In Vitro and In Vivo To characterize the orthogonal orthogonal module biochemically, we produced recombinant forms of 6x-His-PYR1*-$^{MANDI}$, 6x-His-PYR1, GST-HAB1*, and GST-HAB1 in E. coli, as described above, and tested wild type and orthogonal receptors for their ability to inhibit GST-HAB1 activity in vitro, as well as their physical interactions with one another using pull-down assays. To characterize PYR1*-$^{MANDI}$ and HAB1* in vitro, we cloned PYR1*-$^{MANDI}$ into pET28 to generate a 6x-His tagged receptor and cloned HAB1* into pGEX-4T-1 to create a GST-fusion protein. Recombinant 6x-His-PYR1*-$^{MANDI}$ and GST-HAB1* were prepared, as described above in example 1C, and used in experiments with previously prepared 6x-His-PYR1 and GST-HAB1. To conduct pull down assays, the specified recombinant receptor and PP2C (20 and 140 μg respectively), were combined in 500 μl PP2C assay buffer (100 mM Tris-HCl (pH 7.9), 100 mM NaCl, 1 mM $MnCl_2$, 1% β-ME and 0.3% BSA) containing either 10 μM ABA, 10 μM mandipropamid or 1% DMSO carrier solvent as a negative control. The final protein concentrations in the reactions are 1.6 μM receptor and 3.4 μM PP2C. The reactions were incubated for 90 minutes at room temperature (RT) and 20 μl of PrepEase (USB) His-tagged protein purification resin (20 mg) was added. The resin and reaction mixtures were incubated for 30 minutes at RT with gentle shaking at 5 minute intervals. The resin was washed five times and 100 μl of SDS-PAGE buffer was added and boiled for 5 minutes. After centrifugation 20 μl of supernatant was analyzed by SDS-PAGE. The pull-down data, shown in FIG. 8, demonstrate that HAB1* does not bind to wild type PYR1 in the presence of ABA or mandipropamid, however PYR1*-$^{MANDI}$ can bind to wild type HAB1 in response to mandipropamid, which is consistent with previous yeast two hybrid results, which indicated binding, although with ~10-fold less sensitivity to mandipropamid than the orthogonal interaction (FIG. 6). The pull-down reactions do not reveal obvious differences between the amount of HAB* or HAB1 bound by PYR1*-$^{MANDI}$, however this is likely due to the relatively high protein (μM) concentrations in the binding reactions, which are in excess of the nM $K_d$ values measured for ligand bound receptor-PP2C binding measured by surface plasmon resonance (Hao et al., 2011).

Figure 9:
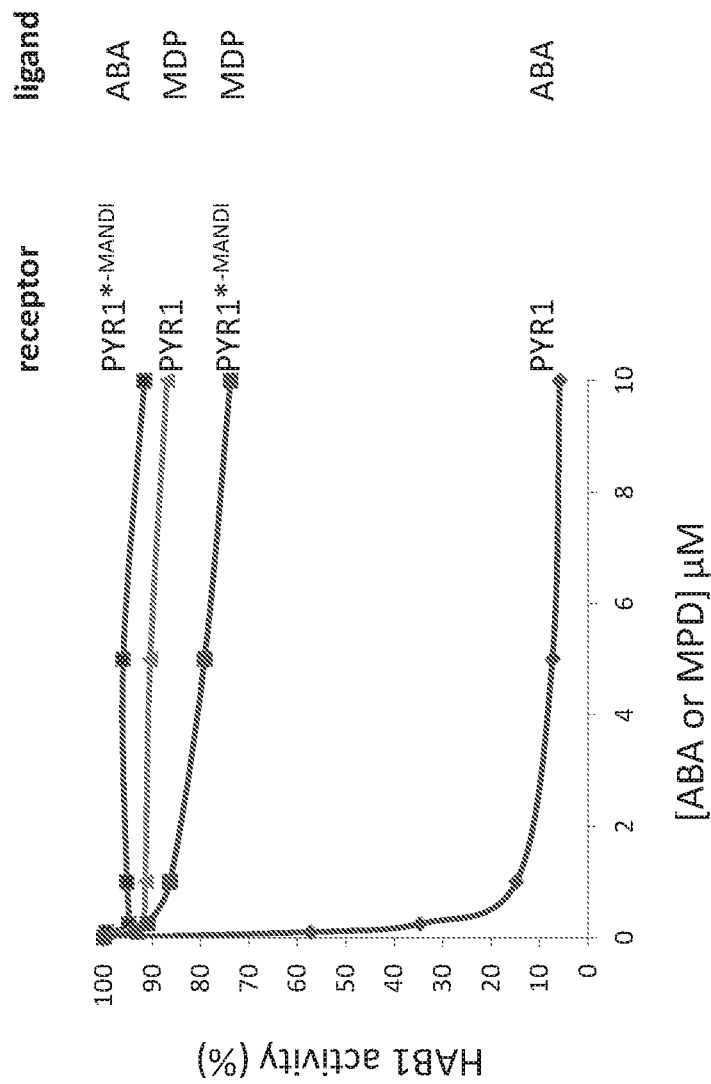
FIG. 9. $PYR1*^{-MANDI}$ does not inhibit HAB1 enzymatic activity in response to either ABA or mandipropamid. The experiment examines the mandipropamid- or ABA-promoted inhibition of HAB1, as measured using in vitro PP2C assays, as described in the Example 4. The data show that $PYR1*^{-MANDI}$ is unable to inhibit the activity of either HAB1, in spite of its ability to physically interact with HAB1. The control data shown for PYR1 inhibition of HAB1 is the same as shown in FIG. 2, as the experiments were conducted at the same time.

According to our current understanding, in order for ABA signaling to be initiated in vivo, PP2C activity must be inhibited to enable accumulation of active SnRK2 kinases. It is therefore essential that PYR1*-$^{MANDI}$ not inhibit HAB1 activity. To examine this, the recombinant 6x-His-PYR1*-$^{MANDI}$ and 6x-His-PYR1 were tested for their ability to inhibit GST-HAB1 PP2C activity in vitro using the proteins prepared above. GST-HAB1 assays were conducted using the following assay conditions: 100 nM 6x-His-PYR1 or 6x-His-PYR1*-$^{MANDI}$, 50 nM GST-HAB1, 100 mM Tris-HCl (pH 7.9), 100 mM NaCl, 1 mM $MnCl_2$, 1% β-me and 0.3% BSA. Reactions were mixed with either differing concentrations of ABA, mandipropamid, or mock DMSO. 4-methylumbeliferyl phosphate was added (1 mM final concentration) to the reactions after 30 minutes equilibration and plates were read by fluorimetry. The PP2C activity values reported are expressed as percent control values, which was calculated by including the carrier solvent (1% DMSO) and the specific receptor assayed, but no ligand. These data (FIG. 9) demonstrate that although the PYR1*-$^{MANDI}$ can bind HAB1 in response to mandipropamid, PYR1*-$^{MANDI}$ does not substantially inhibit wild type HAB1 enzymatic activity.

To characterize the orthogonal interaction in vivo, we conducted pull-down experiments using proteins transiently expressed in N. benthamiana. In these experiments a 6x-His-Tagged GFP-PP2C construct is co-expressed with a GFP-PYR1 construct and the interaction of receptor and PP2C in response to different treatments examined by co-purification using immobilized metal ion affinity chromatography. For these experiments, we made 35S-promoter driven 6x-His-GFP-HAB1, 6x-His-GFP-HAB1*, GFP-PYR1, and GFP-PYR1*-$^{MANDI}$ constructs in the binary plant transformation vector pEGAD and transformed the constructs into Agrobacterium tumefaciens by electroporation. Overnight cultures were harvested by centrifugation and resuspended in infiltration medium containing 10 mM MES pH 5.6, 10 mM MgCl$_2$ and 2 mM acetosyringone. Cultures of Agrobacterium strains expressing a receptor construct, a HAB1 construct and the silencing suppressor p19 were mixed to final OD$_{600S}$ of 0.15, 0.5 and 0.25 in infiltration medium, and infiltrated in N. benthamiana. The ratio of PP2C to receptor used compensates for reduced expression efficiency of the PP2C relative to receptor. Chemical applications of either 50 μM ABA, 50 μM mandipropamid or mock (0.1% DMSO, 0.05% Silwet in H$_2$O) were made 48 hours after infiltration, and tissue harvested 24 hours later. Harvested leaf tissues (~1 g) were ground in liquid N$_2$ by mortar and pestle and extracted in 2 mL of a buffer containing 50 mM Tris-HCl pH 7.6, 150 mM NaCl, 0.1% Nonidet-P40, 1 mM DTT, 1× plant protease inhibitor mix (Sigma), and 10% glycerol. The crude extracts were centrifuged at 4500 rpm for 15 min, and 1.5 ml of supernatant were transferred into a 2 ml tube and 0.025 g of PrepEase His-tagged protein purification resin (USB, OH USA) added. After 30 minutes incubation at 4° C., the resin was collected by brief centrifugation and then washed 3 times with buffer containing 50 mM Tris-HCl pH7.6, 150 mM NaCl, and 0.1% Nonidet-P40. Protein were eluted from the beads by adding 100 μL of SDS-PAGE sample buffer and boiling for 5 minutes. The eluted proteins were separated by SDS-PAGE and then electro-eluted onto nitrocellulose membranes. The proteins were then detected by Western blotting, using anti GFP primary antibody and anti-mouse IgG-HRP conjugated secondary antibody (GE Healthcare, UK) and detected after enhanced chemiluminescence ECL (PerkinElmer, MA USA).

Example 5—Overexpression of PYR1*-$^{MANDI}$ and HAB1* in Arabidopsis

Figure 10:
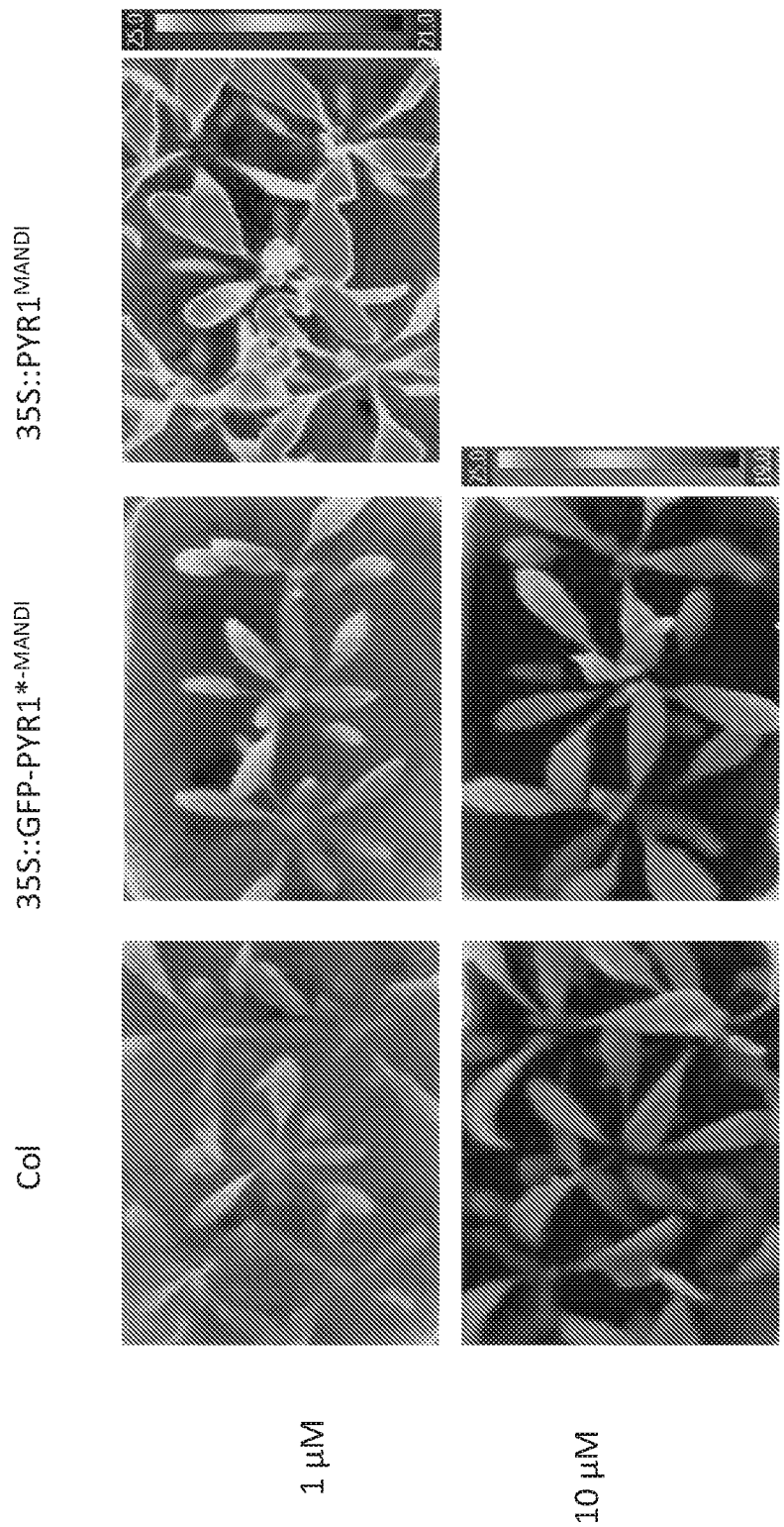
FIG. 10. Activation of $PYR1*^{-MANDI}$ in planta does not elicit an ABA response. The experiment examines the thermal response on 35S::GFP-$PYR1*^{-MANDI}$ transgenic plants to 1 or 10 μM mandipropamid treatment, as described in Example 5. Wild type Columbia and 35S::$PYR1^{MANDI}$ are included as negative and positive controls respectively. The data show that expression of $PYR1*^{-MANDI}$ in planta is not associated with altered ABA responses.

To examine the effects of over-expressing either PYR1*-$^{MANDI}$ or HAB1* in Arabidopsis thaliana, we made 35S-driven GFP-PYR1*-$^{MANDI}$ and GFP-HAB1* constructs by cloning the mutant genes into the binary vector pEGAD, and the resultant plasmids were transformed into Agrobacterium tumefaciens. The floral dip method was used to generate T$_0$ transgenic seed for both constructs and the T$_0$ seed was germinated in soil containing glufosinate to select for transgenic T$_1$ plants. The PYR1*-$^{MANDI}$ T$_1$ plants isolated were grown for ~5 weeks and then treated with mandipropamid, using comparisons to wild type Columbia plants and a previously constructed 35S::PYR1$^{MANDI}$ transgenic strain as controls. The treated plants were thermographed 24 hours after chemical applications to examine leaf temperature, which increases after ABA responses are activated, due to reduced transpiration. To examine different mandipropamid concentrations, the plants were first treated with 1 μM mandipropamid and then 3 days later were treated again with 10 μM mandipropamid. Neither of the treatments elicited substantial alterations in leaf temperature in the 35S::GFP-PYR1*-$^{MANDI}$ transgenic plants, however the 35S::PYR1$^{MANDI}$ plants displayed a strong increase in leaf temperature 24 hours after treatment, consistent with the ability of this protein to bind to endogenous PP2Cs and activate ABA responses. These data are consistent with PYR1*-$^{MANDI}$ being suitably insulated from endogenous wild type signaling factors that it cannot activate ABA responses when activated (FIG. 10).

Figure 11:
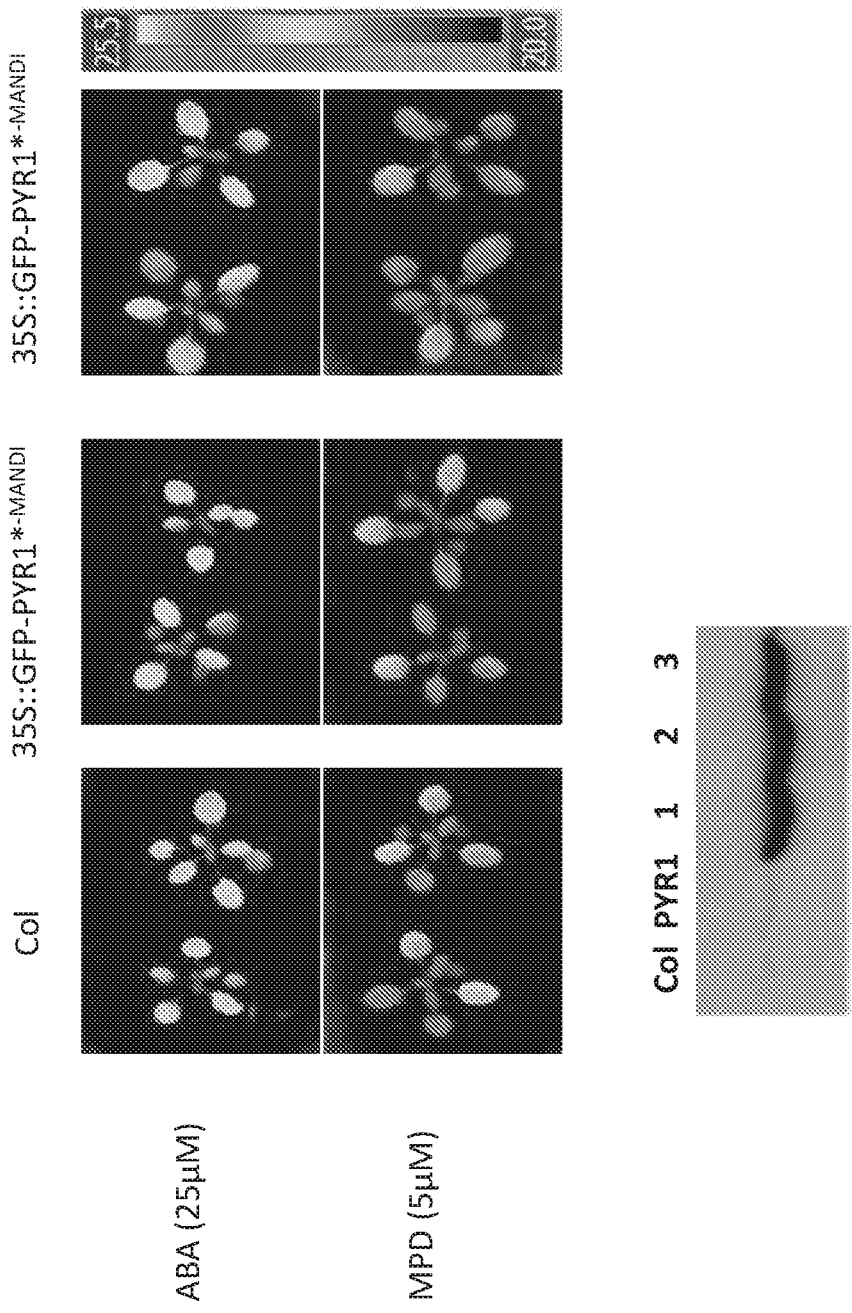
FIG. 11. Activation of $PYR1*^{-MANDI}$ in planta does not elicit an ABA response or inhibit ABA-induced leaf temperature increase. (Upper panel) The experiment examines the thermal response of two independent homozygous 35S::GFP-$PYR1*^{-MANDI}$ transgenic strains #2 and #3 to either 5 μM mandipropamid or 25 μM ABA treatment, as described in Example 5. Wild type Columbia is included as a control. The data show that expression of $PYR1*^{-MANDI}$ in planta is not associated with altered ABA responses. (Lower panel)

Several T$_1$ transgenic seed were propagated and 3 homozygous single insertion transgenic lines identified by glufosinate segregation patterns in the T$_3$ seedlings. GFP-PYR1*-$^{MANDI}$ protein levels were established by western blotting using an anti-GFP antibody, as described above and the three lines had similar levels of protein expression. Two of the 35S:::GFP-PYR1*-$^{MANDI}$ strains and a wild type columbia control were treated with 25 μM ABA and imaged by thermography 24 hours after treatment; these experiments reveal similar leaf temperatures between wild type and the two transgenics (FIG. 10). Similarly, sibling plants of the same two transgenic lines were treated with 5 μM mandipropamid, and the transgenic plants did not reveal differences in leaf temperature in comparison to the wild type control plants (FIG. 11). Together with the experiments conducted on the T$_1$ plants described above, the data suggest that the orthogonal receptor is insulated from the endogenous ABA response pathway.

The HAB1* T$_1$ were propagated and 4 homozygous single insertion transgenic lines identified by glufosinate segregation patterns in the T$_3$ seedlings. GFP-HAB1* protein levels were established by western blotting using an anti-GFP antibody, as described above and two lines with high protein expression levels were selected for further experimentation. Overexpression of wild type HAB1 causes ABA insensitivity, which manifests itself in adult plants by drought sensitivity and reduced leaf temperature due to elevated rates of transpiration. The two transgenic lines were grown alongside wild type columbia and the an allele of abi1 in the Columbia genetic background. The ABA-insensitive abi1 mutant possesses growth defects and reduced leaf temperature, as expected, and the transgenic GFP-HAB1* plants show leaf temperatures similar to wild type plants, indicating that the GFP-HAB1* protein does not strongly impair guard cell ABA responses in plants and is insulated from the endogenous ABA response pathway (FIG. 12).

Example 6—Agrochemical Control of Protein Localization Using the PYR1*-$^{MANDI}$/HAB1* Interaction Module To establish if the orthogonal mandipropamid response module could be used to control protein localization and/or transcriptional responses in vivo, we designed an experimental system where PYR1*-$^{MANDI}$ was localized to the nucleus and a GFP-HAB1* fusion protein was sequestered to the cytosol, which was accomplished using nuclear localization or export sequences. The desired outcome of this configuration is that the subcellular localization of a cytosolic GFP-HAB1* fusion protein shifts towards a nuclear distribution in the presence of mandipropamid via its association with PYR1*-$^{MANDI}$. If successful this could be used to be used to regulate the nuclear localization of transcription factors and/or other nuclear proteins such as CAS9 that require access to their DNA targets to control phenotypic outputs.

The precedent for this logic is exemplified by the ligand controlled association of nuclear hormone receptors (NHRs) with cytoplasmic heat shock proteins (HSPs) as a means of controlling NHR nuclear localization (Pratt, Galigniana, Harrell, & DeFranco, 2004). In the absence of agonists, many NHRs form sequestered cytosolic complexes with HSP70, but will dissociate and enter nuclei after ligand binding, which enables activation of target genes. Inducible transcription factors can be engineered by fusing to nuclear hormone receptors, which has been used to create numerous chemically inducible plant transcription factors, for example inducible flowering time using GR fusions to the transcriptional regulator Constans (Corbesier et al., 2007). Our CIP module can, in principle, be used to engineer similar types of regulation that are under control of an agrochemical and therefore suited for use in agricultural contexts.

To test this idea, we created a nuclear localized version of PYR1*-$^{MANDI}$ (SEQ ID NO:32) and a cytoplasmically localized GFP-HAB1*(SEQ ID NO:33), co-expressed the two components in N. benthamiana, and subsequently examined the localization of GFP-HAB1* in response to mandipropamid using confocal microscopy. To accomplish this, we cloned PYR1*-$^{MANDI}$ into the yeast two hybrid vector pAD, generating a GAL4 activation domain fusion to PYR1*-$^{MANDI}$. The GAL4 activation domain present in pAD contains a synthetic SV40 nuclear localization signal (NLS) at its N-terminus. We used an AD fusion (as opposed to solely adding an NLS to PYR1*$^{-MANDI}$) so that the protein could also be tested in separate experiments for its ability to activate transcription as a split GAL4 system. The AD-PYR1*$^{-MANDI}$ fusion was then amplified by PCR and cloned under the control of the 35S promoter in pEGAD (replacing pEGAD's GFP), creating a construct named 35S::nuc-PYR1*$^{-MANDI}$. We similarly cloned HAB1* into the yeast two hybrid vector pBD to create a BD-HAB1* fusion protein (SEQ ID NO:34). In creating BD-HAB1*, we introduced a synthetic 18 amino acid long Gly-Ser rich linker between BD and HAB1* and added two synthetic nuclear export sequences (NES) to HAB1*'s C-terminus. The nuclear export sequences utilized were derived from previously described NESs (Haasen, Kohler, Neuhaus, & Merkle, 1999; Ossovskaya, Lim, Ota, Schlaepfer, & Ilic, 2008). To generate this construct, HAB1* was amplified from pACT-HAB1* by PCR using and cloned into pBD downstream of the GAL4 DBD. A BsaI site was introduced by site directed mutagenesis between BD and HAB1, at the same time an internal BsaI site was removed. An 14 amino acid long Gly-Ser rich linker flanked by BsaI sites was synthesized and cloned in between pBD and HAB1* using GoldenGate assembly (Engler, Kandzia, & Marillonnet, 2008). The synthetic fusion was then amplified from the resultant plasmid by PCR, using primers that appended 2 nuclear export sequences onto the C-terminus of HAB1. The PCR fragment obtained was cloned into pEGAD in-frame with and downstream of GFP, creating 35S::GFP-cyt-HAB1*.

To characterize these components, 35S::GFP-cyt-HAB1* and 35S::nuc-PYR1*$^{-MANDI}$ were transiently co-expressed in *N. benthamiana*, as described above, and plants treated with a mock or mandipropamid solution (FIG. 13). *Agrobacterium* strains harboring 35S::GFP-cyt-HAB1* and 35S::nuc-PYR1*$^{-MANDI}$ were cultured overnight, centrifuged, and resuspended to a final $OD_{600}$=0.05 of each strain in an infiltration medium composed of 10 mM MES pH 5.6, 10 mM MgCl2, and 2 mM acetosyringone. 48 hours after infiltration, plants were treated with either 50 μM mandipropamid or a mock treatment (0.1% DMSO and 0.05% Silwet). 24 hours later 1-2 leaf segments surrounding infiltration sites were excised and mounted in water for microscopy per treatment. The leaf tissue was scanned manually by epi-fluorescence to identify patches of $GFP^+$ cells and then observed by spinning disk confocal microscopy, collecting ~10 micron deep sections that spanned the entire epidermal cell layer. The Z-series stacks were reconstructed by brightest-point projections in imageJ. Eight to ten $GFP^+$ regions were imaged in this manner. Fluorescence imaging was done using a custom built spinning disk system (Solamere Technology, Inc) with a Yokagawa W1 spinning disk (Yokagawa), EM-CCD camera (Hamamatsu 9100c) and a Nikon Eclipse TE (Nikon) inverted stand. A 40× water immersion lens (1.15 NA) was used with perfluorcarbon immersion liquid (RIAAA-678, Cargille). The microscope's stage is fully motorized and controlled by Micromanager software (www.micromanager.org) with ASI Peizo (300 mm range) and 3 axis DC servo motor controller. GFP was excited with a 445 nm light a solid-state laser (Obis from 40-100 mW) and a 480/40 emission filter (Chroma). All lasers are) and emission filters are from Chroma Technology.

Example 7—Agrochemical Control of Transcription Using the PYR1*$^{-MANDI}$/HAB1* Interaction Module To establish if the orthogonal mandipropamid response module could be used to control transcriptional responses in vivo, we designed an experimental system where PYR1*$^{-MANDI}$ was fused to the GAL4 AD, and HAB1* fused to its BD. Nuclear export sequences were added to the BD-HAB1* component to reduce its access to the nucleus in the absence of mandipropamid and thereby reduce background transcription from the UAS. The constructs were assembled into a plant transformation vector along with a GAL4-responsive UAS in front of a CaMV minimal promoter driving GFP. The plant transformation vector used was a derivative of pCB308 (Xiang, Han, Lutziger, Wang, & Oliver, 1999) in which a kanamycin resistance marker cassette replaces the vector's centrally located uidA and bar expression cassettes. To construct this derivative (called pCB301K), pCB308 was used as template in inverse PCR using primers internal to the T-DNA border sequences that exclude the uidA and bar genes. To the self ligated inverse PCR product Kanamycin resistance cassette which was amplified from pBI121 by PCR was added in the middle of multi cloning site to generate pCB308K.

To construct a vector containing all three components, we sequentially added AD-PYR1*$^{-MANDI}$ (SEQ ID NO:32), BD-HAB1* (SEQ ID NO:34), and then a UAS::GFP cassette (SEQ ID NO:40) that would enable facile replacement with gene of interest. The AD-PYR1*$^{-MANDI}$ expression cassette was amplified by PCR from the 35S::nuc-PYR1*$^{-MANDI}$ construct described above and cloned into pCB301K, to create pCB308K-AD.

To generate the BD-HAB1* construct, HAB1* was amplified from pACT-HAB1* by PCR and cloned into pBD downstream of the GAL4 DBD. A BsaI site was introduced by site directed mutagenesis between the BD and HAB1*, at the same time an internal BsaI site in the vector backbone was removed. A 14 amino acid long Gly-Ser rich linker flanked by BsaI sites was synthesized and cloned in between pBD and HAB1* using GoldenGate assembly (Engler et al., 2008). The resultant plasmid was used as template to introduce Nes. To make BD-Nes-linker-H*-Nes, linker-H* was amplified by PCR using primers in which Nes sequence were added in both primers and pcr product was re-cloned to pBD in downstream of BD. BD-Nes-linker-H*-Nes was amplified by PCR and introduced to pEGAD by replacing GFP. The cassette was amplified and introduced pCB308K-AD to make pCB308K-AD_BD.

A UAS-35S minimal promoter was prepared by primer extension using synthetic oligonucleotides and cloned into pEGAD, replacing its 35S promoter so that GFP expression is controlled by the UAS. The cassette created was amplified from the resultant plasmid by PCR and cloned to pCB301K-AD_BD between the activation domain and binding domain modules, yielding a final construct named pUAS_GFP_mandi.

The resultant construct (pUAS_GFP_mandi) was tested using transient assays in *N. benthamiana*, as described above. *Agrobacterium* (strain GV3101), harboring binary vector containing pUAS_GFP_mandi was mixed with *agrobacterium* containing the p19 suppressor in 0.05 OD600. Infiltrated leaves were treated 50 µM Mandipropamid or mock in 0.1% (DMSO and 0.05% silwet) 24 hr after infiltration. 24 hours later, leaf tissue was collected, frozen in liquid N2, and homogenized by bead beating using Precellys instrument (Bertin Technologies), for 6000 rpm for 30 seconds and then resuspended in SDS sample buffer containing protease inhibitor, separated by SDS-PAGE, electro-blotted onto nitrocellulose membrane and detected using an anti-GFP antibody as described in Example 4 above. FIG. 14 shows that the pUAS_GFP_mandi construct enables mandipropamid inducible GFP production.

Example 8—Agrochemical Control of Gene Expression in *Arabidopsis*

To test the efficacy of our transcriptional circuit in planta, we constructed a 3 component system for inducing genes of interest using the mandipropamid mediated interaction of a BD-PYR1*/AD-HAB1* to drive genes of interest from a GAL4-responsive UAS (FIG. 15A). To do this we constructed a BD-PYR1*-$^{MANDI}$ fusion protein and NLS$_{SV40}$-VP64-HAB1*-N7 fusion protein and used these to drive gene expression from a synthetic UAS-minimal-35S promoter. To make the desired vector, the three required components were separately cloned into vectors that provided necessary elements (such as the Gal4 DNA binding domain, or 35S-promoter-nos-terminator cassettes). After this, the three components were combined into a plant binary transformation vector.

The BD-PYR1*-$^{MANDI}$ fragment was created as follows. PYR1*-$^{MANDI}$ coding sequence was PCR amplified from plasmid DNA using primers that append MfeI sites and the PCR fragment digested and cloned into pBD-Gal4 (Clontech, USA) at its EcoRI site. The resultant BD-PYR1*-$^{MANDI}$ fusion protein was amplified using PCR primers that appended an XmaI site on 5'-end and a BglII site on 3'-end; the resultant fragment was cloned into pEGAD at its AgeI and BamHI sites (Cutler et al., 2000), eliminating pEGAD's GFP and multi-cloning site (MCS) locus, yielding pBD-PYR1*; this created a 35S::BD-PYR1*-Term$_{nos}$ cassette used in subsequent steps.

To create the NLS$_{SV40}$-VP64-HAB1*-N7 component, a synthetic VP64-activation domain linker was prepared by primer extension and cloned at the N-terminus of HAB1* using GoldenGate assembly methods. The resultant VP64-HAB1* fragment was cloned to pAD-Gal4 (Clontech), adding an SV40 nuclear localization signal (NLS) to yield an NLS-VP64-HAB1* fragment with XmaI and XhoI sites on its 5'- and 3'-ends respectively; this fragment was then cloned into pEGAD at its AgeI and XhoI sites, which eliminated pEGAD's 35S-GFP unit; the resultant intermediary vector is called pVP64-HAB1*. To ensure strong nuclear localization, the plant N7 nuclear localization signal (Cutler et al., 2000; Peterson et al., 2016) was added to the protein. To do this, the N7 sequence was amplified by PCR using primers that appended SalI and BglII sites at the 5'- and 3'-ends respectively; this fragment was cloned into pVP64-HAB1* at XhoI and BamHI sites (downstream of HAB1*), yielding pVP64-HAB1*-N7.

The GAL4 UAS component needed to drive expression of target genes was constructed as follows: a UAS-35S minimal promoter cassette was created by primer extension using synthetic oligonucleotides harboring multimerized GAL4 binding sequences and and a minimal 35S promoter (−46 from start site) was cloned into pEGAD at its SacI and AgeI sites, replacing pEGAD's 35S promoter; this resulted in an intermediary vectors called pUAS.

To combine all three components into a single vector, a 35S::NLS-VP64-HAB1*-N7-Nos-terminator cassette was PCR amplified from pVP64-HAB1*-N7 and cloned into pBD-PYR1* into its SacI site, upstream of the BD-PYR1* expression cassette, yielding pAD-BD. Next, the UAS:::GFP-MCS-terminator cassette was amplified with primers that introduce MfeI sites on both ends, digested, and then cloned into pAD-BD between the 35S:NLS-VP64-HAB1*-N7-terminator and 35S:BD-PYR1*-terminator components at an EcoRI site. The final vector, called pMANDI-GFP, has a centrally located MCS that can be used to insert genes of interest downstream of UAS::GFP so that GFP-fusion proteins can be induced by mandipropamid. The T-DNA region of pMANDI-GFP is shown in FIG. 15A. The sequence of the T-DNA region of p-MANDI-GFP is provided as SEQ ID NO: 126.

Having developed a simple induction system, we tested it by examining the expression of the flowering regulator LEAFY. LEAFY cDNA was amplified by PCR and cloned into pMANDI-GFP at its EcoRI and BamHI sites ("pMANDI-UAS-GFP-LEAFY"; SEQ ID NO: 127). We introduced this construct into *Arabidopsis* by *Agrobacterium* mediated transformation using the floral dip method (Clough and Bent, 1998). To test expression, seedlings of T1 plants were identified and a leaf segment cut into two pieces, one of which was transferred to control MS-agar media, and the other transferred to MS-Agar media supplemented with 10 µM mandipropamid. 24 hours after transfer, both tissues were examined using a GFP fluorescence dissecting scope and documented under identical camera and microscope settings (FIG. 15B). These data reveal GFP-LEAFY induction in response to mandipropamid and validate that the system works in planta.

We further set out to establish if the construct's performance could be tuned by altering the expression level of BD-PYR1*-$^{MANDI}$ and/or by adding 5'-UTR elements to our UAS::GFP cassette. The *Arabidopsis* PEX4 gene (At5g25760) has a moderate expression level that is highly consistent across many environmental conditions (Czechowski et al., 2005); we therefore tested the effect of driving BD-PYR1*-$^{MANDI}$ expression by the PEX4 promoter by swapping it with the 35S promoter present in pMANDI-GFP. To do this, we first used PCR to amplify a BD-PYR1*-$^{MANDI}$ fragment from pBD-Gal4-PYR1*-$^{MANDI}$ and cloned it into pEGAD at AgeI and BamHI sites, creating pBD-PYR1*-2, which has slightly different sites available than the pBD-PYR1* vector. To replace the 35S promoter, we PCR amplified a PEX4 promoter fragment from genomic DNA that extended 887 base pairs upstream of PEX4's annotated start codon using primers containing SacI and XmaI sites; this fragment was cloned into the SacI and AgeI sites of pBD-PYR1*-2, resulting in pPEX4-BD-PYR1*. To combine all three components into a single vector, a 35S:: NLS-VP64-HAB1*-N7-Nos-terminator cassette was PCR amplified from pVP64-HAB1*-N7 and cloned pBD-PYR1*-2 into its SacI site, upstream of the PEX4::BD-PYR1* cassette, yielding pAD-PEX4-BD. Next, the UAS:::GFP-MCS-terminator cassette was amplified with primers that introduce MfeI sites on both ends, digested, and then cloned into pAD-PEX4-BD between the 35S:NLS-VP64-H*-N7-terminator and PEX4::BD-PYR1*-terminator components at an EcoRI site, yielding pPEX4-MANDI-GFP.

We then appended two different 5'-UTRs upstream of GFP in both pMANDI-GFP and pPEX4-MANDI-GFP. It has previously been observed that the omega sequence from tomato mosaic virus can both increase induction levels and reduce background expression in a copper-inducible promoter system (Saijo and Nagasawa, 2014); we therefore tested this 71 base pair element ("To71") in the 5'-UTR. In addition, we hypothesized that we might improve induction/background ratios by exploiting UTRs from genes that naturally possess a low basal expression level but are highly induced in response to an external signal. We, therefore, tested the 5'-UTR of MAPKKK18 (At1G05100), a gene that is highly induced by ABA, but otherwise has very low basal induction levels (Okamoto et al., 2013). To do this, the MAPKKK18 (69 bp) and To71 (71 bp) 5'-UTRs were prepared by primer extension using synthetic oligonucleotides that appended XmaI and AgeI sites at the ends; the resultant fragments were cloned into the AgeI site of pEGAD-UAS; the two resultant UAS::UTR-GFP cassettes were cloned into both pAD-BD and pAD-PEX4-BD to generate pMANDI-GFP and pPEX4-MANDI-GFP derivatives with either the MAPKKK18 or To71 5'-UTRs preceding GFP. To investigate the effects of these alterations, the parent and resultant constructs were transformed into Agrobacterium (strain GV3101) and coinfected with Agrobacterium cells containing the p19 suppressor into N. benthamiana leaves and subsequently sprayed 24 hr after infiltration with either 50 µM mandipropamid or a mock solution (0.1% DMSO, 0.05% Silwet). 24 hours after treatment, leaf tissue was collected, frozen in liquid N2, and homogenized by bead beating using a Precellys (Bertin Technologies), at 6000 rpm for 30 seconds and then resuspended in SDS sample buffer containing protease inhibitor, separated by SDS-PAGE, electro-blotted onto nitrocellulose membrane, and detected using an anti-GFP antibody as described in Example 4 above. The results (FIG. 15C) show that replacing the 35S promoter of the BD-PYR1*-$^{MANDI}$ cassette with PEX4 reduces overall induction levels in combination with the base 5'-UTR (which is derived from the 35S promoter). However, the MAPKKK18 or To71 5'-UTRs in combination with PEX4::BD-PYR1*-$^{MANDI}$ increased induction levels and reduced background relative to the starting pMANDI-GFP vector.

Collectively, these examples demonstrate that the orthogonal PYR1*-$^{MANDI}$/HAB1* interaction module can be used to chemically control diverse regulatory processes. The activation domains, nuclear localization and nuclear export sequences, promoters, and terminators can be reconfigured to use native plant-derived sequences (Li et al., 2013; Shieh, Wessler, & Raikhel, 1993; Yamamoto & Obokata, 2008, each of which is incorporated by reference herein).

REFERENCES

Banaszynski, L. A., Chen, L.-C., Maynard-Smith, L. A., Ooi, A. G. L., & Wandless, T. J. (2006). A Rapid, Reversible, and Tunable Method to Regulate Protein Function in Living Cells Using Synthetic Small Molecules. *Cell*, 126(5), 995-1004.

Belshaw, P. J., Ho, S. N., Crabtree, G. R., & Schreiber, S. L. (1996). Controlling protein association and subcellular localization with a synthetic ligand that induces heterodimerization of proteins. *Proceedings of the National Academy of Sciences*, 93(10), 4604-4607.

Bier, D., Thiel, P., Briels, J., & Ottmann, C. (2015). Stabilization of Protein-Protein Interactions in chemical biology and drug discovery. *Progress in Biophysics and Molecular Biology*, 119(1), 10-19.

Clough, S. J., and Bent, A. F. (1998). Floral dip: a simplified method for Agrobacterium-mediated transformation of Arabidopsis thaliana. *Plant J.* 16, 735-743.

Corbesier, L., et al. (2007). FT protein movement contributes to long-distance signaling in floral induction of Arabidopsis. *Science*, 316(5827), 1030-1033.

Cutler, S. R., Ehrhardt, D. W., Griffitts, J. S., and Somerville, C. R. (2000). Random GFP::cDNA fusions enable visualization of subcellular structures in cells of Arabidopsis at a high frequency. *Proc. Natl. Acad. Sci. U.S.A.* 97, 3718-3723.

Cutler, S. R., Rodriguez, P. L., Finkelstein, R. R., & Abrams, S. R. (2010). Abscisic Acid: Emergence of a Core Signaling Network. *Annual Review of Plant Biology*, 61(1), 651-679.

Czechowski, T., Stitt, M., Altmann, T., Udvardi, M. K., and Scheible, W.-R. (2005). Genome-wide identification and testing of superior reference genes for transcript normalization in Arabidopsis. *Plant Physiol.* 139, 5-17.

Engler, C., Kandzia, R., & Marillonnet, S. (2008). A one pot, one step, precision cloning method with high throughput capability. *PloS One*, 3(11), e3647.

Haasen, D., Köhler, C., Neuhaus, G., & Merkle, T. (1999). Nuclear export of proteins in plants: AtXPO1 is the export receptor for leucine-rich nuclear export signals in Arabidopsis thaliana. *The Plant Journal: For Cell and Molecular Biology*, 20(6), 695-705.

Hao, Q., et al. (2011). The molecular basis of ABA-independent inhibition of PP2Cs by a subclass of PYL proteins. *Molecular Cell*, 42(5), 662-672.

Haruki, H., Nishikawa, J., & Laemmli, U. K. (2008). The anchor-away technique: rapid, conditional establishment of yeast mutant phenotypes. *Molecular Cell*, 31(6), 925-932.

Janse, D. M., Crosas, B., Finley, D., & Church, G. M. (2004). Localization to the Proteasome Is Sufficient for Degradation. *The Journal of Biological Chemistry*, 279 (20), 21415-21420.

Liang, F.-S., Ho, W. Q., & Crabtree, G. R. (2011). Engineering the ABA Plant Stress Pathway for Regulation of Induced Proximity. *Science Signaling*, 4(164), rs2.

Licitra, E. J., & Liu, J. O. (1996). A three-hybrid system for detecting small ligand-protein receptor interactions. *Proceedings of the National Academy of Sciences of the United States of America*, 93(23), 12817-12821.

Ma, Y., Szostkiewicz, I., Korte, A., Moes, D., Yang, Y., Christmann, A., & Grill, E. (2009). Regulators of PP2C phosphatase activity function as abscisic acid sensors. *Science*, 324(5930), 1064-1068.

Melcher, K., et al. (2009). A gate-latch-lock mechanism for hormone signalling by abscisic acid receptors. *Nature*, 462(7273), 602-608.

Miyazono, K., et al. (2009). Structural basis of abscisic acid signalling. *Nature*, 462(7273), 609-614.

Mosquna, A., Peterson, F. C., Park, S. Y., Lozano-Juste, J., Volkman, B. F., & Cutler, S. R. (2011). Potent and selective activation of abscisic acid receptors in vivo by mutational stabilization of their agonist-bound conformation. *Proceedings of the National Academy of Sciences*, 108(51), 20838-20843.

Ng, L.-M., et al. (2011). Structural basis for basal activity and autoactivation of abscisic acid (ABA) signaling SnRK2 kinases. *Proceedings of the National Academy of Sciences of the United States of America*, 108(52), 21259-21264.

Nishimura, N., et al. (2009). Structural mechanism of abscisic acid binding and signaling by dimeric PYR1. *Science*, 326(5958), 1373.

Okamoto, M., Peterson, F. C., Defries, A., Park, S.-Y., Endo, A., Nambara, E., Volkman, B. F., and Cutler, S. R. (2013). Activation of dimeric ABA receptors elicits guard cell closure, ABA-regulated gene expression, and drought tolerance. Proc. Natl. Acad. Sci. U.S.A. 110, 12132-12137.

Ossovskaya, V., Lim, S.-T., Ota, N., Schlaepfer, D. D., & Ilic, D. (2008). FAK nuclear export signal sequences. *FEBS Letters*, 582(16), 2402-2406.

Park, S.-Y., et al. (2009). Abscisic Acid Inhibits Type 2C Protein Phosphatases via the PYR/PYL Family of START Proteins. *Science*, 324(5930), 1068-1071.

Park, S. Y., Peterson, F. C., Mosquna, A., Yao, J., Volkman, B. F., & Cutler, S. R. (n.d.). Agrochemical control of plant water use using engineered ABA receptors. *Nature*. http://doi.org/10.1038/nature14123

Peterson, B. A., Haak, D. C., Nishimura, M. T., Teixeira, P. J. P. L., James, S. R., Dangl, J. L., and Nimchuk, Z. L. (2016). Genome-Wide Assessment of Efficiency and Specificity in CRISPR/Cas9 Mediated Multiple Site Targeting in *Arabidopsis*. PLoS One 11, e0162169.

Pratt, W. B., Galigniana, M. D., Harrell, J. M., & DeFranco, D. B. (2004). Role of hsp90 and the hsp90-binding immunophilins in signalling protein movement. *Cellular Signalling*, 16(8), 857-872.

Rutkowska, A., & Schultz, C. (2012). Protein tango: the toolbox to capture interacting partners. *Angewandte Chemie*, 51(33), 8166-8176.

Saijo, T., and Nagasawa, A. (2014). Development of a tightly regulated and highly responsive copper-inducible gene expression system and its application to control of flowering time. Plant Cell Rep. 33, 47-59.

Soon, F.-F., et al. (2012). Molecular Mimicry Regulates ABA Signaling by SnRK2 Kinases and PP2C Phosphatases. *Science*, 335(6064), 85-88.

Yin, P., et al. (2009). Structural insights into the mechanism of abscisic acid signaling by PYL proteins. *Nature Structural & Molecular Biology*, 16(12), 1230-1236.

Zetsche, B., Volz, S. E., & Zhang, F. (2015). A split-Cas9 architecture for inducible genome editing and transcription modulation. *Nature Biotechnology, advance online publication*. http://doi.org/10.1038/nbt.3149

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A plant or a cell comprising a heterologous expression cassette, the expression cassette comprising a promoter operably linked to one or more polynucleotides encoding a first polypeptide comprising a mutated PYR/PYL receptor polypeptide and a second polypeptide comprising a mutated type 2C protein phosphatase (PP2C), wherein the mutated PYR/PYL receptor polypeptide is agonized by an orthogonal ligand that does not significantly agonize a wild-type PYR/PYL receptor polypeptide and wherein the mutated PYR/PYL receptor polypeptide comprises one or more mutations that disrupts binding to a wild-type PP2C, wherein the mutated PP2C comprises one or more mutations that disrupts binding to a wild-type PYR/PYL receptor polypeptide, and wherein the mutated PYR/PYL receptor polypeptide and the mutated PP2C interact with each other, wherein the mutated PYR/PYL receptor polypeptide is at least 95% identical to SEQ ID NO:1 and the mutated PP2C is at least 95% identical to SEQ ID NO:22, and wherein:
   (a) the mutated PYR/PYL receptor polypeptide comprises a mutation corresponding to F61K in SEQ ID NO:1 and the mutated PP2C comprises a mutation corresponding to V393Q in SEQ ID NO:22;
   (b) the mutated PYR/PYL receptor polypeptide comprises a mutation corresponding to S85P in SEQ ID NO:1 and the mutated PP2C comprises a mutation corresponding to E203D in SEQ ID NO:22;
   (c) the mutated PYR/PYL receptor polypeptide comprises a mutation corresponding to S85P in SEQ ID NO:1 and the mutated PP2C comprises a mutation corresponding to E203T in SEQ ID NO:22;
   (d) the mutated PYR/PYL receptor polypeptide comprises a mutation corresponding to S85P in SEQ ID NO:1 and the mutated PP2C comprises a mutation corresponding to E203W in SEQ ID NO:22;
   (e) the mutated PYR/PYL receptor polypeptide comprises a mutation corresponding to T156P in SEQ ID NO:1 and the mutated PP2C comprises a mutation corresponding to I383G in SEQ ID NO:22;
   (f) the mutated PYR/PYL receptor polypeptide comprises a mutation corresponding to T162D in SEQ ID NO:1 and the mutated PP2C comprises a mutation corresponding to V393K in SEQ ID NO:22; or
   (g) the mutated PYR/PYL receptor polypeptide comprises a mutation corresponding to T162D in SEQ ID NO:1 and the mutated PP2C comprises a mutation corresponding to V393R in SEQ ID NO:22.

2. The plant or cell of claim 1, wherein the orthogonal ligand is mandipropamid.

3. The plant or cell of claim 1, wherein the mutated PP2C further comprises one or more mutations that disrupts the catalytic activity of the mutated PP2C.

4. The plant or cell of claim 1, wherein the mutated PYR/PYL receptor polypeptide comprises SEQ ID NO: 19, 20, 21, or 32.

5. The plant or cell of claim 1, wherein the mutated PP2C comprises SEQ ID NO: 30, 31, 33 or 34.

6. The plant or cell of claim 1, wherein the first polypeptide comprises the mutated PYR/PYL receptor polypeptide fused to a transcriptional activation domain and the second polypeptide comprises the mutated PP2C fused to a DNA binding domain, or the first polypeptide comprises the mutated PYR/PYL receptor polypeptide fused to a DNA binding domain and the second polypeptide comprises the mutated PP2C fused to a transcriptional activation domain.

7. A plant cell from the plant of claim 1.

8. A seed, flower, leaf, fruit, processed food, or food ingredient from the plant of claim 1.

9. A method of activating an orthogonal PYR/PYL-PP2C interaction in the plant or cell of claim 1 by contacting the plant or cell with the orthogonal ligand, wherein the step of contacting the plant or cell with the orthogonal ligand activates an interaction between the mutated PYR/PYL and the mutated PP2C but does not significantly activate an endogenous abscisic acid (ABA) signaling pathway in the plant or cell.

10. A method of controlling gene, protein, or phenotype expression in the plant or cell of claim 6, the method comprising contacting the plant or cell with an orthogonal ligand, wherein the step of contacting the plant or cell with the orthogonal ligand activates an interaction between the mutated PYR/PYL and the mutated PP2C, thereby associating the DNA binding domain and the transcriptional activation domain and activating expression of the gene, protein, or phenotype.

11. An expression cassette comprising a promoter operably linked to one or more polynucleotides encoding a mutated PYR/PYL receptor polypeptide and a mutated type 2C protein phosphatase (PP2C), wherein the mutated PYR/PYL receptor polypeptide is agonized by an orthogonal ligand that does not significantly agonize a wild-type PYR/PYL receptor polypeptide and wherein the mutated PYR/PYL receptor polypeptide comprises a mutation that disrupts binding to a wild-type PP2C, wherein the mutated PP2C comprises a mutation that disrupts binding to a wild-type PYR/PYL receptor polypeptide, and wherein the mutated PYR/PYL receptor polypeptide and the mutated PP2C interact with each other, wherein the mutated PYR/PYL receptor polypeptide is at least 95% identical to SEQ ID NO:1 and the mutated PP2C is at least 95% identical to SEQ ID NO:22, and wherein:
   (a) the mutated PYR/PYL receptor polypeptide comprises a mutation corresponding to F61K in SEQ ID NO:1 and the mutated PP2C comprises a mutation corresponding to V393Q in SEQ ID NO:22;
   (b) the mutated PYR/PYL receptor polypeptide comprises a mutation corresponding to S85P in SEQ ID NO:1 and the mutated PP2C comprises a mutation corresponding to E203D in SEQ ID NO:22;
   (c) the mutated PYR/PYL receptor polypeptide comprises a mutation corresponding to S85P in SEQ ID NO:1 and the mutated PP2C comprises a mutation corresponding to E203T in SEQ ID NO:22;

(d) the mutated PYR/PYL receptor polypeptide comprises a mutation corresponding to S85P in SEQ ID NO:1 and the mutated PP2C comprises a mutation corresponding to E203W in SEQ ID NO:22;

(e) the mutated PYR/PYL receptor polypeptide comprises a mutation corresponding to T156P in SEQ ID NO:1 and the mutated PP2C comprises a mutation corresponding to I383G in SEQ ID NO:22;

(f) the mutated PYR/PYL receptor polypeptide comprises a mutation corresponding to T162D in SEQ ID NO:1 and the mutated PP2C comprises a mutation corresponding to V393K in SEQ ID NO:22; or (g) the mutated PYR/PYL receptor polypeptide comprises a mutation corresponding to T162D in SEQ ID NO:1 and the mutated PP2C comprises a mutation corresponding to V393R in SEQ ID NO:22.

12. An expression vector comprising the expression cassette of claim 11.

13. An isolated nucleic acid comprising a polynucleotide encoding a polypeptide comprising a mutated PYR/PYL receptor polypeptide fused to a transcriptional activation domain or a DNA binding domain, wherein the mutated PYR/PYL receptor polypeptide is agonized by an orthogonal ligand that does not significantly agonize a wild-type PYR/PYL receptor polypeptide and wherein the mutated PYR/PYL receptor polypeptide comprises a mutation that disrupts binding to a wild-type PP2C, wherein the mutated PYR/PYL receptor polypeptide is at least 95% identical to SEQ ID NO:1 and wherein:

(a) the mutated PYR/PYL receptor polypeptide comprises a mutation corresponding to F61K in SEQ ID NO:1;

(b) the mutated PYR/PYL receptor polypeptide comprises a mutation corresponding to S85P in SEQ ID NO:1;

(c) the mutated PYR/PYL receptor polypeptide comprises a mutation corresponding to T156P in SEQ ID NO:1; or (d) the mutated PYR/PYL receptor polypeptide comprises a mutation corresponding to T162D in SEQ ID NO:1.

14. An isolated nucleic acid comprising a polynucleotide encoding a polypeptide comprising a mutated type 2C protein phosphatase (PP2C) fused to a transcriptional activation domain or a DNA binding domain, wherein the mutated PP2C comprises a mutation that disrupts binding to a wild-type PYR/PYL receptor polypeptide, wherein the mutated PP2C is at least 95% identical to SEQ ID NO:22, and wherein:

(a) the mutated PP2C comprises a mutation corresponding to V393Q in SEQ ID NO:22;

(b) the mutated PP2C comprises a mutation corresponding to E203D in SEQ ID NO:22;

(c) the mutated PP2C comprises a mutation corresponding to E203T in SEQ ID NO:22;

(d) the mutated PP2C comprises a mutation corresponding to E203W in SEQ ID NO:22;

(e) the mutated PP2C comprises a mutation corresponding to I383G in SEQ ID NO:22;

(f) the mutated PP2C comprises a mutation corresponding to V393K in SEQ ID NO:22; or (g) the mutated PP2C comprises a mutation corresponding to V393R in SEQ ID NO:22.

15. The plant or cell of claim 1, wherein the mutated PYR/PYL receptor polypeptide comprises a mutation corresponding to F61K in SEQ ID NO:1 and the mutated PP2C comprises a mutation corresponding to V393Q in SEQ ID NO:22.

16. The plant or cell of claim 1, wherein the mutated PYR/PYL receptor polypeptide comprises a mutation corresponding to S85P in SEQ ID NO:1 and the mutated PP2C comprises a mutation corresponding to E203D in SEQ ID NO:22.

17. The plant or cell of claim 1, wherein the mutated PYR/PYL receptor polypeptide comprises a mutation corresponding to S85P in SEQ ID NO:1 and the mutated PP2C comprises a mutation corresponding to E203T in SEQ ID NO:22.

18. The plant or cell of claim 1, wherein the mutated PYR/PYL receptor polypeptide comprises a mutation corresponding to S85P in SEQ ID NO:1 and the mutated PP2C comprises a mutation corresponding to E203W in SEQ ID NO:22.

19. The plant or cell of claim 1, wherein the mutated PYR/PYL receptor polypeptide comprises a mutation corresponding to T156P in SEQ ID NO:1 and the mutated PP2C comprises a mutation corresponding to I383G in SEQ ID NO:22.

20. The plant or cell of claim 1, wherein the mutated PYR/PYL receptor polypeptide comprises a mutation corresponding to T162D in SEQ ID NO:1 and the mutated PP2C comprises a mutation corresponding to V393K in SEQ ID NO:22.

21. The plant or cell of claim 1, wherein the mutated PYR/PYL receptor polypeptide comprises a mutation corresponding to T162D in SEQ ID NO:1 and the mutated PP2C comprises a mutation corresponding to V393R in SEQ ID NO:22.

* * * * *

SEQUENCE LISTING

```
<160> NUMBER OF SEQ ID NOS: 127

<210> SEQ ID NO 1
<211> LENGTH: 191
<212> TYPE: PRT
<213> ORGANISM: Arabidopsis thaliana

<400> SEQUENCE: 1

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr Tyr Lys His Phe Ile Lys Ser
    50                  55                  60

Cys Ser Val Glu Gln Asn Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Asp Thr Arg Met Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190
```

<210> SEQ ID NO 2
<211> LENGTH: 221
<212> TYPE: PRT
<213> ORGANISM: Arabidopsis thaliana

<400> SEQUENCE: 2

Met Ala Asn Ser Glu Ser Ser Ser Pro Val Asn Glu Glu Glu Asn
1               5                   10                  15

Ser Gln Arg Ile Ser Thr Leu His His Gln Thr Met Pro Ser Asp Leu
            20                  25                  30

Thr Gln Asp Glu Phe Thr Gln Leu Ser Gln Ser Ile Ala Glu Phe His
        35                  40                  45

Thr Tyr Gln Leu Gly Asn Gly Arg Cys Ser Ser Leu Leu Ala Gln Arg
    50                  55                  60

Ile His Ala Pro Pro Glu Thr Val Trp Ser Val Arg Arg Phe Asp
65                  70                  75                  80

Arg Pro Gln Ile Tyr Lys His Phe Ile Lys Ser Cys Asn Val Ser Glu
                85                  90                  95

Asp Phe Glu Met Arg Val Gly Cys Thr Arg Asp Val Asn Val Ile Ser
            100                 105                 110

Gly Leu Pro Ala Asn Thr Ser Arg Glu Arg Leu Asp Leu Leu Asp Asp
        115                 120                 125

Asp Arg Arg Val Thr Gly Phe Ser Ile Thr Gly Gly Glu His Arg Leu
    130                 135                 140

Arg Asn Tyr Lys Ser Val Thr Thr Val His Arg Phe Glu Lys Glu Glu
145                 150                 155                 160

Glu Glu Glu Arg Ile Trp Thr Val Val Leu Glu Ser Tyr Val Val Asp
                165                 170                 175

Val Pro Glu Gly Asn Ser Glu Glu Asp Thr Arg Leu Phe Ala Asp Thr
            180                 185                 190

Val Ile Arg Leu Asn Leu Gln Lys Leu Ala Ser Ile Thr Glu Ala Met
        195                 200                 205

Asn Arg Asn Asn Asn Asn Asn Ser Ser Gln Val Arg
    210                 215                 220

<210> SEQ ID NO 3
<211> LENGTH: 190
<212> TYPE: PRT
<213> ORGANISM: Arabidopsis thaliana

<400> SEQUENCE: 3

Met Ser Ser Ser Pro Ala Val Lys Gly Leu Thr Asp Glu Glu Gln Lys
1               5                   10                  15

Thr Leu Glu Pro Val Ile Lys Thr Tyr His Gln Phe Glu Pro Asp Pro
            20                  25                  30

Thr Thr Cys Thr Ser Leu Ile Thr Gln Arg Ile His Ala Pro Ala Ser
        35                  40                  45

Val Val Trp Pro Leu Ile Arg Arg Phe Asp Asn Pro Glu Arg Tyr Lys
    50                  55                  60

His Phe Val Lys Arg Cys Arg Leu Ile Ser Gly Asp Gly Asp Val Gly
65                  70                  75                  80

Ser Val Arg Glu Val Thr Val Ile Ser Gly Leu Pro Ala Ser Thr Ser
                85                  90                  95

Thr Glu Arg Leu Glu Phe Val Asp Asp Asp His Arg Val Leu Ser Phe
            100                 105                 110

Arg Val Val Gly Gly Glu His Arg Leu Lys Asn Tyr Lys Ser Val Thr
            115                 120                 125

Ser Val Asn Glu Phe Leu Asn Gln Asp Ser Gly Lys Val Tyr Thr Val
        130                 135                 140

Val Leu Glu Ser Tyr Thr Val Asp Ile Pro Glu Gly Asn Thr Glu Glu
145                 150                 155                 160

Asp Thr Lys Met Phe Val Asp Thr Val Val Lys Leu Asn Leu Gln Lys
                165                 170                 175

Leu Gly Val Ala Ala Thr Ser Ala Pro Met His Asp Glu
            180                 185                 190

<210> SEQ ID NO 4
<211> LENGTH: 209
<212> TYPE: PRT
<213> ORGANISM: Arabidopsis thaliana

<400> SEQUENCE: 4

Met Asn Leu Ala Pro Ile His Asp Pro Ser Ser Ser Thr Thr Thr Thr
1               5                   10                  15

Thr Ser Ser Ser Thr Pro Tyr Gly Leu Thr Lys Asp Glu Phe Ser Thr
            20                  25                  30

Leu Asp Ser Ile Ile Arg Thr His His Thr Phe Pro Arg Ser Pro Asn
        35                  40                  45

Thr Cys Thr Ser Leu Ile Ala His Arg Val Asp Ala Pro Ala His Ala
    50                  55                  60

Ile Trp Arg Phe Val Arg Asp Phe Ala Asn Pro Asn Lys Tyr Lys His
65                  70                  75                  80

Phe Ile Lys Ser Cys Thr Ile Arg Val Asn Gly Asn Gly Ile Lys Glu
                85                  90                  95

Ile Lys Val Gly Thr Ile Arg Glu Val Ser Val Val Ser Gly Leu Pro
            100                 105                 110

Ala Ser Thr Ser Val Glu Ile Leu Glu Val Leu Asp Glu Glu Lys Arg
        115                 120                 125

Ile Leu Ser Phe Arg Val Leu Gly Gly Glu His Arg Leu Asn Asn Tyr
    130                 135                 140

Arg Ser Val Thr Ser Val Asn Glu Phe Val Val Leu Glu Lys Asp Lys
145                 150                 155                 160

Lys Lys Arg Val Tyr Ser Val Val Leu Glu Ser Tyr Ile Val Asp Ile
                165                 170                 175

Pro Gln Gly Asn Thr Glu Glu Asp Thr Arg Met Phe Val Asp Thr Val
            180                 185                 190

Val Lys Ser Asn Leu Gln Asn Leu Ala Val Ile Ser Thr Ala Ser Pro
        195                 200                 205

Thr

<210> SEQ ID NO 5
<211> LENGTH: 207
<212> TYPE: PRT
<213> ORGANISM: Arabidopsis thaliana

<400> SEQUENCE: 5

Met Leu Ala Val His Arg Pro Ser Ser Ala Val Ser Asp Gly Asp Ser
1               5                   10                  15

Val Gln Ile Pro Met Met Ile Ala Ser Phe Gln Lys Arg Phe Pro Ser
            20                  25                  30

```
Leu Ser Arg Asp Ser Thr Ala Ala Arg Phe His Thr His Glu Val Gly
            35                  40                  45

Pro Asn Gln Cys Cys Ser Ala Val Ile Gln Glu Ile Ser Ala Pro Ile
 50                      55                  60

Ser Thr Val Trp Ser Val Val Arg Arg Phe Asp Asn Pro Gln Ala Tyr
 65                  70                  75                  80

Lys His Phe Leu Lys Ser Cys Ser Val Ile Gly Gly Asp Gly Asp Asn
                 85                  90                  95

Val Gly Ser Leu Arg Gln Val His Val Ser Gly Leu Pro Ala Ala
                100                 105                 110

Ser Ser Thr Glu Arg Leu Asp Ile Leu Asp Asp Glu Arg His Val Ile
                115                 120                 125

Ser Phe Ser Val Val Gly Gly Asp His Arg Leu Ser Asn Tyr Arg Ser
                130                 135                 140

Val Thr Thr Leu His Pro Ser Pro Ile Ser Gly Thr Val Val Val Glu
145                 150                 155                 160

Ser Tyr Val Val Asp Val Pro Pro Gly Asn Thr Lys Glu Glu Thr Cys
                165                 170                 175

Asp Phe Val Asp Val Ile Val Arg Cys Asn Leu Gln Ser Leu Ala Lys
                180                 185                 190

Ile Ala Glu Asn Thr Ala Ala Glu Ser Lys Lys Lys Met Ser Leu
                195                 200                 205

<210> SEQ ID NO 6
<211> LENGTH: 203
<212> TYPE: PRT
<213> ORGANISM: Arabidopsis thaliana

<400> SEQUENCE: 6

Met Arg Ser Pro Val Gln Leu Gln His Gly Ser Asp Ala Thr Asn Gly
  1               5                  10                  15

Phe His Thr Leu Gln Pro His Asp Gln Thr Asp Gly Pro Ile Lys Arg
                 20                  25                  30

Val Cys Leu Thr Arg Gly Met His Val Pro Glu His Val Ala Met His
                 35                  40                  45

His Thr His Asp Val Gly Pro Asp Gln Cys Cys Ser Ser Val Val Gln
 50                  55                  60

Met Ile His Ala Pro Pro Glu Ser Val Trp Ala Leu Val Arg Arg Phe
 65                  70                  75                  80

Asp Asn Pro Lys Val Tyr Lys Asn Phe Ile Arg Gln Cys Arg Ile Val
                 85                  90                  95

Gln Gly Asp Gly Leu His Val Gly Asp Leu Arg Glu Val Met Val Val
                100                 105                 110

Ser Gly Leu Pro Ala Val Ser Ser Thr Glu Arg Leu Glu Ile Leu Asp
                115                 120                 125

Glu Glu Arg His Val Ile Ser Phe Ser Val Val Gly Gly Asp His Arg
                130                 135                 140

Leu Lys Asn Tyr Arg Ser Val Thr Thr Leu His Ala Ser Asp Asp Glu
145                 150                 155                 160

Gly Thr Val Val Val Glu Ser Tyr Ile Val Asp Val Pro Pro Gly Asn
                165                 170                 175

Thr Glu Glu Glu Thr Leu Ser Phe Val Asp Thr Ile Val Arg Cys Asn
                180                 185                 190

Leu Gln Ser Leu Ala Arg Ser Thr Asn Arg Gln
                195                 200
```

```
<210> SEQ ID NO 7
<211> LENGTH: 215
<212> TYPE: PRT
<213> ORGANISM: Arabidopsis thaliana

<400> SEQUENCE: 7

Met Pro Thr Ser Ile Gln Phe Gln Arg Ser Thr Ala Ala Glu Ala
1               5                   10                  15

Ala Asn Ala Thr Val Arg Asn Tyr Pro His His Gln Lys Gln Val
                20                  25                  30

Gln Lys Val Ser Leu Thr Arg Gly Met Ala Asp Val Pro Glu His Val
            35                  40                  45

Glu Leu Ser His Thr His Val Val Gly Pro Ser Gln Cys Phe Ser Val
        50                  55                  60

Val Val Gln Asp Val Glu Ala Pro Val Ser Thr Val Trp Ser Ile Leu
65                  70                  75                  80

Ser Arg Phe Glu His Pro Gln Ala Tyr Lys His Phe Val Lys Ser Cys
                85                  90                  95

His Val Val Ile Gly Asp Gly Arg Glu Val Gly Ser Val Arg Glu Val
                100                 105                 110

Arg Val Val Ser Gly Leu Pro Ala Ala Phe Ser Leu Glu Arg Leu Glu
            115                 120                 125

Ile Met Asp Asp Asp Arg His Val Ile Ser Phe Ser Val Val Gly Gly
        130                 135                 140

Asp His Arg Leu Met Asn Tyr Lys Ser Val Thr Thr Val His Glu Ser
145                 150                 155                 160

Glu Glu Asp Ser Asp Gly Lys Lys Arg Thr Arg Val Val Glu Ser Tyr
                165                 170                 175

Val Val Asp Val Pro Ala Gly Asn Asp Lys Glu Glu Thr Cys Ser Phe
                180                 185                 190

Ala Asp Thr Ile Val Arg Cys Asn Leu Gln Ser Leu Ala Lys Leu Ala
            195                 200                 205

Glu Asn Thr Ser Lys Phe Ser
        210                 215

<210> SEQ ID NO 8
<211> LENGTH: 211
<212> TYPE: PRT
<213> ORGANISM: Arabidopsis thaliana

<400> SEQUENCE: 8

Met Glu Met Ile Gly Gly Asp Asp Thr Asp Thr Glu Met Tyr Gly Ala
1               5                   10                  15

Leu Val Thr Ala Gln Ser Leu Arg Leu Arg His Leu His Cys Arg
                20                  25                  30

Glu Asn Gln Cys Thr Ser Val Leu Val Lys Tyr Ile Gln Ala Pro Val
            35                  40                  45

His Leu Val Trp Ser Leu Val Arg Arg Phe Asp Gln Pro Gln Lys Tyr
        50                  55                  60

Lys Pro Phe Ile Ser Arg Cys Thr Val Asn Gly Asp Pro Glu Ile Gly
65                  70                  75                  80

Cys Leu Arg Glu Val Asn Val Lys Ser Gly Leu Pro Ala Thr Thr Ser
                85                  90                  95

Thr Glu Arg Leu Glu Gln Leu Asp Asp Glu Glu His Ile Leu Gly Ile
            100                 105                 110
```

```
Asn Ile Ile Gly Gly Asp His Arg Leu Lys Asn Tyr Ser Ser Ile Leu
            115                 120                 125

Thr Val His Pro Glu Met Ile Asp Gly Arg Ser Gly Thr Met Val Met
    130                 135                 140

Glu Ser Phe Val Val Asp Val Pro Gln Gly Asn Thr Lys Asp Asp Thr
145                 150                 155                 160

Cys Tyr Phe Val Glu Ser Leu Ile Lys Cys Asn Leu Lys Ser Leu Ala
                165                 170                 175

Cys Val Ser Glu Arg Leu Ala Ala Gln Asp Ile Thr Asn Ser Ile Ala
            180                 185                 190

Thr Phe Cys Asn Ala Ser Asn Gly Tyr Arg Glu Lys Asn His Thr Glu
        195                 200                 205

Thr Asn Leu
    210

<210> SEQ ID NO 9
<211> LENGTH: 188
<212> TYPE: PRT
<213> ORGANISM: Arabidopsis thaliana

<400> SEQUENCE: 9

Met Glu Ala Asn Gly Ile Glu Asn Leu Thr Asn Pro Asn Gln Glu Arg
1               5                   10                  15

Glu Phe Ile Arg Arg His His Lys His Glu Leu Val Asp Asn Gln Cys
            20                  25                  30

Ser Ser Thr Leu Val Lys His Ile Asn Ala Pro Val His Ile Val Trp
        35                  40                  45

Ser Leu Val Arg Arg Phe Asp Gln Pro Gln Lys Tyr Lys Pro Phe Ile
    50                  55                  60

Ser Arg Cys Val Val Lys Gly Asn Met Glu Ile Gly Thr Val Arg Glu
65                  70                  75                  80

Val Asp Val Lys Ser Gly Leu Pro Ala Thr Arg Ser Thr Glu Arg Leu
                85                  90                  95

Glu Leu Leu Asp Asp Asn Glu His Ile Leu Ser Ile Arg Ile Val Gly
            100                 105                 110

Gly Asp His Arg Leu Lys Asn Tyr Ser Ser Ile Ile Ser Leu His Pro
        115                 120                 125

Glu Thr Ile Glu Gly Arg Ile Gly Thr Leu Val Ile Glu Ser Phe Val
    130                 135                 140

Val Asp Val Pro Glu Gly Asn Thr Lys Asp Glu Thr Cys Tyr Phe Val
145                 150                 155                 160

Glu Ala Leu Ile Lys Cys Asn Leu Lys Ser Leu Ala Asp Ile Ser Glu
                165                 170                 175

Arg Leu Ala Val Gln Asp Thr Thr Glu Ser Arg Val
            180                 185

<210> SEQ ID NO 10
<211> LENGTH: 187
<212> TYPE: PRT
<213> ORGANISM: Arabidopsis thaliana

<400> SEQUENCE: 10

Met Met Asp Gly Val Glu Gly Gly Thr Ala Met Tyr Gly Gly Leu Glu
1               5                   10                  15

Thr Val Gln Tyr Val Arg Thr His His Gln His Leu Cys Arg Glu Asn
            20                  25                  30
```

Gln Cys Thr Ser Ala Leu Val Lys His Ile Lys Ala Pro Leu His Leu
         35                  40                  45

Val Trp Ser Leu Val Arg Arg Phe Asp Gln Pro Gln Lys Tyr Lys Pro
 50                  55                  60

Phe Val Ser Arg Cys Thr Val Ile Gly Asp Pro Glu Ile Gly Ser Leu
 65                  70                  75                  80

Arg Glu Val Asn Val Lys Ser Gly Leu Pro Ala Thr Thr Ser Thr Glu
                 85                  90                  95

Arg Leu Glu Leu Leu Asp Asp Glu Glu His Ile Leu Gly Ile Lys Ile
             100                 105                 110

Ile Gly Gly Asp His Arg Leu Lys Asn Tyr Ser Ser Ile Leu Thr Val
         115                 120                 125

His Pro Glu Ile Ile Glu Gly Arg Ala Gly Thr Met Val Ile Glu Ser
 130                 135                 140

Phe Val Val Asp Val Pro Gln Gly Asn Thr Lys Asp Glu Thr Cys Tyr
145                 150                 155                 160

Phe Val Glu Ala Leu Ile Arg Cys Asn Leu Lys Ser Leu Ala Asp Val
                165                 170                 175

Ser Glu Arg Leu Ala Ser Gln Asp Ile Thr Gln
            180                 185

<210> SEQ ID NO 11
<211> LENGTH: 183
<212> TYPE: PRT
<213> ORGANISM: Arabidopsis thaliana

<400> SEQUENCE: 11

Met Asn Gly Asp Glu Thr Lys Lys Val Glu Ser Glu Tyr Ile Lys Lys
1               5                   10                  15

His His Arg His Glu Leu Val Glu Ser Gln Cys Ser Ser Thr Leu Val
             20                  25                  30

Lys His Ile Lys Ala Pro Leu His Leu Val Trp Ser Ile Val Arg Arg
         35                  40                  45

Phe Asp Glu Pro Gln Lys Tyr Lys Pro Phe Ile Ser Arg Cys Val Val
 50                  55                  60

Gln Gly Lys Lys Leu Glu Val Gly Ser Val Arg Glu Val Asp Leu Lys
65                  70                  75                  80

Ser Gly Leu Pro Ala Thr Lys Ser Thr Glu Val Leu Glu Ile Leu Asp
                85                  90                  95

Asp Asn Glu His Ile Leu Gly Ile Arg Ile Val Gly Gly Asp His Arg
            100                 105                 110

Leu Lys Asn Tyr Ser Ser Thr Ile Ser Leu His Ser Glu Thr Ile Asp
        115                 120                 125

Gly Lys Thr Gly Thr Leu Ala Ile Glu Ser Phe Val Val Asp Val Pro
130                 135                 140

Glu Gly Asn Thr Lys Glu Glu Thr Cys Phe Phe Val Glu Ala Leu Ile
145                 150                 155                 160

Gln Cys Asn Leu Asn Ser Leu Ala Asp Val Thr Glu Arg Leu Gln Ala
                165                 170                 175

Glu Ser Met Glu Lys Lys Ile
            180

<210> SEQ ID NO 12
<211> LENGTH: 161
<212> TYPE: PRT

<213> ORGANISM: Arabidopsis thaliana

<400> SEQUENCE: 12

Met Glu Thr Ser Gln Lys Tyr His Thr Cys Gly Ser Thr Leu Val Gln
1               5                   10                  15

Thr Ile Asp Ala Pro Leu Ser Leu Val Trp Ser Ile Leu Arg Arg Phe
            20                  25                  30

Asp Asn Pro Gln Ala Tyr Lys Gln Phe Val Lys Thr Cys Asn Leu Ser
        35                  40                  45

Ser Gly Asp Gly Gly Glu Gly Ser Val Arg Glu Val Thr Val Val Ser
    50                  55                  60

Gly Leu Pro Ala Glu Phe Ser Arg Glu Arg Leu Asp Glu Leu Asp Asp
65                  70                  75                  80

Glu Ser His Val Met Met Ile Ser Ile Ile Gly Gly Asp His Arg Leu
                85                  90                  95

Val Asn Tyr Arg Ser Lys Thr Met Ala Phe Val Ala Ala Asp Thr Glu
            100                 105                 110

Glu Lys Thr Val Val Val Glu Ser Tyr Val Val Asp Val Pro Glu Gly
        115                 120                 125

Asn Ser Glu Glu Glu Thr Thr Ser Phe Ala Asp Thr Ile Val Gly Phe
    130                 135                 140

Asn Leu Lys Ser Leu Ala Lys Leu Ser Glu Arg Val Ala His Leu Lys
145                 150                 155                 160

Leu

<210> SEQ ID NO 13
<211> LENGTH: 159
<212> TYPE: PRT
<213> ORGANISM: Arabidopsis thaliana

<400> SEQUENCE: 13

Met Lys Thr Ser Gln Glu Gln His Val Cys Gly Ser Thr Val Val Gln
1               5                   10                  15

Thr Ile Asn Ala Pro Leu Pro Leu Val Trp Ser Ile Leu Arg Arg Phe
            20                  25                  30

Asp Asn Pro Lys Thr Phe Lys His Phe Val Lys Thr Cys Lys Leu Arg
        35                  40                  45

Ser Gly Asp Gly Gly Glu Gly Ser Val Arg Glu Val Thr Val Val Ser
    50                  55                  60

Asp Leu Pro Ala Ser Phe Ser Leu Glu Arg Leu Asp Glu Leu Asp Asp
65                  70                  75                  80

Glu Ser His Val Met Val Ile Ser Ile Ile Gly Gly Asp His Arg Leu
                85                  90                  95

Val Asn Tyr Gln Ser Lys Thr Thr Val Phe Val Ala Ala Glu Glu Glu
            100                 105                 110

Lys Thr Val Val Val Glu Ser Tyr Val Val Asp Val Pro Glu Gly Asn
        115                 120                 125

Thr Glu Glu Glu Thr Thr Leu Phe Ala Asp Thr Ile Val Gly Cys Asn
    130                 135                 140

Leu Arg Ser Leu Ala Lys Leu Ser Glu Lys Met Met Glu Leu Thr
145                 150                 155

<210> SEQ ID NO 14
<211> LENGTH: 164
<212> TYPE: PRT
<213> ORGANISM: Arabidopsis thaliana

<400> SEQUENCE: 14

Met Glu Ser Ser Lys Gln Lys Arg Cys Arg Ser Ser Val Val Glu Thr
1               5                   10                  15

Ile Glu Ala Pro Leu Pro Leu Val Trp Ser Ile Leu Arg Ser Phe Asp
                20                  25                  30

Lys Pro Gln Ala Tyr Gln Arg Phe Val Lys Ser Cys Thr Met Arg Ser
                35                  40                  45

Gly Gly Gly Gly Gly Lys Gly Glu Gly Lys Gly Ser Val Arg Asp
    50                  55                  60

Val Thr Leu Val Ser Gly Phe Pro Ala Asp Phe Ser Thr Glu Arg Leu
65                  70                  75                  80

Glu Glu Leu Asp Asp Glu Ser His Val Met Val Val Ser Ile Ile Gly
                85                  90                  95

Gly Asn His Arg Leu Val Asn Tyr Lys Ser Lys Thr Lys Val Val Ala
                100                 105                 110

Ser Pro Glu Asp Met Ala Lys Lys Thr Val Val Glu Ser Tyr Val
                115                 120                 125

Val Asp Val Pro Glu Gly Thr Ser Gly Glu Asp Thr Ile Phe Phe Val
                130                 135                 140

Asp Asn Ile Ile Arg Tyr Asn Leu Thr Ser Leu Ala Lys Leu Thr Lys
145                 150                 155                 160

Lys Met Met Lys

<210> SEQ ID NO 15
<211> LENGTH: 36
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (2)..(35)
<223> OTHER INFORMATION: Xaa = any amino acid

<400> SEQUENCE: 15

Cys Xaa Ser Xaa Xaa Xaa Xaa Xaa Xaa Ala Pro Xaa Xaa Xaa Xaa
1               5                   10                  15

Trp Xaa Xaa Xaa Xaa Xaa Phe Xaa Xaa Pro Xaa Xaa Xaa Xaa Xaa Phe
                20                  25                  30

Xaa Xaa Xaa Cys
        35

<210> SEQ ID NO 16
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (2)..(24)
<223> OTHER INFORMATION: Xaa = any amino acid

<400> SEQUENCE: 16

Gly Xaa Xaa Arg Xaa Val Xaa Xaa Xaa Ser Xaa Xaa Pro Ala Xaa Xaa
1               5                   10                  15

Ser Xaa Glu Xaa Leu Xaa Xaa Xaa Asp
                20                  25

```
<210> SEQ ID NO 17
<211> LENGTH: 31
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (3)..(30)
<223> OTHER INFORMATION: Xaa = any amino acid

<400> SEQUENCE: 17

Glu Ser Xaa Xaa Val Asp Xaa Pro Xaa Gly Xaa Xaa Xaa Xaa Xaa Thr
1               5                   10                  15

Xaa Xaa Phe Xaa Xaa Xaa Xaa Xaa Xaa Asn Leu Xaa Xaa Leu
            20                  25                  30

<210> SEQ ID NO 18
<211> LENGTH: 45
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (2)..(44)
<223> OTHER INFORMATION: Xaa = any amino acid

<400> SEQUENCE: 18

His Xaa Xaa Xaa Xaa Xaa Xaa Xaa Cys Xaa Ser Xaa Xaa Xaa Xaa
1               5                   10                  15

Xaa Xaa Xaa Ala Pro Xaa Xaa Xaa Xaa Trp Xaa Xaa Xaa Xaa Xaa Phe
            20                  25                  30

Xaa Xaa Pro Xaa Xaa Tyr Lys Xaa Phe Xaa Xaa Xaa Cys
        35                  40                  45

<210> SEQ ID NO 19
<211> LENGTH: 191
<212> TYPE: PRT
<213> ORGANISM: Arabidopsis thaliana

<400> SEQUENCE: 19

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr His Arg His Phe Ile Lys Ser
50                  55                  60

Cys Ser Val Glu Gln Asn Phe Glu Met Arg Val Gly Cys Thr Arg Asp
65                  70                  75                  80

Ile Ile Val Ile Ser Gly Leu Pro Ala Asn Thr Ser Thr Glu Arg Leu
                85                  90                  95

Asp Ile Leu Asp Asp Glu Arg Arg Val Thr Gly Ala Ser Ile Ile Gly
            100                 105                 110

Gly Glu His Arg Leu Thr Asn Tyr Lys Gly Val Thr Thr Val His Arg
        115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Asp Thr Arg Ile Val Val
145                 150                 155                 160
```

Asp Asp Val Val Lys Leu Asn Leu Gln Lys Leu Ala Thr Val Ala Glu
            165                 170                 175

Ala Met Ala Arg Asn Ser Gly Asp Gly Ser Gly Ser Gln Val Thr
        180                 185                 190

<210> SEQ ID NO 20
<211> LENGTH: 191
<212> TYPE: PRT
<213> ORGANISM: Arabidopsis thaliana

<400> SEQUENCE: 20

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr His Arg His Phe Ile Lys Ser
    50                  55                  60

Cys Ser Val Glu Gln Asn Phe Glu Met Arg Val Gly Cys Thr Arg Asp
65                  70                  75                  80

Ile Ile Val Ile Ser Gly Leu Pro Ala Asn Thr Ser Thr Glu Arg Leu
                85                  90                  95

Asp Ile Leu Asp Asp Glu Arg Arg Val Thr Gly Ala Ser Ile Ile Gly
            100                 105                 110

Gly Glu His Arg Leu Thr Asn Tyr Lys Gly Val Thr Thr Val His Arg
        115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Asp Thr Arg Val Val Val
145                 150                 155                 160

Asp Asp Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 21
<211> LENGTH: 191
<212> TYPE: PRT
<213> ORGANISM: Arabidopsis thaliana

<400> SEQUENCE: 21

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr His Arg His Phe Ile Lys Ser
    50                  55                  60

Cys Ser Val Glu Gln Asn Phe Glu Met Arg Val Gly Cys Thr Arg Asp
65                  70                  75                  80

Ile Ile Val Ile Ser Gly Leu Pro Ala Asn Thr Ser Thr Glu Arg Leu
                85                  90                  95

Asp Ile Leu Asp Asp Glu Arg Arg Val Thr Gly Ala Ser Ile Ile Gly
            100                 105                 110

```
Gly Glu His Arg Leu Thr Asn Tyr Lys Gly Val Thr Val His Arg
            115                 120                 125

Phe Glu Lys Glu Asn Arg Ile Trp Thr Val Val Leu Glu Ser Tyr Val
130                 135                 140

Val Asp Met Pro Glu Gly Asn Ser Glu Asp Asp Thr Arg Ile Val Cys
145                 150                 155                 160

Asp Asp Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 22
<211> LENGTH: 511
<212> TYPE: PRT
<213> ORGANISM: Arabidopsis thaliana

<400> SEQUENCE: 22

Met Glu Glu Met Thr Pro Ala Val Ala Met Thr Leu Ser Leu Ala Ala
1               5                   10                  15

Asn Thr Met Cys Glu Ser Ser Pro Val Glu Ile Thr Gln Leu Lys Asn
            20                  25                  30

Val Thr Asp Ala Ala Asp Leu Leu Ser Asp Ser Glu Asn Gln Ser Phe
        35                  40                  45

Cys Asn Gly Gly Thr Glu Cys Thr Met Glu Asp Val Ser Glu Leu Glu
    50                  55                  60

Glu Val Gly Glu Gln Asp Leu Leu Lys Thr Leu Ser Asp Thr Arg Ser
65                  70                  75                  80

Gly Ser Ser Asn Val Phe Asp Glu Asp Val Leu Ser Val Val Glu
                85                  90                  95

Asp Asn Ser Ala Val Ile Ser Glu Gly Leu Leu Val Val Asp Ala Gly
            100                 105                 110

Ser Glu Leu Ser Leu Ser Asn Thr Ala Met Glu Ile Asp Asn Gly Arg
        115                 120                 125

Val Leu Ala Thr Ala Ile Ile Val Gly Glu Ser Ser Ile Glu Gln Val
    130                 135                 140

Pro Thr Ala Glu Val Leu Ile Ala Gly Val Asn Gln Asp Thr Asn Thr
145                 150                 155                 160

Ser Glu Val Val Ile Arg Leu Pro Asp Glu Asn Ser Asn His Leu Val
                165                 170                 175

Lys Gly Arg Ser Val Tyr Glu Leu Asp Cys Ile Pro Leu Trp Gly Thr
            180                 185                 190

Val Ser Ile Gln Gly Asn Arg Ser Glu Met Glu Asp Ala Phe Ala Val
        195                 200                 205

Ser Pro His Phe Leu Lys Leu Pro Ile Lys Met Leu Met Gly Asp His
    210                 215                 220

Glu Gly Met Ser Pro Ser Leu Thr His Leu Thr Gly His Phe Gly
225                 230                 235                 240

Val Tyr Asp Gly His Gly Gly His Lys Val Ala Asp Tyr Cys Arg Asp
                245                 250                 255

Arg Leu His Phe Ala Leu Ala Glu Glu Ile Glu Arg Ile Lys Asp Glu
            260                 265                 270

Leu Cys Lys Arg Asn Thr Gly Glu Gly Arg Gln Val Gln Trp Asp Lys
        275                 280                 285

Val Phe Thr Ser Cys Phe Leu Thr Val Asp Gly Glu Ile Glu Gly Lys
```

```
                290                 295                 300
Ile Gly Arg Ala Val Val Gly Ser Ser Asp Lys Val Leu Glu Ala Val
305                 310                 315                 320

Ala Ser Glu Thr Val Gly Ser Thr Ala Val Ala Leu Val Cys Ser
                325                 330                 335

Ser His Ile Val Val Ser Asn Cys Gly Asp Ser Arg Ala Val Leu Phe
                340                 345                 350

Arg Gly Lys Glu Ala Met Pro Leu Ser Val Asp His Lys Pro Asp Arg
                355                 360                 365

Glu Asp Glu Tyr Ala Arg Ile Glu Asn Ala Gly Gly Lys Val Ile Gln
                370                 375                 380

Trp Gln Gly Ala Arg Val Phe Gly Val Leu Ala Met Ser Arg Ser Ile
385                 390                 395                 400

Gly Asp Arg Tyr Leu Lys Pro Tyr Val Ile Pro Glu Pro Glu Val Thr
                405                 410                 415

Phe Met Pro Arg Ser Arg Glu Asp Glu Cys Leu Ile Leu Ala Ser Asp
                420                 425                 430

Gly Leu Trp Asp Val Met Asn Asn Gln Glu Val Cys Glu Ile Ala Arg
                435                 440                 445

Arg Arg Ile Leu Met Trp His Lys Lys Asn Gly Ala Pro Pro Leu Ala
                450                 455                 460

Glu Arg Gly Lys Gly Ile Asp Pro Ala Cys Gln Ala Ala Ala Asp Tyr
465                 470                 475                 480

Leu Ser Met Leu Ala Leu Gln Lys Gly Ser Lys Asp Asn Ile Ser Ile
                485                 490                 495

Ile Val Ile Asp Leu Lys Ala Gln Arg Lys Phe Lys Thr Arg Thr
                500                 505                 510

<210> SEQ ID NO 23
<211> LENGTH: 434
<212> TYPE: PRT
<213> ORGANISM: Arabidopsis thaliana

<400> SEQUENCE: 23

Met Glu Glu Val Ser Pro Ala Ile Ala Gly Pro Phe Arg Pro Phe Ser
1               5                   10                  15

Glu Thr Gln Met Asp Phe Thr Gly Ile Arg Leu Gly Lys Gly Tyr Cys
                20                  25                  30

Asn Asn Gln Tyr Ser Asn Gln Asp Ser Glu Asn Gly Asp Leu Met Val
                35                  40                  45

Ser Leu Pro Glu Thr Ser Ser Cys Ser Val Ser Gly Ser His Gly Ser
50                  55                  60

Glu Ser Arg Lys Val Leu Ile Ser Arg Ile Asn Ser Pro Asn Leu Asn
65                  70                  75                  80

Met Lys Glu Ser Ala Ala Ala Asp Ile Val Val Asp Ile Ser Ala
                85                  90                  95

Gly Asp Glu Ile Asn Gly Ser Asp Ile Thr Ser Glu Lys Lys Met Ile
                100                 105                 110

Ser Arg Thr Glu Ser Arg Ser Leu Phe Glu Phe Lys Ser Val Pro Leu
                115                 120                 125

Tyr Gly Phe Thr Ser Ile Cys Gly Arg Arg Pro Glu Met Glu Asp Ala
                130                 135                 140

Val Ser Thr Ile Pro Arg Phe Leu Gln Ser Ser Gly Ser Met Leu
145                 150                 155                 160
```

-continued

Asp Gly Arg Phe Asp Pro Gln Ser Ala Ala His Phe Gly Val Tyr
                165                 170                 175

Asp Gly His Gly Gly Ser Gln Val Ala Asn Tyr Cys Arg Glu Arg Met
            180                 185                 190

His Leu Ala Leu Ala Glu Glu Ile Ala Lys Glu Lys Pro Met Leu Cys
        195                 200                 205

Asp Gly Asp Thr Trp Leu Glu Lys Trp Lys Lys Ala Leu Phe Asn Ser
    210                 215                 220

Phe Leu Arg Val Asp Ser Glu Ile Glu Ser Val Ala Pro Glu Thr Val
225                 230                 235                 240

Gly Ser Thr Ser Val Val Ala Val Val Phe Pro Ser His Ile Phe Val
                245                 250                 255

Ala Asn Cys Gly Asp Ser Arg Ala Val Leu Cys Arg Gly Lys Thr Ala
            260                 265                 270

Leu Pro Leu Ser Val Asp His Lys Pro Asp Arg Glu Asp Glu Ala Ala
        275                 280                 285

Arg Ile Glu Ala Ala Gly Gly Lys Val Ile Gln Trp Asn Gly Ala Arg
    290                 295                 300

Val Phe Gly Val Leu Ala Met Ser Arg Ser Ile Gly Asp Arg Tyr Leu
305                 310                 315                 320

Lys Pro Ser Ile Ile Pro Asp Pro Glu Val Thr Ala Val Lys Arg Val
                325                 330                 335

Lys Glu Asp Asp Cys Leu Ile Leu Ala Ser Asp Gly Val Trp Asp Val
            340                 345                 350

Met Thr Asp Glu Glu Ala Cys Glu Met Ala Arg Lys Arg Ile Leu Leu
        355                 360                 365

Trp His Lys Lys Asn Ala Val Ala Gly Asp Ala Ser Leu Leu Ala Asp
    370                 375                 380

Glu Arg Arg Lys Glu Gly Lys Asp Pro Ala Ala Met Ser Ala Ala Glu
385                 390                 395                 400

Tyr Leu Ser Lys Leu Ala Ile Gln Arg Gly Ser Lys Asp Asn Ile Ser
                405                 410                 415

Val Val Val Val Asp Leu Lys Pro Arg Arg Lys Leu Lys Ser Lys Pro
            420                 425                 430

Leu Asn

<210> SEQ ID NO 24
<211> LENGTH: 423
<212> TYPE: PRT
<213> ORGANISM: Arabidopsis thaliana

<400> SEQUENCE: 24

Met Asp Glu Val Ser Pro Ala Val Ala Val Pro Phe Arg Pro Phe Thr
1               5                   10                  15

Asp Pro His Ala Gly Leu Arg Gly Tyr Cys Asn Gly Glu Ser Arg Val
                20                  25                  30

Thr Leu Pro Glu Ser Ser Cys Ser Gly Asp Gly Ala Met Lys Asp Ser
            35                  40                  45

Ser Phe Glu Ile Asn Thr Arg Gln Asp Ser Leu Thr Ser Ser Ser Ser
        50                  55                  60

Ala Met Ala Gly Val Asp Ile Ser Ala Gly Asp Glu Ile Asn Gly Ser
65                  70                  75                  80

Asp Glu Phe Asp Pro Arg Ser Met Asn Gln Ser Glu Lys Lys Val Leu
                85                  90                  95

```
Ser Arg Thr Glu Ser Arg Ser Leu Phe Glu Phe Lys Cys Val Pro Leu
            100                 105                 110

Tyr Gly Val Thr Ser Ile Cys Gly Arg Arg Pro Glu Met Glu Asp Ser
            115                 120                 125

Val Ser Thr Ile Pro Arg Phe Leu Gln Val Ser Ser Ser Ser Leu Leu
        130                 135                 140

Asp Gly Arg Val Thr Asn Gly Phe Asn Pro His Leu Ser Ala His Phe
145                 150                 155                 160

Phe Gly Val Tyr Asp Gly His Gly Gly Ser Gln Val Ala Asn Tyr Cys
                165                 170                 175

Arg Glu Arg Met His Leu Ala Leu Thr Glu Glu Ile Val Lys Glu Lys
            180                 185                 190

Pro Glu Phe Cys Asp Gly Asp Thr Trp Gln Glu Lys Trp Lys Lys Ala
        195                 200                 205

Leu Phe Asn Ser Phe Met Arg Val Asp Ser Glu Ile Glu Thr Val Ala
    210                 215                 220

His Ala Pro Glu Thr Val Gly Ser Thr Ser Val Val Ala Val Val Phe
225                 230                 235                 240

Pro Thr His Ile Phe Val Ala Asn Cys Gly Asp Ser Arg Ala Val Leu
                245                 250                 255

Cys Arg Gly Lys Thr Pro Leu Ala Leu Ser Val Asp His Lys Pro Asp
            260                 265                 270

Arg Asp Asp Glu Ala Ala Arg Ile Glu Ala Ala Gly Gly Lys Val Ile
        275                 280                 285

Arg Trp Asn Gly Ala Arg Val Phe Gly Val Leu Ala Met Ser Arg Ser
    290                 295                 300

Ile Gly Asp Arg Tyr Leu Lys Pro Ser Val Ile Pro Asp Pro Glu Val
305                 310                 315                 320

Thr Ser Val Arg Arg Val Lys Glu Asp Asp Cys Leu Ile Leu Ala Ser
                325                 330                 335

Asp Gly Leu Trp Asp Val Met Thr Asn Glu Glu Val Cys Asp Leu Ala
            340                 345                 350

Arg Lys Arg Ile Leu Leu Trp His Lys Lys Asn Ala Met Ala Gly Glu
        355                 360                 365

Ala Leu Leu Pro Ala Glu Lys Arg Gly Glu Gly Lys Asp Pro Ala Ala
    370                 375                 380

Met Ser Ala Ala Glu Tyr Leu Ser Lys Met Ala Leu Gln Lys Gly Ser
385                 390                 395                 400

Lys Asp Asn Ile Ser Val Val Val Asp Leu Lys Gly Ile Arg Lys
                405                 410                 415

Phe Lys Ser Lys Ser Leu Asn
            420

<210> SEQ ID NO 25
<211> LENGTH: 510
<212> TYPE: PRT
<213> ORGANISM: Arabidopsis thaliana

<400> SEQUENCE: 25

Glu Glu Ile Ser Pro Ala Val Ala Leu Thr Leu Gly Leu Ala Asn Thr
1               5                   10                  15

Met Cys Asp Ser Gly Ile Ser Ser Thr Phe Asp Ile Ser Glu Leu Glu
            20                  25                  30

Asn Val Thr Asp Ala Ala Asp Met Leu Cys Asn Gln Lys Arg Gln Arg
        35                  40                  45
```

-continued

```
Tyr Ser Asn Gly Val Val Asp Cys Ile Met Gly Ser Val Ser Glu Glu
     50                  55                  60

Lys Thr Leu Ser Glu Val Arg Ser Leu Ser Ser Asp Phe Ser Val Thr
 65                  70                  75                  80

Val Gln Glu Ser Glu Glu Asp Glu Pro Leu Val Ser Asp Ala Thr Ile
                 85                  90                  95

Ile Ser Glu Gly Leu Ile Val Val Asp Ala Arg Ser Glu Ile Ser Leu
                100                 105                 110

Pro Asp Thr Val Glu Thr Asp Asn Gly Arg Val Leu Ala Thr Ala Ile
                115                 120                 125

Ile Leu Asn Glu Thr Thr Ile Glu Gln Val Pro Thr Ala Glu Val Leu
    130                 135                 140

Ile Ala Ser Leu Asn His Asp Val Asn Met Glu Val Ala Thr Ser Glu
145                 150                 155                 160

Val Val Ile Arg Leu Pro Glu Glu Asn Pro Asn Val Ala Arg Gly Ser
                165                 170                 175

Arg Ser Val Tyr Glu Leu Glu Cys Ile Pro Leu Trp Gly Thr Ile Ser
                180                 185                 190

Ile Cys Gly Gly Arg Ser Glu Met Glu Asp Ala Val Arg Ala Leu Pro
        195                 200                 205

His Phe Leu Lys Ile Pro Ile Lys Met Leu Met Gly Asp His Glu Gly
    210                 215                 220

Met Ser Pro Ser Leu Pro Tyr Leu Thr Ser His Phe Phe Gly Val Tyr
225                 230                 235                 240

Asp Gly His Gly Gly Ala Gln Val Ala Asp Tyr Cys His Asp Arg Ile
                245                 250                 255

His Ser Ala Leu Ala Glu Glu Ile Glu Arg Ile Lys Glu Glu Leu Cys
                260                 265                 270

Arg Arg Asn Thr Gly Glu Gly Arg Gln Val Gln Trp Glu Lys Val Phe
        275                 280                 285

Val Asp Cys Tyr Leu Lys Val Asp Asp Glu Val Lys Gly Lys Ile Asn
    290                 295                 300

Arg Pro Val Val Gly Ser Ser Asp Arg Met Val Leu Glu Ala Val Ser
305                 310                 315                 320

Pro Glu Thr Val Gly Ser Thr Ala Val Val Ala Leu Val Cys Ser Ser
                325                 330                 335

His Ile Ile Val Ser Asn Cys Gly Asp Ser Arg Ala Val Leu Leu Arg
                340                 345                 350

Gly Lys Asp Ser Met Pro Leu Ser Val Asp His Lys Pro Asp Arg Glu
        355                 360                 365

Asp Glu Tyr Ala Arg Ile Glu Lys Ala Gly Gly Lys Val Ile Gln Trp
    370                 375                 380

Gln Gly Ala Arg Val Ser Gly Val Leu Ala Met Ser Arg Ser Ile Gly
385                 390                 395                 400

Asp Gln Tyr Leu Glu Pro Phe Val Ile Pro Asp Pro Glu Val Thr Phe
                405                 410                 415

Met Pro Arg Ala Arg Glu Asp Glu Cys Leu Ile Leu Ala Ser Asp Gly
                420                 425                 430

Leu Trp Asp Val Met Ser Asn Gln Glu Ala Cys Asp Phe Ala Arg Arg
        435                 440                 445

Arg Ile Leu Ala Trp His Lys Lys Asn Gly Ala Leu Pro Leu Ala Glu
    450                 455                 460
```

```
Arg Gly Val Gly Glu Asp Gln Ala Cys Gln Ala Ala Glu Tyr Leu
465                 470                 475                 480

Ser Lys Leu Ala Ile Gln Met Gly Ser Lys Asp Asn Ile Ser Ile Ile
                485                 490                 495

Val Ile Asp Leu Lys Ala Gln Arg Lys Phe Lys Thr Arg Ser
            500                 505                 510

<210> SEQ ID NO 26
<211> LENGTH: 413
<212> TYPE: PRT
<213> ORGANISM: Arabidopsis thaliana

<400> SEQUENCE: 26

Met Ala Glu Ile Cys Tyr Glu Asn Glu Thr Met Met Ile Glu Thr Thr
1               5                   10                  15

Ala Thr Val Val Lys Lys Ala Thr Thr Thr Arg Arg Arg Glu Arg
                20                  25                  30

Ser Ser Ser Gln Ala Ala Arg Arg Arg Met Glu Ile Arg Arg Phe
            35                  40                  45

Lys Phe Val Ser Gly Glu Gln Glu Pro Val Phe Val Asp Gly Asp Leu
50                  55                  60

Gln Arg Arg Arg Arg Glu Ser Thr Val Ala Ala Ser Thr Ser Thr
65                  70                  75                  80

Val Phe Tyr Glu Thr Ala Lys Glu Val Val Leu Cys Glu Ser Leu
                85                  90                  95

Ser Ser Thr Val Val Ala Leu Pro Asp Pro Glu Ala Tyr Pro Lys Tyr
            100                 105                 110

Gly Val Ala Ser Val Cys Gly Arg Arg Arg Glu Met Glu Asp Ala Val
                115                 120                 125

Ala Val His Pro Phe Phe Ser Arg His Gln Thr Glu Tyr Ser Ser Thr
            130                 135                 140

Gly Phe His Tyr Cys Gly Val Tyr Asp Gly His Gly Cys Ser His Val
145                 150                 155                 160

Ala Met Lys Cys Arg Glu Arg Leu His Glu Leu Val Arg Glu Glu Phe
                165                 170                 175

Glu Ala Asp Ala Asp Trp Glu Lys Ser Met Ala Arg Ser Phe Thr Arg
            180                 185                 190

Met Asp Met Glu Val Val Ala Leu Asn Ala Asp Gly Ala Ala Lys Cys
            195                 200                 205

Arg Cys Glu Leu Gln Arg Pro Asp Cys Asp Ala Val Gly Ser Thr Ala
            210                 215                 220

Val Val Ser Val Leu Thr Pro Glu Lys Ile Ile Val Ala Asn Cys Gly
225                 230                 235                 240

Asp Ser Arg Ala Val Leu Cys Arg Asn Gly Lys Ala Ile Ala Leu Ser
                245                 250                 255

Ser Asp His Lys Pro Asp Arg Pro Asp Glu Leu Asp Arg Ile Gln Ala
            260                 265                 270

Ala Gly Gly Arg Val Ile Tyr Trp Asp Gly Pro Arg Val Leu Gly Val
            275                 280                 285

Leu Ala Met Ser Arg Ala Ile Gly Asp Asn Tyr Leu Lys Pro Tyr Val
            290                 295                 300

Ile Ser Arg Pro Glu Val Thr Val Thr Asp Arg Ala Asn Gly Asp Asp
305                 310                 315                 320

Phe Leu Ile Leu Ala Ser Asp Gly Leu Trp Asp Val Val Ser Asn Glu
                325                 330                 335
```

```
Thr Ala Cys Ser Val Val Arg Met Cys Leu Arg Gly Lys Val Asn Gly
            340                 345                 350

Gln Val Ser Ser Pro Glu Arg Glu Met Thr Gly Val Gly Ala Gly
            355                 360                 365

Asn Val Val Gly Gly Gly Asp Leu Pro Asp Lys Ala Cys Glu Glu
370                 375                 380

Ala Ser Leu Leu Leu Thr Arg Leu Ala Leu Ala Arg Gln Ser Ser Asp
385                 390                 395                 400

Asn Val Ser Val Val Val Asp Leu Arg Arg Asp Thr
            405                 410

<210> SEQ ID NO 27
<211> LENGTH: 442
<212> TYPE: PRT
<213> ORGANISM: Brassica napus

<400> SEQUENCE: 27

Met Ala Asp Ile Cys Tyr Glu Asp Glu Thr Ser Ala Cys Glu Ser Arg
1               5                   10                  15

Pro Leu Trp Ser Ser Arg Lys Trp Arg Ile Gly Val Gln Arg Phe Arg
            20                  25                  30

Met Ser Pro Ser Glu Met Asn Pro Thr Ala Ser Thr Thr Glu Glu Glu
            35                  40                  45

Asp Lys Ser Glu Gly Ile Tyr Asn Lys Arg Asn Lys Gln Glu Glu Tyr
50                  55                  60

Asp Phe Met Asn Cys Ala Ser Ser Pro Ser Gln Ser Ser Pro Glu
65                  70                  75                  80

Glu Glu Ser Val Ser Leu Glu Asp Ser Asp Val Ser Ile Ser Asp Gly
            85                  90                  95

Asn Ser Ser Val Asn Asp Val Ala Val Ile Pro Ser Lys Lys Thr Val
            100                 105                 110

Lys Glu Thr Asp Leu Arg Pro Arg Tyr Gly Val Ala Ser Val Cys Gly
            115                 120                 125

Arg Arg Arg Asp Met Glu Asp Ala Val Ala Leu His Pro Ser Phe Val
130                 135                 140

Arg Lys Gln Thr Glu Phe Ser Arg Thr Arg Trp His Tyr Phe Gly Val
145                 150                 155                 160

Tyr Asp Gly His Gly Cys Ser His Val Ala Ala Arg Cys Lys Glu Arg
            165                 170                 175

Leu His Glu Leu Val Gln Glu Glu Ala Leu Ser Asp Lys Lys Glu Glu
            180                 185                 190

Trp Lys Lys Met Met Glu Arg Ser Phe Thr Arg Met Asp Lys Glu Val
            195                 200                 205

Val Arg Trp Gly Glu Thr Val Met Ser Ala Asn Cys Arg Cys Glu Leu
210                 215                 220

Gln Thr Pro Asp Cys Asp Ala Val Gly Ser Thr Ala Val Ser Val
225                 230                 235                 240

Ile Thr Pro Glu Lys Ile Ile Val Ala Asn Cys Gly Asp Ser Arg Ala
            245                 250                 255

Val Leu Cys Arg Asn Gly Lys Ala Val Pro Leu Ser Thr Asp His Lys
            260                 265                 270

Pro Asp Arg Pro Asp Glu Leu Asp Arg Ile Gln Glu Ala Gly Gly Arg
            275                 280                 285

Val Ile Tyr Trp Asp Gly Ala Arg Val Leu Gly Val Leu Ala Met Ser
```

```
            290                 295                 300
Arg Ala Ile Gly Asp Asn Tyr Leu Lys Pro Tyr Val Thr Ser Glu Pro
305                 310                 315                 320

Glu Val Thr Val Thr Asp Arg Thr Glu Glu Asp Glu Phe Leu Ile Leu
                325                 330                 335

Ala Thr Asp Gly Leu Trp Asp Val Val Thr Asn Glu Ala Ala Cys Thr
                340                 345                 350

Met Val Arg Met Cys Leu Asn Arg Lys Ser Gly Arg Gly Arg Arg Arg
                355                 360                 365

Gly Glu Thr Gln Thr Pro Gly Arg Arg Ser Glu Glu Glu Gly Lys Glu
                370                 375                 380

Glu Glu Glu Lys Val Val Gly Ser Arg Lys Asn Gly Lys Arg Gly Glu
385                 390                 395                 400

Ile Thr Asp Lys Ala Cys Thr Glu Ala Ser Val Leu Leu Thr Lys Leu
                405                 410                 415

Ala Leu Ala Lys His Ser Ser Asp Asn Val Ser Val Val Val Ile Asp
                420                 425                 430

Leu Arg Arg Arg Arg Lys Arg His Val Ala
                435                 440
```

<210> SEQ ID NO 28
<211> LENGTH: 362
<212> TYPE: PRT
<213> ORGANISM: Arabidopsis thaliana

<400> SEQUENCE: 28

```
Met Ala Glu Ile Cys Tyr Glu Val Val Thr Asp Ala Cys Pro Ser Ser
1               5                   10                  15

Val Tyr Glu Ser Thr Pro Ala His Ser Arg Arg Pro Arg Phe Gln
                20                  25                  30

Thr Val Met His Glu Asp Trp Glu Lys Asn Cys Lys Arg Ser Lys Gln
                35                  40                  45

Glu Ala Leu Ala Thr Arg Tyr Ser Ser Ile Pro Arg Ser Ser Arg Glu
                50                  55                  60

Asp Phe Ser Asp Gln Asn Val Asp Val Ser Ser Pro Tyr Gly Val
65                  70                  75                  80

Ser Ser Val Cys Gly Arg Arg Arg Glu Met Glu Asp Ala Val Ala Ile
                85                  90                  95

His Pro Ser Phe Ser Pro Lys Asn Ser Glu Phe Pro Gln His Tyr
                100                 105                 110

Phe Gly Val Tyr Asp Gly His Gly Cys Ser His Val Ala Ala Arg Cys
                115                 120                 125

Arg Glu Arg Leu His Lys Leu Val Gln Glu Glu Leu Ser Ser Asp Met
                130                 135                 140

Glu Asp Glu Glu Glu Trp Lys Thr Thr Met Glu Arg Ser Phe Thr Arg
145                 150                 155                 160

Met Asp Lys Glu Val Val Ser Trp Gly Asp Ser Val Val Thr Ala Asn
                165                 170                 175

Cys Lys Cys Asp Leu Gln Thr Pro Ala Cys Asp Ser Val Gly Ser Thr
                180                 185                 190

Ala Val Val Ser Val Ile Thr Pro Asp Lys Ile Val Val Ala Asn Cys
                195                 200                 205

Gly Asp Ser Arg Ala Val Leu Cys Arg Asn Gly Lys Pro Val Pro Leu
                210                 215                 220
```

Ser Thr Asp His Lys Pro Asp Arg Pro Asp Glu Leu Asp Arg Ile Glu
225                 230                 235                 240

Gly Ala Gly Gly Arg Val Ile Tyr Trp Asp Cys Pro Arg Val Leu Gly
            245                 250                 255

Val Leu Ala Met Ser Arg Ala Ile Gly Asp Asn Tyr Leu Lys Pro Tyr
            260                 265                 270

Val Ser Cys Glu Pro Glu Val Thr Ile Thr Asp Arg Arg Asp Asp Asp
            275                 280                 285

Cys Leu Ile Leu Ala Ser Asp Gly Leu Trp Asp Val Ser Asn Glu
290                 295                 300

Thr Ala Cys Ser Val Ala Arg Met Cys Leu Arg Gly Gly Arg Arg
305                 310                 315                 320

Gln Asp Asn Glu Asp Pro Ala Ile Ser Asp Lys Ala Cys Thr Glu Ala
            325                 330                 335

Ser Val Leu Leu Thr Lys Leu Ala Leu Ala Arg Asn Ser Ser Asp Asn
            340                 345                 350

Val Ser Val Val Val Ile Asp Leu Arg Arg
            355                 360

<210> SEQ ID NO 29
<211> LENGTH: 371
<212> TYPE: PRT
<213> ORGANISM: Arabidopsis thaliana

<400> SEQUENCE: 29

Met Lys Lys Thr Arg Asn Val Ala Ser Ser Pro Ile Glu Cys Val His
1               5                   10                  15

Leu Gln Thr Lys Pro Thr Thr Leu Val Arg Ser Phe Phe Phe Phe
                20                  25                  30

Leu Phe Asn Ser Gln Thr Ile Ser Phe Ile Ile Phe Tyr Leu Phe
            35                  40                  45

Leu Cys Ser Phe Phe Trp Phe Cys Gln Ser Pro Asn Leu Thr Asn Pro
50                  55                  60

Ser Pro Pro Leu Ser Val Ala Pro Leu Arg Gly Asp Ala Asn Ser
65              70                  75                  80

Pro Pro Pro Glu Ser Ser Ser Pro Ala Thr Lys Ser Ser Leu Met
                85                  90                  95

Ile Ser Ser Arg Asp Pro Asn Ala Leu Phe Ser Gly Gly Ile Ser
            100                 105                 110

Phe Leu Ala Gly Val Arg Thr Val Lys Phe Ser Tyr Gly Tyr Ser Ser
            115                 120                 125

Leu Lys Gly Lys Arg Ala Thr Met Glu Asp Tyr Phe Glu Thr Arg Ile
130                 135                 140

Ser Asp Val Asn Gly Gln Met Val Ala Phe Phe Gly Val Phe Asp Gly
145                 150                 155                 160

His Gly Gly Ala Arg Thr Ala Glu Tyr Leu Lys Asn Asn Leu Phe Lys
            165                 170                 175

Asn Leu Val Ser His Asp Asp Phe Ile Ser Asp Thr Lys Lys Ala Ile
            180                 185                 190

Val Glu Val Phe Lys Gln Thr Asp Glu Glu Tyr Leu Ile Glu Glu Ala
            195                 200                 205

Gly Gln Pro Lys Asn Ala Gly Ser Thr Ala Ala Thr Ala Phe Leu Ile
210                 215                 220

Gly Asp Lys Leu Ile Val Ala Asn Val Gly Asp Ser Arg Val Val Ala
225                 230                 235                 240

```
Ser Arg Asn Gly Ser Ala Val Pro Leu Ser Asp Asp His Lys Pro Asp
            245                 250                 255

Arg Ser Asp Glu Arg Gln Arg Ile Glu Asp Ala Gly Phe Ile Ile
            260                 265                 270

Trp Ala Gly Thr Trp Arg Val Gly Ile Leu Ala Val Ser Arg Ala
            275                 280                 285

Phe Gly Asp Lys Gln Leu Lys Pro Tyr Val Ile Ala Glu Pro Glu Ile
            290                 295                 300

Gln Glu Glu Asp Ile Ser Thr Leu Glu Phe Ile Val Val Ala Ser Asp
305                 310                 315                 320

Gly Leu Trp Asn Val Leu Ser Asn Lys Asp Ala Val Ala Ile Val Arg
            325                 330                 335

Asp Ile Ser Asp Ala Glu Thr Ala Ala Arg Lys Leu Val Gln Glu Gly
            340                 345                 350

Tyr Ala Arg Gly Ser Cys Asp Asn Ile Thr Cys Ile Val Val Arg Phe
            355                 360                 365

Glu Val Ser
    370
```

<210> SEQ ID NO 30
<211> LENGTH: 511
<212> TYPE: PRT
<213> ORGANISM: Arabidopsis thaliana

<400> SEQUENCE: 30

```
Met Glu Glu Met Thr Pro Ala Val Ala Met Thr Leu Ser Leu Ala Ala
1               5                   10                  15

Asn Thr Met Cys Glu Ser Ser Pro Val Glu Ile Thr Gln Leu Lys Asn
            20                  25                  30

Val Thr Asp Ala Ala Asp Leu Leu Ser Asp Ser Glu Asn Gln Ser Phe
            35                  40                  45

Cys Asn Gly Gly Thr Glu Cys Thr Met Glu Asp Val Ser Glu Leu Glu
        50                  55                  60

Glu Val Gly Glu Gln Asp Leu Leu Lys Thr Leu Ser Asp Thr Arg Ser
65                  70                  75                  80

Gly Ser Ser Asn Val Phe Asp Glu Asp Val Leu Ser Val Val Glu
            85                  90                  95

Asp Asn Ser Ala Val Ile Ser Glu Gly Leu Leu Val Val Asp Ala Gly
            100                 105                 110

Ser Glu Leu Ser Leu Ser Asn Thr Ala Met Glu Ile Asp Asn Gly Arg
            115                 120                 125

Val Leu Ala Thr Ala Ile Ile Val Gly Glu Ser Ser Ile Glu Gln Val
            130                 135                 140

Pro Thr Ala Glu Val Leu Ile Ala Gly Val Asn Gln Asp Thr Asn Thr
145                 150                 155                 160

Ser Glu Val Val Ile Arg Leu Pro Asp Glu Asn Ser Asn His Leu Val
            165                 170                 175

Lys Gly Arg Ser Val Tyr Glu Leu Asp Cys Ile Pro Leu Trp Gly Thr
            180                 185                 190

Val Ser Ile Gln Gly Asn Ala Ser Glu Met Glu Ala Ala Phe Ala Val
            195                 200                 205

Ser Pro His Phe Leu Lys Leu Pro Ile Lys Met Leu Met Gly Asp His
            210                 215                 220

Glu Gly Met Ser Pro Ser Leu Thr His Leu Thr Gly His Phe Phe Gly
```

```
                    225                 230                 235                 240
            Val Tyr Asp Gly His Gly Gly His Lys Val Ala Asp Tyr Cys Arg Asp
                            245                 250                 255

Arg Leu His Phe Ala Leu Ala Glu Glu Ile Glu Arg Ile Lys Asp Glu
                        260                 265                 270

Leu Cys Lys Arg Asn Thr Gly Glu Gly Arg Gln Val Gln Trp Asp Lys
                        275                 280                 285

Val Phe Thr Ser Cys Phe Leu Thr Val Asp Gly Glu Ile Glu Gly Lys
                    290                 295                 300

Ile Gly Arg Ala Val Val Gly Ser Ser Asp Lys Val Leu Glu Ala Val
            305                 310                 315                 320

Ala Asp Glu Thr Val Gly Ser Thr Ala Val Ala Leu Val Cys Ser
                            325                 330                 335

Ser His Ile Val Val Ser Asn Cys Gly Asp Ser Arg Ala Val Leu Phe
                        340                 345                 350

Arg Gly Lys Glu Ala Met Pro Leu Ser Val Asp His Lys Pro Asp Arg
                    355                 360                 365

Glu Asp Glu Tyr Ala Arg Ile Glu Asn Ala Gly Gly Lys Val Ile Gln
                    370                 375                 380

Trp Gln Gly Ala Arg Val Phe Gly Arg Leu Ala Met Ser Arg Ser Ile
            385                 390                 395                 400

Gly Asp Arg Tyr Leu Lys Pro Tyr Val Ile Pro Glu Pro Glu Val Thr
                            405                 410                 415

Phe Met Pro Arg Ser Arg Glu Asp Glu Cys Leu Ile Leu Ala Ser Asp
                        420                 425                 430

Gly Leu Trp Asp Val Met Asn Asn Gln Glu Val Cys Glu Ile Ala Arg
                    435                 440                 445

Arg Arg Ile Leu Met Trp His Lys Lys Asn Gly Ala Pro Pro Leu Ala
                    450                 455                 460

Glu Arg Gly Lys Gly Ile Asp Pro Ala Cys Gln Ala Ala Ala Asp Tyr
            465                 470                 475                 480

Leu Ser Met Leu Ala Leu Gln Lys Gly Ser Lys Asp Asn Ile Ser Ile
                            485                 490                 495

Ile Val Ile Asp Leu Lys Ala Gln Ala Lys Phe Lys Thr Arg Thr
                        500                 505                 510

<210> SEQ ID NO 31
<211> LENGTH: 508
<212> TYPE: PRT
<213> ORGANISM: Arabidopsis thaliana

<400> SEQUENCE: 31

Met Thr Pro Ala Val Ala Met Thr Leu Ser Leu Ala Ala Asn Thr Met
            1               5                   10                  15

Cys Glu Ser Ser Pro Val Glu Ile Thr Gln Leu Lys Asn Val Thr Asp
                            20                  25                  30

Ala Ala Asp Leu Leu Ser Asp Ser Glu Asn Gln Ser Phe Cys Asn Gly
                        35                  40                  45

Gly Thr Glu Cys Thr Met Glu Asp Val Ser Glu Leu Glu Glu Val Gly
                    50                  55                  60

Glu Gln Asp Leu Leu Lys Thr Leu Ser Asp Thr Arg Ser Gly Ser Ser
            65                  70                  75                  80

Asn Val Phe Asp Glu Asp Asp Val Leu Ser Val Glu Asp Asn Ser
                            85                  90                  95
```

-continued

```
Ala Val Ile Ser Glu Gly Leu Leu Val Val Asp Ala Gly Ser Glu Leu
            100                 105                 110

Ser Leu Ser Asn Thr Ala Met Glu Ile Asp Asn Gly Arg Val Leu Ala
            115                 120                 125

Thr Ala Ile Ile Val Gly Glu Ser Ser Ile Glu Gln Val Pro Thr Ala
            130                 135                 140

Glu Val Leu Ile Ala Gly Val Asn Gln Asp Thr Asn Thr Ser Glu Val
145                 150                 155                 160

Val Ile Arg Leu Pro Asp Glu Asn Ser Asn His Leu Val Lys Gly Arg
                165                 170                 175

Ser Val Tyr Glu Leu Asp Cys Ile Pro Leu Trp Gly Thr Val Ser Ile
            180                 185                 190

Gln Gly Asn Ala Ser Glu Met Glu Ala Ala Phe Ala Val Ser Pro His
            195                 200                 205

Phe Leu Lys Leu Pro Ile Lys Met Leu Met Gly Asp His Glu Gly Met
            210                 215                 220

Ser Pro Ser Leu Thr His Leu Thr Gly His Phe Phe Gly Val Tyr Asp
225                 230                 235                 240

Gly His Gly Gly His Lys Val Ala Asp Tyr Cys Arg Asp Arg Leu His
                245                 250                 255

Phe Ala Leu Ala Glu Glu Ile Glu Arg Ile Lys Asp Glu Leu Cys Lys
            260                 265                 270

Arg Asn Thr Gly Glu Gly Arg Gln Val Gln Trp Asp Lys Val Phe Thr
            275                 280                 285

Ser Cys Phe Leu Thr Val Asp Gly Glu Ile Glu Gly Lys Ile Gly Arg
            290                 295                 300

Ala Val Val Gly Ser Ser Asp Lys Val Leu Glu Ala Val Ala Asp Glu
305                 310                 315                 320

Thr Val Gly Ser Thr Ala Val Ala Leu Val Cys Ser Ser His Ile
            325                 330                 335

Val Val Ser Asn Cys Gly Asp Ser Arg Ala Val Leu Phe Arg Gly Lys
            340                 345                 350

Glu Ala Met Pro Leu Ser Val Asp His Lys Pro Asp Arg Glu Asp Glu
            355                 360                 365

Tyr Ala Arg Ile Glu Asn Ala Gly Gly Lys Val Ile Gln Trp Gln Gly
            370                 375                 380

Ala Arg Val Phe Gly Arg Leu Ala Met Ser Arg Ser Ile Gly Asp Arg
385                 390                 395                 400

Tyr Leu Lys Pro Tyr Val Ile Pro Glu Pro Glu Val Thr Phe Met Pro
                405                 410                 415

Arg Ser Arg Glu Asp Glu Cys Leu Ile Leu Ala Ser Asp Gly Leu Trp
            420                 425                 430

Asp Val Met Asn Asn Gln Glu Val Cys Glu Ile Ala Arg Arg Arg Ile
            435                 440                 445

Leu Met Trp His Lys Lys Asn Gly Ala Pro Pro Leu Ala Glu Arg Gly
            450                 455                 460

Lys Gly Ile Asp Pro Ala Cys Gln Ala Ala Asp Tyr Leu Ser Met
465                 470                 475                 480

Leu Ala Leu Gln Lys Gly Ser Lys Asp Asn Ile Ser Ile Ile Val Ile
            485                 490                 495

Asp Leu Lys Ala Gln Ala Lys Phe Lys Thr Arg Thr
            500                 505
```

<210> SEQ ID NO 32
<211> LENGTH: 330
<212> TYPE: PRT
<213> ORGANISM: Artificial Sequence
<220> FEATURE:
<223> OTHER INFORMATION: Synthetic Construct

<400> SEQUENCE: 32

```
Met Asp Lys Ala Glu Leu Ile Pro Glu Pro Pro Lys Lys Arg Lys
1               5                   10                  15

Val Glu Leu Gly Thr Ala Ala Asn Phe Asn Gln Ser Gly Asn Ile Ala
            20                  25                  30

Asp Ser Ser Leu Ser Phe Thr Phe Thr Asn Ser Ser Asn Gly Pro Asn
        35                  40                  45

Leu Ile Thr Thr Gln Thr Asn Ser Gln Ala Leu Ser Gln Pro Ile Ala
    50                  55                  60

Ser Ser Asn Val His Asp Asn Phe Met Asn Asn Glu Ile Thr Ala Ser
65                  70                  75                  80

Lys Ile Asp Asp Gly Asn Asn Ser Lys Pro Leu Ser Pro Gly Trp Thr
                85                  90                  95

Asp Gln Thr Ala Tyr Asn Ala Phe Gly Ile Thr Thr Gly Met Phe Asn
            100                 105                 110

Thr Thr Thr Met Asp Asp Val Tyr Asn Tyr Leu Phe Asp Asp Glu Asp
        115                 120                 125

Thr Pro Pro Asn Pro Lys Lys Glu Ile Glu Leu Met Pro Ser Glu Leu
    130                 135                 140

Thr Pro Glu Glu Arg Ser Glu Leu Lys Asn Ser Ile Ala Glu Phe His
145                 150                 155                 160

Thr Tyr Gln Leu Asp Pro Gly Ser Cys Ser Ser Leu His Ala Gln Arg
                165                 170                 175

Ile His Ala Pro Pro Glu Leu Val Trp Ser Ile Val Arg Arg Phe Asp
            180                 185                 190

Lys Pro Gln Thr His Arg His Phe Ile Lys Ser Cys Ser Val Glu Gln
        195                 200                 205

Asn Phe Glu Met Arg Val Gly Cys Thr Arg Asp Ile Ile Val Ile Ser
    210                 215                 220

Gly Leu Pro Ala Asn Thr Ser Thr Glu Arg Leu Asp Ile Leu Asp Asp
225                 230                 235                 240

Glu Arg Arg Val Thr Gly Ala Ser Ile Ile Gly Gly Glu His Arg Leu
                245                 250                 255

Thr Asn Tyr Lys Gly Val Thr Val His Arg Phe Glu Lys Glu Asn
            260                 265                 270

Arg Ile Trp Thr Val Val Leu Glu Ser Tyr Val Val Asp Met Pro Glu
        275                 280                 285

Gly Asn Ser Glu Asp Asp Thr Arg Ile Val Asp Asp Val Val Lys
    290                 295                 300

Leu Asn Leu Gln Lys Leu Ala Thr Val Ala Glu Ala Met Ala Arg Asn
305                 310                 315                 320

Ser Gly Asp Gly Ser Gly Ser Gln Val Thr
                325                 330
```

<210> SEQ ID NO 33
<211> LENGTH: 960
<212> TYPE: PRT
<213> ORGANISM: Artificial Sequence
<220> FEATURE:
<223> OTHER INFORMATION: Synthetic Construct

<400> SEQUENCE: 33

```
Met Gly Ser His His His His His Val Ser Lys Gly Glu Leu
1               5                   10                  15

Phe Thr Gly Val Val Pro Ile Leu Val Glu Leu Asp Gly Asp Val Asn
            20                  25                  30

Gly His Lys Phe Ser Val Ser Gly Glu Gly Glu Gly Asp Ala Thr Tyr
                35                  40                  45

Gly Lys Leu Thr Leu Lys Phe Ile Cys Thr Thr Gly Lys Leu Pro Val
    50                  55                  60

Pro Trp Pro Thr Leu Val Thr Thr Leu Thr Tyr Gly Val Gln Cys Phe
65                  70                  75                  80

Ser Arg Tyr Pro Asp His Met Lys Gln His Asp Phe Phe Lys Ser Ala
                85                  90                  95

Met Pro Glu Gly Tyr Val Gln Glu Arg Thr Ile Phe Phe Lys Asp Asp
            100                 105                 110

Gly Asn Tyr Lys Thr Arg Ala Glu Val Lys Phe Glu Gly Asp Thr Leu
        115                 120                 125

Val Asn Arg Ile Glu Leu Lys Gly Ile Asp Phe Lys Glu Asp Gly Asn
130                 135                 140

Ile Leu Gly His Lys Leu Glu Tyr Asn Tyr Asn Ser His Asn Val Tyr
145                 150                 155                 160

Ile Met Ala Asp Lys Gln Lys Asn Gly Ile Lys Val Asn Phe Lys Ile
                165                 170                 175

Arg His Asn Ile Glu Asp Gly Ser Val Gln Leu Ala Asp His Tyr Gln
            180                 185                 190

Gln Asn Thr Pro Ile Gly Asp Gly Pro Val Leu Leu Pro Asp Asn His
        195                 200                 205

Tyr Leu Ser Thr Gln Ser Ala Leu Ser Lys Asp Pro Asn Glu Lys Arg
210                 215                 220

Asp His Met Val Leu Leu Glu Phe Val Thr Ala Ala Gly Ile Thr Leu
225                 230                 235                 240

Gly Met Asp Glu Leu Tyr Lys Ser Gly Ala Ala Ala Ala Ala Ala Ala
                245                 250                 255

Ala Ala Ala Glu Phe Pro Gly Met Lys Leu Leu Ser Ser Ile Glu Gln
            260                 265                 270

Ala Cys Asp Ile Cys Arg Leu Lys Lys Leu Lys Cys Ser Lys Glu Lys
        275                 280                 285

Pro Lys Cys Ala Lys Cys Leu Lys Asn Asn Trp Glu Cys Arg Tyr Ser
290                 295                 300

Pro Lys Thr Lys Arg Ser Pro Leu Thr Arg Ala His Leu Thr Glu Val
305                 310                 315                 320

Glu Ser Arg Leu Glu Arg Leu Glu Gln Leu Phe Leu Leu Ile Phe Pro
                325                 330                 335

Arg Glu Asp Leu Asp Met Ile Leu Lys Met Asp Ser Leu Gln Asp Ile
            340                 345                 350

Lys Ala Leu Leu Thr Gly Leu Phe Val Gln Asp Asn Val Asn Lys Asp
        355                 360                 365

Ala Val Thr Asp Arg Leu Ala Ser Val Glu Thr Asp Met Pro Leu Thr
370                 375                 380

Leu Arg Gln His Arg Ile Ser Ala Thr Ser Ser Ser Glu Glu Ser Ser
385                 390                 395                 400

Asn Lys Gly Gln Arg Gln Leu Thr Val Ser Pro Glu Leu Gly Gly Gly
```

```
                405                 410                 415
Gly Ser Gly Gly Gly Ser Gly Gly Ser Gly Arg Asp Leu Pro Glu
            420             425             430
Met Thr Pro Ala Val Ala Met Thr Leu Ser Leu Ala Ala Asn Thr Met
        435                 440             445
Cys Glu Ser Ser Pro Val Glu Ile Thr Gln Leu Lys Asn Val Thr Asp
    450                 455                 460
Ala Ala Asp Leu Leu Ser Asp Ser Glu Asn Gln Ser Phe Cys Asn Gly
465             470                 475                 480
Gly Thr Glu Cys Thr Met Glu Asp Val Ser Glu Leu Glu Val Gly
            485                 490                 495
Glu Gln Asp Leu Leu Lys Thr Leu Ser Asp Thr Arg Ser Gly Ser Ser
            500             505                 510
Asn Val Phe Asp Glu Asp Asp Val Leu Ser Val Glu Asp Asn Ser
            515                 520                 525
Ala Val Ile Ser Glu Gly Leu Leu Val Asp Ala Gly Ser Glu Leu
            530             535                 540
Ser Leu Ser Asn Thr Ala Met Glu Ile Asp Asn Gly Arg Val Leu Ala
545                 550                 555                 560
Thr Ala Ile Ile Val Gly Glu Ser Ser Ile Glu Gln Val Pro Thr Ala
                565                 570                 575
Glu Val Leu Ile Ala Gly Val Asn Gln Asp Thr Asn Thr Ser Glu Val
            580                 585                 590
Val Ile Arg Leu Pro Asp Glu Asn Ser Asn His Leu Val Lys Gly Arg
            595                 600                 605
Ser Val Tyr Glu Leu Asp Cys Ile Pro Leu Trp Gly Thr Val Ser Ile
            610                 615                 620
Gln Gly Asn Ala Ser Glu Met Glu Ala Ala Phe Ala Val Ser Pro His
625                 630                 635                 640
Phe Leu Lys Leu Pro Ile Lys Met Leu Met Gly Asp His Glu Gly Met
                645                 650                 655
Ser Pro Ser Leu Thr His Leu Thr Gly His Phe Phe Gly Val Tyr Asp
            660                 665                 670
Gly His Gly Gly His Lys Val Ala Asp Tyr Cys Arg Asp Arg Leu His
        675                 680                 685
Phe Ala Leu Ala Glu Glu Ile Glu Arg Ile Lys Asp Glu Leu Cys Lys
        690                 695                 700
Arg Asn Thr Gly Glu Gly Arg Gln Val Gln Trp Asp Lys Val Phe Thr
705             710                 715                 720
Ser Cys Phe Leu Thr Val Asp Gly Glu Ile Glu Gly Lys Ile Gly Arg
            725                 730                 735
Ala Val Val Gly Ser Ser Asp Lys Val Leu Glu Ala Val Ala Asp Glu
            740                 745                 750
Thr Val Gly Ser Thr Ala Val Val Ala Leu Val Cys Ser Ser His Ile
            755                 760                 765
Val Val Ser Asn Cys Gly Asp Ser Arg Ala Val Leu Phe Arg Gly Lys
            770                 775                 780
Glu Ala Met Pro Leu Ser Val Asp His Lys Pro Asp Arg Glu Asp Glu
785                 790                 795                 800
Tyr Ala Arg Ile Glu Asn Ala Gly Gly Lys Val Ile Gln Trp Gln Gly
                805                 810                 815
Ala Arg Val Phe Gly Arg Leu Ala Met Ser Arg Ser Ile Gly Asp Arg
            820                 825                 830
```

```
Tyr Leu Lys Pro Tyr Val Ile Pro Glu Pro Glu Val Thr Phe Met Pro
            835                 840                 845

Arg Ser Arg Glu Asp Glu Cys Leu Ile Leu Ala Ser Asp Gly Leu Trp
        850                 855                 860

Asp Val Met Asn Asn Gln Glu Val Cys Glu Ile Ala Arg Arg Arg Ile
865                 870                 875                 880

Leu Met Trp His Lys Lys Asn Gly Ala Pro Pro Leu Ala Glu Arg Gly
                885                 890                 895

Lys Gly Ile Asp Pro Ala Cys Gln Ala Ala Asp Tyr Leu Ser Met
            900                 905                 910

Leu Ala Leu Gln Lys Gly Ser Lys Asp Asn Ile Ser Ile Ile Val Ile
            915                 920                 925

Asp Leu Lys Ala Gln Ala Lys Phe Lys Thr Arg Thr Leu Asp Leu Ala
            930                 935                 940

Ser Leu Ile Leu Leu Gln Leu Pro Pro Leu Glu Arg Leu Thr Leu Asp
945                 950                 955                 960

<210> SEQ ID NO 34
<211> LENGTH: 693
<212> TYPE: PRT
<213> ORGANISM: Artificial Sequence
<220> FEATURE:
<223> OTHER INFORMATION: Synthetic Construct

<400> SEQUENCE: 34

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
        50                  55                  60

Glu Gln Leu Phe Leu Leu Ile Phe Pro Arg Glu Asp Leu Asp Met Ile
65              70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
            115                 120                 125

Ala Thr Ser Ser Ser Glu Glu Ser Ser Asn Lys Gly Gln Arg Gln Leu
        130                 135                 140

Thr Val Ser Pro Glu Leu Leu Asp Leu Ala Ser Leu Ile Leu Gly Gly
145                 150                 155                 160

Gly Gly Ser Gly Gly Gly Ser Gly Gly Gly Ser Gly Arg Asp Leu Pro
                165                 170                 175

Glu Met Thr Pro Ala Val Ala Met Thr Leu Ser Leu Ala Ala Asn Thr
            180                 185                 190

Met Cys Glu Ser Ser Pro Val Glu Ile Thr Gln Leu Lys Asn Val Thr
            195                 200                 205

Asp Ala Ala Asp Leu Leu Ser Asp Ser Glu Asn Gln Ser Phe Cys Asn
        210                 215                 220

Gly Gly Thr Glu Cys Thr Met Glu Asp Val Ser Glu Leu Glu Glu Val
225                 230                 235                 240
```

-continued

```
Gly Glu Gln Asp Leu Leu Lys Thr Leu Ser Asp Thr Arg Ser Gly Ser
                245                 250                 255

Ser Asn Val Phe Asp Glu Asp Val Leu Ser Val Val Glu Asp Asn
            260                 265                 270

Ser Ala Val Ile Ser Glu Gly Leu Leu Val Val Asp Ala Gly Ser Glu
            275                 280                 285

Leu Ser Leu Ser Asn Thr Ala Met Glu Ile Asp Asn Gly Arg Val Leu
            290                 295                 300

Ala Thr Ala Ile Ile Val Gly Glu Ser Ser Ile Glu Gln Val Pro Thr
305                 310                 315                 320

Ala Glu Val Leu Ile Ala Gly Val Asn Gln Asp Thr Asn Thr Ser Glu
                325                 330                 335

Val Val Ile Arg Leu Pro Asp Glu Asn Ser Asn His Leu Val Lys Gly
                340                 345                 350

Arg Ser Val Tyr Glu Leu Asp Cys Ile Pro Leu Trp Gly Thr Val Ser
            355                 360                 365

Ile Gln Gly Asn Ala Ser Glu Met Glu Ala Ala Phe Ala Val Ser Pro
370                 375                 380

His Phe Leu Lys Leu Pro Ile Lys Met Leu Met Gly Asp His Glu Gly
385                 390                 395                 400

Met Ser Pro Ser Leu Thr His Leu Thr Gly His Phe Phe Gly Val Tyr
                405                 410                 415

Asp Gly His Gly Gly His Lys Val Ala Asp Tyr Cys Arg Asp Arg Leu
            420                 425                 430

His Phe Ala Leu Ala Glu Glu Ile Glu Arg Ile Lys Asp Glu Leu Cys
            435                 440                 445

Lys Arg Asn Thr Gly Glu Gly Arg Gln Val Gln Trp Asp Lys Val Phe
450                 455                 460

Thr Ser Cys Phe Leu Thr Val Asp Gly Glu Ile Glu Gly Lys Ile Gly
465                 470                 475                 480

Arg Ala Val Val Gly Ser Ser Asp Lys Val Leu Glu Ala Val Ala Asp
                485                 490                 495

Glu Thr Val Gly Ser Thr Ala Val Val Ala Leu Val Cys Ser Ser His
            500                 505                 510

Ile Val Val Ser Asn Cys Gly Asp Ser Arg Ala Val Leu Phe Arg Gly
            515                 520                 525

Lys Glu Ala Met Pro Leu Ser Val Asp His Lys Pro Asp Arg Glu Asp
530                 535                 540

Glu Tyr Ala Arg Ile Glu Asn Ala Gly Gly Lys Val Ile Gln Trp Gln
545                 550                 555                 560

Gly Ala Arg Val Phe Gly Arg Leu Ala Met Ser Arg Ser Ile Gly Asp
                565                 570                 575

Arg Tyr Leu Lys Pro Tyr Val Ile Pro Glu Pro Glu Val Thr Phe Met
            580                 585                 590

Pro Arg Ser Arg Glu Asp Glu Cys Leu Ile Leu Ala Ser Asp Gly Leu
            595                 600                 605

Trp Asp Val Met Asn Asn Gln Glu Val Cys Glu Ile Ala Arg Arg
610                 615                 620

Ile Leu Met Trp His Lys Lys Asn Gly Ala Pro Pro Leu Ala Glu Arg
625                 630                 635                 640

Gly Lys Gly Ile Asp Pro Ala Cys Gln Ala Ala Asp Tyr Leu Ser
                645                 650                 655
```

```
Met Leu Ala Leu Gln Lys Gly Ser Lys Asp Asn Ile Ser Ile Ile Val
                660                 665                 670

Ile Asp Leu Lys Ala Gln Ala Lys Phe Lys Thr Arg Thr Leu Asp Leu
            675                 680                 685

Ala Ser Leu Ile Leu
        690

<210> SEQ ID NO 35
<211> LENGTH: 137
<212> TYPE: PRT
<213> ORGANISM: Artificial Sequence
<220> FEATURE:
<223> OTHER INFORMATION: Synthetic Activation Domain (AD) amino acid
      sequence

<400> SEQUENCE: 35

Met Asp Lys Ala Glu Leu Ile Pro Glu Pro Lys Lys Arg Lys
1               5                   10                  15

Val Glu Leu Gly Thr Ala Ala Asn Phe Asn Gln Ser Gly Asn Ile Ala
            20                  25                  30

Asp Ser Ser Leu Ser Phe Thr Phe Thr Asn Ser Ser Asn Gly Pro Asn
        35                  40                  45

Leu Ile Thr Thr Gln Thr Asn Ser Gln Ala Leu Ser Gln Pro Ile Ala
    50                  55                  60

Ser Ser Asn Val His Asp Asn Phe Met Asn Asn Glu Ile Thr Ala Ser
65                  70                  75                  80

Lys Ile Asp Asp Gly Asn Asn Ser Lys Pro Leu Ser Pro Gly Trp Thr
                85                  90                  95

Asp Gln Thr Ala Tyr Asn Ala Phe Gly Ile Thr Thr Gly Met Phe Asn
            100                 105                 110

Thr Thr Thr Met Asp Asp Val Tyr Asn Tyr Leu Phe Asp Asp Glu Asp
        115                 120                 125

Thr Pro Pro Asn Pro Lys Lys Glu Ile
    130                 135

<210> SEQ ID NO 36
<211> LENGTH: 148
<212> TYPE: PRT
<213> ORGANISM: Artificial Sequence
<220> FEATURE:
<223> OTHER INFORMATION: Synthetic DNA Binding Domain (BD) amino acid
      sequence

<400> SEQUENCE: 36

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110
```

Ser Val Glu Thr Asp Met Pro Leu Thr Leu Arg Gln His Arg Ile Ser
            115                 120                 125

Ala Thr Ser Ser Ser Glu Glu Ser Ser Asn Lys Gly Gln Arg Gln Leu
        130                 135                 140

Thr Val Ser Pro
145

<210> SEQ ID NO 37
<211> LENGTH: 7
<212> TYPE: PRT
<213> ORGANISM: Artificial Sequence
<220> FEATURE:
<223> OTHER INFORMATION: Synthetic Nuclear localization sequence

<400> SEQUENCE: 37

Pro Lys Lys Lys Arg Lys Val
1               5

<210> SEQ ID NO 38
<211> LENGTH: 18
<212> TYPE: PRT
<213> ORGANISM: Artificial Sequence
<220> FEATURE:
<223> OTHER INFORMATION: Synthetic Nuclear export sequence

<400> SEQUENCE: 38

Leu Ala Ser Leu Ile Leu Leu Gln Leu Pro Pro Leu Glu Arg Leu Thr
1               5                   10                  15

Leu Asp

<210> SEQ ID NO 39
<211> LENGTH: 8
<212> TYPE: PRT
<213> ORGANISM: Artificial Sequence
<220> FEATURE:
<223> OTHER INFORMATION: Synthetic Nuclear export sequence

<400> SEQUENCE: 39

Leu Asp Leu Ala Ser Leu Ile Leu
1               5

<210> SEQ ID NO 40
<211> LENGTH: 1277
<212> TYPE: DNA
<213> ORGANISM: Artificial Sequence
<220> FEATURE:
<223> OTHER INFORMATION: Synthetic Construct

<400> SEQUENCE: 40
agctccggag tactgtcctc cgagcggagt actgtcctcc gagcggagta ctgtcctccg      60
agcggagtac tgtcctccga gcggagtact gtcctccgag caagaccct tcctctatat     120 aaggaagttc atttcatttg gagagaacac ggggactcta gcgctaccgg tatgggcagc     180
catcatcatc atcatcacgt gagcaagggc gaggagctgt tcaccggggt ggtgcccatc     240
ctggtcgagc tggacggcga cgtaaacggc cacaagttca gcgtgtccgg cgagggcgag     300
ggcgatgcca cctacggcaa gctgaccctg aagttcatct gcaccaccgg caagctgccc     360
gtgccctggc ccaccctcgt gaccaccctg acctacggcg tgcagtgctt cagccgctac     420
cccgaccaca tgaagcagca cgacttcttc aagtccgcca tgcccgaagg ctacgtccag     480
gagcgcacca tcttcttcaa ggacgacggc aactacaaga cccgcgccga ggtgaagttc     540
gagggcgaca cccctggtgaa ccgcatcgag ctgaagggca tcgacttcaa ggaggacggc     600

```
aacatcctgg ggcacaagct ggagtacaac tacaacagcc acaacgtcta tatcatggcc      660
gacaagcaga agaacggcat caaggtgaac ttcaagatcc gccacaacat cgaggacggc      720
agcgtgcagc tcgccgacca ctaccagcag aacacccca tcggcgacgg ccccgtgctg       780
ctgcccgaca ccactacct gagcacccag tccgccctga gcaaagaccc caacgagaag       840
cgcgatcaca tggtcctgct ggagttcgtg accgccgccg ggatcactct cggcatggac      900
gagctgtaca agtccggagc tgcggccgct gccgctgcgg cagcggccga attcccggg       960 ctcgagaagc ttggatccta ggtcgaggcg aatttccccg atcgttcaaa catttggcaa     1020
taaagtttct taagattgaa tcctgttgcc ggtcttgcga tgattatcat ataatttctg     1080
ttgaattacg ttaagcatgt aataattaac atgtaatgca tgacgttatt tatgagatgg     1140
gtttttatga ttagagtccc gcaattatac atttaatacg cgatagaaaa caaaatatag     1200
cgcgcaaact aggataaatt atcgcgcgcg gtgtcatcta tgttactaga tcgggaatta     1260
attcgataag ctagaga                                                    1277
```

<210> SEQ ID NO 41
<211> LENGTH: 191
<212> TYPE: PRT
<213> ORGANISM: Brassica oleracea

<400> SEQUENCE: 41

```
Met Pro Ser Gln Leu Thr Pro Glu Glu Arg Ser Glu Leu Ala Gln Ser
1               5                   10                  15

Ile Ala Glu Phe His Thr Tyr His Leu Gly Pro Gly Ser Cys Ser Ser
                20                  25                  30

Leu His Ala Gln Arg Ile His Ala Pro Pro Glu Ile Val Trp Ser Val
            35                  40                  45

Val Arg Arg Phe Asp Lys Pro Gln Thr Tyr Lys His Phe Ile Lys Ser
        50                  55                  60

Cys Ser Val Glu Asp Gly Phe Glu Met Arg Val Gly Cys Thr Arg Ala
65                  70                  75                  80

Val Asn Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Arg Arg Ile Trp Thr Val Val Leu Glu Ser Tyr Val
    130                 135                 140

Val Asp Met Pro Glu Gly Asn Ser Glu Asp Asp Thr Arg Met Phe Ala
145                 150                 155                 160

Asp Thr Val Val Lys Leu Asn Leu Gln Lys Leu Ala Thr Val Thr Glu
                165                 170                 175

Ala Met Ala Arg Asn Ala Gly Asp Gly Ser Gly Ala Gln Val Thr
            180                 185                 190
```

<210> SEQ ID NO 42
<211> LENGTH: 281
<212> TYPE: PRT
<213> ORGANISM: Brassica oleracea

<400> SEQUENCE: 42

```
Met Pro Ser Glu Leu Thr Gln Glu Glu Arg Ser Lys Leu Thr Gln Ser
1               5                   10                  15
```

Ile Ser Glu Phe His Thr Tyr His Leu Gly Pro Gly Ser Cys Ser Ser
            20                  25                  30

Leu His Ala Gln Arg Ile His Ala Pro Pro Glu Ile Val Trp Ser Val
        35                  40                  45

Val Arg Gln Phe Asp Lys Pro Gln Thr Tyr Lys His Phe Ile Lys Ser
50                  55                  60

Cys Ser Val Glu Glu Gly Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95

Asp Met Leu Asp Asp Glu Arg Arg Val Thr Gly Phe Ser Ile Ile Gly
            100                 105                 110

Gly Glu His Arg Leu Lys Asn Tyr Lys Ser Val Thr Thr Val His Arg
        115                 120                 125

Phe Glu Arg Glu Arg Ile Trp Thr Val Val Leu Glu Ser Tyr Val
    130                 135                 140

Val Asp Met Pro Glu Gly Asn Ser Glu Asp Thr Arg Met Phe Ala
145                 150                 155                 160

Asp Thr Val Val Lys Leu Asn Leu Gln Lys Leu Ala Thr Val Thr Glu
                165                 170                 175

Ala Met Ala Arg Asn Ala Gly Asp Gly Arg Gly Ser Arg Glu Thr Thr
            180                 185                 190

Cys Arg Glu Ser Phe His Leu Ile Thr Ala Phe Glu Lys Gln Arg Gln
        195                 200                 205

Ile Thr Glu Pro Thr Val Tyr Gln Asn Pro Pro Tyr His Thr Gly Met
    210                 215                 220

Thr Pro Glu Pro Arg Thr Ser Thr Val Phe Ile Glu Leu Glu Asp His
225                 230                 235                 240

Arg Thr Leu Pro Gly Asn Leu Thr Pro Thr Thr Glu Glu His Leu Gln
                245                 250                 255

Arg Met Tyr Gln Arg Phe Trp Gly Ile Arg Gln Leu Gln Arg Pro Arg
            260                 265                 270

Gln Ser Phe Gly Glu Arg Gln Ser Ile
        275                 280

<210> SEQ ID NO 43
<211> LENGTH: 453
<212> TYPE: PRT
<213> ORGANISM: Vitis vinifera

<400> SEQUENCE: 43

Met Gln Met Lys Tyr Leu Glu Gly Lys Gln Asn Leu Met Glu Glu Lys
1               5                   10                  15

Gly Glu Lys Gln Cys Ile Pro Met Asp Leu Ala Val Arg Glu Ala Gln
            20                  25                  30

Phe Lys Gly Ser Leu Leu Asp Arg Ile Thr Trp Leu Glu Gln Arg Leu
        35                  40                  45

His Lys Leu Ser Leu Gln Leu Glu Thr Arg Ser Lys Gln Gln Pro His
    50                  55                  60

Pro Ser Arg Met Gln Thr Ala Gly Glu Thr Ser Ser Arg His Gly Pro
65                  70                  75                  80

Lys Lys Glu Leu Ser Cys Ser Phe Pro Val Phe Ser Thr Arg Asn His
                85                  90                  95

Asn His Gly His Lys Gln Thr Ser Gln Phe His Val Pro Arg Phe Glu

```
            100                 105                 110
Tyr Gln Glu Gly Gly Arg Glu Asn Pro Ala Val Val Ile Thr Lys Leu
        115                 120                 125

Thr Pro Phe His His Pro Lys Ile Ile Thr Ile Leu Phe Pro Ile Ser
    130                 135                 140

Asn Tyr Phe Ile Ile Phe Phe Leu Thr Phe Asp Thr Lys Lys Gln
145                 150                 155                 160

Tyr Pro Leu Leu Phe Pro Ile Leu Pro Ser Arg Phe Leu Pro Ile Ser
                165                 170                 175

His Leu Ile Thr Gln Glu Ile Glu Lys Tyr Lys Thr Ser Ser His Phe
            180                 185                 190

Ser Ser Pro Ala Ser Leu Phe Ala Ala Met Asn Lys Ala Glu Thr Ser
        195                 200                 205

Ser Met Ala Glu Ala Glu Ser Glu Asp Ser Thr Thr Thr Pro Thr
    210                 215                 220

Thr His His Leu Thr Ile Pro Pro Gly Leu Thr Gln Pro Glu Phe Gln
225                 230                 235                 240

Glu Leu Ala His Ser Ile Ser Glu Phe His Thr Tyr Gln Val Gly Pro
                245                 250                 255

Gly Gln Cys Ser Ser Leu Leu Ala Gln Arg Val His Ala Pro Leu Pro
            260                 265                 270

Thr Val Trp Ser Val Val Arg Arg Phe Asp Lys Pro Gln Thr Tyr Lys
        275                 280                 285

His Phe Ile Lys Ser Cys His Val Glu Asp Gly Phe Glu Met Arg Val
    290                 295                 300

Gly Cys Leu Arg Asp Val Asn Val Ile Ser Gly Leu Pro Ala Glu Thr
305                 310                 315                 320

Ser Thr Glu Arg Leu Asp Ile Leu Asp Asp Glu Arg His Val Thr Gly
                325                 330                 335

Phe Ser Ile Ile Gly Gly Glu His Arg Leu Arg Asn Tyr Arg Ser Val
            340                 345                 350

Thr Thr Asn His Gly Gly Glu Ile Trp Thr Val Val Leu Glu Ser Tyr
        355                 360                 365

Val Val Asp Met Pro Glu Gly Asn Thr Glu Glu Asp Thr Arg Leu Phe
    370                 375                 380

Ala Asp Thr Val Val Lys Leu Asn Leu Gln Lys Leu Ala Ser Val Thr
385                 390                 395                 400

Glu Val Ser Gln Ser Cys Asn Tyr Pro Cys Gln Phe His Ile Ile Glu
                405                 410                 415

Asn Glu Asp Ile Gln Pro Glu Glu Met Asn Leu Gly Val Leu Thr Thr
            420                 425                 430

Ser Ile Glu Glu Gln Arg Lys Lys Lys Arg Val Val Ala Met Lys Asp
        435                 440                 445

Gly Ser Thr Ser Ser
    450

<210> SEQ ID NO 44
<211> LENGTH: 195
<212> TYPE: PRT
<213> ORGANISM: Vitis vinifera
<220> FEATURE:
<221> NAME/KEY: VARIANT
<222> LOCATION: (193)..(193)
<223> OTHER INFORMATION: Xaa = any amino acid

<400> SEQUENCE: 44
```

```
Met Ala Glu Ala Glu Ser Gly Asp Ser Glu Thr Thr Pro Thr Thr
1               5                   10                  15

His His Leu Thr Ile Pro Pro Gly Leu Thr Gln Pro Glu Phe Gln Glu
            20                  25                  30

Leu Ala His Ser Ile Ser Glu Phe His Thr Tyr Gln Val Gly Pro Gly
            35                  40                  45

Gln Cys Ser Ser Leu Leu Ala Gln Arg Val His Ala Pro Leu Pro Thr
    50                  55                  60

Val Trp Ser Val Val Arg Arg Phe Asp Lys Pro Gln Thr Tyr Lys His
65              70                  75                  80

Phe Ile Lys Ser Cys His Val Glu Asp Gly Phe Glu Met Arg Val Gly
                85                  90                  95

Cys Leu Arg Asp Val Asn Val Ile Ser Gly Leu Pro Ala Glu Thr Ser
                100                 105                 110

Thr Glu Arg Leu Asp Ile Leu Asp Asp Glu Arg His Val Thr Gly Phe
            115                 120                 125

Ser Ile Ile Gly Gly Glu His Arg Leu Arg Asn Tyr Arg Ser Val Thr
    130                 135                 140

Thr Val His Glu Tyr Gln Asn His Gly Gly Glu Ile Trp Thr Val Val
145                 150                 155                 160

Leu Glu Ser Tyr Val Val Asp Met Pro Glu Gly Asn Thr Glu Glu Asp
                165                 170                 175

Thr Arg Leu Phe Ala Asp Thr Val Val Lys Leu Asn Leu Ser Glu Ala
            180                 185                 190

Xaa Arg Arg
    195

<210> SEQ ID NO 45
<211> LENGTH: 217
<212> TYPE: PRT
<213> ORGANISM: Medicago truncatula

<400> SEQUENCE: 45

Met Glu Lys Ala Glu Ser Ser Thr Ala Ser Thr Ser Asp Gln Asp Ser
1               5                   10                  15

Asp Glu Asn His Arg Thr Gln His His Leu Thr Leu Pro Ser Gly Leu
            20                  25                  30

Arg Gln His Glu Phe Asp Ser Leu Ile Pro Phe Ile Asn Ser His His
            35                  40                  45

Thr Tyr Leu Ile Gly Pro Asn Gln Cys Ser Thr Leu Leu Ala Gln Arg
    50                  55                  60

Ile His Ala Pro Pro Gln Thr Val Trp Ser Val Val Arg Ser Phe Asp
65              70                  75                  80

Lys Pro Gln Ile Tyr Lys His Ile Ile Lys Ser Cys Ser Leu Lys Glu
                85                  90                  95

Gly Phe Gln Met Lys Val Gly Cys Thr Arg Asp Val Asn Val Ile Ser
                100                 105                 110

Gly Leu Pro Ala Ala Thr Ser Thr Glu Arg Leu Asp Val Leu Asp Asp
            115                 120                 125

Glu Arg Arg Val Thr Gly Phe Ser Ile Ile Gly Gly Glu His Arg Leu
            130                 135                 140

Lys Asn Tyr Arg Ser Val Thr Ser Val His Gly Phe Gly Asp Gly Asp
145                 150                 155                 160

Asn Gly Gly Glu Ile Trp Thr Val Val Leu Glu Ser Tyr Val Val Asp
```

```
                    165                 170                 175
Val Pro Glu Gly Asn Thr Glu Asp Thr Arg Leu Phe Ala Asp Thr
                180                 185                 190
Val Val Lys Leu Asn Leu Gln Lys Leu Ala Ser Val Thr Glu Gly Lys
            195                 200                 205
Asn Arg Asp Gly Asp Gly Lys Ser His
        210                 215

<210> SEQ ID NO 46
<211> LENGTH: 212
<212> TYPE: PRT
<213> ORGANISM: Oryza sativa

<400> SEQUENCE: 46

Met Glu Gln Gln Glu Glu Val Pro Pro Pro Ala Gly Leu Gly Leu
1               5                   10                  15
Thr Ala Glu Glu Tyr Ala Gln Val Arg Ala Thr Val Glu Ala His His
                20                  25                  30
Arg Tyr Ala Val Gly Pro Gly Gln Cys Ser Ser Leu Leu Ala Gln Arg
            35                  40                  45
Ile His Ala Pro Pro Ala Ala Val Trp Ala Val Arg Arg Phe Asp
    50                  55                  60
Cys Pro Gln Val Tyr Lys His Phe Ile Arg Ser Cys Val Leu Arg Pro
65                  70                  75                  80
Asp Pro His His Asp Asp Asn Gly Asn Asp Leu Arg Pro Gly Arg Leu
                85                  90                  95
Arg Glu Val Ser Val Ile Ser Gly Leu Pro Ala Ser Thr Ser Thr Glu
            100                 105                 110
Arg Leu Asp Leu Leu Asp Asp Ala His Arg Val Phe Gly Phe Thr Ile
        115                 120                 125
Thr Gly Gly Glu His Arg Leu Arg Asn Tyr Arg Ser Val Thr Thr Val
    130                 135                 140
Ser Gln Leu Asp Glu Ile Cys Thr Leu Val Leu Glu Ser Tyr Ile Val
145                 150                 155                 160
Asp Val Pro Asp Gly Asn Thr Glu Asp Thr Arg Leu Phe Ala Asp
                165                 170                 175
Thr Val Ile Arg Leu Asn Leu Gln Lys Leu Lys Ser Val Ser Glu Ala
            180                 185                 190
Asn Ala Asn Ala Ala Ala Ala Ala Ala Pro Pro Pro Pro Pro
        195                 200                 205
Ala Ala Ala Glu
    210

<210> SEQ ID NO 47
<211> LENGTH: 212
<212> TYPE: PRT
<213> ORGANISM: Zea mays

<400> SEQUENCE: 47

Met Asp Gln Gln Gly Ala Gly Gly Asp Ala Glu Val Pro Ala Gly Leu
1               5                   10                  15
Gly Leu Thr Ala Ala Glu Tyr Glu Gln Leu Arg Ser Thr Val Asp Ala
                20                  25                  30
His His Arg Tyr Ala Val Gly Glu Gly Gln Cys Ser Ser Leu Leu Ala
            35                  40                  45
Gln Arg Ile His Ala Pro Pro Glu Ala Val Trp Ala Val Val Arg Arg
```

```
                50                  55                  60
Phe Asp Cys Pro Gln Val Tyr Lys His Phe Ile Arg Ser Cys Ala Leu
 65                  70                  75                  80

Arg Pro Asp Pro Glu Ala Gly Asp Ala Leu Cys Pro Gly Arg Leu Arg
                 85                  90                  95

Glu Val Ser Val Ile Ser Gly Leu Pro Ala Ser Thr Ser Thr Glu Arg
                100                 105                 110

Leu Asp Leu Leu Asp Asp Ala Ala Arg Val Phe Gly Phe Ser Ile Thr
            115                 120                 125

Gly Gly Glu His Arg Leu Arg Asn Tyr Arg Ser Val Thr Thr Val Ser
        130                 135                 140

Glu Leu Ala Val Pro Ala Ile Cys Thr Val Val Leu Glu Ser Tyr Val
145                 150                 155                 160

Val Asp Val Pro Asp Gly Asn Thr Glu Asp Asp Thr Arg Leu Phe Ala
                165                 170                 175

Asp Thr Val Ile Arg Leu Asn Leu Gln Lys Leu Lys Ser Val Ala Glu
            180                 185                 190

Ala Asn Ala Ala Glu Ala Ala Ala Thr Thr Asn Ser Val Leu Leu Pro
        195                 200                 205

Arg Pro Ala Glu
    210

<210> SEQ ID NO 48
<211> LENGTH: 212
<212> TYPE: PRT
<213> ORGANISM: Zea mays
<220> FEATURE:
<221> NAME/KEY: VARIANT
<222> LOCATION: (11)..(11)
<223> OTHER INFORMATION: Xaa = any amino acid

<400> SEQUENCE: 48

Met Asp Gln Gln Gly Ala Gly Gly Asp Ala Xaa Val Pro Ala Gly Leu
 1               5                  10                  15

Gly Leu Thr Ala Ala Glu Tyr Glu Gln Leu Arg Ser Thr Val Asp Ala
                20                  25                  30

His His Arg Tyr Ala Val Gly Glu Gly Gln Cys Ser Ser Leu Leu Ala
            35                  40                  45

Gln Arg Ile His Ala Pro Pro Glu Ala Val Trp Ala Val Val Arg Arg
        50                  55                  60

Phe Asp Cys Pro Gln Val Tyr Lys His Phe Ile Arg Ser Cys Ala Leu
 65                  70                  75                  80

Arg Pro Asp Pro Glu Ala Gly Asp Ala Leu Cys Pro Gly Arg Leu Arg
                 85                  90                  95

Glu Val Ser Val Ile Ser Gly Leu Pro Ala Ser Thr Ser Thr Glu Arg
                100                 105                 110

Leu Asp Leu Leu Asp Asp Ala Ala Arg Val Phe Gly Phe Ser Ile Thr
            115                 120                 125

Gly Gly Glu His Arg Leu Arg Asn Tyr Arg Ser Val Thr Thr Val Ser
        130                 135                 140

Glu Leu Ala Asp Pro Ala Ile Cys Thr Val Val Leu Glu Ser Tyr Val
145                 150                 155                 160

Val Asp Val Pro Asp Gly Asn Thr Glu Asp Asp Thr Arg Leu Phe Ala
                165                 170                 175

Asp Thr Val Ile Arg Leu Asn Leu Gln Lys Leu Lys Ser Val Thr Glu
            180                 185                 190
```

```
Ala Asn Ala Ala Glu Ala Ala Ala Thr Thr Asn Ser Val Leu Leu Pro
        195                 200                 205

Arg Pro Ala Glu
    210

<210> SEQ ID NO 49
<211> LENGTH: 233
<212> TYPE: PRT
<213> ORGANISM: Vitis vinifera

<400> SEQUENCE: 49

Met Asp Pro His His His His Gly Leu Thr Glu Glu Phe Arg Ala
1               5                   10                  15

Leu Glu Pro Ile Ile Gln Asn Tyr His Thr Phe Glu Pro Ser Pro Asn
            20                  25                  30

Thr Cys Thr Ser Leu Ile Thr Gln Lys Ile Asp Ala Pro Ala Gln Val
        35                  40                  45

Val Trp Pro Phe Val Arg Ser Phe Glu Asn Pro Gln Lys Tyr Lys His
    50                  55                  60

Phe Ile Lys Asp Cys Thr Met Arg Gly Asp Gly Val Gly Ser Ile
65                  70                  75                  80

Arg Glu Val Thr Val Val Ser Gly Leu Pro Ala Ser Thr Ser Thr Glu
                85                  90                  95

Arg Leu Glu Ile Leu Asp Asp Glu Lys His Ile Leu Ser Phe Arg Val
            100                 105                 110

Val Gly Gly Glu His Arg Leu Asn Asn Tyr Arg Ser Val Thr Ser Val
        115                 120                 125

Asn Asp Phe Ser Lys Glu Gly Lys Asp Tyr Thr Ile Val Leu Glu Ser
    130                 135                 140

Tyr Ile Val Asp Ile Pro Glu Gly Asn Thr Gly Glu Asp Thr Lys Met
145                 150                 155                 160

Phe Val Asp Thr Val Val Lys Leu Asn Leu Gln Lys Leu Ala Val Val
                165                 170                 175

Ala Ile Thr Ser Leu His Glu Asn Glu Glu Ile Ala Asp Asn Glu Gly
            180                 185                 190

Pro Ser Arg Glu Ile Ser Leu Gln Ser Glu Thr Glu Ser Ala Glu Arg
        195                 200                 205

Gly Asp Glu Arg Arg Asp Gly Asp Gly Pro Ser Lys Ala Cys Asn Arg
    210                 215                 220

Asn Glu Trp His Cys Thr Thr Lys Glu
225                 230

<210> SEQ ID NO 50
<211> LENGTH: 207
<212> TYPE: PRT
<213> ORGANISM: Oryza sativa

<400> SEQUENCE: 50

Met Glu Pro His Met Glu Arg Ala Leu Arg Glu Ala Val Ala Ser Glu
1               5                   10                  15

Ala Glu Arg Arg Glu Leu Glu Gly Val Val Arg Ala His His Thr Phe
            20                  25                  30

Pro Ala Ala Glu Arg Ala Ala Gly Pro Gly Arg Pro Thr Cys Thr
        35                  40                  45

Ser Leu Val Ala Gln Arg Val Asp Ala Pro Leu Ala Ala Val Trp Pro
    50                  55                  60
```

```
Ile Val Arg Gly Phe Ala Asn Pro Gln Arg Tyr Lys His Phe Ile Lys
 65                  70                  75                  80

Ser Cys Glu Leu Ala Ala Gly Asp Gly Ala Thr Val Gly Ser Val Arg
                 85                  90                  95

Glu Val Ala Val Val Ser Gly Leu Pro Ala Ser Thr Ser Thr Glu Arg
            100                 105                 110

Leu Glu Ile Leu Asp Asp Asp Arg His Val Leu Ser Phe Arg Val Val
        115                 120                 125

Gly Gly Asp His Arg Leu Arg Asn Tyr Arg Ser Val Thr Ser Val Thr
130                 135                 140

Glu Phe Ser Ser Pro Ser Ser Pro Pro Arg Pro Tyr Cys Val Val Val
145                 150                 155                 160

Glu Ser Tyr Val Val Asp Val Pro Glu Gly Asn Thr Glu Glu Asp Thr
                165                 170                 175

Arg Met Phe Thr Asp Thr Val Val Lys Leu Asn Leu Gln Lys Leu Ala
            180                 185                 190

Ala Val Ala Thr Ser Ser Ser Pro Ala Ala Gly Asn His His
        195                 200                 205

<210> SEQ ID NO 51
<211> LENGTH: 210
<212> TYPE: PRT
<213> ORGANISM: Oryza sativa

<400> SEQUENCE: 51

Met Glu Pro His Met Glu Arg Ala Leu Arg Glu Ala Val Ala Ser Glu
 1               5                  10                  15

Ala Glu Arg Arg Glu Leu Glu Gly Val Val Arg Ala His His Thr Phe
            20                  25                  30

Pro Ala Ala Glu Arg Ala Ala Gly Pro Gly Arg Arg Pro Thr Cys Thr
        35                  40                  45

Ser Leu Val Ala Gln Arg Val Asp Ala Pro Leu Ala Ala Val Trp Pro
    50                  55                  60

Ile Val Arg Gly Phe Ala Asn Pro Gln Arg Tyr Lys His Phe Ile Lys
 65                  70                  75                  80

Ser Cys Glu Leu Ala Ala Gly Asp Gly Ala Thr Val Gly Ser Val Arg
                 85                  90                  95

Glu Val Ala Val Val Ser Gly Leu Pro Ala Ser Thr Ser Thr Glu Arg
            100                 105                 110

Leu Glu Ile Leu Asp Asp Asp Arg His Val Leu Ser Phe Arg Val Val
        115                 120                 125

Gly Gly Asp His Arg Leu Arg Asn Tyr Arg Ser Val Thr Ser Val Thr
130                 135                 140

Glu Phe Ser Ser Pro Ser Ser Pro Ser Pro Arg Pro Tyr Cys
145                 150                 155                 160

Val Val Val Glu Ser Tyr Val Val Asp Val Pro Glu Gly Asn Thr Glu
                165                 170                 175

Glu Asp Thr Arg Met Phe Thr Asp Thr Val Val Lys Leu Asn Leu Gln
            180                 185                 190

Lys Leu Ala Ala Val Ala Thr Ser Ser Ser Pro Ala Ala Gly Asn
        195                 200                 205

His His
    210
```

```
<210> SEQ ID NO 52
<211> LENGTH: 200
<212> TYPE: PRT
<213> ORGANISM: Zea mays

<400> SEQUENCE: 52

Met Pro Tyr Thr Ala Pro Arg Pro Ser Pro Gln Gln His Ser Arg Val
1               5                   10                  15

Leu Ser Gly Gly Gly Ala Lys Ala Ala Ser His Gly Ala Ser Cys Ala
            20                  25                  30

Ala Val Pro Ala Glu Val Ala Arg His His Glu His Ala Ala Arg Ala
        35                  40                  45

Gly Gln Cys Cys Ser Ala Val Val Gln Ala Ile Ala Ala Pro Val Gly
    50                  55                  60

Ala Val Trp Ser Val Val Arg Arg Phe Asp Arg Pro Gln Ala Tyr Lys
65                  70                  75                  80

His Phe Ile Arg Ser Cys Arg Leu Val Gly Gly Asp Val Ala Val
                85                  90                  95

Gly Ser Val Arg Glu Val Arg Val Ser Gly Leu Pro Ala Thr Ser
                100                 105                 110

Ser Arg Glu Arg Leu Glu Ile Leu Asp Asp Glu Arg Arg Val Leu Ser
            115                 120                 125

Phe Arg Val Val Gly Gly Glu His Arg Leu Ala Asn Tyr Arg Ser Val
130                 135                 140

Thr Thr Val His Glu Ala Gly Ala Gly Ala Gly Thr Gly Thr Val Val
145                 150                 155                 160

Val Glu Ser Tyr Val Val Asp Val Pro His Gly Asn Thr Ala Asp Glu
                165                 170                 175

Thr Arg Val Phe Val Asp Thr Ile Val Arg Cys Asn Leu Gln Ser Leu
            180                 185                 190

Ala Arg Thr Ala Glu Arg Leu Ala
            195                 200

<210> SEQ ID NO 53
<211> LENGTH: 215
<212> TYPE: PRT
<213> ORGANISM: Vitis vinifera

<400> SEQUENCE: 53

Met Pro Ser Asn Pro Pro Lys Ser Ser Leu Val Val His Arg Ile Asn
1               5                   10                  15

Ser Pro Asn Ser Ile Thr Thr Ala Thr Thr Ala Ser Ala Ala Ala Asn
            20                  25                  30

Asn His Asn Thr Ser Thr Met Pro Pro His Lys Gln Val Pro Asp Ala
            35                  40                  45

Val Ser Arg His His Thr His Val Gly Pro Asn Gln Cys Cys Ser
    50                  55                  60

Ala Val Val Gln Gln Ile Ala Ala Pro Val Ser Thr Val Trp Ser Val
65                  70                  75                  80

Val Arg Arg Phe Asp Asn Pro Gln Ala Tyr Lys His Phe Val Lys Ser
                85                  90                  95

Cys His Val Val Val Gly Asp Gly Asp Val Gly Thr Leu Arg Glu Val
                100                 105                 110

His Val Ile Ser Gly Leu Pro Ala Ala Asn Ser Thr Glu Arg Leu Glu
            115                 120                 125

Ile Leu Asp Asp Glu Arg His Val Leu Ser Phe Ser Val Ile Gly Gly
```

-continued

```
                130                 135                 140
Asp His Arg Leu Ser Asn Tyr Arg Ser Val Thr Thr Leu His Pro Ser
145                 150                 155                 160

Pro Ser Ser Thr Gly Thr Val Val Leu Glu Ser Tyr Val Val Asp Ile
                165                 170                 175

Pro Pro Gly Asn Thr Lys Glu Asp Thr Cys Val Phe Val Asp Thr Ile
            180                 185                 190

Val Arg Cys Asn Leu Gln Ser Leu Ala Gln Ile Ala Glu Asn Ala Ala
            195                 200                 205

Gly Cys Lys Arg Ser Ser Ser
        210                 215
```

<210> SEQ ID NO 54
<211> LENGTH: 213
<212> TYPE: PRT
<213> ORGANISM: Nicotiana tabacum

<400> SEQUENCE: 54

```
Met Pro Pro Ser Ser Pro Asp Ser Ser Val Leu Leu Gln Arg Ile Ser
1               5                   10                  15

Ser Asn Thr Thr Pro Asp Phe Ala Cys Lys Gln Ser Gln Gln Leu Gln
                20                  25                  30

Arg Arg Thr Met Pro Ile Pro Cys Thr Thr Gln Val Pro Asp Ser Val
            35                  40                  45

Val Arg Phe His Thr His Pro Val Gly Pro Asn Gln Cys Cys Ser Ala
        50                  55                  60

Val Ile Gln Arg Ile Ser Ala Pro Val Ser Thr Val Trp Ser Val Val
65                  70                  75                  80

Arg Arg Phe Asp Asn Pro Gln Ala Tyr Lys His Phe Val Lys Ser Cys
                85                  90                  95

His Val Ile Val Gly Asp Gly Asp Val Gly Thr Leu Arg Glu Val Arg
            100                 105                 110

Val Ile Ser Gly Leu Pro Ala Ala Ser Ser Thr Glu Arg Leu Glu Ile
        115                 120                 125

Leu Asp Asp Glu Arg His Val Ile Ser Phe Ser Val Val Gly Gly Asp
    130                 135                 140

His Arg Leu Ala Asn Tyr Arg Ser Val Thr Thr Leu His Pro Glu Pro
145                 150                 155                 160

Ser Gly Asp Gly Thr Thr Ile Val Val Glu Ser Tyr Val Val Asp Val
                165                 170                 175

Pro Pro Gly Asn Thr Arg Asp Glu Thr Cys Val Phe Val Asp Thr Ile
            180                 185                 190

Val Lys Cys Asn Leu Thr Ser Leu Ser Gln Ile Ala Val Asn Val Asn
            195                 200                 205

Arg Arg Lys Asp Ser
        210
```

<210> SEQ ID NO 55
<211> LENGTH: 208
<212> TYPE: PRT
<213> ORGANISM: Oryza sativa

<400> SEQUENCE: 55

```
Met Pro Tyr Ala Ala Val Arg Pro Ser Pro Pro Gln Leu Ser Arg
1               5                   10                  15

Pro Ile Gly Ser Gly Ala Gly Gly Gly Lys Ala Cys Pro Ala Val Pro
```

```
                  20                  25                  30

Cys Glu Val Ala Arg Tyr His Glu His Ala Val Gly Ala Gly Gln Cys
             35                  40                  45

Cys Ser Thr Val Val Gln Ala Ile Ala Ala Pro Ala Asp Ala Val Trp
 50                  55                  60

Ser Val Val Arg Arg Phe Asp Arg Pro Gln Ala Tyr Lys Lys Phe Ile
 65                  70                  75                  80

Lys Ser Cys Arg Leu Val Asp Gly Asp Gly Gly Glu Val Gly Ser Val
                 85                  90                  95

Arg Glu Val Arg Val Val Ser Gly Leu Pro Ala Thr Ser Ser Arg Glu
                100                 105                 110

Arg Leu Glu Val Leu Asp Asp Arg Arg Val Leu Ser Phe Arg Ile
             115                 120                 125

Val Gly Gly Glu His Arg Leu Ala Asn Tyr Arg Ser Val Thr Thr Val
             130                 135                 140

His Glu Ala Ala Ala Pro Ala Met Ala Val Val Glu Ser Tyr Val
145                 150                 155                 160

Val Asp Val Pro Pro Gly Asn Thr Trp Glu Glu Thr Arg Val Phe Val
                165                 170                 175

Asp Thr Ile Val Arg Cys Asn Leu Gln Ser Leu Ala Arg Thr Val Glu
                180                 185                 190

Arg Leu Ala Pro Glu Ala Pro Arg Ala Asn Gly Ser Ile Asp His Ala
             195                 200                 205

<210> SEQ ID NO 56
<211> LENGTH: 208
<212> TYPE: PRT
<213> ORGANISM: Oryza sativa

<400> SEQUENCE: 56

Met Pro Tyr Ala Ala Val Arg Pro Ser Pro Pro Gln Leu Ser Arg
 1               5                  10                  15

Pro Ile Gly Ser Gly Ala Gly Gly Lys Ala Cys Pro Ala Val Pro
                 20                  25                  30

Cys Glu Val Ala Arg Tyr His Glu His Ala Val Gly Ala Gly Gln Cys
             35                  40                  45

Phe Ser Thr Val Val Gln Ala Ile Ala Ala Pro Ala Asp Ala Val Trp
 50                  55                  60

Ser Val Val Arg Arg Phe Asp Arg Pro Gln Ala Tyr Lys Lys Phe Ile
 65                  70                  75                  80

Lys Ser Cys Arg Leu Val Asp Gly Asp Gly Gly Glu Val Gly Ser Val
                 85                  90                  95

Arg Glu Val Arg Val Val Ser Gly Leu Pro Ala Thr Ser Ser Arg Glu
                100                 105                 110

Arg Leu Glu Val Leu Asp Asp Arg Arg Val Leu Ser Phe Arg Ile
             115                 120                 125

Val Gly Gly Glu His Arg Leu Ala Asn Tyr Arg Ser Val Thr Thr Val
             130                 135                 140

His Glu Ala Ala Ala Pro Ala Met Ala Val Val Glu Ser Tyr Val
145                 150                 155                 160

Val Asp Val Pro Pro Gly Asn Thr Trp Glu Glu Thr Arg Val Phe Val
                165                 170                 175

Asp Thr Ile Val Arg Cys Asn Leu Gln Ser Leu Ala Arg Thr Val Glu
                180                 185                 190
```

```
Arg Leu Ala Pro Glu Ala Pro Arg Ala Asn Gly Ser Ile Asp His Ala
            195                 200                 205
```

<210> SEQ ID NO 57
<211> LENGTH: 213
<212> TYPE: PRT
<213> ORGANISM: Picea sitchensis

<400> SEQUENCE: 57

```
Met Asp Ile Ile Ala Gly Phe Asp Gln Leu Ser Phe Arg Leu Ser Gly
1               5                   10                  15

Ala Ser Lys Gln Ile Thr Lys Thr Gly Ala Val Gln Tyr Leu Lys Gly
            20                  25                  30

Glu Glu Gly Tyr Gly Glu Trp Leu Lys Glu Val Met Gly Arg Tyr His
        35                  40                  45

Tyr His Ser His Asp Gly Ala Arg Glu Cys Arg Cys Ser Ser Val Val
    50                  55                  60

Val Gln Gln Val Glu Ala Pro Val Ser Val Val Trp Ser Leu Val Arg
65                  70                  75                  80

Arg Phe Asp Gln Pro Gln Val Tyr Lys His Phe Val Ser Asn Cys Phe
                85                  90                  95

Met Arg Gly Asp Leu Lys Val Gly Cys Leu Arg Glu Val Arg Val Val
            100                 105                 110

Ser Gly Leu Pro Ala Ala Thr Ser Thr Glu Arg Leu Asp Ile Leu Asp
        115                 120                 125

Glu Glu Arg His Ile Leu Ser Phe Ser Ile Val Gly Gly Asp His Arg
    130                 135                 140

Leu Asn Asn Tyr Arg Ser Ile Thr Thr Leu His Glu Thr Leu Ile Asn
145                 150                 155                 160

Gly Lys Pro Gly Thr Ile Val Ile Glu Ser Tyr Val Leu Asp Val Pro
                165                 170                 175

His Gly Asn Thr Lys Glu Glu Thr Cys Leu Phe Val Asp Thr Ile Val
            180                 185                 190

Lys Cys Asn Leu Gln Ser Leu Ala His Val Ser Asn His Leu Asn Ser
        195                 200                 205

Thr His Arg Cys Leu
    210
```

<210> SEQ ID NO 58
<211> LENGTH: 207
<212> TYPE: PRT
<213> ORGANISM: Oryza sativa

<400> SEQUENCE: 58

```
Met Glu Ala His Val Glu Arg Ala Leu Arg Glu Gly Leu Thr Glu Glu
1               5                   10                  15

Glu Arg Ala Ala Leu Glu Pro Ala Val Met Ala His His Thr Phe Pro
            20                  25                  30

Pro Ser Thr Thr Thr Ala Thr Thr Ala Ala Ala Thr Cys Thr Ser Leu
        35                  40                  45

Val Thr Gln Arg Val Ala Ala Pro Val Arg Ala Val Trp Pro Ile Val
    50                  55                  60

Arg Ser Phe Gly Asn Pro Gln Arg Tyr Lys His Phe Val Arg Thr Cys
65                  70                  75                  80

Ala Leu Ala Ala Gly Asp Gly Ala Ser Val Gly Ser Val Arg Glu Val
                85                  90                  95
```

```
Thr Val Val Ser Gly Leu Pro Ala Ser Thr Ser Thr Glu Arg Leu Glu
            100                 105                 110

Met Leu Asp Asp Arg His Ile Ile Ser Phe Arg Val Val Gly Gly
        115                 120                 125

Gln His Arg Leu Arg Asn Tyr Arg Ser Val Thr Ser Val Thr Glu Phe
    130                 135                 140

Gln Pro Pro Ala Ala Gly Pro Gly Pro Ala Pro Pro Tyr Cys Val Val
145                 150                 155                 160

Val Glu Ser Tyr Val Val Asp Val Pro Asp Gly Asn Thr Ala Glu Asp
                165                 170                 175

Thr Arg Met Phe Thr Asp Thr Val Val Lys Leu Asn Leu Gln Met Leu
        180                 185                 190

Ala Ala Val Ala Glu Asp Ser Ser Ala Ser Arg Arg Arg Asp
        195                 200                 205
```

<210> SEQ ID NO 59
<211> LENGTH: 216
<212> TYPE: PRT
<213> ORGANISM: Oryza sativa

<400> SEQUENCE: 59

```
Met Pro Tyr Thr Ala Pro Arg Pro Ser Pro Pro Gln His Ser Arg Ile
1               5                   10                  15

Gly Gly Cys Gly Gly Gly Gly Val Leu Lys Ala Ala Gly Ala Ala Gly
            20                  25                  30

His Ala Ala Ser Cys Val Ala Val Pro Ala Glu Val Ala Arg His His
        35                  40                  45

Glu His Ala Ala Gly Val Gly Gln Cys Cys Ser Ala Val Val Gln Ala
    50                  55                  60

Ile Ala Ala Pro Val Asp Ala Val Trp Ser Val Val Arg Arg Phe Asp
65                  70                  75                  80

Arg Pro Gln Ala Tyr Lys His Phe Ile Arg Ser Cys Arg Leu Leu Asp
                85                  90                  95

Gly Asp Gly Asp Gly Gly Ala Val Ala Val Gly Ser Val Arg Glu Val
            100                 105                 110

Arg Val Val Ser Gly Leu Pro Ala Thr Ser Ser Arg Glu Arg Leu Glu
        115                 120                 125

Ile Leu Asp Asp Glu Arg Arg Val Leu Ser Phe Arg Val Val Gly Gly
    130                 135                 140

Glu His Arg Leu Ser Asn Tyr Arg Ser Val Thr Thr Val His Glu Thr
145                 150                 155                 160

Ala Ala Gly Ala Ala Ala Val Val Glu Ser Tyr Val Val Asp Val
                165                 170                 175

Val Pro His Gly Asn Thr Ala Asp Glu Thr Arg Met Phe Val Asp Thr
        180                 185                 190

Ile Val Arg Cys Asn Leu Gln Ser Leu Ala Arg Thr Ala Glu Gln Leu
    195                 200                 205

Ala Leu Ala Ala Pro Arg Ala Ala
210                 215
```

<210> SEQ ID NO 60
<211> LENGTH: 212
<212> TYPE: PRT
<213> ORGANISM: Vitis vinifera

<400> SEQUENCE: 60

Met Pro Ser Ser Leu Gln Leu His Arg Ile Asn Asn Ile Asp Pro Thr
1               5                   10                  15

Thr Val Ala Val Ala Ala Thr Ala Ala Val Asn Cys His Lys Gln Ser
            20                  25                  30

Arg Thr Pro Leu Arg Cys Ala Thr Pro Val Pro Asp Ala Val Ala Ser
            35                  40                  45

Tyr His Ala His Ala Val Gly Pro His Gln Cys Cys Ser Met Val Val
        50                  55                  60

Gln Thr Thr Ala Ala Ala Leu Pro Thr Val Trp Ser Val Val Arg Arg
65                  70                  75                  80

Phe Asp Asn Pro Gln Ala Tyr Lys His Phe Leu Lys Ser Cys His Val
                85                  90                  95

Ile Phe Gly Asp Gly Asp Ile Gly Thr Leu Arg Glu Val His Val Val
                100                 105                 110

Ser Gly Leu Pro Ala Glu Ser Ser Thr Glu Arg Leu Glu Ile Leu Asp
            115                 120                 125

Asp Glu Arg His Val Leu Ser Phe Ser Val Val Gly Gly Asp His Arg
            130                 135                 140

Leu Cys Asn Tyr Arg Ser Val Thr Thr Leu His Pro Ser Pro Thr Gly
145                 150                 155                 160

Thr Gly Thr Val Val Val Glu Ser Tyr Val Val Asp Ile Pro Pro Gly
                165                 170                 175

Asn Thr Lys Glu Asp Thr Cys Val Phe Val Asp Thr Ile Val Lys Cys
                180                 185                 190

Asn Leu Gln Ser Leu Ala Gln Met Ser Glu Lys Leu Thr Asn Asn Asn
            195                 200                 205

Arg Asn Ser Ser
    210

<210> SEQ ID NO 61
<211> LENGTH: 218
<212> TYPE: PRT
<213> ORGANISM: Zea mays

<400> SEQUENCE: 61

Met Pro Cys Leu Gln Ala Ser Ser Pro Gly Ser Met Pro Tyr Gln His
1               5                   10                  15

His Gly Arg Gly Val Gly Cys Ala Ala Glu Ala Gly Ala Ala Val Gly
            20                  25                  30

Ala Ser Ala Gly Thr Gly Thr Arg Cys Gly Ala His Asp Gly Glu Val
            35                  40                  45

Pro Ala Glu Ala Ala Arg His His Glu His Ala Ala Pro Gly Pro Gly
        50                  55                  60

Arg Cys Cys Ser Ala Val Gln Arg Val Ala Pro Ala Glu Ala
65                  70                  75                  80

Val Trp Ser Val Val Arg Arg Phe Asp Gln Pro Gln Ala Tyr Lys Arg
                85                  90                  95

Phe Val Arg Ser Cys Ala Leu Leu Ala Gly Asp Gly Val Gly Thr
                100                 105                 110

Leu Arg Glu Val Arg Val Val Ser Gly Leu Pro Ala Ala Ser Ser Arg
            115                 120                 125

Glu Arg Leu Glu Val Leu Asp Asp Glu Ser His Val Leu Ser Phe Arg
            130                 135                 140

Val Val Gly Gly Glu His Arg Leu Gln Asn Tyr Leu Ser Val Thr Thr
145                 150                 155                 160

Val His Pro Ser Pro Ala Ala Pro Asp Ala Ala Thr Val Val Glu
            165                 170                 175

Ser Tyr Val Val Asp Val Pro Pro Gly Asn Thr Pro Glu Asp Thr Arg
            180                 185                 190

Val Phe Val Asp Thr Ile Val Lys Cys Asn Leu Gln Ser Leu Ala Thr
            195                 200                 205

Thr Ala Glu Lys Leu Ala Leu Ala Ala Val
        210                 215

<210> SEQ ID NO 62
<211> LENGTH: 179
<212> TYPE: PRT
<213> ORGANISM: Physcomitrella patens

<400> SEQUENCE: 62

Met Gln Thr Lys Gly Arg Gln Ala Asp Phe Gln Thr Leu Leu Glu Gly
1               5                   10                  15

Gln Gln Asp Leu Ile Cys Arg Phe His Arg His Glu Leu Gln Pro His
            20                  25                  30

Gln Cys Gly Ser Ile Leu Leu Gln Leu Ile Lys Ala Pro Val Glu Thr
        35                  40                  45

Val Trp Ser Val Ala Arg Ser Phe Asp Lys Pro Gln Val Tyr Lys Arg
    50                  55                  60

Phe Ile Gln Thr Cys Glu Ile Ile Glu Gly Asp Gly Val Gly Gly Ser
65                  70                  75                  80

Ile Arg Glu Val Arg Leu Val Ser Ser Ile Pro Ala Thr Ser Ser Ile
                85                  90                  95

Glu Arg Leu Glu Ile Leu Asp Asp Glu His Ile Ile Ser Phe Arg
            100                 105                 110

Val Leu Gly Gly Gly His Arg Leu Gln Asn Tyr Trp Ser Val Thr Ser
        115                 120                 125

Leu His Ser His Glu Ile Asp Gly Gln Met Gly Thr Leu Val Leu Glu
    130                 135                 140

Ser Tyr Val Val Asp Ile Pro Glu Gly Asn Thr Arg Glu Glu Thr His
145                 150                 155                 160

Met Phe Val Asp Thr Val Arg Cys Asn Leu Lys Ala Leu Ala Gln
                165                 170                 175

Val Ser Glu

<210> SEQ ID NO 63
<211> LENGTH: 229
<212> TYPE: PRT
<213> ORGANISM: Oryza sativa

<400> SEQUENCE: 63

Met Pro Cys Ile Pro Ala Ser Ser Pro Gly Ile Pro His Gln His Gln
1               5                   10                  15

His Gln His His Arg Ala Leu Ala Gly Val Gly Met Ala Val Gly Cys
            20                  25                  30

Ala Ala Glu Ala Ala Val Ala Ala Ala Gly Val Ala Gly Thr Arg Cys
        35                  40                  45

Gly Ala His Asp Gly Glu Val Pro Met Glu Val Ala Arg His His Glu
    50                  55                  60

His Ala Glu Pro Gly Ser Gly Arg Cys Cys Ser Ala Val Val Gln His
65                  70                  75                  80

```
Val Ala Ala Pro Ala Pro Ala Val Trp Ser Val Val Arg Arg Phe Asp
                85                  90                  95

Gln Pro Gln Ala Tyr Lys Arg Phe Val Arg Ser Cys Ala Leu Leu Ala
            100                 105                 110

Gly Asp Gly Gly Val Gly Thr Leu Arg Glu Val Arg Val Val Ser Gly
        115                 120                 125

Leu Pro Ala Ala Ser Ser Arg Glu Arg Leu Glu Ile Leu Asp Asp Glu
    130                 135                 140

Ser His Val Leu Ser Phe Arg Val Val Gly Gly Glu His Arg Leu Lys
145                 150                 155                 160

Asn Tyr Leu Ser Val Thr Thr Val His Pro Ser Pro Ser Ala Pro Thr
                165                 170                 175

Ala Ala Thr Val Val Val Glu Ser Tyr Val Val Asp Val Pro Pro Gly
            180                 185                 190

Asn Thr Pro Glu Asp Thr Arg Val Phe Val Asp Thr Ile Val Lys Cys
        195                 200                 205

Asn Leu Gln Ser Leu Ala Lys Thr Ala Glu Lys Leu Ala Ala Gly Ala
    210                 215                 220

Arg Ala Ala Gly Ser
225

<210> SEQ ID NO 64
<211> LENGTH: 229
<212> TYPE: PRT
<213> ORGANISM: Oryza sativa

<400> SEQUENCE: 64

Met Pro Cys Ile Pro Ala Ser Ser Pro Gly Ile Pro His Gln His Gln
1               5                   10                  15

His Gln His His Arg Ala Leu Ala Gly Val Gly Met Ala Val Gly Cys
            20                  25                  30

Ala Ala Glu Ala Ala Val Ala Ala Ala Gly Val Ala Gly Thr Arg Cys
        35                  40                  45

Gly Ala His Asp Gly Glu Val Pro Met Glu Val Ala Arg His His Glu
    50                  55                  60

His Ala Glu Pro Gly Ser Gly Arg Cys Cys Ser Ala Val Val Gln His
65                  70                  75                  80

Val Ala Ala Pro Ala Ala Val Trp Ser Val Val Arg Arg Phe Asp
                85                  90                  95

Gln Pro Gln Ala Tyr Lys Arg Phe Val Arg Ser Cys Ala Leu Leu Ala
            100                 105                 110

Gly Asp Gly Gly Val Gly Thr Leu Arg Glu Val Arg Val Val Ser Gly
        115                 120                 125

Leu Pro Ala Ala Ser Ser Arg Glu Arg Leu Glu Ile Leu Asp Asp Glu
    130                 135                 140

Ser His Val Leu Ser Phe Arg Val Val Gly Gly Glu His Arg Leu Lys
145                 150                 155                 160

Asn Tyr Leu Ser Val Thr Thr Val His Pro Ser Pro Ser Ala Pro Thr
                165                 170                 175

Ala Ala Thr Val Val Val Glu Ser Tyr Val Val Asp Val Pro Pro Gly
            180                 185                 190

Asn Thr Pro Glu Asp Thr Arg Val Phe Val Asp Thr Ile Val Lys Cys
        195                 200                 205

Asn Leu Gln Ser Leu Ala Lys Thr Ala Glu Lys Leu Ala Ala Gly Ala
    210                 215                 220
```

Arg Ala Ala Gly Ser
225

<210> SEQ ID NO 65
<211> LENGTH: 205
<212> TYPE: PRT
<213> ORGANISM: Medicago truncatula

<400> SEQUENCE: 65

Met Pro Ser Pro Val Gln Phe Gln Arg Phe Asp Ser Asn Thr Ala Ile
1               5                   10                  15

Thr Asn Gly Val Asn Cys Pro Lys Gln Ile Gln Ala Cys Arg Tyr Ala
            20                  25                  30

Leu Ser Ser Leu Lys Pro Thr Val Ser Val Pro Glu Thr Val Val Asp
        35                  40                  45

His His Met His Val Val Gly Gln Asn Gln Cys Tyr Ser Val Val Ile
    50                  55                  60

Gln Thr Ile Asn Ala Ser Val Ser Thr Val Trp Ser Val Arg Arg
65                  70                  75                  80

Phe Asp Tyr Pro Gln Gly Tyr Lys His Phe Val Lys Ser Cys Asn Val
                85                  90                  95

Val Ala Ser Gly Asp Gly Ile Arg Val Gly Ala Leu Arg Glu Val Arg
            100                 105                 110

Leu Val Ser Gly Leu Pro Ala Val Ser Ser Thr Glu Arg Leu Asp Ile
        115                 120                 125

Leu Asp Glu Glu Arg His Val Ile Ser Phe Ser Val Val Gly Gly Val
    130                 135                 140

His Arg Cys Arg Asn Tyr Arg Ser Val Thr Thr Leu His Gly Asp Gly
145                 150                 155                 160

Asn Gly Gly Thr Val Val Ile Glu Ser Tyr Val Val Asp Val Pro Gln
                165                 170                 175

Gly Asn Thr Lys Glu Glu Thr Cys Ser Phe Ala Asp Thr Ile Val Arg
            180                 185                 190

Cys Asn Leu Gln Ser Leu Val Gln Ile Ala Glu Lys Leu
        195                 200                 205

<210> SEQ ID NO 66
<211> LENGTH: 212
<212> TYPE: PRT
<213> ORGANISM: Zea mays

<400> SEQUENCE: 66

Met Pro Phe Ala Ala Ser Arg Thr Ser Gln Gln Gln His Ser Arg Val
1               5                   10                  15

Ala Thr Asn Gly Arg Ala Val Ala Val Cys Ala Gly His Ala Gly Val
            20                  25                  30

Pro Asp Glu Val Ala Arg His His Glu His Ala Val Ala Ala Gly Gln
        35                  40                  45

Cys Cys Ala Ala Met Val Gln Ser Ile Ala Ala Pro Val Asp Ala Val
    50                  55                  60

Trp Ser Leu Val Arg Arg Phe Asp Gln Pro Gln Arg Tyr Lys Arg Phe
65                  70                  75                  80

Ile Arg Ser Cys His Leu Val Asp Gly Asp Gly Ala Glu Val Gly Ser
                85                  90                  95

Val Arg Glu Leu Leu Leu Val Ser Gly Leu Pro Ala Glu Ser Ser Arg
            100                 105                 110

Glu Arg Leu Glu Ile Arg Asp Asp Glu Arg Val Ile Ser Phe Arg
            115                 120                 125

Val Leu Gly Gly Asp His Arg Leu Ala Asn Tyr Arg Ser Val Thr Thr
130                 135                 140

Val His Glu Ala Ala Pro Ser Gln Asp Gly Arg Pro Leu Thr Met Val
145                 150                 155                 160

Val Glu Ser Tyr Val Val Asp Val Pro Pro Gly Asn Thr Val Glu Glu
                165                 170                 175

Thr Arg Ile Phe Val Asp Thr Ile Val Arg Cys Asn Leu Gln Ser Leu
            180                 185                 190

Glu Gly Thr Val Ile Arg Gln Leu Glu Ile Ala Ala Met Pro His Asp
        195                 200                 205

Asp Asn Gln Asn
    210

<210> SEQ ID NO 67
<211> LENGTH: 233
<212> TYPE: PRT
<213> ORGANISM: Zea mays

<400> SEQUENCE: 67

Met Arg Glu Arg Asn Ser Ser Ile Asp Gln Glu His Gln Arg Gly Ser
1               5                   10                  15

Ser Ser Arg Ser Thr Met Pro Phe Ala Ala Ser Arg Thr Ser Gln Gln
            20                  25                  30

Gln His Ser Arg Val Ala Thr Asn Gly Arg Ala Val Ala Val Cys Ala
        35                  40                  45

Gly His Ala Gly Val Pro Asp Glu Val Ala Arg His His Glu His Ala
    50                  55                  60

Val Ala Ala Gly Gln Cys Cys Ala Ala Met Val Gln Ser Ile Ala Ala
65                  70                  75                  80

Pro Val Asp Ala Val Trp Ser Leu Val Arg Arg Phe Asp Gln Pro Gln
                85                  90                  95

Arg Tyr Lys Arg Phe Ile Arg Ser Cys His Leu Val Asp Gly Asp Gly
            100                 105                 110

Ala Glu Val Gly Ser Val Arg Glu Leu Leu Leu Val Ser Gly Leu Pro
        115                 120                 125

Ala Glu Ser Ser Arg Glu Arg Leu Glu Ile Arg Asp Asp Glu Arg Arg
    130                 135                 140

Val Ile Ser Phe Arg Val Leu Gly Gly Asp His Arg Leu Ala Asn Tyr
145                 150                 155                 160

Arg Ser Val Thr Thr Val His Glu Ala Ala Pro Ser Gln Asp Gly Arg
                165                 170                 175

Pro Leu Thr Met Val Val Glu Ser Tyr Val Val Asp Val Pro Pro Gly
            180                 185                 190

Asn Thr Val Glu Glu Thr Arg Ile Phe Val Asp Thr Ile Val Arg Cys
        195                 200                 205

Asn Leu Gln Ser Leu Glu Gly Thr Val Ile Arg Gln Leu Glu Ile Ala
    210                 215                 220

Ala Met Pro His Asp Asp Asn Gln Asn
225                 230

<210> SEQ ID NO 68
<211> LENGTH: 194
<212> TYPE: PRT

<213> ORGANISM: Physcomitrella patens

<400> SEQUENCE: 68

Met Met Gln Glu Lys Gln Gly Arg Pro Asp Phe Gln Phe Leu Leu Glu
1               5                   10                  15

Gly Gln Gln Asp Leu Ile Cys Arg Phe His Lys His Glu Leu Leu Pro
            20                  25                  30

His Gln Cys Gly Ser Ile Leu Leu Gln Gln Ile Lys Ala Pro Val Gln
        35                  40                  45

Thr Val Trp Leu Ile Val Arg Arg Phe Asp Glu Pro Gln Val Tyr Lys
    50                  55                  60

Arg Phe Ile Gln Arg Cys Asp Ile Val Glu Gly Asp Val Val Gly
65                  70                  75                  80

Ser Ile Arg Glu Val Gln Leu Val Ser Ser Ile Pro Ala Thr Ser Ser
                85                  90                  95

Ile Glu Arg Leu Glu Ile Leu Asp Asp Glu His Ile Ile Ser Phe
            100                 105                 110

Arg Val Leu Gly Gly Gly His Arg Leu Gln Asn Tyr Trp Ser Val Thr
        115                 120                 125

Ser Leu His Arg His Glu Ile Gln Gly Gln Met Gly Thr Leu Val Leu
    130                 135                 140

Glu Ser Tyr Val Val Asp Ile Pro Asp Gly Asn Thr Arg Glu Thr
145                 150                 155                 160

His Thr Phe Val Asp Thr Val Arg Cys Asn Leu Lys Ala Leu Ala
            165                 170                 175

Gln Val Ser Glu Gln Lys His Leu Leu Asn Ser Asn Glu Lys Pro Ala
            180                 185                 190

Ala Pro

<210> SEQ ID NO 69
<211> LENGTH: 191
<212> TYPE: PRT
<213> ORGANISM: Vitis vinifera

<400> SEQUENCE: 69

Met Lys Val Tyr Ser Pro Ser Gln Ile Leu Ala Glu Arg Gly Pro Arg
1               5                   10                  15

Ala Gln Ala Met Gly Asn Leu Tyr His Thr His Leu Leu Pro Asn
            20                  25                  30

Gln Cys Ser Ser Leu Val Val Gln Thr Thr Asp Ala Pro Leu Pro Gln
        35                  40                  45

Val Trp Ser Met Val Arg Arg Phe Asp Arg Pro Gln Ser Tyr Lys Arg
    50                  55                  60

Phe Val Arg Gly Cys Thr Leu Arg Arg Gly Lys Gly Val Gly Ser
65                  70                  75                  80

Val Arg Glu Val Asn Ile Val Ser Gly Leu Pro Ala Glu Ile Ser Leu
                85                  90                  95

Glu Arg Leu Asp Lys Leu Asp Asp Leu His Val Met Arg Phe Thr
            100                 105                 110

Val Ile Gly Gly Asp His Arg Leu Ala Asn Tyr His Ser Thr Leu Thr
        115                 120                 125

Leu His Glu Asp Glu Asp Gly Val Arg Lys Thr Val Met Glu
    130                 135                 140

Ser Tyr Val Val Asp Val Pro Gly Gly Asn Ser Ala Gly Glu Thr Cys
145                 150                 155                 160

```
Tyr Phe Ala Asn Thr Ile Ile Gly Phe Asn Leu Lys Ala Leu Ala Ala
                165                 170                 175

Val Thr Glu Thr Met Ala Leu Lys Ala Asn Ile Pro Ser Gly Phe
            180                 185                 190
```

<210> SEQ ID NO 70
<211> LENGTH: 217
<212> TYPE: PRT
<213> ORGANISM: Physcomitrella patens

<400> SEQUENCE: 70

```
Met Gln Gln Val Lys Gly Arg Gln Asp Phe Gln Arg Leu Leu Glu Ala
1               5                   10                  15

Gln Gln Asp Leu Ile Cys Arg Tyr His Thr His Glu Leu Lys Ala His
            20                  25                  30

Gln Cys Gly Ser Ile Leu Leu Gln Gln Ile Lys Val Pro Leu Pro Ile
        35                  40                  45

Val Trp Ala Ile Val Arg Ser Phe Asp Lys Pro Gln Val Tyr Lys Arg
    50                  55                  60

Phe Ile Gln Thr Cys Lys Ile Thr Glu Gly Asp Gly Gly Val Gly Ser
65                  70                  75                  80

Ile Arg Glu Val His Leu Val Ser Ser Val Pro Ala Thr Cys Ser Ile
                85                  90                  95

Glu Arg Leu Glu Ile Leu Asp Asp Glu Lys His Ile Ile Ser Phe Arg
            100                 105                 110

Val Leu Gly Gly Gly His Arg Leu Gln Asn Tyr Ser Ser Val Ser Ser
        115                 120                 125

Leu His Glu Leu Glu Val Glu Gly His Pro Cys Thr Leu Val Leu Glu
    130                 135                 140

Ser Tyr Met Val Asp Ile Pro Asp Gly Asn Thr Arg Glu Glu Thr His
145                 150                 155                 160

Met Phe Val Asp Thr Val Val Arg Cys Asn Leu Lys Ser Leu Ala Gln
                165                 170                 175

Ile Ser Glu Gln Gln Tyr Asn Lys Asp Cys Leu Gln Gln Lys Gln His
            180                 185                 190

Asp Gln Gln Gln Met Tyr Gln Gln Arg His Pro Pro Leu Pro Pro Ile
        195                 200                 205

Pro Ile Thr Asp Lys Asn Met Glu Arg
    210                 215
```

<210> SEQ ID NO 71
<211> LENGTH: 195
<212> TYPE: PRT
<213> ORGANISM: Physcomitrella patens

<400> SEQUENCE: 71

```
Met Arg Phe Asp Ile Gly His Asn Asp Val Arg Gly Phe Phe Thr Cys
1               5                   10                  15

Glu Glu Glu His Ala Tyr Ala Leu His Ser Gln Thr Val Glu Leu Asn
            20                  25                  30

Gln Cys Gly Ser Ile Leu Met Gln Gln Ile His Ala Pro Ile Glu Val
        35                  40                  45

Val Trp Ser Ile Val Arg Ser Phe Gly Ser Pro Gln Ile Tyr Lys Lys
    50                  55                  60

Phe Ile Gln Ala Cys Ile Leu Thr Val Gly Asp Gly Val Gly Ser
65                  70                  75                  80
```

```
Ile Arg Glu Val Phe Leu Val Ser Gly Val Pro Ala Thr Ser Ser Ile
                85                  90                  95

Glu Arg Leu Glu Ile Leu Asp Asp Glu Lys His Val Phe Ser Phe Arg
            100                 105                 110

Val Leu Lys Gly Gly His Arg Leu Gln Asn Tyr Arg Ser Val Thr Thr
        115                 120                 125

Leu His Glu Gln Glu Val Asn Gly Arg Gln Thr Thr Thr Val Leu Glu
    130                 135                 140

Ser Tyr Val Val Asp Val Pro Asp Gly Asn Thr Arg Glu Glu Thr His
145                 150                 155                 160

Met Phe Ala Asp Thr Val Val Met Cys Asn Leu Lys Ser Leu Ala Gln
                165                 170                 175

Val Ala Glu Trp Arg Ala Met Gln Gly Ile Thr Gln Gln Leu Ser Thr
            180                 185                 190

Ser Ser Leu
        195

<210> SEQ ID NO 72
<211> LENGTH: 172
<212> TYPE: PRT
<213> ORGANISM: Vitis vinifera

<400> SEQUENCE: 72

Met Gly Asn Leu Tyr His Thr His His Leu Leu Pro Asn Gln Cys Ser
1               5                   10                  15

Ser Leu Val Val Gln Thr Thr Asp Ala Pro Leu Pro Gln Val Trp Ser
            20                  25                  30

Met Val Arg Arg Phe Asp Arg Pro Gln Ser Tyr Lys Arg Phe Val Arg
        35                  40                  45

Gly Cys Thr Leu Arg Arg Gly Lys Gly Gly Val Gly Ser Val Arg Glu
    50                  55                  60

Val Asn Ile Val Ser Gly Leu Pro Ala Glu Ile Ser Leu Glu Arg Leu
65                  70                  75                  80

Asp Lys Leu Asp Asp Asp Leu His Val Met Arg Phe Thr Val Ile Gly
                85                  90                  95

Gly Asp His Arg Leu Ala Asn Tyr His Ser Thr Leu Thr Leu His Glu
            100                 105                 110

Asp Glu Glu Asp Gly Val Arg Lys Thr Val Val Met Glu Ser Tyr Val
        115                 120                 125

Val Asp Val Pro Gly Gly Asn Ser Ala Gly Glu Thr Cys Tyr Phe Ala
    130                 135                 140

Asn Thr Ile Ile Gly Phe Asn Leu Lys Ala Leu Ala Ala Val Thr Glu
145                 150                 155                 160

Thr Met Ala Leu Lys Ala Asn Ile Pro Ser Gly Phe
                165                 170

<210> SEQ ID NO 73
<211> LENGTH: 196
<212> TYPE: PRT
<213> ORGANISM: Picea sitchensis

<400> SEQUENCE: 73

Met Glu Asp Leu Ser Ser Trp Arg Gly Arg Ala Met Trp Leu Gly
1               5                   10                  15

Asn Pro Pro Ser Glu Ser Glu Leu Val Cys Arg His His Arg His Glu
            20                  25                  30
```

```
Leu Gln Gly Asn Gln Cys Ser Ser Phe Leu Val Lys His Ile Arg Ala
        35                  40                  45

Pro Val His Leu Val Trp Ser Ile Val Arg Thr Phe Asp Gln Pro Gln
 50                  55                  60

Lys Tyr Lys Pro Phe Val His Ser Cys Ser Val Arg Gly Gly Ile Thr
 65                  70                  75                  80

Val Gly Ser Ile Arg Asn Val Asn Val Lys Ser Gly Leu Pro Ala Thr
                 85                  90                  95

Ala Ser Glu Glu Arg Leu Glu Ile Leu Asp Asp Asn Glu His Val Phe
            100                 105                 110

Ser Ile Lys Ile Leu Gly Gly Asp His Arg Leu Gln Asn Tyr Ser Ser
            115                 120                 125

Ile Ile Thr Val His Pro Glu Ile Ile Asp Gly Arg Pro Gly Thr Leu
        130                 135                 140

Val Ile Glu Ser Tyr Val Val Asp Val Pro Glu Gly Asn Thr Arg Glu
145                 150                 155                 160

Glu Thr Arg Phe Phe Val Glu Ala Leu Val Lys Cys Asn Leu Lys Ser
                165                 170                 175

Leu Ala Asp Val Ser Glu Arg Leu Ala Ser Gln His Thr Glu Leu
            180                 185                 190

Leu Glu Arg Thr
        195

<210> SEQ ID NO 74
<211> LENGTH: 185
<212> TYPE: PRT
<213> ORGANISM: Solanum tuberosum

<400> SEQUENCE: 74

Met Asn Ala Asn Gly Phe Cys Gly Val Glu Lys Glu Tyr Ile Arg Lys
 1               5                  10                  15

His His Leu His Glu Pro Lys Glu Asn Gln Cys Ser Ser Phe Leu Val
             20                  25                  30

Lys His Ile Arg Ala Pro Val His Leu Val Trp Ser Leu Val Arg Arg
         35                  40                  45

Phe Asp Gln Pro Gln Lys Tyr Lys Pro Phe Ile Ser Arg Cys Ile Val
 50                  55                  60

Gln Gly Asp Leu Glu Ile Gly Ser Leu Arg Glu Val Asp Val Lys Ser
 65                  70                  75                  80

Gly Leu Pro Ala Thr Thr Ser Thr Glu Arg Leu Glu Leu Leu Asp Asp
                 85                  90                  95

Glu Glu His Ile Leu Ser Val Arg Ile Val Gly Gly Asp His Arg Leu
            100                 105                 110

Arg Asn Tyr Ser Ser Val Ile Ser Val His Pro Glu Val Ile Asp Gly
            115                 120                 125

Arg Pro Gly Thr Val Val Leu Glu Ser Phe Val Val Asp Val Pro Glu
        130                 135                 140

Gly Asn Thr Lys Asp Glu Thr Cys Tyr Phe Val Glu Ala Leu Ile Asn
145                 150                 155                 160

Cys Asn Leu Lys Ser Leu Ala Asp Ile Ser Glu Arg Val Ala Val Gln
                165                 170                 175

Asp Arg Thr Glu Pro Ile Asp Gln Val
            180                 185
```

```
<210> SEQ ID NO 75
<211> LENGTH: 190
<212> TYPE: PRT
<213> ORGANISM: Medicago truncatula

<400> SEQUENCE: 75
```

Met Asn Asn Gly Cys Glu Gln Gln Gln Tyr Ser Val Ile Glu Thr Gln
1               5                   10                  15

Tyr Ile Arg Arg His His Lys His Asp Leu Arg Asp Asn Gln Cys Ser
            20                  25                  30

Ser Ala Leu Val Lys His Ile Lys Ala Pro Val His Leu Val Trp Ser
        35                  40                  45

Leu Val Arg Arg Phe Asp Gln Pro Gln Lys Tyr Lys Pro Phe Ile Ser
    50                  55                  60

Arg Cys Ile Met Gln Gly Asp Leu Ser Ile Gly Ser Val Arg Glu Val
65                  70                  75                  80

Asn Val Lys Ser Gly Leu Pro Ala Thr Thr Ser Thr Glu Arg Leu Glu
                85                  90                  95

Gln Leu Asp Asp Glu Glu His Ile Leu Gly Ile Arg Ile Val Gly Gly
            100                 105                 110

Asp His Arg Leu Arg Asn Tyr Ser Ser Ile Ile Thr Val His Pro Gly
        115                 120                 125

Val Ile Asp Gly Arg Pro Gly Thr Met Val Ile Glu Ser Phe Val Val
    130                 135                 140

Asp Val Pro Glu Gly Asn Thr Lys Asp Glu Thr Cys Tyr Phe Val Glu
145                 150                 155                 160

Ala Leu Ile Arg Tyr Asn Leu Ser Ser Leu Ala Asp Val Ser Glu Arg
                165                 170                 175

Met Ala Val Gln Gly Arg Thr Asp Pro Ile Asn Ile Asn Pro
            180                 185                 190

```
<210> SEQ ID NO 76
<211> LENGTH: 185
<212> TYPE: PRT
<213> ORGANISM: Vitis vinifera

<400> SEQUENCE: 76
```

Met Ser Gly Tyr Gly Cys Ile Lys Met Glu Asp Glu Tyr Ile Arg Arg
1               5                   10                  15

His His Arg His Glu Ile Arg Asp Asn Gln Cys Ser Ser Ser Leu Val
            20                  25                  30

Lys His Ile Lys Ala Pro Val His Leu Val Trp Ser Leu Val Arg Ser
        35                  40                  45

Phe Asp Gln Pro Gln Lys Tyr Lys Pro Phe Val Ser Arg Cys Ile Val
    50                  55                  60

Gln Gly Asp Leu Glu Ile Gly Ser Val Arg Glu Val Asn Val Lys Ser
65                  70                  75                  80

Gly Leu Pro Ala Thr Thr Ser Thr Glu Arg Leu Glu Leu Leu Asp Asp
                85                  90                  95

Glu Glu His Ile Phe Gly Met Arg Ile Val Gly Gly Asp His Arg Leu
            100                 105                 110

Lys Asn Tyr Ser Ser Ile Val Thr Val His Pro Glu Ile Ile Asp Gly
        115                 120                 125

Arg Pro Gly Thr Leu Val Ile Glu Ser Phe Val Val Asp Val Pro Asp
    130                 135                 140

Gly Asn Thr Lys Asp Glu Thr Cys Tyr Phe Val Glu Ala Leu Ile Lys

```
145                 150                 155                 160
Cys Asn Leu Lys Ser Leu Ala Asp Val Ser Glu Arg Leu Ala Ile Gln
                165                 170                 175

Asp Arg Thr Glu Pro Ile Asp Arg Met
            180                 185

<210> SEQ ID NO 77
<211> LENGTH: 185
<212> TYPE: PRT
<213> ORGANISM: Vitis vinifera

<400> SEQUENCE: 77

Met Asn Gly Asn Gly Leu Ser Ser Met Glu Ser Glu Tyr Ile Arg Arg
1               5                   10                  15

His His Arg His Glu Pro Ala Glu Asn Gln Cys Ser Ser Ala Leu Val
                20                  25                  30

Lys His Ile Lys Ala Pro Val Pro Leu Val Trp Ser Leu Val Arg Arg
            35                  40                  45

Phe Asp Gln Pro Gln Lys Tyr Lys Pro Phe Ile Ser Arg Cys Val Val
50                  55                  60

Gln Gly Asn Leu Glu Ile Gly Ser Leu Arg Glu Val Asp Val Lys Ser
65                  70                  75                  80

Gly Leu Pro Ala Thr Thr Ser Thr Glu Arg Leu Glu Leu Leu Asp Asp
                85                  90                  95

Asp Glu His Ile Leu Ser Met Arg Ile Ile Gly Gly Asp His Arg Leu
            100                 105                 110

Arg Asn Tyr Ser Ser Ile Ile Ser Leu His Pro Glu Ile Ile Asp Gly
        115                 120                 125

Arg Pro Gly Thr Met Val Ile Glu Ser Tyr Val Val Asp Val Pro Glu
    130                 135                 140

Gly Asn Thr Lys Asp Glu Thr Cys Tyr Phe Val Glu Ala Leu Ile Lys
145                 150                 155                 160

Cys Asn Leu Lys Ser Leu Ala Asp Val Ser Glu Arg Leu Ala Val Gln
                165                 170                 175

Asp Arg Thr Glu Pro Ile Asp Arg Met
            180                 185

<210> SEQ ID NO 78
<211> LENGTH: 208
<212> TYPE: PRT
<213> ORGANISM: Oryza sativa

<400> SEQUENCE: 78

Met Glu Ala His Val Glu Arg Ala Leu Arg Glu Gly Leu Thr Glu Glu
1               5                   10                  15

Glu Arg Ala Ala Leu Glu Pro Ala Val Met Ala His His Thr Phe Pro
                20                  25                  30

Pro Ser Thr Thr Thr Ala Thr Ala Ala Ala Thr Cys Thr Ser Leu
            35                  40                  45

Val Thr Gln Arg Val Ala Ala Pro Val Arg Ala Val Trp Pro Ile Val
50                  55                  60

Arg Ser Phe Gly Asn Pro Gln Arg Tyr Lys His Phe Val Arg Thr Cys
65                  70                  75                  80

Ala Leu Ala Ala Gly Asn Gly Pro Ser Phe Gly Ser Val Arg Glu Val
                85                  90                  95

Thr Val Val Ser Gly Pro Ser Arg Leu Pro Pro Gly Thr Glu Arg Leu
```

```
            100                 105                 110
Glu Met Leu Asp Asp Arg His Ile Ile Ser Phe Arg Val Val Gly
        115                 120                 125

Gly Gln His Arg Leu Arg Asn Tyr Arg Ser Val Thr Ser Val Thr Glu
    130                 135                 140

Phe Gln Pro Pro Ala Ala Gly Pro Gly Pro Ala Pro Pro Tyr Cys Val
145                 150                 155                 160

Val Val Glu Ser Tyr Val Val Asp Val Pro Asp Gly Asn Thr Ala Glu
                165                 170                 175

Asp Thr Arg Met Phe Thr Asp Thr Val Val Lys Leu Asn Leu Gln Met
            180                 185                 190

Leu Ala Ala Val Ala Glu Asp Ser Ser Ala Ser Arg Arg Arg Asp
        195                 200                 205

<210> SEQ ID NO 79
<211> LENGTH: 186
<212> TYPE: PRT
<213> ORGANISM: Capsicum annuum

<400> SEQUENCE: 79

Met Met Asn Ala Asn Gly Phe Ser Gly Val Glu Lys Glu Tyr Ile Arg
1               5                   10                  15

Lys His His Leu His Gln Pro Lys Glu Asn Gln Cys Ser Ser Phe Leu
            20                  25                  30

Val Lys His Ile Arg Ala Pro Val His Leu Val Trp Ser Leu Val Arg
        35                  40                  45

Arg Phe Asp Gln Pro Gln Lys Tyr Lys Pro Phe Val Ser Arg Cys Ile
    50                  55                  60

Ala Gln Gly Asp Leu Glu Ile Gly Ser Leu Arg Glu Val Asp Val Lys
65                  70                  75                  80

Ser Gly Leu Pro Ala Thr Thr Ser Thr Glu Arg Leu Glu Leu Leu Asp
                85                  90                  95

Asp Glu Glu His Ile Leu Ser Phe Arg Ile Ile Gly Gly Asp His Arg
            100                 105                 110

Leu Arg Asn Tyr Ser Ser Ile Ile Ser Leu His Pro Glu Val Ile Asp
        115                 120                 125

Gly Arg Pro Gly Thr Leu Val Ile Glu Ser Phe Val Val Asp Val Pro
    130                 135                 140

Gln Gly Asn Thr Lys Asp Glu Thr Cys Tyr Phe Val Glu Ala Leu Ile
145                 150                 155                 160

Asn Cys Asn Leu Lys Ser Leu Ala Asp Val Ser Glu Arg Leu Ala Val
                165                 170                 175

Gln Asp Arg Thr Glu Pro Ile Asp Gln Val
            180                 185

<210> SEQ ID NO 80
<211> LENGTH: 186
<212> TYPE: PRT
<213> ORGANISM: Populus trichocarpa

<400> SEQUENCE: 80

Met Asn Gly Ser Asp Ala Tyr Ser Ala Thr Glu Ala Gln Tyr Val Arg
1               5                   10                  15

Arg His His Lys His Glu Pro Arg Glu Asn Gln Cys Thr Ser Ala Leu
            20                  25                  30

Val Lys His Ile Lys Ala Pro Ala His Leu Val Trp Ser Leu Val Arg
```

```
                35                  40                  45
Arg Phe Asp Gln Pro Gln Arg Tyr Lys Pro Phe Val Ser Arg Cys Val
 50                  55                  60

Met Asn Gly Glu Leu Gly Ile Gly Ser Val Arg Glu Val Asn Val Lys
 65                  70                  75                  80

Ser Gly Leu Pro Ala Thr Thr Ser Thr Glu Arg Leu Glu Leu Leu Asp
                 85                  90                  95

Asp Glu Glu His Ile Leu Gly Val Gln Ile Val Gly Gly Asp His Arg
                100                 105                 110

Leu Lys Asn Tyr Ser Ser Ile Met Thr Val His Pro Glu Phe Ile Asp
            115                 120                 125

Gly Arg Pro Gly Thr Leu Val Ile Glu Ser Phe Ile Val Asp Val Pro
130                 135                 140

Asp Gly Asn Thr Lys Asp Glu Thr Cys Tyr Phe Val Glu Ala Leu Ile
145                 150                 155                 160

Arg Cys Asn Leu Lys Ser Leu Ala Asp Val Ser Glu Arg Met Ala Val
                165                 170                 175

Gln Asp Arg Val Glu Pro Val Asn Gln Phe
            180                 185

<210> SEQ ID NO 81
<211> LENGTH: 185
<212> TYPE: PRT
<213> ORGANISM: Capsicum annuum

<400> SEQUENCE: 81

Met Asn Ala Asn Gly Phe Ser Gly Val Glu Lys Glu Tyr Ile Arg Lys
 1               5                  10                  15

His His Leu His Gln Pro Lys Glu Asn Gln Cys Ser Ser Phe Leu Val
                20                  25                  30

Lys His Ile Arg Ala Pro Val His Leu Val Trp Ser Leu Val Arg Arg
            35                  40                  45

Phe Asp Gln Pro Gln Lys Tyr Lys Pro Phe Val Ser Arg Cys Ile Ala
 50                  55                  60

Gln Gly Asp Leu Glu Ile Gly Ser Leu Arg Glu Val Asp Val Lys Ser
 65                  70                  75                  80

Gly Leu Pro Ala Thr Thr Ser Thr Glu Arg Leu Glu Leu Leu Asp Asp
                 85                  90                  95

Glu Glu His Ile Leu Ser Phe Arg Ile Ile Gly Gly Asp His Arg Leu
                100                 105                 110

Arg Asn Tyr Ser Ser Ile Ile Ser Leu His Pro Glu Val Ile Asp Gly
            115                 120                 125

Arg Pro Gly Thr Leu Val Ile Glu Ser Phe Val Val Asp Val Pro Gln
130                 135                 140

Gly Asn Thr Lys Asp Glu Thr Cys Tyr Phe Val Glu Ala Leu Ile Asn
145                 150                 155                 160

Cys Asn Leu Lys Ser Leu Ala Asp Val Ser Glu Arg Leu Ala Val Gln
                165                 170                 175

Asp Arg Thr Glu Pro Ile Asp Gln Val
            180                 185

<210> SEQ ID NO 82
<211> LENGTH: 186
<212> TYPE: PRT
<213> ORGANISM: Populus trichocarpa
```

<400> SEQUENCE: 82

```
Met Asn Gly Ser Asp Ala Tyr Ser Ala Thr Glu Ala Gln Tyr Val Arg
1               5                   10                  15

Arg His His Lys His Glu Pro Arg Glu Asn Gln Cys Thr Ser Ala Leu
            20                  25                  30

Val Lys His Ile Lys Ala Pro His Leu Val Trp Ser Leu Val Arg
        35                  40                  45

Arg Phe Asp Gln Pro Gln Arg Tyr Lys Pro Phe Val Ser Arg Cys Val
    50                  55                  60

Met Asn Gly Glu Leu Gly Ile Gly Ser Val Arg Glu Val Asn Val Lys
65                  70                  75                  80

Ser Gly Leu Pro Ala Thr Thr Ser Thr Glu Arg Leu Glu Leu Leu Asp
                85                  90                  95

Asp Glu Glu His Ile Leu Gly Val Gln Ile Val Gly Gly Asp His Arg
            100                 105                 110

Leu Lys Asn Tyr Ser Ser Ile Met Thr Val His Pro Glu Phe Ile Asp
        115                 120                 125

Gly Arg Pro Gly Thr Leu Val Ile Glu Ser Phe Ile Val Asp Val Pro
    130                 135                 140

Asp Gly Asn Thr Lys Asp Glu Thr Cys Tyr Phe Val Lys Ala Leu Ile
145                 150                 155                 160

Arg Cys Asn Leu Lys Ser Leu Ala Asp Val Ser Glu Arg Met Ala Val
                165                 170                 175

Gln Asp Arg Val Glu Pro Val Asn Gln Phe
            180                 185
```

<210> SEQ ID NO 83
<211> LENGTH: 188
<212> TYPE: PRT
<213> ORGANISM: Pisum sativum

<400> SEQUENCE: 83

```
Met Asn Asn Gly Gly Glu Gln Tyr Ser Ala Ile Glu Thr Gln Tyr Ile
1               5                   10                  15

Arg Arg Arg His Lys His Asp Leu Arg Asp Asn Gln Cys Ser Ser Ala
            20                  25                  30

Leu Val Lys His Ile Lys Ala Pro Val His Leu Val Trp Ser Leu Val
        35                  40                  45

Arg Arg Phe Asp Gln Pro Gln Lys Tyr Lys Pro Phe Val Ser Arg Cys
    50                  55                  60

Ile Met Gln Gly Asp Leu Gly Ile Gly Ser Val Arg Glu Val Asn Val
65                  70                  75                  80

Lys Ser Gly Leu Pro Ala Thr Thr Ser Thr Glu Arg Leu Glu Gln Leu
                85                  90                  95

Asp Asp Glu Glu His Ile Leu Gly Ile Arg Ile Val Gly Gly Asp His
            100                 105                 110

Arg Leu Arg Asn Tyr Ser Ser Val Ile Thr Val His Pro Glu Val Ile
        115                 120                 125

Asp Gly Arg Pro Gly Thr Met Val Ile Glu Ser Phe Val Val Asp Val
    130                 135                 140

Pro Glu Gly Asn Thr Arg Asp Glu Thr Cys Tyr Phe Val Glu Ala Leu
145                 150                 155                 160

Ile Arg Gly Asn Leu Ser Ser Leu Ala Asp Val Ser Glu Arg Met Ala
                165                 170                 175
```

Val Gln Gly Arg Thr Asp Pro Ile Asn Val Asn Pro
            180                 185

<210> SEQ ID NO 84
<211> LENGTH: 177
<212> TYPE: PRT
<213> ORGANISM: Vitis vinifera

<400> SEQUENCE: 84

Met Glu Ala Gln Val Ile Cys Arg His Ala His Glu Pro Arg Glu
1               5                   10                  15

Asn Gln Cys Ser Ser Val Leu Val Arg His Val Lys Ala Pro Ala Asn
                20                  25                  30

Leu Val Trp Ser Leu Val Arg Arg Phe Asp Gln Pro Gln Lys Tyr Lys
            35                  40                  45

Pro Phe Val Ser Arg Cys Val Val Gln Gly Asp Leu Arg Ile Gly Ser
        50                  55                  60

Val Arg Glu Val Asn Val Lys Thr Gly Leu Pro Ala Thr Thr Ser Thr
65                  70                  75                  80

Glu Arg Leu Glu Leu Phe Asp Asp Glu His Val Leu Gly Ile Lys
                85                  90                  95

Ile Leu Asp Gly Asp His Arg Leu Arg Asn Tyr Ser Ser Val Ile Thr
                100                 105                 110

Val His Pro Glu Ile Ile Asp Gly Arg Pro Gly Thr Leu Val Ile Glu
            115                 120                 125

Ser Phe Val Val Asp Val Pro Glu Gly Asn Thr Lys Asp Asp Thr Cys
        130                 135                 140

Tyr Phe Val Arg Ala Leu Ile Asn Cys Asn Leu Lys Cys Leu Ala Glu
145                 150                 155                 160

Val Ser Glu Arg Met Ala Met Leu Gly Arg Val Glu Pro Ala Asn Ala
                165                 170                 175

Val

<210> SEQ ID NO 85
<211> LENGTH: 178
<212> TYPE: PRT
<213> ORGANISM: Vitis vinifera

<400> SEQUENCE: 85

Met Met Glu Ala Gln Val Ile Cys Arg His Ala His Glu Pro Arg
1               5                   10                  15

Glu Asn Gln Cys Ser Ser Val Leu Val Arg His Val Lys Ala Pro Ala
                20                  25                  30

Asn Leu Val Trp Ser Leu Val Arg Arg Phe Asp Gln Pro Gln Lys Tyr
            35                  40                  45

Lys Pro Phe Val Ser Arg Cys Val Val Gln Gly Asp Leu Arg Ile Gly
        50                  55                  60

Ser Val Arg Glu Val Asn Val Lys Thr Gly Leu Pro Ala Thr Thr Ser
65                  70                  75                  80

Thr Glu Arg Leu Glu Leu Phe Asp Asp Glu His Val Leu Gly Ile
                85                  90                  95

Lys Ile Leu Asp Gly Asp His Arg Leu Arg Asn Tyr Ser Ser Val Ile
                100                 105                 110

Thr Val His Pro Glu Ile Ile Asp Gly Arg Pro Gly Thr Leu Val Ile
            115                 120                 125

Glu Ser Phe Val Val Asp Val Pro Glu Gly Asn Thr Lys Asp Asp Thr

```
                130               135               140
Cys Tyr Phe Val Arg Ala Leu Ile Asn Cys Asn Leu Lys Cys Leu Ala
145                 150                 155                 160

Glu Val Ser Glu Arg Met Ala Met Leu Gly Arg Val Glu Pro Ala Asn
                165                 170                 175

Ala Val

<210> SEQ ID NO 86
<211> LENGTH: 193
<212> TYPE: PRT
<213> ORGANISM: Arachis hypogaea
<220> FEATURE:
<221> NAME/KEY: VARIANT
<222> LOCATION: (162)..(162)
<223> OTHER INFORMATION: Xaa = any amino acid

<400> SEQUENCE: 86

Met Met Asn Gly Ser Cys Gly Gly Gly Gly Gly Glu Ala Tyr Gly
1               5                   10                  15

Ala Ile Glu Ala Gln Tyr Ile Arg Arg His His Arg His Glu Pro Arg
                20                  25                  30

Asp Asn Gln Cys Thr Ser Ala Leu Val Lys His Ile Arg Ala Pro Val
            35                  40                  45

His Leu Val Trp Ser Leu Val Arg Arg Phe Asp Gln Pro Gln Lys Tyr
    50                  55                  60

Lys Pro Phe Val Ser Arg Cys Ile Met Gln Gly Asp Leu Gly Ile Gly
65                  70                  75                  80

Ser Val Arg Glu Val Asn Val Lys Ser Gly Leu Pro Ala Thr Thr Ser
                85                  90                  95

Thr Glu Arg Leu Glu Gln Leu Asp Asp Glu His Ile Leu Gly Ile
                100                 105                 110

Arg Ile Val Gly Gly Asp His Arg Leu Arg Asn Tyr Ser Ser Ile Ile
            115                 120                 125

Thr Val His Pro Glu Val Ile Glu Gly Arg Pro Gly Thr Met Val Ile
    130                 135                 140

Glu Ser Phe Val Val Asp Val Pro Asp Gly Asn Thr Lys Asp Glu Thr
145                 150                 155                 160

Cys Xaa Phe Val Glu Ala Leu Ile Arg Cys Asn Leu Ser Ser Leu Ala
                165                 170                 175

Asp Val Ser Glu Arg Met Ala Val Gln Gly Arg Thr Asp Pro Ile Asn
                180                 185                 190

Gln

<210> SEQ ID NO 87
<211> LENGTH: 217
<212> TYPE: PRT
<213> ORGANISM: Zea mays

<400> SEQUENCE: 87

Met Val Val Glu Met Asp Gly Gly Val Gly Val Ala Ala Gly Gly Gly
1               5                   10                  15

Gly Gly Ala Gln Thr Pro Ala Pro Ala Pro Pro Arg Arg Trp Arg Leu
                20                  25                  30

Ala Asp Glu Arg Cys Asp Leu Arg Ala Met Glu Thr Asp Tyr Val Arg
            35                  40                  45

Arg Phe His Arg His Glu Pro Arg Asp His Gln Cys Ser Ser Ala Val
    50                  55                  60
```

```
Ala Lys His Ile Lys Ala Pro Val His Leu Val Trp Ser Leu Val Arg
 65                  70                  75                  80

Arg Phe Asp Gln Pro Gln Leu Phe Lys Pro Phe Val Ser Arg Cys Glu
                 85                  90                  95

Met Lys Gly Asn Ile Glu Ile Gly Ser Val Arg Glu Val Asn Val Lys
            100                 105                 110

Ser Gly Leu Pro Ala Thr Arg Ser Thr Glu Arg Leu Glu Leu Leu Asp
            115                 120                 125

Asp Asp Glu Arg Ile Leu Ser Val Arg Phe Val Gly Gly Asp His Arg
        130                 135                 140

Leu Gln Asn Tyr Ser Ser Ile Leu Thr Val His Pro Glu Val Ile Asp
145                 150                 155                 160

Gly Arg Pro Gly Thr Leu Val Ile Glu Ser Phe Val Val Asp Val Pro
                165                 170                 175

Asp Gly Asn Thr Lys Asp Glu Thr Cys Tyr Phe Val Glu Ala Leu Leu
            180                 185                 190

Lys Cys Asn Leu Arg Ser Leu Ala Glu Val Ser Glu Gly Gln Val Ile
            195                 200                 205

Met Asp Gln Thr Glu Pro Leu Asp Arg
    210                 215
```

<210> SEQ ID NO 88
<211> LENGTH: 217
<212> TYPE: PRT
<213> ORGANISM: Zea mays

<400> SEQUENCE: 88

```
Met Val Val Glu Met Asp Gly Val Gly Val Ala Ala Ala Gly Gly
1               5                   10                  15

Gly Gly Ala Gln Thr Pro Ala Pro Pro Pro Arg Arg Trp Arg Leu
             20                  25                  30

Ala Asp Glu Arg Cys Asp Leu Arg Ala Met Glu Thr Asp Tyr Val Arg
        35                  40                  45

Arg Phe His Arg His Glu Pro Arg Asp His Gln Cys Ser Ser Ala Val
 50                  55                  60

Ala Lys His Ile Lys Ala Pro Val His Leu Val Trp Ser Leu Val Arg
 65                  70                  75                  80

Arg Phe Asp Gln Pro Gln Leu Phe Lys Pro Phe Val Ser Arg Cys Glu
                 85                  90                  95

Met Lys Gly Asn Ile Glu Ile Gly Ser Val Arg Glu Val Asn Val Lys
            100                 105                 110

Ser Gly Leu Pro Ala Thr Arg Ser Thr Glu Arg Leu Glu Leu Leu Asp
            115                 120                 125

Asp Asp Glu Arg Ile Leu Ser Val Arg Phe Val Gly Gly Asp His Arg
        130                 135                 140

Leu Gln Asn Tyr Ser Ser Ile Leu Thr Val His Pro Glu Val Ile Asp
145                 150                 155                 160

Gly Arg Pro Gly Thr Leu Val Ile Glu Ser Phe Val Val Asp Val Pro
                165                 170                 175

Asp Gly Asn Thr Lys Asp Glu Thr Cys Tyr Phe Val Glu Ala Leu Leu
            180                 185                 190

Lys Cys Asn Leu Arg Ser Leu Ala Glu Val Ser Glu Gly Gln Val Ile
            195                 200                 205

Met Asp Gln Thr Glu Pro Leu Asp Arg
```

```
              210                 215

<210> SEQ ID NO 89
<211> LENGTH: 206
<212> TYPE: PRT
<213> ORGANISM: Oryza sativa

<400> SEQUENCE: 89

Met Asn Gly Val Gly Gly Ala Gly Gly Ala Ala Gly Lys Leu Pro
1               5                   10                  15

Met Val Ser His Arg Arg Val Gln Trp Arg Leu Ala Asp Glu Arg Cys
            20                  25                  30

Glu Leu Arg Glu Glu Met Glu Tyr Ile Arg Arg Phe His Arg His
        35                  40                  45

Glu Pro Ser Ser Asn Gln Cys Thr Ser Phe Ala Ala Lys His Ile Lys
    50                  55                  60

Ala Pro Leu His Thr Val Trp Ser Leu Val Arg Arg Phe Asp Gln Pro
65                  70                  75                  80

Gln Leu Phe Lys Pro Phe Val Arg Asn Cys Val Met Arg Glu Asn Ile
                85                  90                  95

Ile Ala Thr Gly Cys Ile Arg Glu Val Asn Val Gln Ser Gly Leu Pro
            100                 105                 110

Ala Thr Arg Ser Thr Glu Arg Leu Glu Leu Leu Asp Asp Asn Glu His
        115                 120                 125

Ile Leu Lys Val Asn Phe Ile Gly Gly Asp His Met Leu Lys Asn Tyr
    130                 135                 140

Ser Ser Ile Leu Thr Val His Ser Glu Val Ile Asp Gly Gln Leu Gly
145                 150                 155                 160

Thr Leu Val Val Glu Ser Phe Ile Val Asp Val Pro Glu Gly Asn Thr
                165                 170                 175

Lys Asp Asp Ile Ser Tyr Phe Ile Glu Asn Val Leu Arg Cys Asn Leu
            180                 185                 190

Arg Thr Leu Ala Asp Val Ser Glu Glu Arg Leu Ala Asn Pro
        195                 200                 205

<210> SEQ ID NO 90
<211> LENGTH: 206
<212> TYPE: PRT
<213> ORGANISM: Oryza sativa

<400> SEQUENCE: 90

Met Asn Gly Ala Gly Gly Ala Gly Gly Ala Ala Gly Lys Leu Pro
1               5                   10                  15

Met Val Ser His Arg Gln Val Gln Trp Arg Leu Ala Asp Glu Arg Cys
            20                  25                  30

Glu Leu Arg Glu Glu Met Glu Tyr Ile Arg Gln Phe His Arg His
        35                  40                  45

Glu Pro Ser Ser Asn Gln Cys Thr Ser Phe Val Ala Lys His Ile Lys
    50                  55                  60

Ala Pro Leu Gln Thr Val Trp Ser Leu Val Arg Arg Phe Asp Gln Pro
65                  70                  75                  80

Gln Leu Phe Lys Pro Phe Val Arg Lys Cys Val Met Arg Glu Asn Ile
                85                  90                  95

Ile Ala Thr Gly Cys Val Arg Glu Val Asn Val Gln Ser Gly Leu Pro
            100                 105                 110

Ala Thr Arg Ser Thr Glu Arg Leu Glu Leu Leu Asp Asp Asn Glu His
```

```
                   115                 120                 125
Ile Leu Lys Val Lys Phe Ile Gly Gly Asp His Met Leu Lys Asn Tyr
        130                 135                 140

Ser Ser Ile Leu Thr Ile His Ser Glu Val Ile Asp Gly Gln Leu Gly
145                 150                 155                 160

Thr Leu Val Val Glu Ser Phe Val Val Asp Ile Pro Glu Gly Asn Thr
                165                 170                 175

Lys Asp Asp Ile Cys Tyr Phe Ile Glu Asn Ile Leu Arg Cys Asn Leu
        180                 185                 190

Met Thr Leu Ala Asp Val Ser Glu Glu Arg Leu Ala Asn Pro
        195                 200                 205
```

<210> SEQ ID NO 91
<211> LENGTH: 205
<212> TYPE: PRT
<213> ORGANISM: Oryza sativa

<400> SEQUENCE: 91

```
Met Val Glu Val Gly Gly Gly Ala Ala Glu Ala Ala Gly Arg Arg
1               5                  10                  15

Trp Arg Leu Ala Asp Glu Arg Cys Asp Leu Arg Ala Ala Glu Thr Glu
            20                  25                  30

Tyr Val Arg Arg Phe His Arg His Glu Pro Arg Asp His Gln Cys Ser
        35                  40                  45

Ser Ala Val Ala Lys His Ile Lys Ala Pro Val His Leu Val Trp Ser
    50                  55                  60

Leu Val Arg Arg Phe Asp Gln Pro Gln Leu Phe Lys Pro Phe Val Ser
65                  70                  75                  80

Arg Cys Glu Met Lys Gly Asn Ile Glu Ile Gly Ser Val Arg Glu Val
                85                  90                  95

Asn Val Lys Ser Gly Leu Pro Ala Thr Arg Ser Thr Glu Arg Leu Glu
            100                 105                 110

Leu Leu Asp Asp Asn Glu His Ile Leu Ser Val Arg Phe Val Gly Gly
        115                 120                 125

Asp His Arg Leu Lys Asn Tyr Ser Ser Ile Leu Thr Val His Pro Glu
    130                 135                 140

Val Ile Asp Gly Arg Pro Gly Thr Leu Val Ile Glu Ser Phe Val Val
145                 150                 155                 160

Asp Val Pro Glu Gly Asn Thr Lys Asp Glu Thr Cys Tyr Phe Val Glu
                165                 170                 175

Ala Leu Leu Lys Cys Asn Leu Lys Ser Leu Ala Glu Val Ser Glu Arg
            180                 185                 190

Leu Val Cys Gln Gly Pro Asn Arg Ala Pro Ser Thr Arg
        195                 200                 205
```

<210> SEQ ID NO 92
<211> LENGTH: 204
<212> TYPE: PRT
<213> ORGANISM: Oryza sativa

<400> SEQUENCE: 92

```
Met Val Glu Val Gly Gly Gly Ala Ala Glu Ala Ala Gly Arg Arg
1               5                  10                  15

Trp Arg Leu Ala Asp Glu Arg Cys Asp Leu Arg Ala Ala Glu Thr Glu
            20                  25                  30

Tyr Val Arg Arg Phe His Arg His Glu Pro Arg Asp His Gln Cys Ser
```

```
                35                  40                  45
Ser Ala Val Ala Lys His Ile Lys Ala Pro Val His Leu Val Trp Ser
 50                  55                  60

Leu Val Arg Arg Phe Asp Gln Pro Gln Leu Phe Lys Pro Phe Val Ser
 65                  70                  75                  80

Arg Cys Glu Met Lys Gly Asn Ile Glu Ile Gly Ser Val Arg Glu Val
                 85                  90                  95

Asn Val Lys Ser Gly Leu Pro Ala Thr Arg Ser Thr Glu Arg Leu Glu
                100                 105                 110

Leu Leu Asp Asp Asn Glu His Ile Leu Ser Val Arg Phe Val Gly Gly
                115                 120                 125

Asp His Arg Leu Lys Asn Tyr Ser Ser Ile Leu Thr Val His Pro Glu
            130                 135                 140

Val Ile Asp Gly Arg Pro Gly Thr Leu Val Ile Glu Ser Phe Val Val
145                 150                 155                 160

Asp Val Pro Glu Gly Asn Thr Lys Asp Glu Thr Cys Tyr Phe Val Glu
                165                 170                 175

Ala Leu Leu Lys Cys Asn Leu Lys Ser Leu Ala Glu Val Ser Glu Arg
                180                 185                 190

Leu Val Val Lys Asp Gln Thr Glu Pro Leu Asp Arg
                195                 200

<210> SEQ ID NO 93
<211> LENGTH: 199
<212> TYPE: PRT
<213> ORGANISM: Medicago truncatula

<400> SEQUENCE: 93

Met Glu Lys Met Asn Gly Thr Glu Asn Gly Val Phe Asn Ser Thr
  1               5                  10                  15

Glu Met Glu Tyr Ile Arg Arg His His Asn Gln Gln Pro Gly Glu Asn
                 20                  25                  30

Gln Cys Ser Ser Ala Leu Val Lys His Ile Arg Ala Pro Val Pro Leu
             35                  40                  45

Val Trp Ser Leu Val Arg Arg Phe Asp Gln Pro Gln Lys Tyr Lys Pro
 50                  55                  60

Phe Val Ser Arg Cys Val Val Arg Gly Asn Leu Glu Ile Gly Ser Leu
 65                  70                  75                  80

Arg Glu Val Asp Val Lys Ser Gly Leu Pro Ala Thr Thr Ser Thr Glu
                 85                  90                  95

Arg Leu Glu Val Leu Asp Asp Asn Glu His Ile Leu Ser Ile Arg Ile
                100                 105                 110

Ile Gly Gly Asp His Arg Leu Arg Asn Tyr Ser Ser Ile Met Ser Leu
            115                 120                 125

His Pro Glu Ile Ile Asp Gly Arg Pro Gly Thr Leu Val Ile Glu Ser
        130                 135                 140

Phe Val Val Asp Val Pro Glu Gly Asn Thr Lys Asp Glu Thr Cys Tyr
145                 150                 155                 160

Phe Val Glu Ala Leu Ile Lys Cys Asn Leu Lys Ser Leu Ser Asp Val
                165                 170                 175

Ser Glu Gly His Ala Val Gln Asp Leu Thr Glu Pro Leu Asp Arg Val
                180                 185                 190

His Glu Leu Leu Ile Ser Gly
            195
```

<210> SEQ ID NO 94
<211> LENGTH: 199
<212> TYPE: PRT
<213> ORGANISM: Medicago truncatula

<400> SEQUENCE: 94

Met Glu Lys Met Asn Gly Thr Glu Asn Asn Gly Val Phe Asn Ser Thr
1               5                   10                  15

Glu Met Glu Tyr Ile Arg Arg His His Asn Gln Gln Pro Gly Glu Asn
            20                  25                  30

Gln Cys Ser Ser Ala Leu Val Lys His Ile Arg Ala Pro Val Pro Leu
        35                  40                  45

Val Trp Ser Leu Val Arg Arg Phe Asp Gln Pro Gln Lys Tyr Lys Pro
    50                  55                  60

Phe Val Ser Arg Cys Val Val Arg Gly Asn Leu Glu Ile Gly Ser Leu
65                  70                  75                  80

Arg Glu Val Asp Val Lys Ser Gly Leu Pro Ala Thr Thr Ser Thr Glu
                85                  90                  95

Arg Leu Glu Val Leu Asp Asp Asn Glu His Ile Leu Ser Ile Arg Ile
            100                 105                 110

Ile Gly Gly Asp His Arg Leu Arg Asn Tyr Ser Ser Ile Met Ser Leu
        115                 120                 125

His Pro Glu Ile Ile Asp Gly Arg Pro Gly Thr Leu Val Ile Glu Ser
    130                 135                 140

Phe Val Val Asp Val Pro Glu Gly Asn Thr Lys Asp Glu Thr Cys Tyr
145                 150                 155                 160

Phe Val Glu Ala Leu Ile Lys Cys Asn Leu Lys Ser Leu Ser Asp Val
                165                 170                 175

Ser Glu Gly His Ala Ala Gln Asp Leu Thr Glu Pro Leu Asp Arg Met
            180                 185                 190

His Glu Leu Leu Ile Ser Gly
        195

<210> SEQ ID NO 95
<211> LENGTH: 197
<212> TYPE: PRT
<213> ORGANISM: Zea mays

<400> SEQUENCE: 95

Met Val Gly Leu Val Gly Gly Ser Thr Ala Arg Ala Glu His Val Val
1               5                   10                  15

Ala Asn Ala Gly Gly Glu Ala Glu Tyr Val Arg Arg Met His Arg His
            20                  25                  30

Ala Pro Thr Glu His Gln Cys Thr Ser Thr Leu Val Lys His Ile Lys
        35                  40                  45

Ala Pro Val His Leu Val Trp Gln Leu Val Arg Arg Phe Asp Gln Pro
    50                  55                  60

Gln Arg Tyr Lys Pro Phe Val Arg Asn Cys Val Val Arg Gly Asp Gln
65                  70                  75                  80

Leu Glu Val Gly Ser Leu Arg Asp Val Asn Val Lys Thr Gly Leu Pro
                85                  90                  95

Ala Thr Thr Ser Thr Glu Arg Leu Glu Gln Leu Asp Asp Asp Leu His
            100                 105                 110

Ile Leu Gly Val Lys Phe Val Gly Gly Asp His Arg Leu Gln Asn Tyr
        115                 120                 125

```
Ser Ser Ile Ile Thr Val His Pro Glu Ser Ile Asp Gly Arg Pro Gly
    130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Asn Ser Leu Ala Glu Val Ser Glu Gln Leu Ala Val Glu Ser Pro Thr
            180                 185                 190

Ser Leu Ile Asp Gln
        195

<210> SEQ ID NO 96
<211> LENGTH: 197
<212> TYPE: PRT
<213> ORGANISM: Zea mays

<400> SEQUENCE: 96

Met Val Gly Leu Val Gly Gly Ser Thr Ala Arg Ala Glu His Val Val
1               5                   10                  15

Ala Asn Ala Gly Gly Glu Ala Glu Tyr Val Arg Arg Met His Arg His
            20                  25                  30

Ala Pro Thr Glu His Gln Cys Thr Ser Thr Leu Val Lys His Ile Lys
        35                  40                  45

Ala Pro Val His Leu Val Trp Glu Leu Val Arg Arg Phe Asp Gln Pro
    50                  55                  60

Gln Arg Tyr Lys Pro Phe Val Arg Asn Cys Val Val Arg Gly Asp Gln
65                  70                  75                  80

Leu Glu Val Gly Ser Leu Arg Asp Val Asn Val Lys Thr Gly Leu Pro
                85                  90                  95

Ala Thr Thr Ser Thr Glu Arg Leu Glu Gln Leu Asp Asp Asp Leu His
            100                 105                 110

Ile Leu Gly Val Lys Phe Val Gly Gly Asp His Arg Leu Gln Asn Tyr
        115                 120                 125

Ser Ser Ile Ile Thr Val His Pro Glu Ser Ile Asp Gly Arg Pro Gly
    130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Asn Ser Leu Ala Glu Val Ser Glu Gln Leu Ala Val Glu Ser Pro Thr
            180                 185                 190

Ser Leu Ile Asp Gln
        195

<210> SEQ ID NO 97
<211> LENGTH: 212
<212> TYPE: PRT
<213> ORGANISM: Zea mays

<400> SEQUENCE: 97

Met Val Met Val Glu Met Asp Gly Gly Val Gly Gly Gly Gly Gly Gly
1               5                   10                  15

Gly Gln Thr Pro Ala Pro Arg Arg Trp Arg Leu Ala Asp Glu Arg Cys
            20                  25                  30

Asp Leu Arg Ala Met Glu Thr Asp Tyr Val Arg Arg Phe His Arg His
        35                  40                  45
```

```
Glu Pro Arg Glu His Gln Cys Ser Ser Ala Val Ala Lys His Ile Lys
 50                  55                  60

Ala Pro Val His Leu Val Trp Ser Leu Val Arg Arg Phe Asp Gln Pro
 65                  70                  75                  80

Gln Leu Phe Lys Pro Phe Val Ser Arg Cys Glu Met Lys Gly Asn Ile
                 85                  90                  95

Glu Ile Gly Ser Val Arg Glu Val Asn Val Lys Ser Gly Leu Pro Ala
                100                 105                 110

Thr Arg Ser Thr Glu Arg Leu Glu Leu Leu Asp Asp Asn Glu His Ile
            115                 120                 125

Leu Ser Val Arg Phe Val Gly Gly Asp His Arg Leu Gln Asn Tyr Ser
130                 135                 140

Ser Ile Leu Thr Val His Pro Glu Val Ile Asp Gly Arg Pro Gly Thr
145                 150                 155                 160

Leu Val Ile Glu Ser Phe Val Asp Val Pro Asp Gly Asn Thr Lys
                165                 170                 175

Asp Glu Thr Cys Tyr Phe Val Gly Ala Leu Leu Lys Cys Asn Leu Lys
            180                 185                 190

Ser Leu Ala Glu Val Ser Glu Arg Gln Val Val Lys Asp Gln Thr Glu
            195                 200                 205

Pro Leu Asp Arg
    210

<210> SEQ ID NO 98
<211> LENGTH: 205
<212> TYPE: PRT
<213> ORGANISM: Oryza sativa

<400> SEQUENCE: 98

Met Asn Gly Ala Gly Gly Ala Gly Gly Ala Ala Ala Gly Lys Leu Pro
  1               5                  10                  15

Met Val Ser His Arg Arg Val Gln Cys Arg Leu Ala Asp Lys Arg Cys
                 20                  25                  30

Glu Leu Arg Glu Glu Glu Met Glu Tyr Ile Arg Gln Phe His Arg His
             35                  40                  45

Glu Pro Ser Ser Asn Gln Cys Thr Ser Phe Val Ala Lys His Ile Lys
 50                  55                  60

Ala Pro Leu Gln Thr Val Trp Ser Leu Val Arg Arg Phe Asp Gln Pro
 65                  70                  75                  80

Gln Leu Phe Lys Pro Phe Val Arg Lys Cys Val Met Arg Glu Asn Ile
                 85                  90                  95

Ile Val Thr Gly Cys Val Arg Glu Val Asn Val Gln Ser Gly Leu Pro
                100                 105                 110

Ala Thr Arg Ser Thr Glu Arg Leu Glu Leu Leu Asp Asp Asn Glu His
            115                 120                 125

Ile Leu Lys Val Lys Phe Ile Gly Gly Asp His Met Leu Lys Asn Tyr
130                 135                 140

Ser Ser Ile Leu Thr Ile His Ser Glu Val Ile Asp Gly Gln Leu Gly
145                 150                 155                 160

Thr Leu Val Val Glu Ser Phe Val Asp Ile Pro Asp Gly Asn Thr
                165                 170                 175

Lys Asp Asp Ile Cys Tyr Phe Ile Glu Asn Val Leu Arg Cys Asn Leu
            180                 185                 190

Met Thr Leu Ala Asp Val Ser Glu Glu Arg Leu Ala Asn
            195                 200                 205
```

<210> SEQ ID NO 99
<211> LENGTH: 197
<212> TYPE: PRT
<213> ORGANISM: Zea mays

<400> SEQUENCE: 99

Met Val Gly Leu Val Gly Gly Ser Thr Ala Arg Ala Glu His Val Val
1               5                   10                  15

Ala Asn Ala Gly Gly Glu Thr Glu Tyr Val Arg Arg Leu His Arg His
                20                  25                  30

Ala Pro Ala Glu His Gln Cys Thr Ser Thr Leu Val Lys His Ile Lys
            35                  40                  45

Ala Pro Val His Leu Val Trp Glu Leu Val Arg Ser Phe Asp Gln Pro
        50                  55                  60

Gln Arg Tyr Lys Pro Phe Val Arg Asn Cys Val Val Arg Gly Asp Gln
65                  70                  75                  80

Leu Glu Val Gly Ser Leu Arg Asp Val Asn Val Lys Thr Gly Leu Pro
                85                  90                  95

Ala Thr Thr Ser Thr Glu Arg Leu Glu Gln Leu Asp Asp Asp Leu His
            100                 105                 110

Ile Leu Gly Val Lys Phe Val Gly Gly Asp His Arg Leu Gln Asn Tyr
        115                 120                 125

Ser Ser Ile Ile Thr Val His Pro Glu Ser Ile Asp Gly Arg Pro Gly
    130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Lys Ser Leu Ala Glu Val Ser Glu Gln Leu Ala Val Glu Ser Pro Thr
            180                 185                 190

Ser Pro Ile Asp Gln
        195

<210> SEQ ID NO 100
<211> LENGTH: 206
<212> TYPE: PRT
<213> ORGANISM: Oryza sativa

<400> SEQUENCE: 100

Met Asn Gly Val Gly Gly Ala Gly Gly Ala Ala Gly Lys Leu Pro
1               5                   10                  15

Met Val Ser His Arg Arg Val Gln Trp Arg Leu Ala Asp Glu Arg Cys
                20                  25                  30

Glu Leu Arg Glu Glu Met Glu Tyr Ile Arg Arg Phe His Arg His
            35                  40                  45

Glu Pro Ser Ser Asn Gln Cys Thr Ser Phe Ala Ala Lys His Ile Lys
        50                  55                  60

Ala Pro Leu His Thr Val Trp Ser Leu Val Arg Arg Phe Asp Gln Pro
65                  70                  75                  80

Gln Leu Phe Lys Pro Phe Val Arg Asn Cys Val Met Arg Glu Asn Ile
                85                  90                  95

Ile Ala Thr Gly Cys Ile Arg Glu Val Asn Val Gln Ser Gly Leu Pro
            100                 105                 110

Ala Thr Arg Ser Thr Glu Arg Leu Glu Leu Leu Asp Asp Asn Glu His
        115                 120                 125

```
Ile Leu Lys Val Lys Phe Ile Gly Gly Asp His Met Leu Lys Asn Tyr
        130                 135                 140

Ser Ser Ile Leu Thr Val His Ser Glu Val Ile Asp Gly Gln Leu Gly
145                 150                 155                 160

Thr Leu Val Val Glu Ser Phe Ile Val Asp Val Leu Glu Gly Asn Thr
                165                 170                 175

Lys Asp Asp Ile Ser Tyr Phe Ile Glu Asn Val Leu Arg Cys Asn Leu
            180                 185                 190

Arg Thr Leu Ala Asp Val Ser Glu Glu Arg Leu Ala Asn Pro
        195                 200                 205

<210> SEQ ID NO 101
<211> LENGTH: 209
<212> TYPE: PRT
<213> ORGANISM: Oryza sativa

<400> SEQUENCE: 101

Met Val Gly Leu Val Gly Gly Gly Trp Arg Val Gly Asp Asp Ala
1               5                   10                  15

Ala Gly Gly Gly Gly Gly Ala Val Ala Gly Ala Ala Ala Ala
            20                  25                  30

Ala Glu Ala Glu His Met Arg Arg Leu His Ser His Ala Pro Gly Glu
        35                  40                  45

His Gln Cys Ser Ser Ala Leu Val Lys His Ile Lys Ala Pro Val His
    50                  55                  60

Leu Val Trp Ser Leu Val Arg Ser Phe Asp Gln Pro Gln Arg Tyr Lys
65                  70                  75                  80

Pro Phe Val Ser Arg Cys Val Val Arg Gly Gly Asp Leu Glu Ile Gly
                85                  90                  95

Ser Val Arg Glu Val Asn Val Lys Thr Gly Leu Pro Ala Thr Thr Ser
            100                 105                 110

Thr Glu Arg Leu Glu Leu Leu Asp Asp Glu His Ile Leu Ser Val
        115                 120                 125

Lys Phe Val Gly Gly Asp His Arg Leu Arg Asn Tyr Ser Ser Ile Val
130                 135                 140

Thr Val His Pro Glu Ser Ile Asp Gly Arg Pro Gly Thr Leu Val Ile
145                 150                 155                 160

Glu Ser Phe Val Val Asp Val Pro Asp Gly Asn Thr Lys Asp Glu Thr
                165                 170                 175

Cys Tyr Phe Val Glu Ala Val Ile Lys Cys Asn Leu Thr Ser Leu Ala
            180                 185                 190

Glu Val Ser Glu Arg Leu Ala Val Gln Ser Pro Thr Ser Pro Leu Glu
        195                 200                 205

Gln

<210> SEQ ID NO 102
<211> LENGTH: 180
<212> TYPE: PRT
<213> ORGANISM: Oryza sativa

<400> SEQUENCE: 102

Met Val Glu Met Asp Ala Gly Gly Arg Pro Glu Pro Ser Pro Ser
1               5                   10                  15

Gly Gln Cys Ser Ser Ala Val Thr Met Arg Ile Asn Ala Pro Val His
            20                  25                  30
```

```
Leu Val Trp Ser Ile Val Arg Arg Phe Glu Glu Pro His Ile Phe Gln
            35                  40                  45

Pro Phe Val Arg Gly Cys Thr Met Arg Gly Ser Thr Ser Leu Ala Val
 50                  55                  60

Gly Cys Val Arg Glu Val Asp Phe Lys Ser Gly Phe Pro Ala Lys Ser
 65                  70                  75                  80

Ser Val Glu Arg Leu Glu Ile Leu Asp Asp Lys Glu His Val Phe Gly
                85                  90                  95

Val Arg Ile Ile Gly Gly Asp His Arg Leu Lys Asn Tyr Ser Ser Val
                100                 105                 110

Leu Thr Ala Lys Pro Glu Val Ile Asp Gly Glu Pro Ala Thr Leu Val
            115                 120                 125

Ser Glu Ser Phe Val Val Asp Val Pro Glu Gly Asn Thr Ala Asp Glu
130                 135                 140

Thr Arg His Phe Val Glu Phe Leu Ile Arg Cys Asn Leu Arg Ser Leu
145                 150                 155                 160

Ala Met Val Ser Gln Arg Leu Leu Leu Ala Gln Gly Asp Leu Ala Glu
                165                 170                 175

Pro Pro Ala Gln
            180

<210> SEQ ID NO 103
<211> LENGTH: 176
<212> TYPE: PRT
<213> ORGANISM: Vitis vinifera

<400> SEQUENCE: 103

Met Asn Gly Asn Gly Leu Ser Ser Met Glu Ser Glu Tyr Ile Arg Arg
 1                5                  10                  15

His His Arg His Glu Pro Ala Glu Asn Gln Cys Ser Ser Ala Leu Val
                20                  25                  30

Lys His Ile Lys Ala Pro Val Pro Leu Val Trp Ser Leu Val Arg Arg
            35                  40                  45

Phe Asp Gln Pro Gln Lys Tyr Lys Pro Phe Ile Ser Arg Cys Val Val
 50                  55                  60

Gln Gly Asn Leu Glu Ile Gly Ser Leu Arg Glu Val Asp Val Lys Ser
 65                  70                  75                  80

Gly Leu Pro Ala Thr Thr Ser Thr Glu Arg Leu Glu Leu Leu Asp Asp
                85                  90                  95

Asp Glu His Ile Leu Ser Met Arg Ile Ile Gly Gly Asp His Arg Leu
                100                 105                 110

Arg Asn Tyr Ser Ser Ile Ile Ser Leu His Pro Glu Ile Ile Asp Gly
            115                 120                 125

Arg Pro Gly Thr Met Val Ile Glu Ser Tyr Val Val Asp Val Pro Glu
130                 135                 140

Gly Asn Thr Lys Asp Glu Thr Cys Tyr Phe Ser Leu Ala Asp Val Ser
145                 150                 155                 160

Glu Arg Leu Ala Val Ala Gly Thr Val Thr Glu Pro Ile Asp Arg Met
                165                 170                 175

<210> SEQ ID NO 104
<211> LENGTH: 180
<212> TYPE: PRT
<213> ORGANISM: Oryza sativa

<400> SEQUENCE: 104
```

```
Met Val Glu Met Asp Ala Gly Gly Arg Pro Glu Ser Pro Pro Ser
1               5                   10                  15

Gly Gln Cys Ser Ser Ala Val Thr Met Arg Ile Asn Ala Pro Val His
            20                  25                  30

Leu Val Trp Ser Ile Val Arg Arg Phe Glu Glu Pro His Ile Phe Gln
            35                  40                  45

Pro Phe Val Arg Gly Cys Thr Met Arg Gly Ser Thr Ser Leu Ala Val
        50                  55                  60

Gly Cys Val Arg Glu Val Asp Phe Lys Ser Gly Phe Ser Ala Lys Ser
65                  70                  75                  80

Ser Val Glu Arg Leu Glu Ile Leu Asp Asp Lys Glu His Val Phe Gly
                85                  90                  95

Val Arg Ile Ile Gly Gly Asp His Arg Leu Lys Asn Tyr Ser Ser Val
            100                 105                 110

Leu Thr Ala Lys Pro Glu Val Ile Asp Gly Glu Pro Ala Thr Leu Val
            115                 120                 125

Ser Glu Ser Phe Val Ile Asp Val Pro Glu Gly Asn Thr Ala Asp Glu
        130                 135                 140

Thr Arg His Phe Val Glu Phe Leu Ile Arg Cys Asn Leu Arg Ser Leu
145                 150                 155                 160

Ala Met Val Ser Gln Arg Leu Leu Leu Ala Gln Gly Asp Leu Ala Glu
                165                 170                 175

Pro Pro Ala Gln
            180

<210> SEQ ID NO 105
<211> LENGTH: 215
<212> TYPE: PRT
<213> ORGANISM: Oryza sativa

<400> SEQUENCE: 105

Met Pro Cys Ile Pro Ala Ser Ser Pro Gly Ile Pro His Gln His Gln
1               5                   10                  15

His Gln His His Arg Ala Leu Ala Gly Val Gly Met Ala Val Gly Cys
            20                  25                  30

Ala Ala Glu Ala Ala Val Ala Ala Ala Gly Val Ala Gly Thr Arg Cys
            35                  40                  45

Gly Ala His Asp Gly Glu Val Pro Met Glu Val Ala Arg His His Glu
        50                  55                  60

His Ala Glu Pro Gly Ser Gly Arg Cys Cys Ser Ala Val Val Gln His
65                  70                  75                  80

Val Ala Ala Pro Ala Ala Val Trp Ser Val Val Arg Arg Phe Asp
                85                  90                  95

Gln Pro Gln Ala Tyr Lys Arg Phe Val Arg Ser Cys Ala Leu Leu Ala
            100                 105                 110

Gly Asp Gly Gly Leu Gly Lys Val Arg Glu Arg Leu Glu Ile Leu Asp
            115                 120                 125

Asp Glu Ser His Val Leu Ser Phe Arg Val Val Gly Gly Glu His Arg
        130                 135                 140

Leu Lys Asn Tyr Leu Ser Val Thr Val His Pro Ser Pro Ser Ala
145                 150                 155                 160

Pro Thr Ala Ala Thr Val Val Glu Ser Tyr Val Val Asp Val Pro
                165                 170                 175

Pro Gly Asn Thr Pro Glu Asp Thr Arg Val Phe Val Asp Thr Ile Val
            180                 185                 190
```

Lys Cys Asn Leu Gln Ser Leu Ala Lys Thr Ala Glu Lys Leu Ala Ala
            195                 200                 205

Gly Ala Arg Ala Ala Gly Ser
    210                 215

<210> SEQ ID NO 106
<211> LENGTH: 186
<212> TYPE: PRT
<213> ORGANISM: Rheum australe

<400> SEQUENCE: 106

Met Asn Gly Asp Gly Tyr Gly Gly Ser Glu Glu Phe Val Lys Arg
1               5                   10                  15

Tyr His Glu His Val Leu Ala Asp His Gln Cys Ser Ser Val Leu Val
                20                  25                  30

Glu His Ile Asn Ala Pro Leu His Leu Val Trp Ser Leu Val Arg Ser
            35                  40                  45

Phe Asp Gln Pro Gln Lys Tyr Lys Pro Phe Val Ser Arg Cys Val Val
        50                  55                  60

Gln Gly Gly Asp Leu Glu Ile Gly Ser Val Arg Glu Val Asp Val Lys
65                  70                  75                  80

Ser Gly Leu Pro Ala Thr Thr Ser Met Glu Glu Leu Glu Leu Leu Asp
                85                  90                  95

Asp Lys Glu His Val Leu Arg Val Lys Phe Val Gly Gly Asp His Arg
            100                 105                 110

Leu Lys Asn Tyr Ser Ser Ile Val Ser Leu His Pro Glu Ile Ile Gly
        115                 120                 125

Gly Arg Ser Gly Thr Met Val Ile Glu Ser Phe Ile Val Asp Ile Ala
130                 135                 140

Asp Gly Asn Thr Lys Glu Glu Thr Cys Tyr Phe Ile Glu Ser Leu Ile
145                 150                 155                 160

Asn Cys Asn Leu Lys Ser Leu Ser Cys Val Ser Glu Arg Leu Ala Val
                165                 170                 175

Glu Asp Ile Ala Glu Arg Ile Ala Gln Met
            180                 185

<210> SEQ ID NO 107
<211> LENGTH: 254
<212> TYPE: PRT
<213> ORGANISM: Oryza sativa

<400> SEQUENCE: 107

Met Val Gly Leu Val Gly Gly Gly Trp Arg Val Gly Asp Asp Ala
1               5                   10                  15

Ala Gly Gly Gly Gly Gly Ala Val Ala Ala Gly Ala Ala Ala
                20                  25                  30

Ala Glu Ala Glu His Met Arg Arg Leu His Ser Gln Gly Pro Arg Arg
            35                  40                  45

Ala Pro Val Gln Leu Arg Ala Arg Gln Ala His Gln Gly Ser Cys Ser
        50                  55                  60

Pro Pro Arg Ile Glu Cys Ala Asn Phe Ala Val Phe Leu Ala Ala Arg
65                  70                  75                  80

Asp Pro Lys Ile Val Trp Ser Leu Val Arg Ser Phe Asp Gln Pro Gln
                85                  90                  95

Arg Tyr Lys Pro Phe Val Ser Arg Cys Val Val Arg Gly Gly Asp Leu
            100                 105                 110

```
Glu Ile Gly Ser Val Arg Glu Val Asn Val Lys Thr Gly Leu Pro Ala
            115                 120                 125

Thr Thr Ser Thr Glu Arg Leu Glu Leu Leu Asp Asp Asp Glu His Ile
130                 135                 140

Leu Ser Val Lys Phe Val Gly Asp His Arg Leu Arg Asn Tyr Ser
145                 150                 155                 160

Ser Ile Val Thr Val His Pro Glu Ser Ile Asp Gly Arg Pro Gly Thr
                165                 170                 175

Leu Val Ile Glu Ser Phe Val Val Asp Val Pro Asp Gly Asn Thr Lys
            180                 185                 190

Asp Glu Thr Cys Tyr Phe Val Glu Ala Val Ile Lys Cys Asn Leu Thr
                195                 200                 205

Ser Leu Ala Glu Met Val Arg Met Ile Ser Leu Val Leu Pro Phe Met
        210                 215                 220

Leu Val Asp Arg Met Ser Gly Ile Thr Cys Glu Ser His Leu Glu Thr
225                 230                 235                 240

Thr Leu Val Arg Cys Gly Glu Tyr Ala Val Leu Ala His Val
                245                 250
```

<210> SEQ ID NO 108
<211> LENGTH: 186
<212> TYPE: PRT
<213> ORGANISM: Oryza sativa

<400> SEQUENCE: 108

```
Met Glu Pro His Met Glu Arg Ala Leu Arg Glu Ala Val Ala Ser Glu
1               5                   10                  15

Ala Glu Arg Arg Glu Leu Glu Gly Val Val Arg Ala His His Thr Gly
            20                  25                  30

Trp Asn Ala Pro Leu Ala Ala Val Trp Pro His Arg Ala Arg Val Arg
        35                  40                  45

Pro Thr Arg Ser Gly Thr Ser Thr Ser Ser Arg Ala Ser Ser Pro
    50                  55                  60

Pro Gly Asp Gly Ala Thr Val Gly Ser Val Arg Glu Val Ala Val Val
65                  70                  75                  80

Ser Gly Leu Pro Ala Ser Thr Ser Thr Glu Arg Leu Glu Ile Leu Asp
                85                  90                  95

Asp Asp Arg His Val Leu Ser Phe Arg Val Val Gly Gly Asp His Arg
            100                 105                 110

Leu Arg Asn Tyr Arg Ser Val Thr Ser Val Thr Glu Phe Ser Ser Pro
        115                 120                 125

Ser Ser Pro Pro Arg Pro Tyr Cys Val Val Val Glu Ser Tyr Val Val
    130                 135                 140

Asp Val Pro Glu Gly Asn Thr Glu Glu Asp Thr Arg Met Phe Thr Asp
145                 150                 155                 160

Thr Val Val Lys Leu Asn Leu Gln Lys Leu Ala Ala Val Ala Thr Ser
                165                 170                 175

Ser Ser Pro Pro Ala Ala Gly Asn His His
        180                 185
```

<210> SEQ ID NO 109
<211> LENGTH: 150
<212> TYPE: PRT
<213> ORGANISM: Oryza sativa

<400> SEQUENCE: 109

-continued

```
Met Glu Val Val Trp Ser Ile Val Arg Arg Phe Glu Pro His Ile
1               5                   10                  15

Phe Gln Pro Phe Val Arg Gly Cys Thr Met Arg Gly Ser Thr Ser Leu
                20                  25                  30

Ala Val Gly Cys Val Arg Glu Val Asp Phe Lys Ser Gly Phe Pro Ala
            35                  40                  45

Lys Ser Ser Val Glu Arg Leu Glu Ile Leu Asp Asp Lys Glu His Val
50                  55                  60

Phe Gly Val Arg Ile Ile Gly Gly Asp His Arg Leu Lys Asn Tyr Ser
65                  70                  75                  80

Ser Val Leu Thr Ala Lys Pro Glu Val Ile Asp Gly Pro Ala Thr
                85                  90                  95

Leu Val Ser Glu Ser Phe Val Val Asp Val Pro Glu Gly Asn Thr Ala
                100                 105                 110

Asp Glu Thr Arg His Phe Val Glu Phe Leu Ile Arg Cys Asn Leu Arg
                115                 120                 125

Ser Leu Ala Met Val Ser Gln Arg Leu Leu Leu Ala Gln Gly Asp Leu
130                 135                 140

Ala Glu Pro Pro Gly Gln
145                 150
```

<210> SEQ ID NO 110
<211> LENGTH: 206
<212> TYPE: PRT
<213> ORGANISM: Oryza sativa

<400> SEQUENCE: 110

```
Met Pro Tyr Thr Ala Pro Arg Pro Ser Pro Pro Gln His Ser Arg Ile
1               5                   10                  15

Gly Gly Cys Gly Gly Gly Val Leu Lys Ala Ala Gly Ala Ala Gly
                20                  25                  30

His Ala Ala Ser Cys Val Ala Val Pro Ala Glu Val Ala Arg His His
            35                  40                  45

Glu His Ala Ala Gly Val Gly Gln Cys Cys Ser Ala Val Val Gln Ala
50                  55                  60

Ile Ala Ala Pro Val Asp Ala Val Trp Arg Thr Ser Thr Ser Ser Gly
65                  70                  75                  80

Ala Ala Ala Ser Trp Thr Ala Thr Ala Thr Ala Gly Pro Leu Pro Val
                85                  90                  95

Gly Ser Val Arg Glu Phe Arg Val Leu Ser Gly Leu Pro Gly Thr Ser
                100                 105                 110

Ser Arg Glu Arg Leu Glu Ile Leu Asp Asp Glu Arg Arg Val Leu Ser
                115                 120                 125

Phe Arg Val Val Gly Gly Glu His Arg Leu Ser Asn Tyr Arg Ser Val
                130                 135                 140

Thr Thr Val His Glu Thr Ala Ala Gly Ala Ala Ala Val Val Val
145                 150                 155                 160

Glu Ser Tyr Val Val Asp Val Pro His Gly Asn Thr Ala Asp Glu Thr
                165                 170                 175

Arg Met Phe Val Asp Thr Ile Val Arg Cys Asn Leu Gln Ser Leu Ala
                180                 185                 190

Arg Thr Ala Glu Gln Leu Ala Leu Ala Ala Pro Arg Ala Ala
                195                 200                 205
```

```
<210> SEQ ID NO 111
<211> LENGTH: 396
<212> TYPE: PRT
<213> ORGANISM: Vitis vinifera
<220> FEATURE:
<221> NAME/KEY: VARIANT
<222> LOCATION: (61)..(277)
<223> OTHER INFORMATION: Xaa = any amino acid

<400> SEQUENCE: 111

Met Pro Ile Ser Ser Leu Pro Phe Ser Leu Tyr Thr Val Thr Pro Asn
 1               5                  10                  15

Pro Leu Lys Leu Ile Thr Thr His Ala His Ala Phe Thr Pro His Thr
            20                  25                  30

His Ile Phe Thr Leu Lys Phe Met Ser His Thr Tyr Cys Pro His Ile
        35                  40                  45

His His Ile Thr Ser Ile His Tyr Thr His Leu Leu Xaa Pro Ile Pro
    50                  55                  60

His Met Pro Leu Gln Pro Pro Leu Pro Pro His Pro Ile Leu Pro Ser
65                  70                  75                  80

Met Pro Ala Phe Gln His Leu Tyr Ser Thr Asn Gln His Leu Gln Val
                85                  90                  95

Ala Leu Phe Ser Ala Arg Gly Pro Asn Ile Arg Asp Phe Asn Phe Gln
            100                 105                 110

Asp Ala Asp Leu Leu Lys Leu Asp Ile Leu Ala Pro Gly Ser Leu Ile
        115                 120                 125

Trp Ala Ala Trp Ser Pro Asn Gly Thr Asp Glu Ala Asn Tyr Val Gly
    130                 135                 140

Glu Gly Ser Pro Thr Val Ala Met Ile Ala Lys Arg Gly Pro Arg His
145                 150                 155                 160

Gly Lys Tyr Met Ala Phe Cys Xaa Met Tyr Arg Asp Asn Val Ala Pro
                165                 170                 175

Lys Gly Val Asn Xaa Ala Val Ala Thr Val Lys Thr Lys Arg Thr Ile
            180                 185                 190

Gln Leu Lys Thr Ser Leu Glu Ile Ala Cys His Tyr Ala Gly Ile Asn
        195                 200                 205

Ile Ser Gly Ile Asn Gly Glu Val Met Pro Gly Gln Trp Glu Tyr Gln
    210                 215                 220

Val Gly Pro Gly Gln Cys Ser Ser Leu Leu Ala Gln Arg Val His Val
225                 230                 235                 240

Pro Leu Ser Ala Val Gly Ser Val Val His Arg Phe Asp Lys Pro Gln
                245                 250                 255

Arg Tyr Gln His Val Ile Lys Ser Cys Arg Ile Glu Asp Gly Phe Glu
            260                 265                 270

Met Arg Met Gly Xaa Leu Arg Asp Val Asn Ile Ile Ser Gly Leu Pro
        275                 280                 285

Thr Ala Thr Asn Thr Gly Arg Leu Asp Met Gln Asp Asp Glu Arg His
    290                 295                 300

Val Thr Arg Cys Pro His Gln Arg Gln Ser Glu Ser Lys Tyr Thr Glu
305                 310                 315                 320

Asn Asn Asn Ser Asp Ala Ser Ser Ile Lys Ser Pro Ile Asn Gly Pro
                325                 330                 335

Ser Glu His Leu Lys Thr Ala Ala Ser Pro Lys Thr Glu Ser Ile Ile
            340                 345                 350

Val Ile Asp Thr Ser Lys Phe Leu Asn Glu Glu Asp Phe Glu Gly Lys
        355                 360                 365
```

Asp Glu Thr Ser Ser Asn Gln Val Gln Ile Glu Asp Glu Asn Trp
            370                 375                 380

Glu Thr Arg Phe Pro Asn Thr Asp Ala Gly Ile Trp
385                 390                 395

<210> SEQ ID NO 112
<211> LENGTH: 443
<212> TYPE: PRT
<213> ORGANISM: Vitis vinifera
<220> FEATURE:
<221> NAME/KEY: VARIANT
<222> LOCATION: (5)..(443)
<223> OTHER INFORMATION: Xaa = any amino acid

<400> SEQUENCE: 112

Met Pro Ser Ala Xaa Lys Ser Ser Thr Val Pro Leu Ser Leu Xaa Gln
1               5                   10                  15

Phe Lys Leu Gly Leu Arg His Gly His Arg Val Ile Pro Trp Gly Asp
                20                  25                  30

Leu Asp Ser Leu Ala Met Leu Gln Arg Gln Leu Asp Val Asp Ile Leu
            35                  40                  45

Val Thr Gly His Thr His Arg Phe Thr Ala Tyr Lys His Glu Gly Gly
50                  55                  60

Val Val Ile Asn Pro Gly Ser Ala Thr Gly Ala Phe Gly Ser Ile Thr
65                  70                  75                  80

Tyr Asp Val Asn Pro Ser Phe Val Leu Met Asp Ile Asp Gly Leu Arg
                85                  90                  95

Val Val Val Cys Val Tyr Glu Leu Ile Asp Glu Thr Ala Asn Ile Ile
            100                 105                 110

Lys Glu Leu His Ala Arg Lys Ile Ser Phe Gly Thr Lys Ser Met Ile
        115                 120                 125

Xaa Cys Leu Leu Leu Lys Arg Arg Ser Thr Pro Lys Phe Arg Arg Lys
130                 135                 140

Lys Leu Phe Leu Phe Gln Cys Arg Val Gln Met Thr Leu Thr Leu Thr
145                 150                 155                 160

Asn Leu Ala Val Ser Gly Ile Ala Gln Thr Leu Gln Val Asp Gln Trp
                165                 170                 175

Thr Val Cys Ala Leu Ile Phe Met Thr Arg Arg Asp Ile His Leu Asp
            180                 185                 190

Lys Ala Arg Phe Leu Asp Phe Lys Asp Met Gly Lys Leu Leu Ala Asp
        195                 200                 205

Ala Ser Gly Leu Arg Lys Ala Leu Ser Gly Gly Xaa Val Thr Ala Gly
    210                 215                 220

Met Ala Ile Phe Asp Thr Met Arg His Ile Arg Pro Asp Val Pro Thr
225                 230                 235                 240

Val Cys Val Gly Leu Ala Ala Val Ala Met Ile Ala Lys Arg Gly Pro
                245                 250                 255

Arg His Gly Lys Tyr Met Ala Phe Cys Pro Met Tyr Arg Asp Asn Val
            260                 265                 270

Ala Pro Lys Gly Val Asn Val Ala Val Val Thr Val Lys Thr Lys Arg
        275                 280                 285

Thr Ile Gln Leu Lys Thr Ser Leu Glu Ile Ala Cys His Tyr Ala Gly
    290                 295                 300

Ile Asn Ile Ser Gly Ile Asn Gly Glu Val Met Pro Gly Gln Trp Glu
305                 310                 315                 320

```
Tyr Gln Val Gly Pro Gly Gln Cys Ser Ser Leu Leu Ala Gln Arg Val
                325                 330                 335

His Val Pro Leu Ser Ala Val Gly Ser Val Val His Arg Phe Asp Lys
            340                 345                 350

Pro Gln Arg Tyr Gln His Val Ile Lys Ser Cys Arg Ile Glu Asp Gly
        355                 360                 365

Phe Glu Met Arg Met Gly Arg Leu Arg Asp Val Asn Ile Ile Ser Gly
370                 375                 380

Leu Pro Thr Ala Thr Asn Thr Gly Arg Leu Asp Met Gln Asp Asp Glu
385                 390                 395                 400

Xaa His Val Thr Arg Cys Pro His Gln Arg Gln Ser Glu Ser Lys Tyr
                405                 410                 415

Thr Glu Asn Asn Asn Ser Asp Ala Ser Ser Val Lys Ser Pro Ile Asn
            420                 425                 430

Gly Pro Ser Glu His Leu Lys Thr Ala Ala Xaa
            435                 440

<210> SEQ ID NO 113
<211> LENGTH: 95
<212> TYPE: PRT
<213> ORGANISM: Oryza sativa

<400> SEQUENCE: 113

Glu Ile Gly Ser Val Arg Glu Val Asn Val Lys Thr Gly Leu Pro Ala
1               5                   10                  15

Thr Thr Ser Thr Glu Arg Leu Glu Leu Leu Asp Asp Asp Glu His Ile
            20                  25                  30

Leu Ser Val Lys Phe Val Gly Gly Asp His Arg Leu Arg Asn Tyr Ser
        35                  40                  45

Ser Ile Val Thr Val His Pro Glu Ser Ile Asp Gly Arg Pro Gly Thr
    50                  55                  60

Leu Val Ile Glu Ser Phe Val Val Asp Val Pro Asp Gly Asn Thr Lys
65                  70                  75                  80

Asp Glu Thr Cys Tyr Phe Val Glu Ala Val Ile Lys Cys Asn Leu
                85                  90                  95

<210> SEQ ID NO 114
<211> LENGTH: 191
<212> TYPE: PRT
<213> ORGANISM: Zea mays

<400> SEQUENCE: 114

Met Val Val Glu Met Asp Gly Val Gly Val Ala Ala Gly Gly
1               5                   10                  15

Gly Gly Ala Gln Thr Pro Ala Pro Pro Pro Arg Arg Trp Arg Leu
            20                  25                  30

Ala Asp Glu Arg Cys Asp Leu Arg Ala Met Glu Thr Asp Tyr Val Arg
        35                  40                  45

Arg Phe His Arg His Glu Pro Arg Asp His Gln Cys Ser Ser Ala Val
    50                  55                  60

Ala Lys His Ile Lys Ala Pro Val His Leu Val Trp Ser Leu Val Arg
65                  70                  75                  80

Arg Phe Asp Gln Pro Gln Leu Phe Lys Pro Phe Val Ser Arg Cys Glu
                85                  90                  95

Met Lys Gly Asn Ile Glu Ile Gly Ser Val Arg Glu Val Asn Val Lys
            100                 105                 110
```

Ser Gly Leu Pro Ala Thr Arg Ser Thr Glu Arg Leu Glu Leu Leu Asp
            115                 120                 125

Asp Asp Glu Arg Ile Leu Ser Val Arg Phe Val Gly Asp His Arg
    130                 135                 140

Leu Gln Val Cys Ser Val Leu His Leu Ser Ile Phe Cys Ala Ala His
145                 150                 155                 160

Ala Arg Tyr Phe Ala His His Leu Lys Cys Val Leu Glu Phe Leu Cys
                165                 170                 175

Gln Met His Leu Asp Val Leu Pro Cys Asp Asp Ala Ile Leu Glu
            180                 185                 190

<210> SEQ ID NO 115
<211> LENGTH: 239
<212> TYPE: PRT
<213> ORGANISM: Oryza sativa

<400> SEQUENCE: 115

Met Asn Gly Cys Thr Gly Gly Ala Gly Val Ala Ala Gly Arg Leu
1               5                   10                  15

Pro Ala Val Ser Leu Gln Gln Ala Gln Trp Lys Leu Val Asp Glu Arg
                20                  25                  30

Cys Glu Leu Arg Glu Glu Glu Met Glu Tyr Val Arg Arg Phe His Arg
            35                  40                  45

His Glu Ile Gly Ser Asn Gln Cys Asn Ser Phe Ile Ala Lys His Val
        50                  55                  60

Arg Ala Pro Leu Gln Asn Val Trp Ser Leu Val Arg Arg Phe Asp Gln
65                  70                  75                  80

Pro Gln Ile Tyr Lys Pro Phe Val Arg Lys Cys Val Met Arg Gly Asn
                85                  90                  95

Val Glu Thr Gly Ser Val Arg Glu Ile Ile Val Gln Ser Gly Leu Pro
            100                 105                 110

Ala Thr Arg Ser Ile Glu Arg Leu Glu Phe Leu Asp Asp Asn Glu Tyr
                115                 120                 125

Ile Leu Arg Val Lys Phe Ile Gly Gly Asp His Met Leu Lys Lys Arg
        130                 135                 140

Ile Pro Lys Lys Thr Tyr Ala Ile Ser Ser Arg Thr Cys Ser Asp Ser
145                 150                 155                 160

Ala Ile Ile Ala Val Gly Gln Ser Asn Cys Ala Pro Glu Ile Thr Ala
                165                 170                 175

Met Asn Gly Gly Val Ser Ile Gln Pro Trp Leu Ile Leu Ala Phe
            180                 185                 190

Phe Ser Ser Pro Ser Asn Gln Thr Asn Pro Asp Ser Leu Arg Asp Met
                195                 200                 205

His Pro Gly Ser Trp Phe Gln Ile Leu Leu Val Leu Ala Met Phe Thr
            210                 215                 220

Cys Ser Lys Gly Ser Val Leu Pro Pro Ser Glu Lys Val Asn Val
225                 230                 235

<210> SEQ ID NO 116
<211> LENGTH: 48
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (4)..(45)
<223> OTHER INFORMATION: Xaa = any amino acid

```
<400> SEQUENCE: 116

Val Gly Arg Xaa Val Xaa Val Xaa Ser Gly Leu Pro Ala Xaa Xaa Ser
1               5                   10                  15

Xaa Glu Xaa Leu Xaa Xaa Xaa Asp Xaa Xaa Xaa Xaa Xaa Xaa Phe
            20                  25                  30

Xaa Xaa Xaa Gly Gly Xaa His Arg Leu Xaa Asn Tyr Xaa Ser Val Thr
            35                  40                  45

<210> SEQ ID NO 117
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (2)..(32)
<223> OTHER INFORMATION: Xaa = any amino acid

<400> SEQUENCE: 117

Val Xaa Glu Ser Tyr Xaa Val Asp Xaa Pro Xaa Gly Asn Xaa Xaa Xaa
1               5                   10                  15

Xaa Thr Xaa Xaa Phe Xaa Asp Xaa Xaa Xaa Xaa Xaa Asn Leu Gln Xaa
            20                  25                  30

Leu

<210> SEQ ID NO 118
<211> LENGTH: 50
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (2)..(50)
<223> OTHER INFORMATION: Xaa = any amino acid

<400> SEQUENCE: 118

His Xaa His Xaa Xaa Xaa Xaa Xaa Gln Cys Xaa Ser Xaa Leu Val Lys
1               5                   10                  15

Xaa Ile Xaa Ala Pro Xaa His Xaa Val Trp Ser Xaa Val Arg Arg Phe
            20                  25                  30

Asp Xaa Pro Gln Lys Tyr Lys Pro Phe Xaa Ser Arg Cys Xaa Val Xaa
            35                  40                  45

Gly Xaa
    50

<210> SEQ ID NO 119
<211> LENGTH: 65
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (2)..(65)
<223> OTHER INFORMATION: Xaa = any amino acid

<400> SEQUENCE: 119

Glu Xaa Gly Xaa Xaa Arg Glu Val Xaa Xaa Lys Ser Gly Leu Pro Ala
1               5                   10                  15

Thr Xaa Ser Thr Glu Xaa Leu Glu Xaa Leu Asp Asp Xaa Glu His Ile
            20                  25                  30
```

```
Leu Xaa Ile Xaa Ile Xaa Gly Gly Asp His Arg Leu Lys Asn Tyr Ser
        35          40                  45

Ser Xaa Xaa Xaa His Xaa Glu Xaa Ile Xaa Gly Xaa Xaa Gly Thr
50              55                  60

Xaa
65

<210> SEQ ID NO 120
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(37)
<223> OTHER INFORMATION: Xaa = any amino acid

<400> SEQUENCE: 120

Xaa Xaa Glu Ser Phe Val Val Asp Val Pro Xaa Gly Asn Thr Lys Xaa
1               5                   10                  15

Xaa Thr Cys Xaa Phe Val Glu Xaa Leu Ile Xaa Cys Asn Leu Xaa Ser
            20                  25                  30

Leu Ala Xaa Xaa Xaa Glu Arg Leu
        35              40

<210> SEQ ID NO 121
<211> LENGTH: 44
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (2)..(42)
<223> OTHER INFORMATION: Xaa = any amino acid

<400> SEQUENCE: 121

Cys Xaa Ser Xaa Xaa Val Xaa Thr Ile Xaa Ala Pro Leu Xaa Leu Val
1               5                   10                  15

Trp Ser Ile Leu Arg Xaa Phe Asp Xaa Pro Xaa Xaa Xaa Xaa Xaa Phe
            20                  25                  30

Val Lys Xaa Cys Xaa Xaa Xaa Ser Gly Xaa Gly Gly
            35                  40

<210> SEQ ID NO 122
<211> LENGTH: 49
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (5)..(46)
<223> OTHER INFORMATION: Xaa = any amino acid

<400> SEQUENCE: 122

Gly Ser Val Arg Xaa Val Thr Xaa Val Ser Xaa Xaa Pro Ala Xaa Phe
1               5                   10                  15

Ser Xaa Glu Arg Leu Xaa Glu Leu Asp Asp Glu Ser His Val Met Xaa
            20                  25                  30

Xaa Ser Ile Ile Gly Gly Xaa His Arg Leu Val Asn Tyr Xaa Ser Lys
        35                  40                  45
```

Thr

<210> SEQ ID NO 123
<211> LENGTH: 899
<212> TYPE: DNA
<213> ORGANISM: Artificial Sequence
<220> FEATURE:
<223> OTHER INFORMATION: Synthetic Construct

<400> SEQUENCE: 123

```
gagctcccac aacagacctg aaagaggctg caatagttgt cataagaatc aatcctctgc    60
ttcaacgtcg gagacaacct cgcatacaaa tgtcgaaacc acatctcacg gtacagaaga   120
cagaacacat ggtcgttgtc tacgtaagga gcaatcgctt ccacacttgg ccacggcgtg   180
tccttgaaca gacgctccga tatgctctgg aacgatgtct cacacatctg gtggatctcg   240
tacacgttct tatcccttat gtgtctgtac atgtgtgaca cgaacgactt caccgaatcc   300
ggcaccatat ttgggtcgta cccactctcc ctctcccccg gaccttcctc atactcattg   360
ctgctcgcca tttctcgccgg atcaattctt agcggccgca acaatgttag ctcttaactc   420
actaccaccg cctagggttt ccttattacc accggttcta tcatccggtt tcgtttcctt   480
attaccaccg gttctatcat ccggttatgt tttttataa agtcatttta ataaaacttt   540
ctatggttcg gaaaaaaaaa acttcacata atcatcgcta ttctctctct ctctctctct   600
ctctctctct ctcgctctca tatttgcagg taaagcttcg ttgattcgtc ctctttatgt   660
tcaattatag tttcgcatcc ctcctatgtc tttctttcta gatcttaaag cagagtcatt   720
gcttaaccct aattatcact gttcttgtat aaaacacttt tcacctaatc attgagattg   780
ttacgggatc tgataattgc gtctgtgaat tacaagaaat tagggtttat ttcttcttga   840
ttttagattg atcttttttgc agttgacaat tcgttctctt tgggaaatta gagcccggg   899
```

<210> SEQ ID NO 124
<211> LENGTH: 81
<212> TYPE: DNA
<213> ORGANISM: Artificial Sequence
<220> FEATURE:
<223> OTHER INFORMATION: Synthetic Construct

<400> SEQUENCE: 124

```
cccgggaaac attcaaaaaa aaaaaaaaac cattttttttt ttcttactca aatcttttttt    60
agtatcattc tccaaaccgg t                                                 81
```

<210> SEQ ID NO 125
<211> LENGTH: 83
<212> TYPE: DNA
<213> ORGANISM: Artificial Sequence
<220> FEATURE:
<223> OTHER INFORMATION: Synthetic Construct

<400> SEQUENCE: 125

```
cccggggtat ttttacaaca attaccaaca acaacaacaa acaacaacaa cattacattt    60
tacattctac aactacaacc ggt                                              83
```

<210> SEQ ID NO 126
<211> LENGTH: 8774
<212> TYPE: DNA
<213> ORGANISM: Artificial Sequence
<220> FEATURE:
<223> OTHER INFORMATION: Synthetic pMANDI-UAS-GFP T-DNA region

<400> SEQUENCE: 126

```
ggtttacccg ccaatatatc ctgtcaaaca ctgatagttt aaactgaagg cgggaaacga      60
caatctgatc atgagcggag aattaaggga gtcaggcctt aattaagagc tcgcatgccc     120
tttcagaaag aatgctaacc cacagatggt tagagaggct tacgcagcag gtctcatcaa     180
gacgatctac ccgagcaata atctccagga aatcaaatac cttcccaaga aggttaaaga     240
tgcagtcaaa agattcagga ctaactgcat caagaacaca gagaaagata tatttctcaa     300
gatcagaagt actattccag tatggacgat tcaaggcttg cttcacaaac caaggcaagt     360
aatagagatt ggagtctcta aaaaggtagt tcccactgaa tcaaaggcca tggagtcaaa     420
gattcaaata gaggacctaa cagaactccc cgtaaagact ggcgaacagt tcatacagag     480
tctcttacga ctcaatgaca agaagaaaat cttcgtcaac atggtggagc acgacacgct     540
tgtctactcc aaaaatatca aagatacagt ctcagaagac caaagggcaa ttgagacttt     600
tcaacaaagg gtaatatccg gaaacctcct cggattccat tgcccagcta tctgtcactt     660
tattgtgaag atagtggaaa aggaaggtgg ctcctacaaa tgccatcatt gcgataaagg     720
aaaggccatc gttgaagatg cctctgccga cagtggtccc aaagatggac ccccacccac     780
gaggagcatc gtggaaaaag aagacgttcc aaccacgtct tcaaagcaag tggattgatg     840
tgatatctcc actgacgtaa gggatgacgc acaatcccac tatccttcgc aagacccttc     900
ctctatataa ggaagttcat ttcatttgga gagaacacgg gggactctag cgctaccggg     960
tgcaaagatg gataaagcgg aattaattcc cgagcctcca aaaagaaga gaaaggtcga    1020 attgggtacc gccgacgctt tggacgactt cgacttggac atgttgggtt ctgatgccct    1080
ggacgatttc gatctcgata tgctaggcag cgacgcatta gatgactttg acttagatat    1140
gctcgggtcc gacgcgcttg atgatttcga cctagacatg ctgggaggtt ctggtggtgg    1200
ttctggtggt ggttctggtc gtgatttacc tgagatgact cccgcagttg caatgactct    1260
tagcttagca gccaacacca tgtgtgaatc atcacctgtc gagatcactc agctaaagaa    1320
cgttactgat gcagctgact tgttatctga ttctgaaaat caaagctttt gcaacggagg    1380
gactgaatgc actatggaag atgtttctga actggaagag gtaggtgaac aggatttgtt    1440 gaaaactta tccgatacga aagcgggtc ttccaatgtt tttgatgaag acgatgtatt    1500
gtctgttgtg gaggataata gtgctgtcat aagtgagggc ttgttagttg ttgatgcagg    1560
ctctgaatta agcttgtcta atacagctat ggaaatagat aacgggcgag ttcttgcaac    1620
cgcgattatc gtaggcgaat caagcattga gcaggttccc accgcggaag ttcttatcgc    1680
gggtgtaaat caggatacca atacttcgga ggttgtcatt agattgccag atgaaaatag    1740
taatcatctg gtgaaaggga gaagtgttta tgaactagat tgtataccgc tttggggcac    1800
ggtttccatt caagggaatg cgtctgagat ggaggctgct tttgccgtgt cacctccattt    1860 tctgaaacta cccatcaaaa tgcttatggg ggaccatgag ggtatgagtc aagcctcac     1920 acacctcaca ggtcattttt tcggtgttta tgatggtcat ggaggccata aggttgctga    1980
ctattgccga gatagactcc attttgcttt ggctgaagaa atagaacgta taaaagacga    2040
attatgcaag aggaatacag gagagggtag gcaggtgcag tgggataaag tcttcacgag    2100
ttgttttcta actgtcgatg gtgagattga aggaaaaatt ggtagagccg ttgttggttc    2160
ttctgataag gttcttgagg ctgttgcgga tgagaccgta ggatcaactg ctgttgttgc    2220
cttggtttgc tcatcacata tagtagtttc taactgcggt gattcgaggg cggttttatt    2280
ccgtggcaaa gaagccatgc ccttgtcagt tgatcacaaa ccagatagag aggatgaata    2340
```

```
tgcaagaata gaaaatgctg gaggcaaagt tatacaatgg caaggcgcac gtgttttgg    2400 tcgtctcgcc atgtctaggt ccatcggtga cagatatctg aagccatatg tgatcccaga   2460
accggaagtg acattcatgc ctcggtcaag agaagacgag tgtctcatac tagccagtga   2520
cggtctttgg gatgtaatga caaccaaga agtctgcgaa atagcaagga gacggatatt    2580
gatgtggcac aagaagaacg gtgcaccgcc tctagcagag agaggcaaag gaatagatcc    2640
agcttgccaa gccgcagctg actacctctc aatgcttgct ctacaaaaag gaagtaaaga   2700
caacatctcc atcattgtga ttgacttgaa agctcaagca aagttcaaga ccagaaccct    2760
cgacaagcgc gaggaacagg cccggaaggc gaaagtgaac aatgagaaga aaacagaaat    2820
cgttaaacct gagagctgct caaacgaggg agacgttaag gatcttaaga ggaaagactc    2880
tgaggatggc aacgaaggag aggaagagga agctagctca aaacctaaga aaccaaaggt    2940
ggcactctca catctccaag acattgacga caccgaagca gaccaagaag aagaatgaag    3000
atcctaggtc gaggcgaatt tccccgatcg ttcaaacatt tggcaataaa gtttcttaag    3060
attgaatcct gttgccggtc ttgcgatgat tatcatataa tttctgttga attacgttaa    3120
gcatgtaata attaacatgt aatgcatgac gttatttatg agatgggttt ttatgattag    3180
agtcccgcaa ttatacattt aatacgcgat agaaaacaaa atatagcgcg caaactagga    3240
taaattatcg cgcgcggtgt catctatgtt actagatcgg gaattaattc gataagctag    3300
agagaattgg ccttaattaa cagctccgga gtactgtcct ccgagcggag tactgtcctc    3360
cgagcggagt actgtcctcc gagcggagta ctgtcctccg agcggagtac tgtcctccga    3420
ggcaagaccc ttcctctata taggaagtt catttcattt ggagagaaca cggggactct    3480
agcgctaccg gtatgggcag ccatcatcat catcatcacg tgagcaaggg cgaggagctg    3540
ttcaccgggg tggtgcccat cctggtcgag ctggacggcg acgtaaacgg ccacaagttc    3600
agcgtgtccg gcgagggcga gggcgatgcc acctacggca agctgaccct gaagttcatc    3660
tgcaccaccg gcaagctgcc cgtgccctgg cccaccctcg tgaccaccct gacctacggc    3720
gtgcagtgct tcagccgcta ccccgaccac atgaagcagc acgacttctt caagtccgcc    3780
atgcccgaag gctacgtcca ggagcgcacc atcttcttca aggacgacgg caactacaag    3840
acccgcgccg aggtgaagtt cgagggcgac accctggtga accgcatcga gctgaagggc    3900
atcgacttca aggaggacgg caacatcctg gggcacaagc tggagtacaa ctacaacagc    3960
cacaacgtct atatcatggc cgacaagcag aagaacggca tcaaggtgaa cttcaagatc    4020
cgccacaaca tcgaggacgg cagcgtgcag ctcgccgacc actaccagca gaacaccccc    4080
atcggcgacg gccccgtgct gctgcccgac aaccactacc tgagcaccca gtccgccctg    4140
agcaaagacc ccaacgagaa gcgcgatcac atggtcctgc tggagttcgt gaccgccgcc    4200
gggatcactc tcggcatgga cgagctgtac aagtccggag ctgcggccgc tgccgctgcg    4260
gcagcggccg aattccccgg gctcgagaag cttggatcct aggtcgaggc gaatttcccc    4320
gatcgttcaa acatttggca ataaagtttc ttaagattga atcctgttgc cggtcttgcg    4380
atgattatca tataatttct gttgaattac gttaagcatg taataattaa catgtaatgc    4440
atgacgttat ttatgagatg gttttttatg attagagtcc cgcaattata catttaatac    4500
gcgatagaaa acaaaatata gcgcgcaaac taggataaat tatcgcgcgc ggtgtcatct    4560
atgttactag atcgggaatt aattcgataa gctagagaca attcgagctc gcatgcctgc    4620
aggtccccag attagccttt tcaatttcag aaagaatgct aacccacaga tggtttagag    4680
aggcttacgc agcaggtctc atcaagacga tctaccccgag caataatctc caggaaatca    4740
```

| | |
|---|---|
| aataccttcc caagaaggtt aaagatgcag tcaaaagatt caggactaac tgcatcaaga | 4800 |
| acacagagaa agatatattt ctcaagatca gaagtactat tccagtatgg acgattcaag | 4860 |
| gcttgcttca caaccaagg caagtaatag agattggagt ctctaaaaag gtagttccca | 4920 |
| ctgaatcaaa ggccatggag tcaaagattc aaatagagga cctaacagaa ctccccgtaa | 4980 |
| agactggcga acagttcata cagagtctct tacgactcaa tgacaagaag aaaatcttcg | 5040 |
| tcaacatggt ggagcacgac acgcttgtct actccaaaaa tatcaaagat acagtctcag | 5100 |
| aagaccaaag ggcaattgag acttttcaac aaagggtaat atccggaaac ctcctcggat | 5160 |
| tccattgccc agctatctgt cactttattg tgaagatagt ggaaaaggaa ggtggctcct | 5220 |
| acaaatgcca tcattgcgat aaaggaaagg ccatcgttga agatgcctct gccgacagtg | 5280 |
| gtcccaaaga tggaccccca cccacgagga gcatcgtgga aaaagaagac gttccaacca | 5340 |
| cgtcttcaaa gcaagtggat tgatgtgata tctccactga cgtaagggat gacgcacaat | 5400 |
| cccactatcc ttcgcaagac ccttcctcta tataaggaag ttcatttcat ttggagagaa | 5460 |
| cacgggggac tctagcgcta ccggtatgaa gctactgtct tctatcgaac aagcatgcga | 5520 |
| tatttgccga cttaaaaagc tcaagtgctc caagaaaaaa ccgaagtgcg ccaagtgtct | 5580 |
| gaagaacaac tgggagtgtc gctactctcc caaaaccaaa agatctccgc tgactagggc | 5640 |
| acatctgaca gaagtggaat caaggctaga aagactggaa cagctatttc tactgatttt | 5700 |
| tcctcgagaa gaccttgaca tgattttgaa aatggattct ttacaggata taaaagcatt | 5760 |
| gttaacagga ttatttgtac aagataatgt gaataaagat gccgtcacag atagattggc | 5820 |
| ttcagtggag actgatatgc ctctaacatt gagacagcat agaataagtg cgacatcatc | 5880 |
| atcggaagag agtagtaaca aaggtcaaag acagttgact gtatcggtct cggaattgat | 5940 |
| gccttcggag ttaacaccag aagaacgatc ggaactaaaa aactcaatcg ccgagttcca | 6000 |
| cacataccaa ctcgatccag gaagctgttc atcactccac gcgcaacgaa tccacgcgcc | 6060 |
| tccggaactc gtctggtcaa tcgtacgacg attcgacaaa ccacaaacac accgccactt | 6120 |
| catcaaatcc tgctccgtcg aacaaaactt cgagatgcgc gtcggatgca cgcgcgacat | 6180 |
| catcgtcatc agtggattac cggcgaacac atcaacggaa agactcgata tactcgacga | 6240 |
| cgaacggaga gttaccggag ccagtatcat cggaggcgaa cataggctga cgaattacaa | 6300 |
| aggcgttacg acggtgcatc ggttcgagaa agagaatcgg atctgacgg tggttttgga | 6360 |
| atcttacgtc gttgatatgc cggaaggtaa ctcggaggat gatactcgta ttgttgtgga | 6420 |
| tgacgttgtg aagcttaatt tgcagaaact cgcgacggtt gctgaagcta tggctcgtaa | 6480 |
| ctccggtgac ggaagtggtt ctcaggtgac gtgaagatcc taggtcgagg cgaatttccc | 6540 |
| cgatcgttca acatttggc aataaagttt cttaagattg aatcctgttg ccggtcttgc | 6600 |
| gatgattatc atataatttc tgttgaatta cgttaagcat gtaataatta acatgtaatg | 6660 |
| catgacgtta tttatgagat gggtttttat gattagagtc ccgcaattat acatttaata | 6720 |
| cgcgatagaa aacaaatata gcgcgcaaac tagataaatt atcgcgcgcg tgtcatcta | 6780 |
| tgttactaga tcgggaatta attcgatagc tagagatccg tcaacatggt ggagcacgac | 6840 |
| acgcttgtct actccaaaaa tatcaaagat acagtctcag aagaccaaag ggcaattgag | 6900 |
| acttttcaac aaagggtaat atccggaaac ctcctcggat tccattgccc agctatctgt | 6960 |
| cactttattg tgaagatagt ggaaaaggaa ggtggctcct acaaatgcca tcattgcgat | 7020 |
| aaaggaaagg ccatcgttga agatgcctct gccgacagtg gtcccaaaga tggaccccca | 7080 |

| | |
|---|---|
| cccacgagga gcatcgtgga aaaagaagac gttccaacca cgtcttcaaa gcaagtggat | 7140 |
| tgatgtgata tctccactga cgtaagggat gacgcacaat cccactatcc ttcgcaagac | 7200 |
| ccttcctcta tataaggaag ttcatttcat ttggagagga cagacctgca ggtcgatcca | 7260 |
| tgagcccaga acgacgcccg gccgacatcc gccgtgccac cgaggcggac atgccggcgg | 7320 |
| tctgcaccat cgtcaaccac tacatcgaga caagcacggt caacttccgt accgagccgc | 7380 |
| aggaaccgca ggagtggacg gacgacctcg tccgtctgcg ggagcgctat ccctggctcg | 7440 |
| tcgccgaggt ggacggcgag gtcgccggca tcgcctacgc gggcccctgg aaggcacgca | 7500 |
| acgcctacga ctggacggcc gagtcgaccg tgtacgtctc ccccgccac cagcggacgg | 7560 |
| gactgggctc cacgctctac acccacctgc tgaagtccct ggaggcacag ggcttcaaga | 7620 |
| gcgtggtcgc tgtcatcggg ctgcccaacg acccgagcgt gcgcatgcac gaggcgctcg | 7680 |
| gatatgcccc ccgcggcatg ctgcgggcgg ccggcttcaa gcacgggaac tggcatgacg | 7740 |
| tgggtttctg gcagctggac ttcagcctgc cggtaccgcc ccgtccggtc ctgcccgtca | 7800 |
| ccgagatctg atctcacgcg tctaggatcg acctgcagat cgttcaaaca tttggcaata | 7860 |
| aagtttctta agattgaatc ctgttgccgg tcttgcgatg attatcatct aatttctgtt | 7920 |
| gaattacgtt aagcatgtaa taattaacat gtaatgcatg acgttattta tgagatgggt | 7980 |
| ttttatgatt agagtcccgc aattatacat ttaatacgcg atagaaaaca aaatatagcg | 8040 |
| cgcaaactag gataaattat cgcgcgcggt gtcatctatg ttactagatc tctagcttga | 8100 |
| tatcgaatta attcactggc cgtcgtttta caacgtcgtg actgggaaaa ccctggcgtt | 8160 |
| acccaactta atcgccttgc agcacatccc cctttcgcca gctggcgtaa tagcgaagag | 8220 |
| gcccgcaccg atcgcccttc ccaacagttg cgcagcctga atggcgcccg ctcctttcgc | 8280 |
| tttcttccct cctttctcg ccacgttcgc cggctttccc cgtcaagctc taaatcgggg | 8340 |
| gctcccttta gggttccgat ttagtgcttt acggcacctc gaccccaaaa aacttgattt | 8400 |
| gggtgatggt tcacgtagtg ggccatcgcc ctgatagacg ttttttcgcc ctttgacgtt | 8460 |
| ggagtccacg ttctttaata gtggactctt gttccaaact ggaacaacac tcaaccctat | 8520 |
| ctcgggctat tcttttgatt tataagggat tttgccgatt tcggaaccac catcaaacag | 8580 |
| gattttcgcc tgctggggca aaccagcgtg gaccgcttgc tgcaactctc tcagggccag | 8640 |
| gcggtgaagg gcaatcagct gttgcccgtc tcactggtga aaagaaaaac caccccagta | 8700 |
| cattaaaaac gtccgcaatg tgttattaag ttgtctaagc gtcaatttgt ttacaccaca | 8760 |
| atatatcctg ccac | 8774 |

<210> SEQ ID NO 127
<211> LENGTH: 10019
<212> TYPE: DNA
<213> ORGANISM: Artificial Sequence
<220> FEATURE:
<223> OTHER INFORMATION: Synthetic pMANDI-UAS-GFP-LEAFY

<400> SEQUENCE: 127

| | |
|---|---|
| ggtttacccg ccaatatatc ctgtcaaaca ctgatagttt aaactgaagg cgggaaacga | 60 |
| caatctgatc atgagcggag aattaaggga gtcaggcctt aattaagagc tcgcatgccc | 120 |
| tttcagaaag aatgctaacc cacagatggt tagagaggct tacgcagcag gtctcatcaa | 180 |
| gacgatctac ccgagcaata atctccagga aatcaaatac cttcccaaga aggttaaaga | 240 |
| tgcagtcaaa agattcagga ctaactgcat caagaacaca gagaaagata tatttctcaa | 300 |
| gatcagaagt actattccag tatggacgat tcaaggcttg cttcacaaac caaggcaagt | 360 |

```
aatagagatt ggagtctcta aaaaggtagt tcccactgaa tcaaaggcca tggagtcaaa      420
gattcaaata gaggacctaa cagaactccc cgtaaagact ggcgaacagt tcatacagag      480
tctcttacga ctcaatgaca agaagaaaat cttcgtcaac atggtggagc acgacacgct      540
tgtctactcc aaaaatatca agatacagt ctcagaagac caaagggcaa ttgagacttt       600
tcaacaaagg gtaatatccg gaaacctcct cggattccat tgcccagcta tctgtcactt      660
tattgtgaag atagtggaaa aggaaggtgg ctcctacaaa tgccatcatt gcgataaagg      720
aaaggccatc gttgaagatg cctctgccga cagtggtccc aaagatggac ccccacccac      780
gaggagcatc gtgaaaaag aagacgttcc aaccacgtct tcaaagcaag tggattgatg       840
tgatatctcc actgacgtaa gggatgacgc acaatcccac tatccttcgc aagacccttc      900
ctctatataa ggaagttcat ttcatttgga gagaacacgg gggactctag cgctaccggg      960
tgcaaagatg gataaagcgg aattaattcc cgagcctcca aaaagaaga gaaaggtcga      1020
attgggtacc gccgacgctt tggacgactt cgacttggac atgttgggtt ctgatgccct     1080
ggacgatttc gatctcgata tgctaggcag cgacgcatta gatgactttg acttagatat     1140
gctcgggtcc gacgcgcttg atgatttcga cctagacatg ctgggaggtt ctggtggtgg     1200
ttctggtggt ggttctggtc gtgatttacc tgagatgact cccgcagttg caatgactct     1260
tagcttagca gccaacacca tgtgtgaatc atcacctgtc gagatcactc agctaaagaa     1320
cgttactgat gcagctgact tgttatctga ttctgaaaat caaagctttt gcaacggagg     1380
gactgaatgc actatggaag atgtttctga actggaagag gtaggtgaac aggatttgtt     1440
gaaaacttta tccgatacga gaagcgggtc ttccaatgtt tttgatgaag acgatgtatt     1500
gtctgttgtg gaggataata gtgctgtcat aagtgagggc ttgttagttg ttgatgcagg     1560
ctctgaatta agcttgtcta atacagctat ggaaatagat aacgggcgag ttcttgcaac     1620
cgcgattatc gtaggcgaat caagcattga gcaggttccc accgcggaag ttcttatcgc     1680
gggtgtaaat caggatacca atacttcgga ggttgtcatt agattgccag atgaaaatag     1740
taatcatctg gtgaaaggga gaagtgttta tgaactagat tgtataccgc tttggggcac     1800
ggtttccatt caagggaatg cgtctgagat ggaggctgct tttgccgtgt cacctcattt     1860
tctgaaacta cccatcaaaa tgcttatggg ggaccatgag ggtatgagtc caagcctcac     1920
acacctcaca ggtcattttt tcggtgttta tgatggtcat ggaggccata aggttgctga     1980
ctattgccga gatagactcc attttgcttt ggctgaagaa atagaacgta taaagacga      2040
attatgcaag aggaatacag gagagggtag gcaggtgcag tgggataaag tcttcacgag     2100
ttgttttcta actgtcgatg gtgagattga aggaaaaatt ggtagagccg ttgttggttc     2160
ttctgataag gttcttgagg ctgttgcgga tgagaccgta ggatcaactg ctgttgttgc     2220
cttggttttgc tcatcacata tagtagtttc taactgcggt gattcgaggg cggttttatt     2280
ccgtggcaaa gaagccatgc ccttgtcagt tgatcacaaa ccagatagag aggatgaata     2340
tgcaagaata gaaaatgctg gaggcaaagt tatacaatgg caaggcgcac gtgttttggg     2400
tcgtctcgcc atgtctaggt ccatcggtga cagatatctg aagccatatg tgatcccaga     2460
accggaagtg acattcatgc ctcggtcaag agaagacgag tgtctcatac tagccagtga     2520
cggtctttgg gatgtaatga acaaccaaga agtctgcgaa atagcaagga cggatatt      2580
gatgtggcac aagaagaacg gtgcaccgcc tctagcagag agaggcaaag gaatagatcc     2640
agcttgccaa gccgcagctg actacctctc aatgcttgct ctacaaaaag gaagtaaaga     2700
```

```
caacatctcc atcattgtga ttgacttgaa agctcaagca aagttcaaga ccagaaccct    2760
cgacaagcgc gaggaacagg cccggaaggc gaaagtgaac aatgagaaga aaacagaaat    2820
cgttaaacct gagagctgct caaacgaggg agacgttaag gatcttaaga ggaaagactc    2880
tgaggatggc aacgaaggag aggaagagga agctagctca aaacctaaga aaccaaaggt    2940
ggcactctca catctccaag acattgacga caccgaagca gaccaagaag aagaatgaag    3000
atcctaggtc gaggcgaatt tccccgatcg ttcaaacatt tggcaataaa gtttcttaag    3060
attgaatcct gttgccggtc ttgcgatgat tatcatataa tttctgttga attacgttaa    3120
gcatgtaata attaacatgt aatgcatgac gttatttatg agatgggttt ttatgattag    3180
agtcccgcaa ttatacattt aatacgcgat agaaaacaaa atatagcgcg caaactagga    3240
taaattatcg cgcgcggtgt catctatgtt actagatcgg gaattaattc gataagctag    3300
agagaattgg ccttaattaa cagctccgga gtactgtcct ccgagcggag tactgtcctc    3360
cgagcggagt actgtcctcc gagcggagta ctgtcctccg agcggagtac tgtcctccga    3420
ggcaagaccc ttcctctata taaggaagtt catttcattt ggagagaaca cggggactct    3480
agcgctaccg gtatgggcag ccatcatcat catcatcacg tgagcaaggg cgaggagctg    3540
ttcaccgggg tggtgcccat cctggtcgag ctggacggcg acgtaaacgg ccacaagttc    3600
agcgtgtccg gcgagggcga gggcgatgcc acctacggca agctgaccct gaagttcatc    3660
tgcaccaccg gcaagctgcc cgtgccctgg cccaccctcg tgaccaccct gacctacggc    3720
gtgcagtgct tcagccgcta ccccgaccac atgaagcagc acgacttctt caagtccgcc    3780
atgcccgaag gctacgtcca ggagcgcacc atcttcttca aggacgacgg caactacaag    3840
acccgcgccg aggtgaagtt cgagggcgac accctggtga accgcatcga gctgaagggc    3900
atcgacttca aggaggacgg caacatcctg gggcacaagc tggagtacaa ctacaacagc    3960
cacaacgtct atatcatggc cgacaagcag aagaacggca tcaaggtgaa cttcaagatc    4020
cgccacaaca tcgaggacgg cagcgtgcag ctcgccgacc actaccagca gaacacccccc   4080
atcggcgacg gccccgtgct gctgcccgac aaccactacc tgagcaccca gtccgccctg    4140
agcaaagacc ccaacgagaa gcgcgatcac atggtcctgc tggagttcgt gaccgccgcc    4200
gggatcactc tcggcatgga cgagctgtac aagtccggag ctgcggccgc tgccgctgcg    4260
gcagcggccg aattcatgga ccctgaaggt ttcacgagtg gcttattccg gtggaaccca    4320
acgagagcat tggttcaagc accacctccg gttccacctc cgctgcagca acagccggtg    4380
acaccgcaga cggctgcttt tgggatgcga cttggtggtt tagagggact attcggtccg    4440
tacggtatac gtttctacac ggcggcgaag atagcggagt taggttttac ggcgagcacg    4500
cttgtgggta tgaaggacga ggagcttgaa gagatgatga atagtctctc tcatatctttt    4560
cgttgggagc ttcttgttgg tgaacggtac ggtatcaaag ctgccgttag agctgaacgg    4620
agacgattgc aagaagagga ggaagaggaa tcttctagac gccgtcattt gctactctcc    4680
gccgctggtg attccggtac tcatcacgct cttgatgctc tctcccaaga agggttatct    4740
gaggaaccgg tgcagcaaca agaccagact gatgcggcgg ggaataacgg cggaggagga    4800
agtggttact gggacgcagg tcaaggaaag atgaagaagc aacagcagca gagacggaga    4860
aagaaaccaa tgctgacgtc agtggaaacc gacgaagacg tcaacgaagg tgaggatgac    4920
gacgggatgg ataacggcaa cggaggtagt ggtttgggga cagagagaca gagggagcat    4980
ccgtttatcg taacggagcc tggggaagtg gcacgtggca aaaagaacgg cttagattat    5040
ctgttccact tgtacgaaca atgccgtgag ttccttcttc aggtccagac aattgctaaa    5100
```

```
gaccgtggcg aaaaatgccc caccaaggtg acgaaccaag tattcaggta cgcgaagaaa    5160
tcaggagcga gttacataaa caagcctaaa atgcgacact acgttcactg ttacgctctc    5220
cactgcctag acgaagaagc ttcaaatgct ctcagaagag cgtttaaaga acgcggtgag    5280
aacgttggct catggcgtca ggcttgttac aagccacttg tgaacatcgc ttgtcgtcat    5340
ggctgggata tagacgccgt cttaacgct catcctcgtc tctctatttg gtatgttcca    5400
acaaagctgc gtcagctttg ccatttggag cggaacaatg cggttgctgc ggctgcggct    5460
ttagttggcg gtattagctg taccggatcg tcgacgtctg gacgtggtgg atgcggcggc    5520
gacgacttgc gtttcggagg atcctaggtc gaggcgaatt cccccgatcg ttcaaacatt    5580
tggcaataaa gtttcttaag attgaatcct gttgccggtc ttgcgatgat tatcatataa    5640
tttctgttga attacgttaa gcatgtaata attaacatgt aatgcatgac gttatttatg    5700
agatgggttt ttatgattag agtcccgcaa ttatacattt aatacgcgat agaaaacaaa    5760
atatagcgcg caaactagga taaattatcg cgcgcggtgt catctatgtt actagatcgg    5820
gaattaattc gataagctag agacaattcg agctcgcatg cctgcaggtc cccagattag    5880
cctttttcaat ttcagaaaga atgctaaccc acagatggtt tagagaggct tacgcagcag    5940
gtctcatcaa gacgatctac ccgagcaata atctccagga aatcaaatac cttcccaaga    6000
aggttaaaga tgcagtcaaa agattcagga ctaactgcat caagaacaca gagaaagata    6060
tatttctcaa gatcagaagt actattccag tatggacgat tcaaggcttg cttcacaaac    6120
caaggcaagt aatagagatt ggagtctcta aaaaggtagt tcccactgaa tcaaaggcca    6180
tggagtcaaa gattcaaata gaggacctaa cagaactccc cgtaaagact ggcgaacagt    6240
tcatacagag tctcttacga ctcaatgaca agaagaaaat cttcgtcaac atggtggagc    6300
acgacacgct tgtctactcc aaaaatatca agatacagt ctcagaagac caaagggcaa    6360
ttgagacttt tcaacaaagg gtaatatccg gaaacctcct cggattccat tgcccagcta    6420
tctgtcactt tattgtgaag atagtggaaa aggaaggtgg ctcctacaaa tgccatcatt    6480
gcgataaagg aaaggccatc gttgaagatg cctctgccga cagtggtccc aaagatggac    6540
ccccacccac gaggagcatc gtggaaaaag aagacgttcc aaccacgtct tcaaagcaag    6600
tggattgatg tgatatctcc actgacgtaa gggatgacgc acaatcccac tatccttcgc    6660
aagacccttc ctctatataa ggaagttcat ttcatttgga gagaacacgg gggactctag    6720
cgctaccggt atgaagctac tgtcttctat cgaacaagca tgcgatattt gccgacttaa    6780
aaagctcaag tgctccaaag aaaaaccgaa gtgcgccaag tgtctgaaga caactgggga    6840
gtgtcgctac tctcccaaaa ccaaaagatc tccgctgact agggcacatc tgacagaagt    6900
ggaatcaagg ctagaaagac tggaacagct atttctactg atttttcctc gagaagacct    6960
tgacatgatt ttgaaaatgg attctttaca ggatataaaa gcattgttaa caggattatt    7020
tgtacaagat aatgtgaata agatgccgt cacagataga ttggcttcag tggagactga    7080
tatgcctcta acattgagac agcatagaat aagtgcgaca tcatcatcgg aagagagtag    7140
taacaaggt caaagacagt tgactgtatc ggtctcggaa ttgatgcctt cggagttaac    7200
accagaagaa cgatcggaac taaaaaactc aatcgccgag ttccacacat accaactcga    7260
tccaggaagc tgttcatcac tccacgcgca acgaatccac gcgcctccgg aactcgtctg    7320
gtcaatcgta cgacgattcg acaaaccaca aacacaccgc cacttcatca atcctgctc    7380
cgtcgaacaa aacttcgaga tgcgcgtcgg atgcacgcgc gacatcatcg tcatcagtgg    7440
```

```
attaccggcg aacacatcaa cggaaagact cgatatactc gacgacgaac ggagagttac    7500
cggagccagt atcatcggag gcgaacatag gctgacgaat tacaaaggcg ttacgacggt    7560
gcatcggttc gagaaagaga atcggatctg gacggtggtt ttggaatctt acgtcgttga    7620
tatgccggaa ggtaactcgg aggatgatac tcgtattgtt gtggatgacg ttgtgaagct    7680
taatttgcag aaactcgcga cggttgctga agctatggct cgtaactccg gtgacggaag    7740
tggttctcag gtgacgtgaa gatcctaggt cgaggcgaat ttccccgatc gttcaaacat    7800
ttggcaataa agtttcttaa gattgaatcc tgttgccggt cttgcgatga ttatcatata    7860
atttctgttg aattacgtta agcatgtaat aattaacatg taatgcatga cgttatttat    7920
gagatgggtt tttatgatta gagtcccgca attatacatt taatacgcga tagaaaacaa    7980
atatagcgcg caaactagat aaattatcgc gcgcggtgtc atctatgtta ctagatcggg    8040
aattaattcg atagctagag atccgtcaac atggtggagc acgacacgct tgtctactcc    8100
aaaaatatca agatacagt  ctcagaagac caaagggcaa ttgagacttt tcaacaaagg    8160
gtaatatccg gaaacctcct cggattccat tgcccagcta tctgtcactt tattgtgaag    8220
atagtggaaa aggaaggtgg ctcctacaaa tgccatcatt gcgataaagg aaaggccatc    8280
gttgaagatg cctctgccga cagtggtccc aaagatggac ccccacccac gaggagcatc    8340
gtggaaaaag aagacgttcc aaccacgtct tcaaagcaag tggattgatg tgatatctcc    8400
actgacgtaa gggatgacgc acaatcccac tatccttcgc aagacccttc ctctatataa    8460
ggaagttcat tcatttggag aggacagac  ctgcaggtcg atccatgagc ccagaacgac    8520
gcccggccga catccgccgt gccaccgagg cggacatgcc ggcggtctgc accatcgtca    8580
accactacat cgagacaagc acggtcaact tccgtaccga gccgcaggaa ccgcaggagt    8640
ggacggacga cctcgtccgt ctgcgggagc gctatccctg gctcgtcgcc gaggtggacg    8700
gcgaggtcgc cggcatcgcc tacgcgggcc cctggaaggc acgcaacgcc tacgactgga    8760
cggccgagtc gaccgtgtac gtctccccc  gccaccagcg gacgggactg gctccacgc     8820
tctacaccca cctgctgaag tccctggagg cacagggctt caagagcgtg gtcgctgtca    8880
tcgggctgcc caacgacccg agcgtgcgca tgcacgaggc gctcggatat gcccccgcg     8940
gcatgctgcg ggcggccggc ttcaagcacg ggaactggca tgacgtgggt ttctggcagc    9000
tggacttcag cctgccggta ccgccccgtc cggtcctgcc cgtcaccgag atctgatctc    9060
acgcgtctag gatcgacctg cagatcgttc aaacatttgg caataaagtt tcttaagatt    9120
gaatcctgtt gccggtcttg cgatgattat catctaattt ctgttgaatt acgttaagca    9180
tgtaataatt aacatgtaat gcatgacgtt atttatgaga tgggttttta tgattagagt    9240
cccgcaatta tacatttaat acgcgataga aacaaaata tagcgcgcaa actaggataa    9300
attatcgcgc gcggtgtcat ctatgttact agatctctag cttgatatcg aattaattca    9360
ctggccgtcg ttttacaacg tcgtgactgg gaaaaccctg gcgttaccca acttaatcgc    9420
cttgcagcac atcccccttt cgccagctgg cgtaatagcg aagaggcccg caccgatcgc    9480
ccttcccaac agttgcgcag cctgaatggc gccgctcct  ttcgctttct tcccttcctt    9540
tctcgccacg ttcgccggct ttccccgtca gctctaaat  cggggctcc ctttagggtt     9600
ccgatttagt gctttacggc acctcgaccc caaaaaactt gatttgggtg atggttcacg    9660
tagtgggcca tcgccctgat agacggtttt tcgccctttg acgttggagt ccacgttctt    9720
taatagtgga ctcttgttcc aaactggaac aacactcaac cctatctcgg gctattcttt    9780
tgatttataa gggattttgc cgatttcgga accaccatca aacaggattt tcgcctgctg    9840
```

```
gggcaaacca gcgtggaccg cttgctgcaa ctctctcagg gccaggcggt gaagggcaat   9900
cagctgttgc ccgtctcact ggtgaaaaga aaaaccaccc cagtacatta aaaacgtccg   9960
caatgtgtta ttaagttgtc taagcgtcaa tttgtttaca ccacaatata tcctgccac  10019
```